(12) United States Patent
Görgens et al.

(10) Patent No.: US 8,304,371 B2
(45) Date of Patent: Nov. 6, 2012

(54) INSECTICIDAL ARYLPYRROLINES

(75) Inventors: Ulrich Görgens, Ratingen (DE); Yasushi Yoneta, Hanyu (JP); Tetsuya Murata, Oyama (JP); Jun Mihara, Oyama (JP); Kei Domon, Oyama (JP); Eiichi Shimojo, Oyama (JP); Katsuhiko Shibuya, Shimotsuke (JP); Teruyuki Ichihara, Oyama (JP)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 12/863,980

(22) PCT Filed: Jan. 29, 2009

(86) PCT No.: PCT/EP2009/000559
§ 371 (c)(1),
(2), (4) Date: Sep. 21, 2010

(87) PCT Pub. No.: WO2009/097992
PCT Pub. Date: Aug. 13, 2009

(65) Prior Publication Data
US 2011/0003690 A1    Jan. 6, 2011

(30) Foreign Application Priority Data

Feb. 7, 2008  (JP) ................ 2008-027241
May 30, 2008  (JP) ................ 2008-143120
Oct. 22, 2008  (EP) ................ 08167339

(51) Int. Cl.
*A01C 1/06*  (2006.01)
*A01N 43/653*  (2006.01)
*A01N 43/36*  (2006.01)
*A01N 43/56*  (2006.01)
*A01N 43/50*  (2006.01)
*A01N 43/647*  (2006.01)
*A01N 43/713*  (2006.01)
*A01N 43/40*  (2006.01)
*A01P 7/04*  (2006.01)

(52) U.S. Cl. ........ 504/100; 514/422; 514/429; 548/518; 548/565

(58) Field of Classification Search ............... 504/100; 514/422, 429; 548/518, 565
See application file for complete search history.

(56) References Cited

U.S. PATENT DOCUMENTS

| 2,969,392 | A | 1/1961 | Schaeffer |
| 4,759,832 | A | 7/1988 | Degner et al. |
| 5,627,181 | A | 5/1997 | Riedl et al. |
| 5,656,644 | A | 8/1997 | Adams et al. |
| 2007/0111984 | A1 | 5/2007 | Naidu et al. |

FOREIGN PATENT DOCUMENTS

| DE | 137927 | 10/1979 |
| EP | 1 538 138 | 6/2005 |
| JP | 2007/016017 | 1/2007 |
| JP | 2007/091708 | 4/2007 |
| JP | 2007/106756 | 4/2007 |
| JP | 2008/122375 | 10/2008 |
| WO | 2004/103991 | 12/2004 |
| WO | 2007/030847 | 3/2007 |
| WO | 2007/070606 | 6/2007 |
| WO | 2007/074789 | 7/2007 |
| WO | 2007/075459 | 7/2007 |
| WO | 2007/079162 | 7/2007 |
| WO | 2007/105814 | 9/2007 |
| WO | 2007/123853 | 11/2007 |
| WO | 2007/123855 | 11/2007 |
| WO | 2007/125984 | 11/2007 |

OTHER PUBLICATIONS

Kitano et al., Synthesis, (2006), vol. 3, p. 405-410. (provided by Applicants).*
International Search Report based on PCT/EP2009/000559 dated May 13, 2009 (15 pages).
Kitano et al.; "A Convenient Method for the Preparation of Benzyl Isocyanides" Synthesis, vol. 3, 2006, pp. 405-410, XP002525680 Example 4F.
Kuhn et al.: "The Synthesis of Pyrroles With Insecticidal Activity" Pesticide Science, Elsevier Applied Science Publisher, Barking, GB, vol. 41, No. 3, Jan. 1, 1994, pp. 279-286, XP002084185, ISSN: 0031-613X; p. 284; Compound 9.
Tsuge et al.; "Cycloadditions of N-Benzylideneaminoacetonitrile As a Synthetic Equivalent of Methanenitrile Benzylide" Chemistry Letters, pp. 1601-1604, 1985, The Chemical Society of Japan.
Padwa et al.; "Silyl-Substituted Thioimidates As Nitrile Ylide Equivalents"; J. Org. Chem.; 1987, 52, pp. 1027-1035.

* cited by examiner

*Primary Examiner* — Yong Chu
(74) *Attorney, Agent, or Firm* — Baker Donelson Bearman, Caldwell & Berkowitz, PC

(57) ABSTRACT

The invention relates to novel arylpyrroline compounds of formula (I) which having excellent insecticidal activity and which can thus be used as an insecticide is provided.

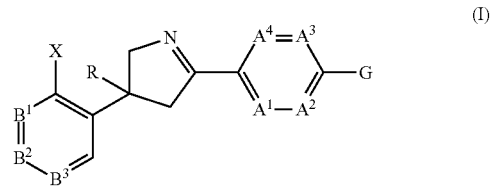

20 Claims, No Drawings

INSECTICIDAL ARYLPYRROLINES

CROSS REFERENCE TO RELATED APPLICATIONS

This application is a §371 National Stage Application of PCT/EP2009/000559 filed Jan. 29, 2009, which claims priority to Japanese Application 2008-027241 filed Feb. 7, 2008, Japanese Application 2008-143120 filed May 30, 2008 and European Application 08167339.4 filed Oct. 22, 2008.

BACKGROUND OF THE INVENTION

1. Field of the Invention

The present invention relates to novel arylpyrrolines and their use as insecticides, as well as to processes for the preparation of the arylpyrrolines.

2. Description of Related Art

From Japanese Patent Application Laid-open No. 2007-91708 it is known that dihydroazole-substituted benzamide compounds may be used as pest controlling agents. Moreover, from several published patent applications it is known, that certain isoxazoline derivatives can also be used as pest controlling agents (cf. WO 2005/085216, WO 2007/026965, WO 2007/074789, WO 2007/070606, WO 2007/075459, WO 2007/079162, WO 2007/105814, WO 2007/125984, Japanese Patent Application Laid-open No. 2007-16017, Japanese Patent Application Laid-open No. 2007-106756, and Japanese Patent Application Laid-open No. 2007-30847). The use of 5-membered heterocyclic compounds as pest controlling agents has been described in WO 2007/123853, and the same use of pyrazoline compounds has been described in WO 2007/123855.

Since ecological and economic demands on modern plant treatment agents are continually increasing, particularly in respect to the amount applied, residue formation, selectivity, toxicity and favourable production methodology, and also because, for example, resistance problems can occur, there is the on-going task to develop new plant treatment agents that at least in certain areas are able to demonstrate advantages over known agents.

The inventors of the present invention devotedly conducted research to create a novel compound exhibiting higher effects and having a wide spectrum as an insecticide. As a result they found novel arylpyrrolines, which exhibit high activity, a wide spectrum and safety, and, furthermore, are effective against pests that are resistant to organic phosphorus agents or carbamate agents.

SUMMARY OF THE INVENTION

Thus, this invention is directed to arylpyrroline compounds of formula (I)

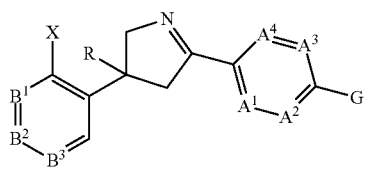

wherein

G represents an optionally substituted saturated or unsaturated 5- or 6-membered heterocyclic group, or represents a chemical group characterized by the following formula:

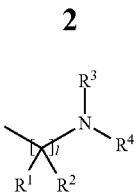

wherein $R^1$ and $R^2$ each independently represent hydrogen; optionally substituted alkyl, cycloalkyl, haloalkyl, cyclohaloalkyl, alkenyl, alkynyl, haloalkenyl, haloalkynyl; cyano; optionally substituted alkoxycarbony, or alkoxythiocarbonyl; or R1 and R2 together with the carbon atom to which they are attached form a 3 to 6-membered carbocyclic ring;

R3 represents hydrogen; amino; hydroxyl; optionally substituted alkoxy, alkylcarbonylamino, alkylimino, alkyl, cycloalkyl, haloalkyl; cyano; optionally substituted alkenyl, alkynyl, alkylcarbonyl, or is selected from the following groups $CH_2$—R5, C(=O)R5, C(=S)R5;

R4 represents a chemical group selected among hydrogen; cyano; carbonyl; thiocarbonyl; optionally substituted alkylcarbonyl, alkylthiocarbonyl, haloalkylcarbonyl, haloalkylthiocarbonyl, alkylaminocarbonyl, alkylaminothiocarbonyl, dialkylaminocarbonyl, dialkylaminothiocarbonyl, alkoxyaminocarbonyl, alkoxyaminothiocarbonyl, alkoxycarbonyl, alkoxythiocarbonyl, thioalkoxycarbonyl, thioalkoxythiocarbonyl, alkylsulfonyl, haloalkylsulfonyl; or a chemical group selected among cycloalkylcarbonyl, alkenylcarbonyl, alkynylcarbonyl, cycloalkylalkylcarbonyl, alkylsulfenylalkylcarbonyl, alkylsulfinylalkylcarbonyl, alkylsulfonylalkylcarbonyl, alkylcarbonylalkylcarbonyl, cyclalkylaminocarbonyl, alkenylaminocarbonyl, alkynylaminocarbonyl; or is selected from the groups $C(=O)R^5$ and $C(=S)R^5$;

or

R3 and R4 together with the nitrogen atom to which they are bound, form a 3- to 6-membered heterocyclic ring which may be substituted with a substituent X, or may be substituted with a keto, thioketo or nitroimino group;

R5 represents optionally substituted phenyl, or an optionally substituted heterocyclic ring;

R represents optionally substituted alkyl, or haloalkyl;

A1, A2, A3 and A4 each independently represents a group C—Y; or nitrogen, under the proviso that only 2 of the chemical groups A1, A2, A3 and A4 may stand for nitrogen at the same time or if A1 and A2 both represent C—Y, then both Y, together with the carbon atoms to which they are attached to, may form a 5- or 6-membered aromatic ring;

B1, B2 and B3 each independently represent C—X or nitrogen; under the proviso that only 2 of the chemical groups B1, B2, and B3 may stand for nitrogen at the same time;

X each independently represents hydrogen, halogen, optionally substituted haloalkyl; nitro; optionally substituted alkyl, alkoxyl; cyano, optionally substituted haloalkoxyl, alkylsulfenyl, alkylsulfinyl, alkylsulfonyl, haloalkylsulfenyl, haloalkylsulfinyl, haloalkylsulfonyl; hydroxyl, thiol, amino, optionally substituted acylamino, alkoxycarbonylamino, haloalkoxycarbonylamino, alkoxyimino, haloalkoxyimino, alkylsulfonylamino; or sulfur pentafluoride;

Y each independently represents hydrogen; halogen; optionally substituted haloalkyl; nitro; optionally substituted alkyl, cycloalkyl, cyclohaloalkyl, alkoxyl; cyano, optionally substituted haloalkoxyl, alkylsulfenyl, alkylsulfinyl, alkylsulfonyl, haloalkylsulfenyl, haloalkylsulfinyl, haloalkylsulfonyl, alkylsulfonyloxy, haloalkylsulfonyloxy, alkylaminosulfonyl, haloalkylaminosulfonyl, dialkylaminosulfonyl, di(haloalkyl)aminosulfonyl; hydroxyl; thiol; amino; optionally substituted alkylamino, dialkylamino, acylamino, alkoxycarbonylamino, haloalkoxycarbonylamino, alkylsulfonylamino, haloalkylsulfonylamino, trialkylsilyl, alkoxyimino, haloalkoxyimino, alkoxyiminoalkyl, haloalkoxy-iminoalkyl, alkylsulfinylimino, alkylsulfinyliminoalkyl, alkylsulfinyliminoalkylcarbonyl, alkylsulfoxyimino, alkylsulfoxyiminoalkyl, alkoxycarbonyl, alkylcarbonyl, aminocarbonyl, alkylaminocarbonyl, aminothiocarbonyl, alkylaminothiocarbonyl, dialkylaminocarbonyl, or dialkylaminothiocarbonyl; and 1 stands for 1, 2 or 3.

DETAILED DESCRIPTION OF A PREFERRED EMBODIMENT

In a first embodiment the invention is directed to arylpyrroline compounds of formula (I),
wherein
G is selected from the group consisting of optionally substituted 5-membered heterocyclic groups G1 to G9:

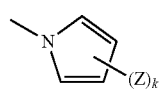

G1

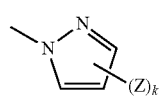

G2

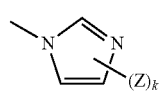

G3

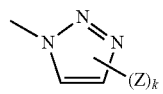

G4

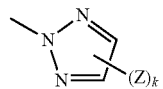

G5

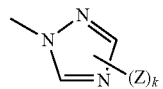

G6

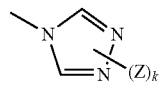

G7

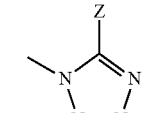

G8

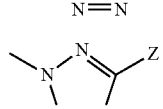

G9 or represents a chemical group characterized by the following formula:

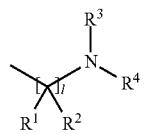

wherein
$R^1$ and $R^2$ each independently represent hydrogen; optionally substituted $C_{1-12}$ alkyl, $C_{3-8}$ cycloalkyl, $C_{1-12}$ haloalkyl, $C_{3-8}$ cyclohaloalkyl, $C_{2-12}$ alkenyl, $C_{2-12}$, alkynyl, $C_{2-12}$ haloalkenyl, $C_{2-12}$ haloalkynyl; cyano; optionally substituted $C_{1-12}$ alkoxy-carbonyl, $C_{1-12}$ alkoxy-thiocarbonyl, or $R^1$ and $R^2$ together with the carbon atom to which they are attached may form a 3 to 6-membered carbocyclic ring;

$R^3$ represents hydrogen; amino; hydroxyl; optionally substituted $C_{1-12}$ alkoxy, $C_{1-12}$ alkylcarbonylamino, $C_{1-12}$ alkylimino, $C_{1-12}$ alkyl, $C_{3-8}$ cycloalkyl, $C_{1-12}$ haloalkyl, cyano, $C_{2-12}$ alkenyl, $C_{2-12}$ alkynyl, $C_{1-12}$ alkyl-carbonyl; or is selected from the following groups $CH_2$—$R^5$, $C(=O)R^5$, $C(=S)R^5$;

$R^4$ represents a chemical group selected among hydrogen; cyano; carbonyl; thiocarbonyl; optionally substituted $C_{1-12}$ alkyl-carbonyl, $C_{1-12}$ alkyl-thiocarbonyl, $C_{1-12}$ haloalkyl-carbonyl, $C_{1-12}$ haloalkyl-thiocarbonyl, $C_{1-12}$ alkylamino-carbonyl, $C_{1-12}$ alkylamino-thiocarbonyl, $C_{2-24}$ (total carbon number) dialkylamino-carbonyl, $C_{2-24}$ (total carbon number) dialkylamino-thiocarbonyl, $C_{1-12}$ alkoxyamino-carbonyl, $C_{1-12}$ alkoxyamino-thiocarbonyl, $C_{1-12}$ alkoxy-carbonyl, $C_{1-12}$ alkoxy-thiocarbonyl, $C_{1-12}$ thioalkoxy-carbonyl, $C_{1-12}$ thioalkoxy-thiocarbonyl, $C_{1-12}$ alkylsulfonyl, $C_{1-12}$ haloalkylsulfonyl; or a chemical group selected among $C_{4-13}$ cycloalkylcarbonyl, $C_{3-13}$ alkenylcarbonyl, $C_{3-13}$ alkynylcarbonyl, $C_{5-25}$cycloalkylalkylcarbonyl, $C_{3-25}$ alkylsulfenylalkylcarbonyl, $C_{3-25}$ alkylsulfinylalkylcarbonyl. $C_{3-25}$ alkylsulfonylalkylcarbonyl, $C_{4-26}$ alkylcarbonylalkylcarbonyl, $C_{4-13}$ cyclalkylaminocarbonyl, $C_{3-13}$ alkenylaminocarbonyl, $C_{3-13}$ minocarbony alkynylal; or is selected from the groups $C(=O)R^5$ and $C(=S)R^5$; or $R^3$ and $R^4$ together with the nitrogen atom to which they are bound, form a 3- to 6-membered heterocyclic ring which may be substituted with a substituent X, or may be substituted with a keto, thioketo or nitroimino group;

$R^5$ represents optionally substituted phenyl, or an optionally substituted saturated or unsaturated heterocyclic ring:

Z each independently represents halogen, optionally substituted C1-12 haloalkyl; nitro; optionally substituted C1-12 alkoxyl; cyano; optionally substituted C1-12 haloalkoxyl, C1-12 alkylsulfenyl, C1-12 alkylsulfinyl, C1-12 alkylsulfonyl, C1-12 haloalkylsulfenyl, C1-12 haloalkylsulfinyl, C1-12 haloalkylsulfonyl; hydroxyl or thiol;

k represents 0, 1, 2, 3 or 4;

R represents optionally substituted C1-12 alkyl, or C1-12 haloalkyl;

A1, A2, A3 and A4 each independently represents a group C—Y; or nitrogen, under the proviso that only 2 of the chemical groups A1, A2, A3 and A4 may stand for nitrogen at the same time; or if A1 and A2 both represent C—Y, then both Y, together with the carbon atoms to which they are attached to, may form a 5- or 6-membered aromatic ring;

B1, B2 and B3 each independently represents a group C—X; or nitrogen under the proviso that only 2 of the chemical groups B1, B2, and B3 may stand for nitrogen at the same time;

X each independently represents hydrogen; halogen; optionally substituted C1-12 haloalkyl; nitro; optionally substituted C1-12 alkyl, C1-12 alkoxyl, cyano, optionally substituted C1-12 haloalkoxyl, C1-12 alkylsulfenyl, C1-12 alkylsulfinyl, C1-12 alkylsulfonyl, C1-12 haloalkylsulfenyl, C1-12 haloalkylsulfinyl, C1-12 haloalkylsulfonyl; hydroxyl, thiol; amino; optionally substituted C1-12 acylamino, C1-12 alkoxy-carbonylamino, C1-12 haloalkoy-carbonylamino, C1-12 alkoxy-imino, C1-12 haloalkoxy-imino, C1-12 alkylsulfonylamino; or sulfur pentafluoride;

Y each independently represents hydrogen; halogen; optionally substituted C1-12haloalkyl; nitro; optionally substituted C1-12 alkyl, C3-8 cycloalkyl, C3-8 cyclohaloalkyl, C1-12 alkoxyl; cyano, optionally substituted C1-12 haloalkoxyl, C1-12 alkylsulfenyl, C1-12 alkylsulfinyl, C1-12 alkylsulfonyl, C1-12 haloalkylsulfenyl, C1-12 haloalkylsulfinyl, C1-12 haloalkylsulfonyl, C1-12 alkylsulfonyloxy, C1-12 haloalkylsulfonyloxy, C1-12 alkylaminosulfonyl, C1-12 haloalkylaminosulfonyl, C2-24 (total carbon number) dialkylaminosulfonyl, C2-24 (total carbon number)di(haloalkyl)aminosulfonyl; hydroxyl; thiol; amino; optionally substituted C1-12 alkylamino, C2-24 (total carbon number) dialkylamino, C1-12 acylamino, C1-12 alkoxycarbonylamino, C1-12 haloalkoxycarbonylamino, C1-12 alkylsulfonylamino, C1-12 haloalkylsulfonylamino, C1-12 trialkylsilyl, C1-12 alkoxyimino, C1-12 haloalkoxyimino, C1-12 alkoxyiminoalkyl, C1-12 haloalkoxy-iminoalkyl, C1-12 alkylsulfinylimino, C1-12 alkylsulfinyliminoalkyl, C1-12 alkylsulfinylimino-C1-12 alkylcarbonyl, C1-12 alkylsulfoxyimino, C1-12 alkylsulfoxyimino-C1-12 alkyl, C1-12 alkoxycarbonyl, C1-12 alkylcarbonyl, aminocarbonyl, C1-12 alkylaminocarbonyl, aminothiocarbonyl, C1-12 alkylaminothiocarbonyl, C2-12 (total carbon number)dialkylaminocarbonyl, or C2-12 (total carbon number)dialkylaminothiocarbonyl; and l stands for 1, 2 or 3.

In a second embodiment the invention is directed to arylpyrroline compounds of formula (I), wherein G is selected from the group consisting of optionally substituted heterocyclic groups G1 to G9:

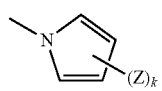  G1

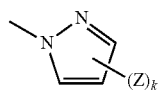  G2

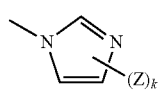  G3

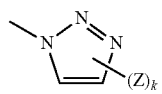  G4

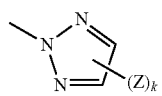  G5

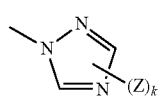  G6

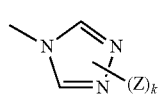  G7

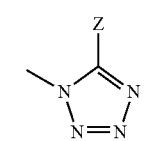  G8

-continued

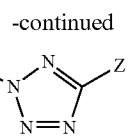  G9 or represents a chemical group characterized by the following formula:

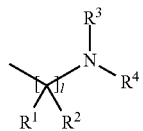

$R^1$ and $R^2$ each independently represent hydrogen; optionally substituted $C_{1-6}$ alkyl, $C_{3-6}$ cycloalkyl, $C_{1-6}$ haloalkyl, cyclohaloalkyl, $C_{3-6}$ alkenyl, $C_{2-6}$ alkynyl, $C_{2-12}$ haloalkenyl, $C_{2-6}$ haloalkynyl; cyano; optionally substituted $C_{1-6}$ alkoxycarbonyl, $C_{1-6}$ alkoxy-thiocarbonyl, or R1 and R2 together with the carbon atom to which they are attached may form a 3 to 6-membered carbocyclic ring;

R3 represents hydrogen; amino; hydroxyl; optionally substituted C1-6 alkoxy, C1-6 alkyl-carbonylamino, C1-6 alkylimino, C1-6 alkyl, C3-6 cycloalkyl, C1-6 haloalkyl, cyano, C2-6 alkenyl, C2-6 alkynyl, C1-6 alkyl-carbonyl; or is selected from the following groups CH2-R5, C(=O)R5, C(=S)R5;

R4 represents a chemical group selected among hydrogen; cyano; carbonyl; thiocarbonyl; optionally substituted C1-6 alkyl-carbonyl, C1-6 alkyl-thiocarbonyl, C1-6 haloalkyl-carbonyl, C1-6 haloalkyl-thiocarbonyl, C1-6 alkylamino-carbonyl, C1-6 alkylamino-thiocarbonyl, C2-12 (total carbon number) dialkylamino-carbonyl, C2-12 (total carbon number) dialkylamino-thiocarbonyl, C1-6 alkoxyamino-carbonyl, C1-6 alkoxyamino-thiocarbonyl, C1-6 alkoxy-carbonyl, C1-6 alkoxy-thiocarbonyl, C1-6 thioalkoxy-carbonyl, C1-6 thioalkoxy-thiocarbonyl, C1-6 alkylsulfonyl, C1-6 haloalkylsulfonyl; or a chemical group selected among C4-7 cycloalkylcarbonyl, C3-7 alkenylcarbonyl, C3-7 alkynylcarbonyl, C5-13 cycloalkylalkylcarbonyl, C3-13 alkylsulfenylalkylcarbonyl, C3-13 alkylsulfinylalkylcarbonyl, C3-13 alkylsulfonylalkylcarbonyl, C4-14 alkylcarbonylalkylcarbonyl, C4-7 cyclalkylaminocarbonyl, C3-7 alkenylaminocarbonyl, C3-7 alkynylaminocarbonyl; or is selected from the groups C(=O)R5 and C(=S)R5;

or R3 and R4 together with the nitrogen atom to which they are bound, form a 3- to 6-membered heterocyclic ring which may be substituted with a substituent X, or may be substituted with a keto, thioketo or nitroimino group;

R5 represents optionally substituted phenyl, or an optionally substituted saturated or unsaturated heterocyclic ring;

Z each independently represents halogen, optionally substituted C1-6 haloalkyl; nitro; optionally substituted C1-6 alkoxyl; cyano; optionally substituted C1-6 haloalkoxyl, C1-6 alkylsulfenyl, C1-6 alkylsulfinyl, C1-6 alkylsulfonyl, C1-6 haloalkylsulfenyl, C1-6 haloalkylsulfinyl, C1-6 haloalkylsulfonyl; hydroxyl or thiol;

k represents 0, 1, 2, 3 or 4;

R represents optionally substituted C1-6 alkyl, or C1-6 haloalkyl;

A1, A2, A3 and A4 each independently represents a group C—Y; or nitrogen, under the proviso that only 2 of the chemical groups A1, A2, A3 and A4 may stand for nitrogen at the same time; or if A1 and A2 both represent C—Y, then both Y, together with the carbon atoms to which they are attached to, may form a 5- or 6-membered aromatic ring;

B1, B2 and B3 each independently represents a group C—X; or nitrogen under the proviso that only 2 of the chemical groups B1, B2, and B3 may stand for nitrogen at the same time;

X each independently represents hydrogen; halogen; optionally substituted C1-6 haloalkyl; nitro; optionally substituted C1-6 alkyl, C1-6 alkoxyl, cyano, optionally substituted C1-6 haloalkoxyl, C1-6 alkylsulfenyl, C1-6 alkylsulfinyl, C1-6 alkylsulfonyl, C1-6 haloalkylsulfenyl, C1-6 haloalkylsulfinyl, C1-6 haloalkylsulfonyl; hydroxyl; thiol; amino; optionally substituted C1-6 acylamino, C1-6 alkoxycarbonylamino, C1-6 haloalkoy-carbonylamino, C1-6 alkoxy-imino, C1-6 haloalkoxy-imino, C1-6 alkylsulfonylamino; or sulfur pentafluoride;

Y each independently represents hydrogen; halogen; optionally substituted C1-6haloalkyl; nitro; optionally substituted C1-6 alkyl, C3-6 cycloalkyl, C3-6 cyclohaloalkyl, C1-6 alkoxyl; cyano, optionally substituted C1-6 haloalkoxyl, C1-6 alkylsulfenyl, C1-6 alkylsulfinyl, C1-6 alkylsulfonyl, C1-6 haloalkylsulfenyl, C1-6 haloalkylsulfinyl, C1-6 haloalkylsulfonyl, C1-6 alkylsulfonyloxy, C1-6 haloalkylsulfonyloxy, C1-6 alkylaminosulfonyl, C1-6 haloalkylaminosulfonyl, C2-12 (total carbon number) dialkylaminosulfonyl, C2-12 (total carbon number)di(haloalkyl)aminosulfonyl; hydroxyl; thiol; amino; optionally substituted C1-6 alkylamino, C2-12 (total carbon number) dialkylamino, C1-6 acylamino, C1-6 alkoxycarbonylamino, C1-6 haloalkoxycarbonylamino, C1-6 alkylsulfonylamino, C1-6 haloalkylsulfonylamino, C1-6 trialkylsilyl, C1-6 alkoxyimino, C1-6 haloalkoxyimino, C1-6 alkoxyiminoalkyl, C1-6 haloalkoxy-iminoalkyl, C1-4 alkylsulfinylimino, C1-4 alkylsulfinylimino C1-6 alkyl, C1-4 alkylsulfinylimino-C1-5 alkylcarbonyl, C1-4 alkylsulfoxyimino, C1-4 alkylsulfoxyimino-C1-4 alkyl, C1-6 alkoxycarbonyl, C1-6 alkylcarbonyl, aminocarbonyl, C1-6 alkylaminocarbonyl, aminothiocarbonyl, C1-6 alkylaminothiocarbonyl, C2-12 (total carbon number)dialkylaminocarbonyl, or $C_{2-12}$ (total carbon number)dialkylaminothiocarbonyl; and l stands for 1, 2 or 3.

The compounds according to the invention have asymmetric carbons, and thus the compounds also include optically active species. Moreover, the present invention also includes N-oxides and salts of the compounds according to the invention.

In an embodiment A, arylpyrroline compounds of the following structures (I-a), (b), (I-d), (I-e) and (I-f), wherein the chemical groups G, $B^1$ to $B^3$, X, R are as defined herein, and wherein each of $Y_1, Y_2, Y_1$ and $Y_4$ are as defined herein for Y, are preferred.

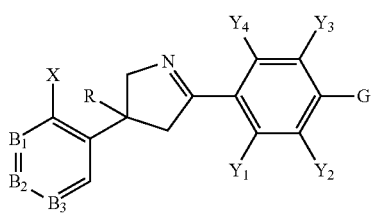
(I-a)

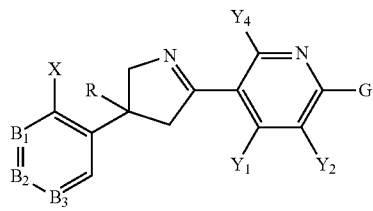
(I-b)

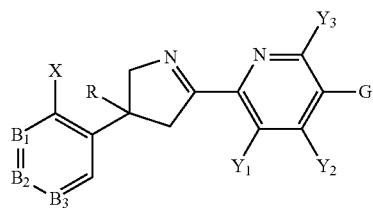
(I-c)

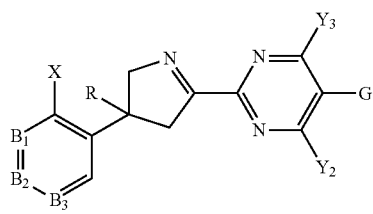
(I-d)

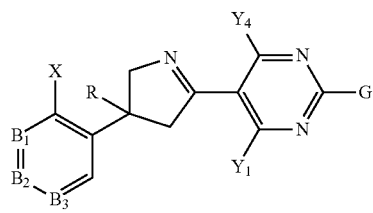
(I-e)

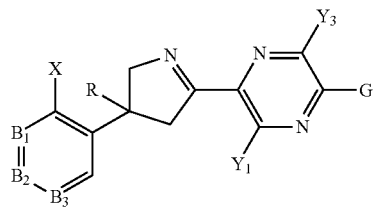
(I-f)

In an embodiment B, the invention is directed to compounds as defined in embodiment A, wherein G is selected among G1 to G9, preferably among G1, G2 and G6.

In an embodiment C, the invention is directed to compounds as defined in embodiment A, wherein G stands for a group

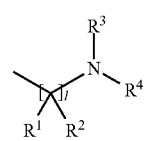

and wherein $R^1$ and $R^2$ are as defined herein, and wherein or $R^3$ and $R^4$ together with the nitrogen atom to which they are bound, form a 3- to 6-membered cyclic ring or a heterocycle, preferably selected among G1 to G9, which may be substituted with a substituent X, or may be substituted with a keto, thioketo or nitroimino group;

In an embodiment D and E, respectively, the invention is directed to arylpyrroline compounds of the following structures (I-g) and (I-h), respectively, wherein the chemical groups G, R are as defined herein, and wherein each of $Y_1, Y_2, Y_3$ and $Y_4$ are as defined herein for Y, and wherein $X_0, X_1, X_2$ and $X_3$ are as defined herein for X are preferred.

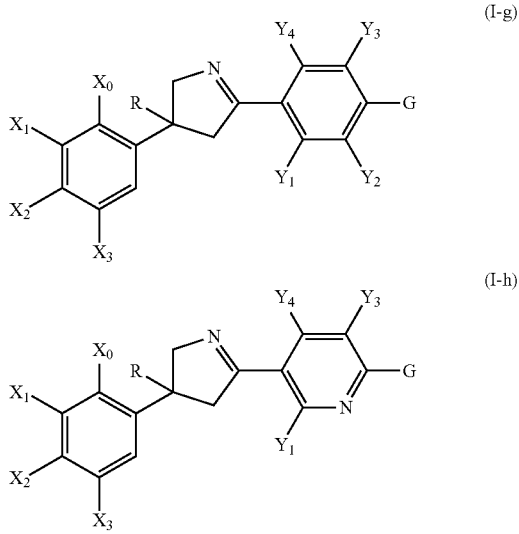

In an embodiment F, the invention is directed to compounds as defined in embodiment D or E, wherein G is selected among G1 to G9, preferably among G1, G2 and G6.

In an embodiment G, the invention is directed to compounds as defined in embodiment D or E, wherein G stands for a group

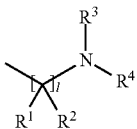

and wherein $R^1$ and $R^2$ are as defined herein, and wherein $R^3$ and $R^4$ together with the nitrogen atom to which they are bound, form a 3- to 6-membered cyclic ring or a heterocycle, preferably selected among G1 to G9, which may be substituted with a substituent X, or may be substituted with a keto, thioketo or nitroimino group;

In an embodiment H, the invention is directed to compounds as defined in embodiment D or E, wherein G stands for a group

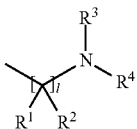

and wherein $R^1$ and $R^2$, $R^3$ and $R^4$ are as defined herein.

The compounds according to the present invention exhibit a potent insecticidal action.

In the present specification,

The term "alkyl" used either alone or combined with other terms such as "aminoalkyl" or "haloalkyl" includes straight-chained or branched alkyl containing up to 12 carbon atoms, such as methyl, ethyl, n- or iso-propyl; n-, iso-, secondary- or tertiary-butyl; n-pentyl, n-hexyl, n-heptyl, n-octyl, n-nonyl, n-decyl, n-undecyl or n-dodecyl, and preferably represents alkyl having 1 to 6 carbon atoms.

The term "halogen" or "halo" used either alone or combined with other terms such as "haloalkyl" includes fluorine, chlorine, bromine or iodine.

The term "haloalkyl" used either alone or combined with other terms refers to alkyl groups which are partially or fully substituted with halogen atoms which may be the same or different. Examples of "haloalkyl" includes among others chemical groups like $CF_3$, $CH_3F$, $CHF_2$, $CH_2CHF_2$, $CCl_3$, $CH_2Cl$, $CHCl_2$, $CF_2CF_3$, $CH_2CF_3$, $CH_2CH_2Cl$, $CH_2CH_2F$, $CHClCH_3$, $CHFCH_3$, $CH_2CHFCl$, $CHCl_2$, $CF_2CF_2H$, $CH_2CF_3$.

The term "cycloalkyl" used either alone or combined with other terms preferably stands for cycloalkyl groups having 3 to 8 carbon atoms, such as cyclopropyl, cyclobutyl, cyclopentyl, cyclohexyl, cycloheptyl or cyclooctyl, and preferably represents cycloalkyl having 3 to 7 carbon atoms.

The term "alkenyl" used either alone or combined with other terms preferably stands for alkenyl having 2 to 6 or 2 to 5 carbon atoms. Examples include vinyl, allyl, 1-propenyl, 1-, 2-, or 3-butenyl or 1-pentenyl. More preferred it stands for alkenyl having 2 to 4 carbon atoms.

The term "alkynyl" used either alone or combined with other terms preferably stands for alkynyl having 2 to 6 or 2 to 5 carbon atoms. Examples include ethynyl, propargyl, 1-propynyl, but-3-ynyl or pent-4-ynyl. More preferred it stands for alkynyl having 2 to 4 carbon atoms.

The term "heterocyclic group" used either alone or combined with other terms preferably stands for a 5- or 6-membered heterocyclic group containing at least one of N, O and S as a heteroatom. Typically a heterocyclic group contains no more than 4 nitrogens, 2 oxygens and 2 sulfur atoms. The cyclic group, the ring, can be saturated, unsaturated or partially saturated. If not mentioned otherwise, than a heterocyclic group can be can be attached through any available carbon or heteroatom. The term additionally includes fused heterocyclic group which may then be benzo-condensed. Heterocyclic group include for example furyl, thienyl, pyrrolyl, isoxazolyl, pyrazolyl, oxazolyl, oxathiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl or quinolyl.

The term "acylamino" includes groups like alkylcarbonylamino, cycloalkylcarbonylamino or benzoylamino.

The term "optionally substituted" means unsubstituted, or substituted with at least one substituent "J", which is selected among $C_{1-6}$Alkyl, $C_{2-6}$Alkenyl, $C_{2-6}$Alkynyl, $C_{3-6}$Cycloalkyl, Chloro, Fluoro, Bromo, Iodo, $NO_2$, $NR_xR_y$, $N_3$, CN, SCN, $OR_x$, SH, $SF_5$, $COOR_x$, $C(O)R_x$, $CONR_xR_y$, $N=C(R_x)OR_y$, $SO_2NR_xR_y$, Phenyl, 5 or 6-membered heterocycles, whereas $R_x$ and $R_y$ independently of each other stands for H, $C_{1-6}$alkyl or $C_{1-6}$haloalkyl. The substituent J preferably stands for methyl, ethyl, i-propyl, $C_3$-Cycloalkyl. Chloro, Fluoro, Bromo, Iodo, $NO_2$, $NH_2$, $NMe_2$, NHMe, CN, SCN, OH, OMe, SH, $SF_5$, COOH, COOMe, C(O)H, COMe, $CONH_2COMe_2$, N=CHOH, N=CHOMe, N=CMeOH, $SO_2NHMe$, $SO_2NH_2$, $SO_2NMe_2$, Phenyl, a group G1 to G9 as defined herein, or pyridine.

The term "fluorine reagents" means "fluorine-containing reagents". Such reagents are known in the art and include for example HF as well as potassium fluoride, tetramethylammonium fluoride, tetraethylammonium fluoride or tetrabutylammonium fluoride.

The term "alkyl halide" stands for haloalkanes, such as fluoroalkanes, chloroalkanes, bromoalkanes and iodoalkanes, having from 1 to 6 carbon atoms.

The compounds according to the invention can be obtained by preparation methods generally known in the art, in combination with the production methods (a) to (g) or (p) as described herein.

Thus, the invention is also directed to a preparation method (a) for the preparation of compounds according to the invention, comprising the step of shifting an imino double bond in compounds of the formula (II):

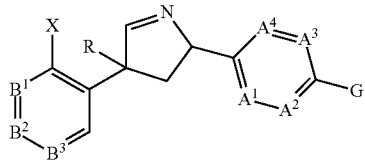

(II)

wherein
$A^1$ to $A^4$, $B^1$ to $B^3$, X, R and G have the same meanings as defined herein, in the presence of an alkali metal base.

The invention is moreover directed to a preparation method (b) for the preparation of compounds according to the invention wherein G stands for G1, G6 or G8, comprising reacting compounds of the formula (III):

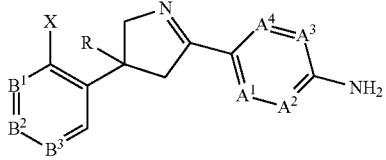

(III)

wherein
$A^1$ to $A^4$, $B^1$ to $B^3$, and X, R have the same meanings as defined herein, with either dialkoxytetrahydrofuran (e.g. dimethoxytetrahydrofuran), 1,2-diformylhydrazine, or sodium azide and trialkyl orthoformate.

The invention is also directed to a preparation method (c) for the preparation of compounds according to the invention, wherein G stands for G2, comprising reacting compounds of the formula (IV):

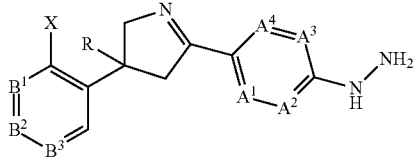

(IV)

$A^1$ to $A^4$, $B^1$ to $B^3$, X, and R have the same meanings as defined herein, with, 1,1,3,3-tetraalkoxypropane (e.g. 1,1,3,3-tetraethoxypropane).

The invention is also directed to a preparation method (d) for the preparation of compounds according to the invention, wherein G stands for G2, G3, G4, G5, G6, G8 or G9, comprising reacting compounds of the formula (V):

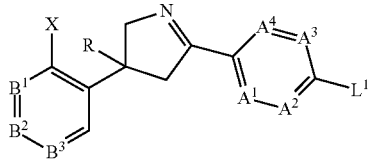

(V)

wherein
$A^1$ to $A^4$, $B^1$ to $B^3$, X, and R have the same meanings as defined herein, and wherein $L^1$ represents halogen, or a haloalkylsulfonyloxy group having 1 to 4 carbon atoms, with a chemical group G2-H, G3-H, G4-H, G5-H, G6-H, G8-H or G9-H.

The invention is also directed to a preparation method (e) for the preparation of compounds according to the invention, comprising reacting compounds of the formula (VI):

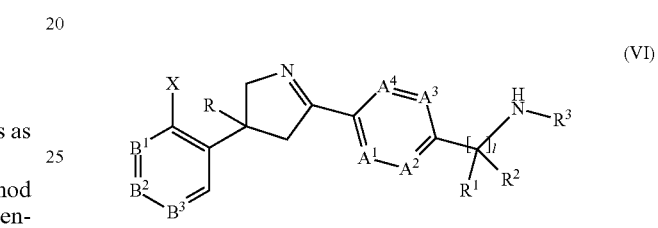

(VI)

wherein $A^1$ to $A^4$, $B^1$ to $B^3$, X, R, $R^1$ to $R^3$ and l have the same meanings as defined herein, with compounds of the formula (VII):

$$R^4-L \quad (VII)$$

wherein $R^4$ has the same meaning as defined herein; and L represents halogen, alkylsulfonyloxy, arylsulfonyloxy or alkylcarbonyloxy.

The invention is also directed to a preparation method (f) for the preparation of compounds according to the invention, comprising reacting compounds of the formula (VIII):

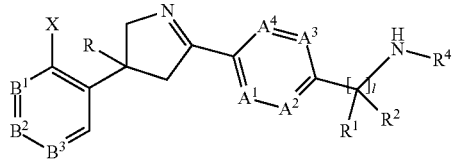

(VIII)

wherein $A^1$ to $A^4$, $B^1$ to $B^3$, X, R, $R^1$, $R^2$, $R^4$ and l have the same meanings as defined herein, with compounds of the formula (IX):

$$R^3-L \quad (IX)$$

wherein $R^3$ has the same meaning as defined herein; and L represents halogen, alkylsulfonyloxy, arylsulfonyloxy or alkylcarbonyloxy.

The invention is also directed to a preparation method (g) for the preparation of compounds according to the invention, comprising reacting compounds of the formula (X):

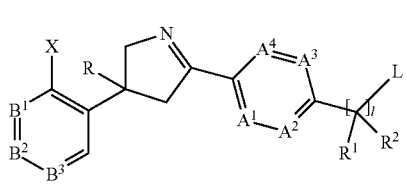

(X)

wherein $A^1$ to $A^4$, $B^1$ to $B^3$, X, R, $R^1$, $R^2$, L and l have the same meanings as defined herein, with compounds of the formula (XI):

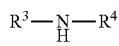

(XI)

wherein $R^3$ and $R^4$ have the same meanings as defined herein.

The invention is moreover directed to a preparation method (p) for the preparation of compounds according to the invention, comprising reacting compounds of the formula (XII):

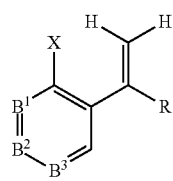

(XII)

wherein $B^1$ to $B^3$, X and R have the same meanings as defined herein, with compounds of the formula (XXXVI):

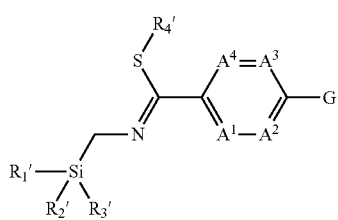

(XXXVI)

wherein $R_1'$, $R_2'$ and $R_3'$ each independently represents optionally substituted alkyl preferably $C_{1-12}$ alkyl, or optionally substituted phenyl; and $R_4'$ represents hydrogen; or is selected among optionally substituted alkyl, preferably $C_{1-12}$ alkyl optionally substituted alkenyl, preferably $C_{2-12}$ alkenyl, optionally substituted alkynyl, preferably $C_{2-12}$ alkynyl or optionally substituted benzyl;

and $A^1$ to $A^4$ and G have the same meanings as defined herein.

The invention is also directed to a preparation method (h) for the preparation of compounds according to the invention, comprising reacting compounds of the formula (XX):

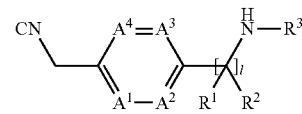

(XX)

with compounds of the formula (XII), to obtain compounds of the formula (XXI):

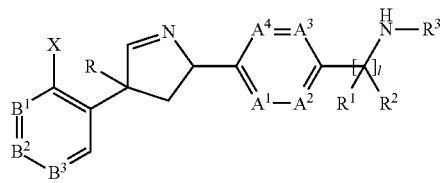

(XXI)

wherein $A^1$ to $A^4$, $B^1$ to $B^3$, X, R, $R^1$ to $R^3$ and l have the same meanings as defined herein, followed by the step of shifting an imino double bond under basic conditions as described for example for preparation method (a).

The invention is also directed to a preparation method (i) for the preparation of compounds according to the invention, comprising reacting compounds of the formula (XXII):

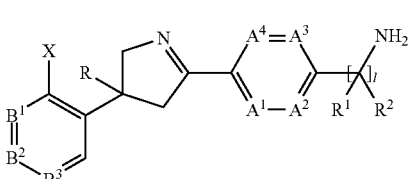

(XXII)

wherein $A^1$ to $A^4$, $B^1$ to $B^3$, X, R, $R^1$ to $R^3$ and l have the same meanings as defined herein, with compounds of the formula (IX).

The invention is moreover directed to a preparation method (j) or the preparation of compounds according to the invention, comprising reacting compounds of the formula (X) with compounds of the formula (XXIII):

$$R^3 - NH_2 \quad (XXIII)$$

wherein $R^3$ is as defined herein.

The production methods (a) to (g) and (p) are illustrated by the following reaction schemes Reaction scheme 1 - Production method (a):

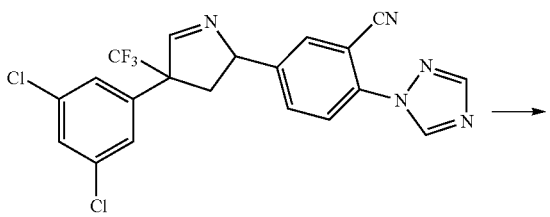

-continued

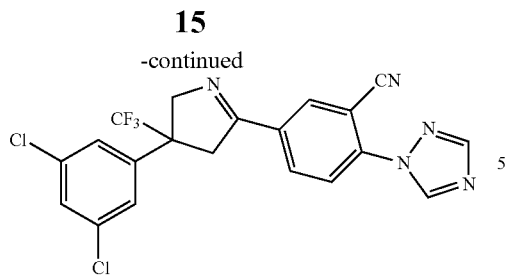

Here, 5-[4-(3,5-dichlorophenyl)-4-(trifluoromethyl)-3,4-dihydro-2H-pyrrol-2-yl]-2-(1H-1,2,4-triazol-1-yl)benzonitrile is used as starting material.

Reaction scheme 2 - Production method (b):

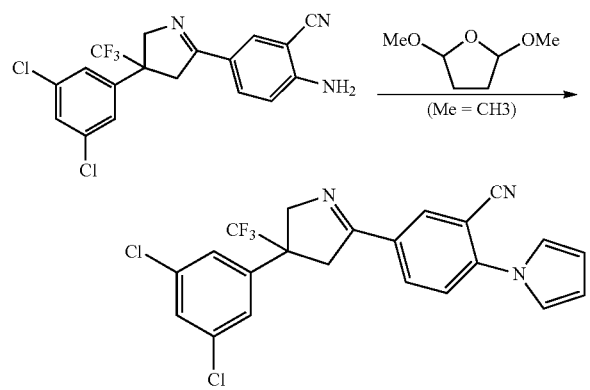

Here, 2-amino-5-[3-(3,5-dichlorophenyl)-3-(trifluoromethyl)-3,4-dihydro-2H-pyrrol-5-yl]benzo-nitrite and 2,5-dimethoxytetrahydrofuran are used as starting materials.

Reaction scheme 3-Production method (c):

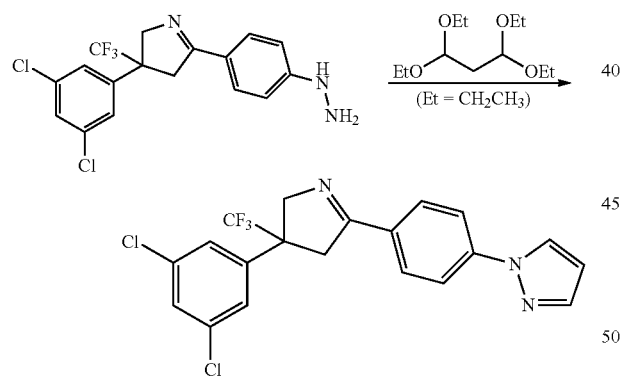

Here, 3-(3,5-dichlorophenyl)-5-(4-hydrazinophenyl)-3-(trifluoromethyl)-3,4-dihydro-2H-pyrrole and 1,1,3,3-tetra-ethoxypropane are used as starting materials.

Reaction scheme 4 - Production method (d):

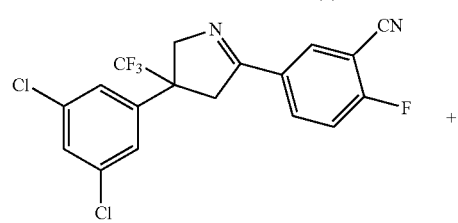

-continued

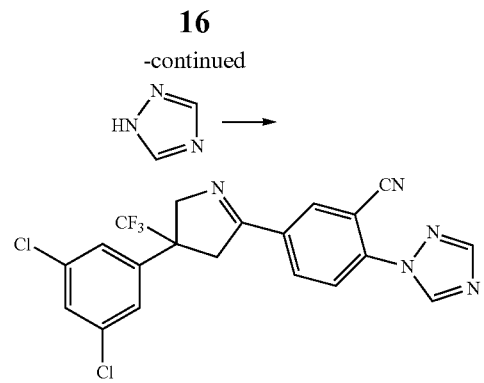

Here, 5-[3-(3,5-dichlorophenyl)-3-(trifluoromethyl)-3,4-dihydro-2H-pyrrol-5-yl]-2-fluorobenzo-nitrile and 1H-1,2,4-triazole are used as starting materials.

Reaction scheme 5 - Production method (e):

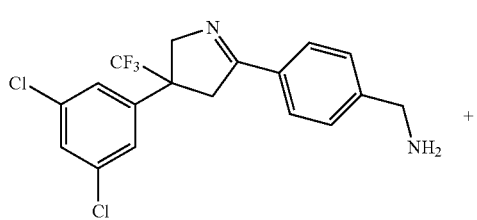

Here, 1-{4-[3-(3,5-dichlorophenyl)-3-(trifluoromethyl)-3,4-dihydro-2H-pyrrol-5-yl]phenyl}-methanamine and acetyl chloride are used as starting materials.

Reaction scheme 6 - Production method (f):

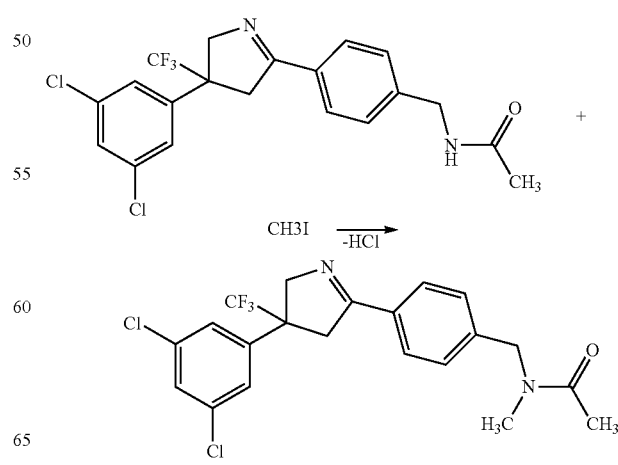

Here, N-{4-[3-(3,5-dichlorophenyl)-3-(trifluoromethyl)-3,4-dihydro-2H-pyrrol-5-yl]benzy}-acetamide and iodomethane are used as starting materials.

Reaction scheme 7 - Production method (g):

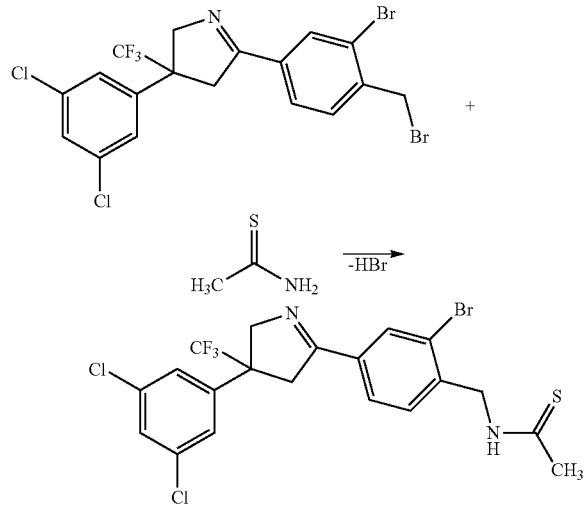

Here, 5-[3-bromo-4-(bromomethyl)phenyl]-3-(3,5-dichlorophenyl)-3-(trifluoromethyl)-3,4-dihydro-2H-pyrrole and thioacetamide are used as starting materials.

Reaction scheme 8 - Production method (p):

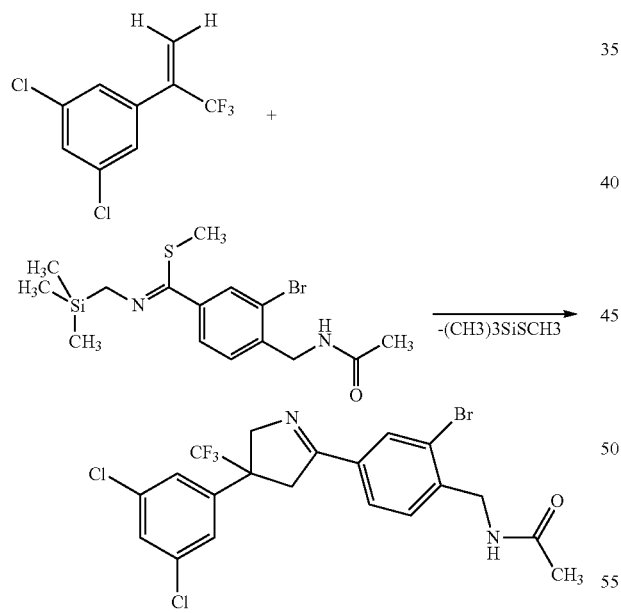

Here, 1,3-dichloro-5-(3,3,3-trifluoropropo-1-en-2-yl)benzene and methyl 4-[(acetylamino)methyl]-3-bromo-N-[(trimethylsilyl)methyl]benzenecarbodimidethioate are used as starting materials.

Compounds of formula (II), which can be used as starting materials in the production method (a), are novel compounds, and can be synthesized using similar or the same methods as described in EP-A-1538138.

Compounds of formula (II) can be prepared by reacting compounds of the formula (XII).

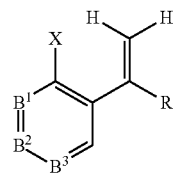

(XII)

wherein $B^1$ to $B^3$, X and R have the same meanings as defined herein, with compounds of the formula (XIII):

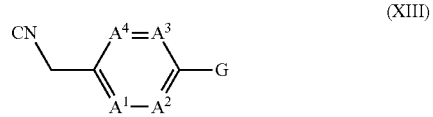

(XIII)

wherein $A^1$ to $A^4$ and G have the same meanings as defined herein, preferably, in the presence of a metal catalyst.

As compounds (II) and in an embodiment J, compounds of the following structures (II-a), (II-b), (II-c), (II-e) and (II-f), wherein the chemical groups G, $B^1$ to $B^3$, X, R are as defined herein, and wherein each of $Y_1$, $Y_2$, $Y_3$ and $Y_4$ are as defined herein for Y, are preferred.

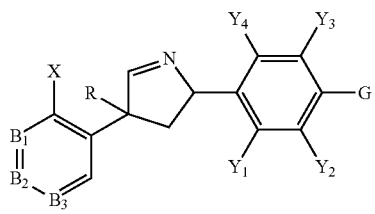

(II-a)

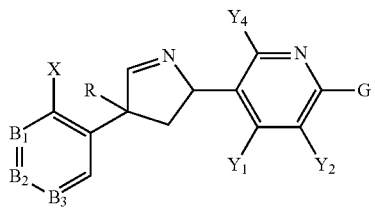

(II-b)

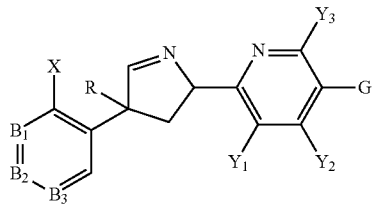

(II-c)

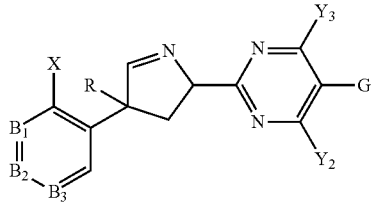

(II-d)

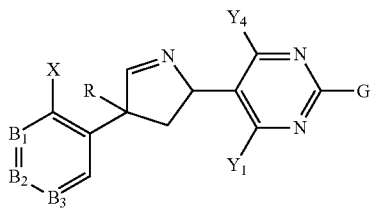
(II-e)

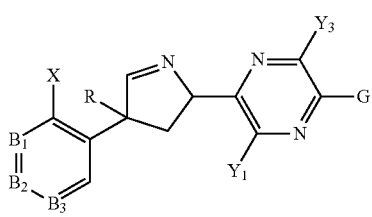
(II-f)

In an embodiment K, the invention is directed to compounds as defined in embodiment J, wherein G is selected among G1 to G9, preferably among G1, G2 and G6.

In an embodiment L, the invention is directed to compounds as defined in embodiment wherein G stands for a group

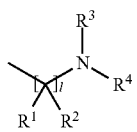

and wherein $R^1$ and $R^2$ are as defined herein, and wherein or $R^3$ and $R^4$ together with the nitrogen atom to which they are bound, form a 3- to 6-membered cyclic ring or a heterocycle, preferably selected among G1 to G9, which may be substituted with a substituent X, or may be substituted with a keto, thioketo or nitroimino group;

In an embodiment M and N, respectively, the invention is directed to compounds of the following structures (II-g) and (II-h), respectively, wherein the chemical groups U, R are as defined herein, and wherein each of $Y_1$, $Y_2$, $Y_3$ and $Y_4$ are as defined herein for Y, and wherein $X_0$, $X_1$, $X_2$ and $X_3$ are as defined herein for X are preferred.

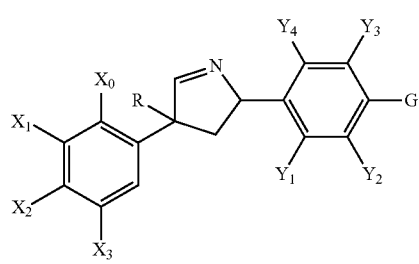
(II-g)

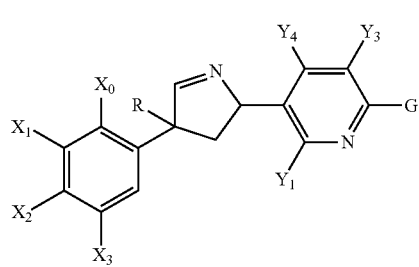
(II-h)

In an embodiment O, the invention is directed to compounds as defined in embodiment M or N, wherein G is selected among G1 to G9, preferably among G1, G2 and G6.

In an embodiment P, the invention is directed to compounds as defined in embodiment M or N, wherein G stands for a group

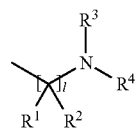

and wherein $R^1$ and $R^2$ are as defined herein, and wherein $R^3$ and $R^4$ together with the nitrogen atom to which they are bound, form a 3- to 6-membered cyclic ring or a heterocycle, preferably selected among G1 to G9, which may be substituted with a substituent X, or may be substituted with a keto, thioketo or nitroimino group;

In an embodiment Q, the invention is directed to compounds as defined in embodiment M or N, wherein G stands for a group

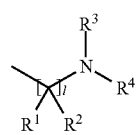

and wherein $R^1$ and $R^2$, $R^3$ and $R^4$ are as defined herein.

Compounds of formula (II) are for example 5-[4-(3,5-Dichlorophenyl)-4-(trifluoromethyl)-3,4-dihydro-2H-pyrrol-2-yl]-2-(1H-1,2,4-triazol-1-yl)benzonitrile, and N-{2-bromo-4-[4-(3,5-dichlorophenyl)-4-(trifluoromethyl)-3,4-dihydro-2H-pyrrol-2-yl]benzyl}acetamide.

Compounds of formula (XII) are described in The Journal of Organic Chemistry, Vol. 56, p. 7336-7340 (1991); ibid. Vol. 59, p. 2898-2901 (1994); Journal of Fluorine Chemistry, Vol. 95, p. 167-170 (1999) or WO 2005/5085216. Such compounds are for example [1-(Trifluoromethyl)vinyl]benzene, 1,3-Difluoro-5-[1-(trifluoromethyl)vinyl]benzene, 1-Chloro-3-[1-(trifluoromethyl)vinyl]benzene, 1,3-Dichloro-5-[1-(trifluoromethyl)vinyl]benzene, 1-Trifluoromethyl-3-[1-(trifluoromethyl)vinyl]benzene, 1-Trifluoromethyl-4-[1-(trifluoromethyl) vinyl]benzene, 1,3-bis(trifluoromethyl)-5-[1-(trifluoromethyl)vinyl]benzene, 1,3-Dibromo-5-[1-(trifluoromethyl)vinyl]benzene, 1,2,3-Trichloro-5-[1-(trifluoromethyl)vinyl]benzene, and 1-Fluoro-2-(trifluoromethyl)-4-[1-(trifluoromethyl)vinyl]benzene.

Compounds of formula (XIII) can be synthesized by the methods described in Chem. Lett., p. 697-698 (1977) and/or can be obtained by reacting compounds of the formula (XIV) with ethyl formate

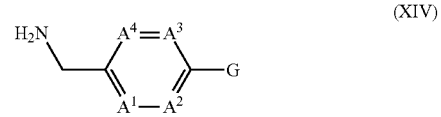
(XIV)

to obtain compounds of the formula (XV):

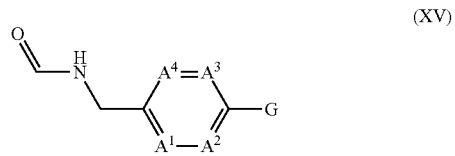
(XV)

wherein A1 to A4 and G have the same meanings as defined herein, followed by the steps of halogenation, dehalogenation and hydrogenation.

Reaction scheme 9 shows a synthesis method for the preparation of compounds of the formula (XIV), wherein G represents an optionally substituted saturated or unsaturated 5- or 6-membered heterocyclic group.

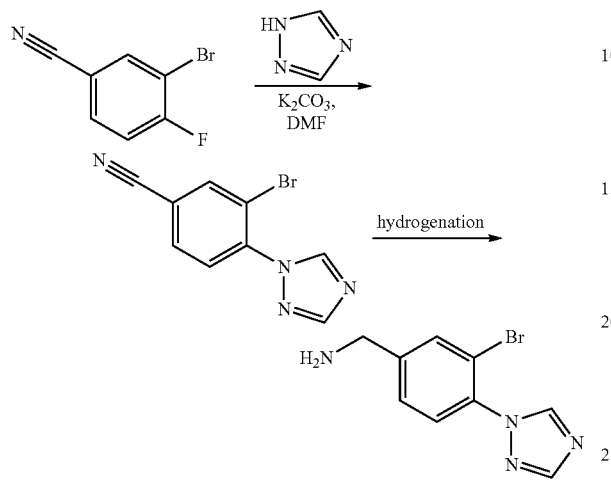

wherein DMF stands for N,N-dimethylformamide; and the hydrogenation, is done as described in US 2007/111984 A.

Reaction scheme 10 shows a synthesis method for the preparation of compounds of the formula (XIV), wherein G represents a chemical group —$(CR^1R^2)_l$—$NR^3R^4$ as defined herein.

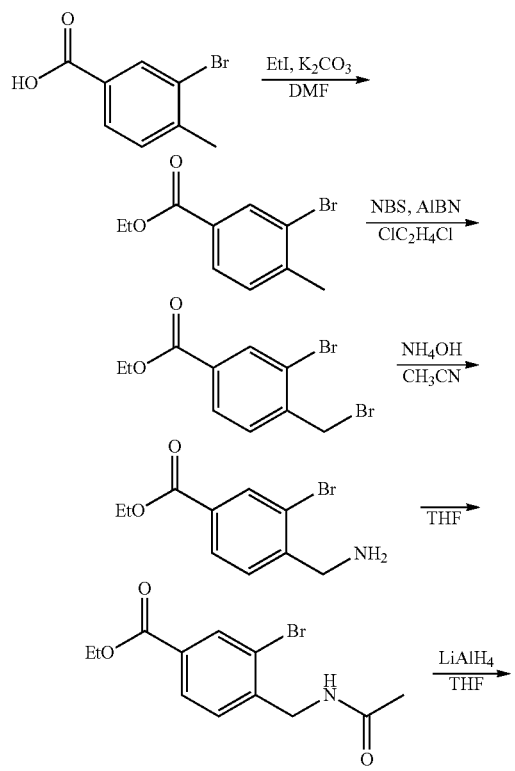

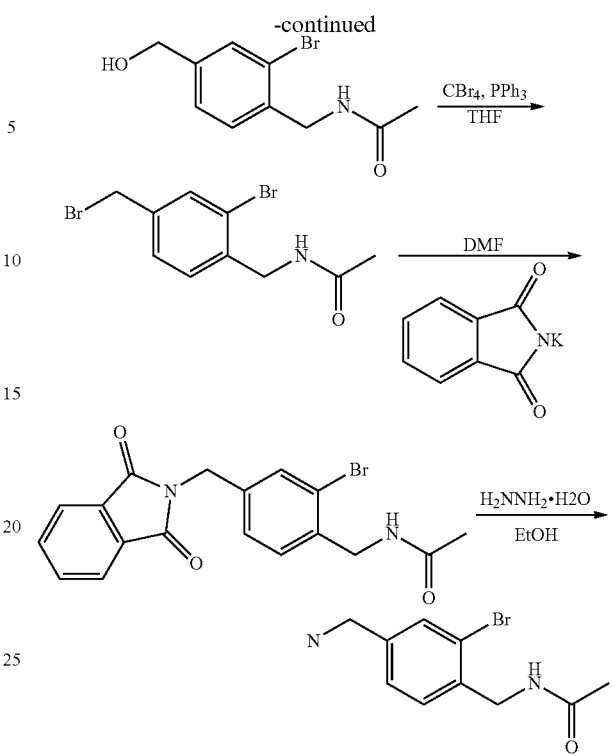

*1 Anhydrous acetic acid, wherein EtI stands for ethyl iodide, NBS stands for N-bromosuccinimide. AIBN stands for azobisisobutyronitrile, and DMF stands for N,N-dimethylformamide.

Compounds of the formula (XV) are, for example, N-[3-Bromo-4-(1H-1,2,4-triazol-1-yl)benzyl]formamide, and N-{2-bromo-4-[(formylamino)methyl]benzyl}acetamide.

Additionally, the production method (a) can be carried out as described in Japanese Patent Application Laid-Open No. 2007-91708 and Chem. Lett., p. 1601-1604 (1985).

The reaction of the production method (a) can be performed in an appropriate diluent, and by using an alkali metal base such as sodium carbonate, potassium carbonate, sodium hydrogen carbonate, potassium hydrogen carbonate, sodium acetate, potassium acetate, sodium methoxide, sodium ethoxide or potassium tert-butoxide; an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane or imidazole; as the base; at temperatures from about −78 to about 200° C., preferably from −10 to about 100° C. Furthermore, the reaction can be performed at different pressures, such as normal pressure, i.e. 1013 mbar, or under reduced pressure, i.e. below 1013 mbar. The reaction time may vary and is from 0.1 to 72 hours, preferably from 1 to 24 hours.

Appropriate diluents for production method (a) include for example aliphatic, cycloaliphatic and aromatic hydrocarbons (optionally, may be chlorinated), for example, pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers, for example, ethyl ether, methyl ethyl ether, isopropyl ether, butyl ether, dioxane, dimethoxyethane (DME), tetrahydrofuran (TI-IF), diethylene glycol dimethyl ether (DGM) and the like; ketones, for example, acetone, methyl ethyl ketone (MEK), methyl isopropyl ketone, methyl isobutyl ketone (MIBK) and the like; nitriles, for example, acetonitrile, propionitrile, acrylonitrile and the like; alcohols, for example, methanol, ethanol, isopropanol, butanol, ethylene glycol and the like; esters, for example, ethyl acetate, amyl acetate and the like; acid amides, for example, dimethylformamide (DMF), dmethylacetamide (MDA), N-methylpyrrolidone, 1,3-dimethyl-2-imidazolidinone, hexamethylphosphoric triamide (HMPA) and the like; sulfones and sulfoxides, for example, dimethylsulfoxide (DMSO), sulfolane and the like; and bases, for example, pyridine and the like.

In carrying out the production method (a), for example, when 1 mole of the compounds of formula (II) is reacted with abuse in an amount of 1 mole or in a slightly excess amount, in a diluent such as THF, compounds according to the invention can be obtained.

The compounds of formula (III), which can be used as starting materials, in the production method (b), are novel compounds, and can be synthesized according to the following preparation methods and reaction schemes. Compounds of formula (III) can be prepared by reacting compounds of the formula (XII) with compounds of the formula (XVI):

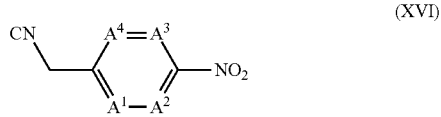

to obtain compounds of the formula (XVII):

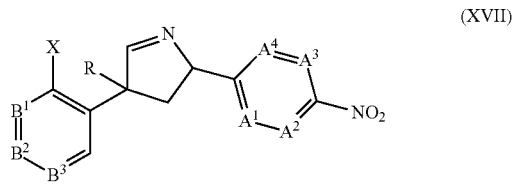

wherein A1 to A4, B1 to B3, R and X have the same meanings as the defined herein, followed by the step of shifting an imino double bond under basic conditions (e.g. in the presence of an alkali metal base) and the reduction of the —NO2 group.

Compounds of the formula (XVI) are, for example, 2-Fluoro-4-isocyanatomethyl-1-nitrobenzene, 2-Bromo-4-isocyanatomethyl-1-nitrobenzene, 2-Iodo-4-isocyanatomethyl-1-nitrobenzene, 2-Methyl-4-isocyanatomethyl-1-nitrobenzene and 2-Cyano-4-isocyanatomethyl-1-nitrobenzene.

Representative Compounds of formula (III) are, for example, 4-[3-(3,5-Dichlorophenyl)-3-(trifluoromethyl)-3,4-dihydro-2H-pyrrol-5-yl]aniline, and 2-Bromo-4-[3-(3,5-dichlorophenyl)-3-(trifluoromethyl)-3,4-dihydro-2H-pyrrol-5-yl]aniline.

Dialkoxytetrahydrofuran is for example, 2,5-Dimethoxytetrahydrofuran, and 2,5-Diethoxy-tetrahydrofuran.

The reaction of the production method (b) can be performed in an appropriate diluent at temperatures from 0 to about 200° C., and preferably from room temperature i.e. about 20° C. to about 150° C. Furthermore, the reaction can be performed at different pressures, such as normal pressure, i.e. 1013 mbar, or under a pressure over or under normal pressure (reduced pressure). The reaction time may vary from 0.1 to 72 hours, preferably from 1 to 24 hours.

Appropriate diluents in production method (b) include for example aliphatic hydrocarbons (hexane, cyclohexane, benzene, toluene, xylene and others), acids (acetic acid, propionic acid), aromatic hydrocarbons (benzene, toluene, xylene, chlorobenzene and others), ethers (diethyl ether, dibutyl ether, dimethoxyethane (DME), tetrahydrofuran, dioxane and others), acid amides (dimethylformamide (DMF), dimethylacetamide (DME), N-methylopyrrolidone and others), acids (acetic acid, propionic acid), nitriles (acetonitrile, propionitrile and others), dimethylsulfoxide (DMSO), and solvent mixtures thereof.

In carrying out the production method (b), for example, when 1 mole of the compounds of formula (III) is reacted with 1 mole to 5 moles of 2,5-dimethoxytetrahydrofuran in a diluent such as acetic acid, compounds, according to the invention can be obtained.

In the case where a reaction with 1,2-diformylhydrazine is carried out in the production method (b), the reaction can be performed in the presence of a base, such as organic bases (e.g. triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane and imidazole, and trialkylhalosilane) and trialkylhalosilane, such as Trimethylchlorosilane, Triethylchlorosilane and Trimethylbromosilane.

In carrying out the production method, when 1 mole of the compounds of formula (III) is reacted with 1 to 5 moles of 1,2-diformylhydrazine, 1 to 10 moles of the base, and 1 to 25 moles of trialkylhalosilane, in a large excess of pyridine, compounds according to the invention can be obtained.

In the case that in production method (b), sodium azide is reacted with trialkyl orthoformate, examples of the trialkyl orthoformate include trimethyl orthoformate and triethyl orthoformate.

In carrying out the production method, when 1 mole of the compounds of formula (III) is reacted with 1 to 3 moles of sodium azide and 1 to 10 moles of trialkyl orthoformate in an appropriate diluent such as acetic acid, the compounds, according to the invention can be obtained.

The compounds of formula (IV), which can be used as starting material in the production method (c), are novel compounds, and can be synthesized by subjecting compounds of formula (III) to the well known "Sandmeyer" reaction, and followed by a reduction reaction.

Representative compounds of formula (IV) are, for example, 3-(3,5-Dichlorophenyl)-1-(4-hydrazinophenyl)-3-(trifluoromethyl)-3,4-dihydro-2H-pyrrole and 3-(3,5-Dichlorophenyl)-1-(4-hydrazino-3-methylphenyl)-3-(trifluoromethyl)-3,4-dihydro-2H-pyrrole.

Suitable 1,1,3,3-Tetraalkoxypropanes are for example 1,1,3,3-Tetramethoxypropane and 1,1,3,3-Tetraethoxypropane, The reaction of the production method (c) can be performed in an appropriate diluent at temperatures and pressure as described for production method (b).

In carrying out the production method (c), for example, when 1 mole of the compounds of formula (IV) is reacted with 1 mole to 5 moles of 1,1,3,3-tetraalkoxypropane in a diluent such as ethanol, and if necessary, in the presence of a catalytic amount of an acid such as sulfuric acid, the compounds according to the invention can be obtained.

The compounds of formula (V), which can be used as starting materials in the production method (d), are known compounds, and can be synthesized by reacting the compounds of the formula (XII) with compounds of the formula (XVIII):

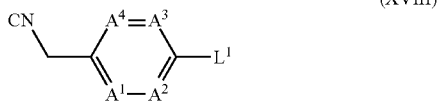
(XVIII)

to obtain compounds of the following formula:

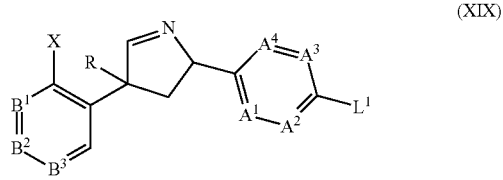
(XIX)

wherein A1 to A4, B1 to B3, R, X and L1 have the same meanings as defined herein, followed by the step of shifting an imino double under basic conditions.

The compounds of the formula (XVIII) can be synthesized according to the method for producing the compounds of the formula (XIII). Specific compounds of the formula (XVIII) are, for example, 2-Fluoro-5-isocyanatomethyl-nitrobenzene and 2-Fluoro-5-isocyanatomethyl-benzonitrile.

Representative compounds of the formula (V) used in the production method (d) are, for example, 5-[3-(3,5-dichlorophenyl)-3-(trifluoromethyl)-3,4-dihydro-2H-pyrrol-5-yl]-2-fluorobenzonitrile and 5-{3-[3,5-bis(trifluoromethyl)phenyl]-3-(trifluoromethyl)-3,4-dihydro-2H-pyrrol-5-yl}-2-fluorobenzonitrile.

Many of the compounds represented by the formulas G2-H, G3-H, G4-H, G5-H, G6-H, G8-H and G9-H, which are the starting material in the production method (d), are known compounds, and specific examples thereof include 1H-Imidazole, 1H-Pyrazole, 4-Methyl-1H-pyrazole, 4-Fluoro-1H-pyrazole, 4-Chloro-1H-pyrazole, 4-Bromo-1H-pyrazole, 4-Iodo-1H-pyrazole, 4-Nitro-1H-pyrazole, 3-Trifluoromethyl-1H-pyrazole, 4-Trifluoromethyl-1H-pyrazole, 4-Cyano-1H-pyrazole, 1H-1,2,3-triazole, 1H-1,2,4-triazole, 1H-tetrazole, 5-Methyl-1H-tetrazole, 5-(Methylthio)-1H-tetrazole.

The reaction of the production method (d) can be performed in an appropriate diluent and using an alkali metal base as exemplified at the reaction method (a) at reaction conditions (temperatures, pressure, reactiontime) as described for production method (a).

In carrying out the production method (d), for example, when 1 mole of the compounds of formula (V) is reacted with 1 mole to 3 moles of G6-H in a diluent such as DMF, in the presence of 1 mole to 3 moles of a base, the compounds according to the invention can be obtained.

The compounds of formula (VI), which can be used as starting materials in the production method (e) can be obtained by the methods (g) and (h) to (j) as described herein.

The compounds of formula (XX) used in the production method (h) can be synthesized according to the procedure described for the preparation of compounds of formula (XIII), and are for example, 1-[2-Bromo-4-(isocyanomethyl)phenyl]-N-methylmethanamine and N-benzyl-1-[2-bromo-4-(isocyanomethyl)phenyl]methanamine.

The compounds of formula (XXI) can be synthesized according to the procedure described for the preparation of compounds of formula (II). Compounds of formula (XXI) are for example, 1-{2-Bromo-4-[4-(3,5-dichlorophenyl)-4-(trifluoromethyl)-3,4-dihydro-2H-pyrrol-2-yl]phenyl}-N-methylmethanamine and N-benzyl-1-{2-bromo-4-[4-(3,5-dichlorophenyl)-4-(trifluoromethyl)-3,4-dihydro-2H-pyrrol-2-yl]phenyl}methanamine.

The compounds of the formula (XXII) can be synthesized according to the procedure described for the preparation of compounds of formula (I). Compounds of formula (XXII) are for example, 1-{2-Bromo-4-[3-(3,5-dichlorophenyl)-3-(trifluoromethyl)-3,4-dihydro-2H-pyrrol-5-yl]phenyl}methanamine and 2-(Aminomethyl)-5-[3-(3,5-dichlorophenyl)-3-(trifluoromethyl)-3,4-dihydro-2H-pyrrol-5-yl]benzonitrile.

Suitable compounds of the formula (VII) for use in the preparation method are for example acetyl chloride, propionyl chloride, pivaloyl chloride, acryloyl chloride, methyl chloroformate, N,N-dimethylcarbamoyl chloride, cyclopropylcarbonyl chloride, N,N-dimethylthiocarbamoyl chloride, benzoyl chloride, nicotinyl chloride, anhydrous acetic acid, anhydrous trifluoroacetic acid or methanesulfonyl chloride.

The reaction of the production method (e) can be performed in an appropriate diluent and by using an alkali metal base as exemplified at the production method (a) at conditions (temperature, pressure, reaction time) as described for production method (a).

In carrying out the production method (e), for example, when 1 mole of the compounds of formula (VI) is reacted with 1 mole to 3 moles of the compounds of formula (VII) in a diluent such as DMF, in the presence of 1 mole to 3 moles of a base, the compound according to the present invention can be obtained.

Suitable compounds of the formula (VI for the use in the production method (f), can be obtained by the production methods (g) and (k) to (m).

Production Method (k)

A method for the preparation of compounds of formula (VIII) comprising
a step (a) of reacting compounds of the formula (XXIV) with the compounds of the formula (XII),

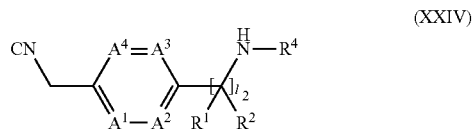
(XXIV)

to obtain compounds of the formula (XXV):

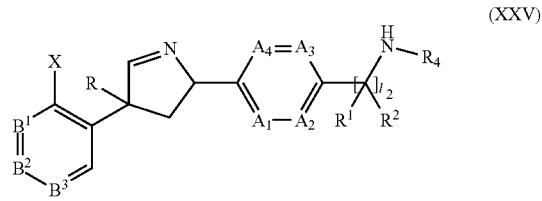
(XXV)

wherein $A^1$ to $A^4$, $B^1$ to $B^3$, X, R, $R^1$, $R^2$, $R^4$ and l have the same meanings as defined herein; and
a step (b) of shifting an imino double bond under basic conditions.

Production Method (l)
A method of reacting the compounds of the formula (XXII) with the compounds of the formula (VII).

Production Method (m)

A method of reacting the compounds of the formula (X) with compounds of the following formula:

(XXVI)

wherein $R^4$ has the same meaning as defined herein.

Compounds of the formula (XXIV) can be synthesized according to the procedure described for the preparation of compounds of formula (XIII). Representative compounds of formula (XXIV) are for example, N-[2-fluoro-4-(isocyanatomethyl)benzyl]acetamide, N-[2-bromo-4-(isocyanatomethyl)benzyl]acetamide, N-[2-iodo-4-(isocyanatomethyl)benzyl]acetamide, N-[2-methyl-4-(isocyanatomethyl)benzyl]acettamida and N-[2-cyano-4-(isocyanatomethyl)benzyl]acetamide.

The compounds of the formula (XXV) can be synthesized according to the procedure described for the preparation of compounds of formula (II). Representative examples are for example, N-{2-bromo-4-[4-(3,5-dichlorophenyl)-4-(trifluoromethyl)-3,4-dihydro-2H-pyrrol-2-yl]benzyl}acetamide and N-{2-bromo-4-[4-(3,5-dichlorophenyl)-4-(trifluoromethyl)-3,4-dihydro-2H-pyrrol-2-yl]benzyl}benzamide.

The compounds of the formula (XXII) in the aforementioned production method (1) correspond to compounds of the formula (VI) wherein R3 stands for hydrogen.

Suitable compounds of the formula (XXVI) for the use in the production method (m) are, for example, formamide, acetamide, propionamide, 2,2,2-trifluoroacetamide, benzamide, ethyl carbamate or ethanethioamide.

Production method (f) can be performed under the same conditions as described for production method (e).

Suitable compounds of formula (X) for the use in the production method (g) can be obtained by the production methods (n) or (o).

Production Method (n)

A method of reacting compounds of the following formula:

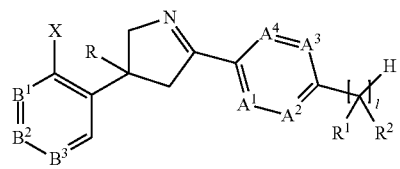
(XXVII)

wherein A1 to A4, B1 to B3, X, R, R1, R2 and l have the same meanings as defined herein, with a halogenating agent.

Production Method (o)

A method for the preparation of compounds to the invention, comprising reducing compounds of the formula (XXVIII):

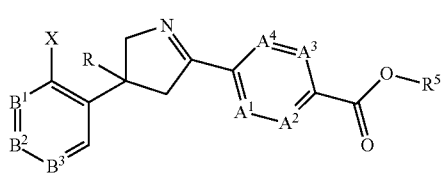
(XXVIII)

wherein $A^1$ to $A^4$, $B^1$ to $B^3$, X, and R have the same meanings as defined herein; and wherein $R^5$ stands for an alkyl group, to obtain compounds of the formula (XXIX):

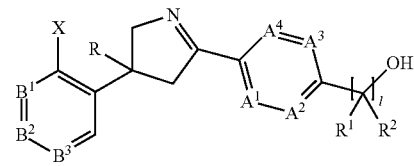
(XXIX)

wherein $A^1$ to $A^4$, $B^1$ to $B^3$, X, R, $R^1$, $R^2$ and l have the same meanings as defined herein, and then reacting the compound (XXIX) with methanesulfonyl chloride or a halogenating agent.

The compounds of the formula (XXVII) can be obtained, for example, by reacting compounds of the formula (XXX):

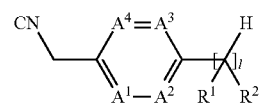
(XXX)

wherein $A^1$ to $A^4$, $R^1$, $R^2$ and l have the same meanings as defined herein,
with compounds of the formula (XII) to obtain compounds of the following formula (XXXI):

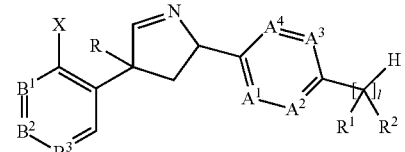
(XXXI)

wherein $A^1$ to $A^4$, $B^1$ to $B^3$, X, R, $R^1$, $R^2$ and l have the same meanings as defined herein, followed by the step of shifting an imino double bond under basic conditions.

The compounds of the formula (XXVIII) can be obtained, by reacting compounds of the formula (XXXII):

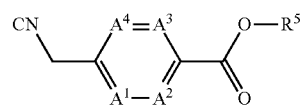
(XXXII)

wherein $A^1$ to $A^4$, and $R^5$ have the same meanings as defined herein,
with the compounds of the formula (XII) to obtain compounds of the formula (XXXIII):

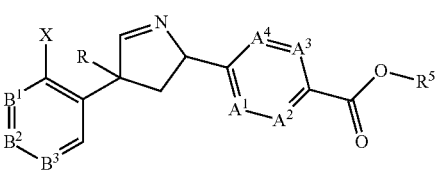
(XXXIII)

wherein $A^1$ to $A^4$, $B^1$ to $B^3$, X, $R^1$, $R^5$ have the same meanings as defined herein, followed by the step of shifting an imino double bond under basic conditions.

Representative compounds of the formula (XXX) are for example, 2-Bromo-4-(isocyanomethyl)-1-methylbenzene, 2-Cyano-4-(isocyanomethyl)-1-methylbenzene and 2-Bromo-4-(isocyanomethyl)-1-ethylbenzene.

Moreover, compounds of the formula (XXXVIII)

(XXXVIII)

wherein $A^1$ to $A^4$, $B^1$ to $B^3$, X, R, $R^1$, $R^2$, $R_{5'}$ and l have the same meanings as defined herein,
can also be synthesized by reacting compounds of the formula (XXXVII)

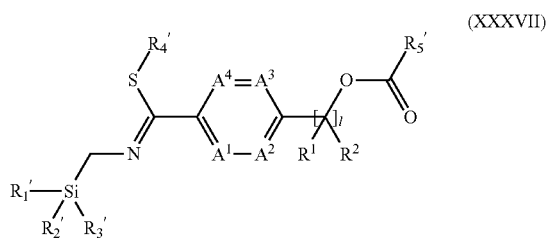

(XXXVII)

wherein
$R^1$, $R^2$, $A^1$ to $A^4$ and l have the same meanings as defined herein, and wherein $R_1'$, $R_2'$ and $R_3'$ each independently represent optionally substituted alkyl or optionally substituted phenyl; and R4' represents hydrogen; or a chemical group selected among optionally substituted alkyl, alkenyl, alkynyl; or optionally substituted benzyl; and $R_5'$ represents hydrogen, optionally substituted alkyl or optionally substituted phenyl;
with compounds of formula (XII), if appropriate, in the presence of a fluorine reagent and alkyl halide (preferably methyl iodide when R4' represents hydrogen).

Compounds of formula (XXIX) can be synthesized by subjecting the compounds of formula (XXXVIII) to a hydrolysis using known procedures.

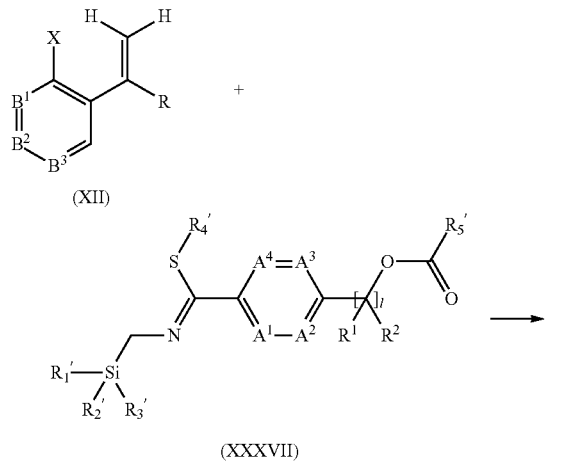

(XXXVII)

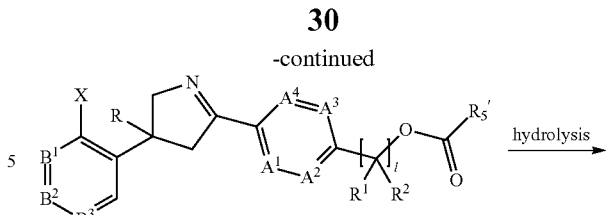

(XXXVIII)

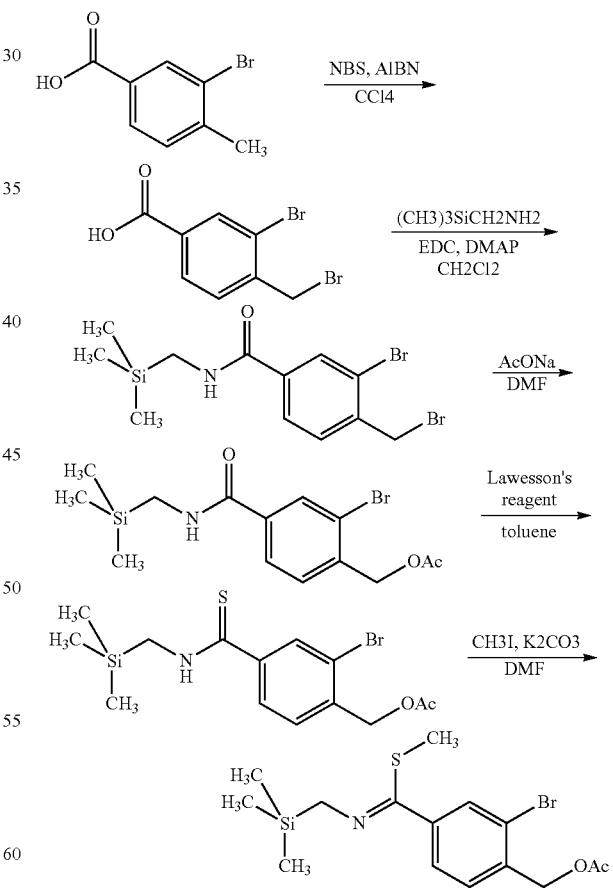

(XXIX)

Compounds of formula (XXIX) are then reacted with methanesulfonyl chloride or a halogenating agent to yield compounds according to the invention.

Compounds of the formula (XXXVII) can be synthesized according to reaction process illustrated in reaction scheme 11.

Reaction scheme 11:

wherein NBS stands for N-bromosuccinimide, AIBN stands for azobisisobutyronitrile, EDC stands for 1-ethyl-3-(3-dimethylaminopropyl)-carbodiimide, DMAP stands for 4-(dimethylamino)pyridine, DMF stands for N,N-dimethylformamide and Lawesson's reagent stands for 2,4-bis(4-methoxyphenyl)-1,3-dithia-2,4-diphosphetane-2,4-disulfide.

Compounds of the formula (XXXVII) are for example, 2-Bromo-4-[(methyl-sulfanyl){[(trimethylsilyl)methyl]imino}methyl]benzyl acetate, 2-Chloro-4-[(methylsulfanyl)-{[(trimethylsilyl)methyl]imino}methyl]benzyl acetate, 2-Trifluoromethyl-4-[(methylsulfanyl){[(trimethylsilyl)methyl]imino}methyl]benzyl acetate, {6-[(methylsulfanyl){[(trimethylsilyl)-methyl]imino}methyl]-2-(trifluoromethyl)pyridin-3-yl}methyl acetate, and {6-[(methylsulfanyl)-{[(trimethylsilyl)methyl]imino}methyl]-4-(trifluoromethyl)pyridin-3-yl}methyl acetate.

Additionally, the production method for the preparation of compounds of the formula (XXXVIII) can be carried out according to the methods described in The Journal of Organic Chemistry, Vol. 52, p. 1027-1035 (1987).

The production method for the preparation of compounds of the formula (XXXVIII) can be performed in an appropriate diluent, by using a fluorine reagent such as potassium fluoride, or tetramethylammonium fluoride, tetraethylammonium fluoride or tetrabutylammonium fluoride and can be performed at temperatures from about −78 to about 100° C., preferably −10 to about 50° C. Furthermore, it is desirable to perform the reaction at normal pressure, i.e. 1013 mbar but the reaction can also be operated under pressure i.e. above 1013 mbar or under reduced pressure i.e. under 1013 mbar. The reaction time is from 0.1 to 10 hours, preferably from 1 to 5 hours.

In carrying out the production method of the compounds of the formula (XXXVIII), for example, when 1 mole of the compounds of formula (XXXVII) is reacted with 1 mole of the compounds of formula (XII) in a diluent such as THF, in the presence of 0.1 mole of fluorination agent, such as tetrabutylammonium floride, the compound of formula (XXXVIII) can be obtained.

Compounds of the formula (XXXVIII) are for example, 2-Bromo-4-[3-(3,5-dichlorophenyl)-3-(trifluoromethyl)-3,4-dihydro-2H-pyrrol-5-yl]benzyl acetate, 2-Chloro-4-[3-(3,5-dichlorophenyl)-3-(trifluoromethyl)-3,4-dihydro-2H-pyrrol-5-yl]benzyl acetate, 2-Cyano-4-[3-(3,5-dichlorophenyl)-3-(trifluoromethyl)-3,4-dihydro-2H-pyrrol-5-yl]benzyl acetate, 2-Trifluoromethyl-4-[3-(3,5-dichlorophenyl)-3-(trifluoromethyl)-3,4-dihydro-2H-pyrrol-5-yl]benzyl acetate, 2-Bromo-4-[3-(3 dibromophenyl)-3-(trifluoromethyl)-3,4-dihydro-2H-pyrrol-5-yl]benzyl acetate, 2-Chloro-4-[3-(3,5-dibromophenyl)-3-(trifluoromethyl)-3,4-dihydro-2H-pyrrol-5-yl]benzyl acetate, 2-Cyano-4-[3-(3,5-dibromophenyl)-3-(trifluoromethyl)-3,4-dihydro-2H-pyrrol-5-yl]benzyl acetate, 2-Trifluoromethyl-4-[3-(3,5-dibromophenyl)-3-(trifluoromethyl)-3,4-dihydro-2H-pyrrol-5-yl]benzyl acetate, 2-Bromo-4-[3-(3,5-bistrifluoromethylphenyl)-3-(trifluoromethyl)-3,4-dihydro-2H-pyrrol-5-yl]benzyl acetate, 2-Chloro-4-[3-(3,5-bistrifluoromethylphenyl)-3-(trifluoromethyl)-3,4-dihydro-2H-pyrrol-5-yl]benzyl acetate, 2-Cyano-4-[3-(3,5-bistrifluoromethylphenyl)-3-(trifluoromethyl)-3,4-dihydro-2H-pyrrol-5-yl]benzyl acetate, 2-Trifluoromethyl-4-[3-(3,5-bistrifluoromethylphenyl)-3-(trifluoromethyl)-3,4-dihydro-2H-pyrrol-5-yl]benzyl acetate, 2-Bromo-4-[3-(3,4,5-trichlorophenyl)-1-(trifluoromethyl)-3,4-dihydro-2H-pyrrol-5-yl]benzyl acetate, 2-Chloro-4-[3-(3,4,5-trichlorophenyl)-3-(trifluoromethyl)-3,4-dihydro-2H-pyrrol-5-yl]benzyl acetate, 2-Cyano-4-[3-(3,4,5-trichlorophenyl)-3-(trifluoromethyl)-3,4-dihydro-2H-pyrrol-5-yl]benzyl acetate, 2-Trifluoromethyl-4-[3-(3,4,5-trichlorophenyl)-3-(trifluoromethyl)-3,4-dihydro-2H-pyrrol-5-yl]benzyl acetate, {6-[3-(3,5-dichlorophenyl)-3-(trifluoromethyl)-3,4-dihydro-2H-pyrrol-5-yl]-2-(trifluoromethyl)pyridin-3-yl}methyl acetate and {6-[3-(3,5-dichlorophenyl)-3-(trifluoromethyl)-3,4-dihydro-2H-pyrrol-5-yl]-4-(trifluoromethyl)pyridin-3-yl}methyl acetate.

Suitable amide compounds of the formula (XI) in the production method (g) are for example, acetamide, 2,2,2-trifluoroacetamide, 2,2,2-trifluoro-N-methylacetamide, pyrrolidin-2-one, piperidin-2-one and N-(pyridin-2-ylmethyl)acetamide.

The production method (g) can be performed under the same conditions as described for production method (e).

Compounds of the formula (II), formula (XIII), formula (XV), formula (XX) and formula (XXIV) are novel compounds.

The compounds of formulae (XIII) and (XV) are represented by the general formula (XXXIV)

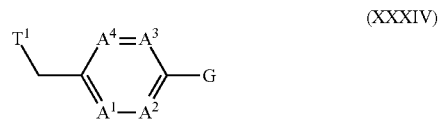

wherein T1 represents —N—CH═O or —N═C; and wherein A1 to A4 and G have the same meanings as defined herein.

Compounds of the general formula (XXXIV) are useful intermediates for the preparation of compounds according to the invention. Namely, as compounds according to the invention can be prepared by reacting a compound of formula (XII) with a compound of formula (XXXIV) to give a compound of formula (II) and subsequently inducing the shifting of the imino double bond under basic conditions such as described in preparation method (a).

The compounds of formulae (XX) and (XXIV) are represented by the general formula (XXXV)

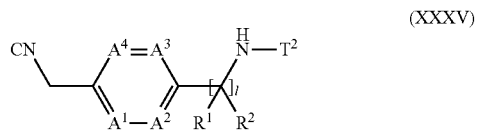

wherein $T^2$ represents $R^3$ or $R^4$; and $A^1$ to $A^4$, $R^1$, $R^2$, $R^3$, $R^4$ and l have the same meanings as defined herein.

Compounds of the general formula (XXXV) are useful intermediates for the preparation of compounds according to the invention. Namely, as compounds according to the invention can be prepared by reacting a compound of formula (XII) with a compound of formula (XXXV) to give a compound of formula (II) and subsequently inducing the shifting of the imino double bond under basic conditions such as described in preparation method (a).

Compounds of formula (XXXV) can be understood as being compounds of formula (XXXIV) wherein $T^1$ stands for CN and G stands for a group

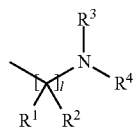

wherein either R3 or R4 stands for H and wherein A1 to A4 and $R^1$, R2 and either R3 or R4 and 1 have the meanings as defined herein.

Reaction scheme 12 shows a synthesis method for the preparation of compounds of the formula (XXXVI), wherein G represents an optionally substituted saturated or unsaturated 5- or 6-membered heterocyclic group.

Reaction scheme 12

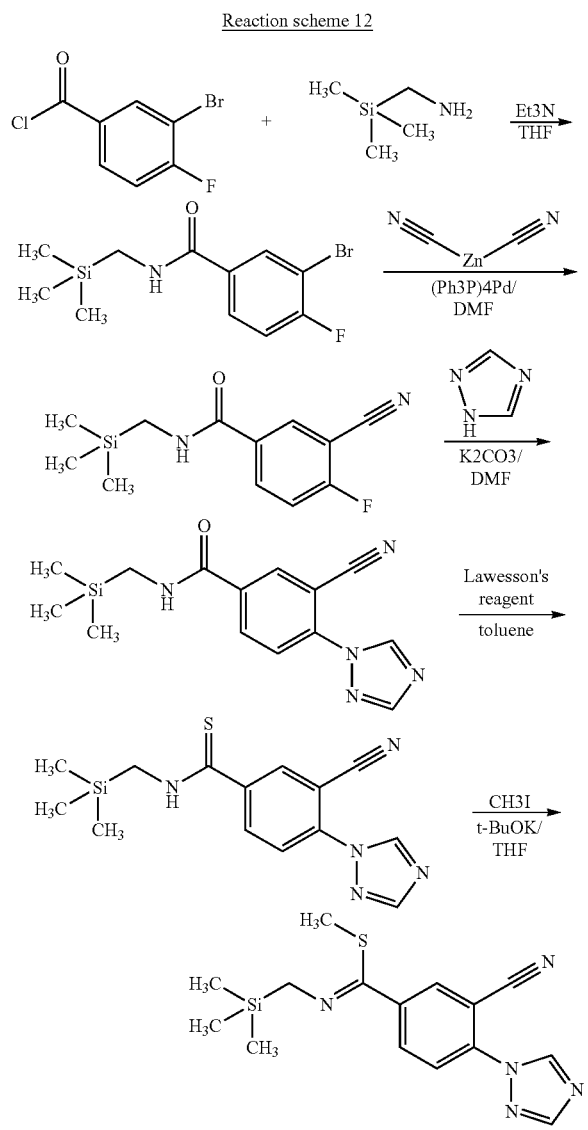

wherein Et3N represents triethylamine, THF represents tetrahydrofuran, (Ph3P)4Pd represents tetrakis(triphenylphosphine)palladium, DMF represents N,N-dimethylformamide, Lawesson's reagent represents 2,4-bis(4-methoxyphenyl)-1,3-dithia-2,4-diphosphetane-2,4-disulfide and t-BuOK represents t-butoxycarbonyl.

Reaction scheme 13 shows a synthesis method for the preparation of compounds of the formula (XXXVI), wherein G represents a chemical group —(CR$^1$R$^2$), —NR$^3$R$^4$ as defined herein.

Reaction scheme 13

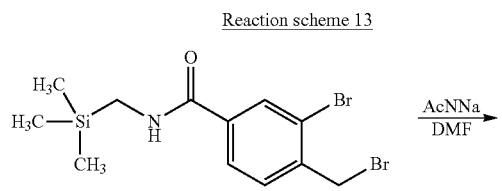

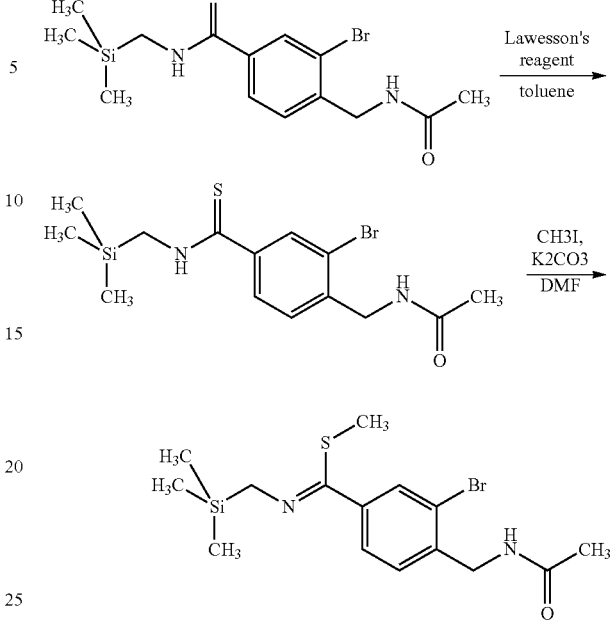

wherein AcNH2 represents Ammoniumacetate, NaH represents sodiumhydride, DMF represents N,N-dimethylformamide and Lawesson's reagent represents 2,4-bis(4-methoxyphenyl)-1,3-dithia-2,4-diphosphetane-2,4-disulfide.

Compounds of the formula (XXXVI) are for example, Methyl 3-bromo-4-(1H-1,2,4-triazol-1-yl)-N-[(trimethylsilyl)methyl]benzenecarbimidothioate, Methyl 3-chloro-4-(1H-1,2,4-triazol-1-yl)-N-[(trimethylsilyl)methyl]benzenecarbimidothioate, Methyl 3-trifluoromethyl-4-(1H-1,2,4-triazol-1-yl)-N-[(trimethylsilyl)methyl]benzenecarbimidothioate, Methyl 3-cyano-4-(1H-1,2,4-triazol-1-yl)-N-[(trimethylsilyl)methyl]benzenecarbimidothioate, Ethyl 3-bromo-4-(1H-1,2,4-triazol-1-yl)-N-[(trimethylsilyl)methyl]benzenecarbimidothioate, Methyl 3-bromo-4-(1H-1,2,4-triazol-1-yl)-N-[(triethylsilyl)methyl]benzenecarbimidothioate, Methyl 3-bromo-4-(1H-1,2,4-triazol-1-yl)-N-[(t-butyldimethylsilyl)methyl]benzenecarbimidothioate, Methyl 4-[(acetylamino)methyl]-3-bromo-N-[(trimethylsilyl)methyl]benzenecarbimidothioate, Methyl 4-[(acetylamino)methyl]-3-chloro-N-[(trimethylsilyl)methyl]benzenecarbimidothioate, Methyl 4-[(acetylamino)methyl]-3-trifluoromethyl-N-[(trimethylsilyl)methyl]benzenecarbimidothioate, Methyl 4-[(acetylamino)methyl]-3-cyano-N-[(trimethylsilyl)methyl]benzenecarbimidothioate, Ethyl 4-[(acetylamino)methyl]-3-bromo-N-[(trimethylsilyl)methyl]benzenecarbimidothioate, Methyl 4-[(acetylamino)methyl]-3-bromo-N-[(triethylsilyl)methyl]benzenecarbimidothioate and Methyl 4-[(acetylamino)methyl]-3-bromo-N-[(t-butyldimethylsilyl)methyl]benzenecarbimidothioate.

The production method (p) can be performed under the same conditions as described for the production method of compounds of the formula (XXXVIII).

The compounds of the formulae (XXXVI) and (XXXVII) are represented by the general formula (XXXIX).

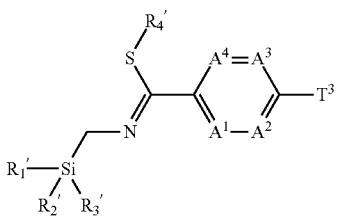

(XXXIX)

wherein T³ stands for a halogen, such as Fluor, Chlor, Brom or Iod, the chemical group G as defined in herein or represents one of the following chemical group:

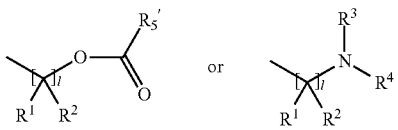

wherein R¹, R², R³, R⁴, R₅' and l have the same meanings as the aforementioned, and R₁', R₂', R₃', R₄' and A¹ to A⁴ have the same meanings as the defined herein.

Compounds of the general formula (XXXIX) are useful intermediates for the preparation of compounds according to the invention. Namely, as compounds according to the invention can be prepared by reacting a compound of formula (XII) with a compound of formula (XXXIX) in the presence of a fluorine reagent if R4' does not stand for H. In case that R4' stands for H, the reaction can be carried out in a one pot reaction by firstly adding an alkyl halid, such as methyl iodide and then adding a fluorine reagent.

Compounds of the formula (XXXIX) are for example those mentioned in the respective tables as well as methyl 3-cyano-4-fluoro-N-[(trimethylsilyl)methyl]benzenecarbimidothioate.

According to the invention it is preferred that in every compound which is described herein by using a general formula (such as for example compounds (XIII), (XV), (XXXIV), (XX), (XXIV), (XXXV), (XXXVI), (XXXVII), (XXXIX)), particularly in such compounds which are useful for the preparation of compounds according to the invention, at least 3 of the groups A1 to A4 stand for C—Y, whereas A1 and A4 both stand for C—Y and/or wherein at least 2 of the groups B1 to B3 stand for C—X and, if appropriate, R stands for CF3.

It is particularly preferred that in any such compounds all groups A¹ to A⁴ stand for C—Y, and/or all of the groups B¹ to B³ stand for C—X and, if appropriate, R stands for CF₃.

The compounds according to the present invention show a potent insecticidal action and can therefore be used as an insecticide. Furthermore, the compounds according to the present invention exhibit a strong control effect against harmful insects, without imposing any harmful side effects of drug to cultivated plants. The compounds of the present invention can thus be used for the control of a wide range of pest species, for example, harmful sucking insects, chewing insects, as well as other plant parasitic pests, storage insects, hygiene pests and the like, and can be applied for the purpose of disinfestations and extermination thereof. Harmful animal pest are for example:

As for insects, coleopterans, for example, *Callosobruchus chinensis*, *Sitophilus zeamais*, *Tribolium castaneum*, *Epilachna vigintioctomaculata*, *Agriotes fuscicollis*, *Anomala rufocuprea*, *Leptinotarsa decemlineata*, *Diabrotica* spp., *Monochamus alternatus*, *Lissorhoptrus oryzophilus*, *Lyctus bruneus*, *Aulacophora femoralis*; lepidopterans, for example, *Lymantria dispar*, *Malacosoma neustria*), *Pieris rapae*, *Spodoptera litura*, *Mamestra brassicae*, *Chilo suppressalis*), *Pyrausta nubilalis*, *Ephestia cautella*, *Adoxophyes orana*, *Carpocapsa pomonella*, *Agrotisfucosa*, *Galleria mellonella*, *Plutella maculipennis*, *Heliothis virescens*, *Phyllocnistis citrella*; hemipterans, for example, *Nephotettix cincticeps*, *Nilaparvata lugens*, *Pseudococcus comstocki*, *Unaspis yanonensis*, *Myzus persicas*, *Aphis pomi*, *Aphis gossypii*, *Rhopalosiphum pseudobrassicas*, *Stephanitis nashi*, *Nezara* spp., *Trialeurodes vaporariorm*, *Psylla* spp.; thysanopterans, for example, *Thrips palmi*, *Franklinella occidental*; orthopterans, for example, *Blatella germanica*, *Periplaneta americana*, *Gryllotalpa Africana*, *Locusta migratoria migratoriodes*; isopterans, for example, *Reticulitermes speratus*, *Coptotermes formosanus*; dipterans, for example, *Musca domestica*, *Aedes aegypti*, *Hylemia platura*, *Culex pipiens*, *Anopheles sinensis*, *Culex tritaeniorhynchus*, *Liriomyza trifolii*.

As for acari, for example, *Tetranychus cinnabarinus*, *Tetranychus urticae*, *Panonychus citri*, *Aculops pelekassi*, *Tarsonemus* spp.

As for nematodes, for example, *Meloidogyne incognita*, *Bursaphelenchus lignicolus Mamiya* et *Kiyohara*, *Aphelenchoides besseyi*, *Heterodera glycines*, *Pratylenchus* spp.

Additionally, the compounds according to the present invention show a good plant tolerance and favourable toxicity to warm-blooded animals and being tolerated well by the environment, and thus are suitable for protecting plants and plant parts.

Application of the compounds of the invention may result in increasing the harvest yields, improving the quality of the harvested material. Additionally, the compounds can be used for controlling animal pests, in particular insects, arachnids, helminths, nematodes and molluscs, which are encountered in agriculture, in horticulture, the field of veterinary medicine, in forests, in gardens and leisure facilities, in the protection of stored products and of materials, and in the hygiene sector. They may be preferably employed as plant protection agents. They are active against normally sensitive and resistant species and against all or some stages of development. These pests include inter alia:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro*, *Aceria sheldoni*, *Aculops* spp., *Aculus* spp., *Amblyomma* spp., *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Hemitarsonemus* spp., *Hyalomma* spp., *Ixodes* spp., *Latrodectus mactans*, *Metatetranychus* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apogonia* spp., *Atomaria* spp., *Attagenus* spp., *Bruchidius obtectus*, *Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica. Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp. *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp. *Sphenophorus* spp., *Sternechus* spp., *Symphyletes* spp., *Tenebrio molitor, Tribolium* spp., *Trogoderma* spp., *Tychius* spp., *Xylotrechus* spp. *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp. *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control protozoa, such as Eimeria.

From the order of the Heteroptera, for example. *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp. *Pentomidae, Piesma quadrata, Piezodorus, Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example. *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp. *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Moueilia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber*.

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp. *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella. Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella gerrnanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The terms "parts", "parts of plants" and "plant parts" have been explained above.

Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive "synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits urea better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin. phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds according to the invention at a suitable concentration.

Furthermore, in the field of veterinary medicine, the novel compounds of the present invention can be effectively used against various harmful animal parasitic pests (endoparasites and ectoparasites), for example, insects and helminthes. Examples of such animal parasitic pests include the pests as described below. Examples of the insects include *Gasterophilus* spp., *Stomoxys* spp., *Trichodectes* spp., *Rhodnius* spp., *Ctenocephalides canis*, *Cimx lecturius*, *Ctenocephalides felis*, *Lucilia cuprina*, and the like. Examples of acari include *Ornithodoros* spp., *Ixodes* spp., *Boophilus* spp., and the like.

In the veterinary fields, i.e. in the field of veterinary medicine, the active compounds according to the present invention are active against animal parasites, in particular ectoparasites or endoparasites. The term endoparasites includes in particular helminths, such as cestodes, nematodes or trematodes, and protozoae, such as coccidia. Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include:

From the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;* from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi;* from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp. *Hybomitra* spp., *Atylotus* spp., *Tabanus* spp. *Haematopota* spp., *Philipomyia* spp., *Braula* spp., *Musca* spp. *Hydrotaea* spp., *Stomoxys* spp., *Haematobia* spp., *Morellia* spp., *Fannia* spp., *Glossina* spp., *Calliphora* spp., *Lucilia* spp. *Chrysomyia* spp. *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp. *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorrhoidalis, Gasterophilus inermis, Gasterophilus nasalis, Gasterophilus nigricornis, Gasterophilus pecorum, Braula coeca;* from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis;* from the order of the *Heteropterida*, for example *Cimex* spp., *Triatoma* spp., *Rhodnius* spp., *Panstrongylus* spp.

From the order of the *Blattarida*, for example *Blatta orientalis, Periplaneta americana, Blattela germanica, Supella* spp. (e.g. *Suppella longipalpa*);

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp. *Raillietia* spp., *Pneumonyssus* spp., *Sternostoma* spp., *Varroa* spp., *Acarapis* spp.; particular examples are: *Argas persicus, Argas reflexus. Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina. Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;* from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp. *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes*

*ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoae, which attack animals. Animals include agricultural livestock such as, for example, cattle, sheep, goats, horses, pigs, donkeys, camels, buffaloes, rabbits, chickens, turkeys, ducks, geese, cultured fish, honeybees. Moreover, animals include domestic animals—also referred to as companion animals—such as, for example, dogs, cats, cage birds, aquarium fish and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it is desirable to prevent or interrupt the uptake of blood by the parasites from the hosts (when applicable). Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

Generally, when used for the treatment of animals the active compounds according to the invention can be applied directly. Preferably they are applied as pharmaceutical compositions which may contain pharmaceutically acceptable excipients and/or auxiliaries which are known in the art.

In the veterinary field and in animal keeping, the active compounds are applied (=administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The active compounds may be formulated as shampoo or as suitable formulations usable in aerosols, unpressurized sprays, for example pump sprays and atomizer sprays.

When used for livestock, poultry, domestic animals and the like, the active compounds according to the invention can be applied as formulations (for example powders, wettable powders ["WP"], emulsions, emulsifiable concentrates ["EC"], flowables, homogeneous solutions, and suspension concentrates ["SC"]) which comprise the active compounds in an amount of from 1 to 80% by weight, either directly or after dilution (e.g. 100- to 10 000-fold dilution), or else as a chemical bath.

When used in the veterinary field the active compounds according to the invention may be used in combination with suitable synergists or other active compounds, such as for example, acaricides, insecticides, anthelmintics, anti-protozoal drugs.

In the present invention, a substance having an insecticidal action against pests including all of these is referred to as an insecticide.

An active compound of the present invention can be prepared in conventional formulation forms, when used as an insecticide. Examples of the formulation forms include solutions, emulsions, wettable powders, water dispersible granules, suspensions, powders, foams, pastes, tablets, granules, aerosols, active compound-infiltrated natural and synthetic materials, microcapsules, seed coating agents, formulations used with a combustion apparatus (for example, fumigation and smoking cartridges, cans, coils or the like as the combustion apparatus), ULV (cold mist, warm mist), and the like.

These formulations can be produced by methods that are known per se. For example, a formulation can be produced by mixing the active compound with a developer, that is, a liquid diluent or carrier; a liquefied gas diluent or carrier; a solid diluent or carrier, and optionally with a surfactant, that is, an emulsifier and/or dispersant and/or foaming agent.

In the case where water is used as the developer, for example, an organic solvent can also be used as an auxiliary solvent.

Examples of the liquid diluent or carrier include aromatic hydrocarbons (for example, xylene, toluene, alkylnaphthalene and the like), chlorinated aromatic or chlorinated aliphatic hydrocarbons (for example, chlorobenzenes, ethylene chlorides, methylene chlorides), aliphatic hydrocarbons (for example, cyclohexanes), paraffins (for example, mineral oil fractions), alcohols (for example, butanol, glycols and their ethers, esters and the like), ketones (for example, acetone, methyl ethyl ketone, methyl isobutyl ketone, cyclohexanone and the like), strongly polar solvents (for example, dimethylformamide, dimethylsulfoxide and the like), water and the like.

The liquefied gas diluent or carrier may be those which are gaseous at normal temperature and normal pressure, for example, aerosol propellants such as butane, propane, nitrogen gas, carbon dioxide and halogenated hydrocarbons.

Examples of the solid diluent include pulverized natural minerals (for example, kaolin, clay, talc, chalk, quartz, attapulgite, montmorillonite, diatomaceous earth, and the like), pulverized synthetic minerals (for example, highly dispersed silicic acid, alumina, silicates and the like), and the like.

Examples of the solid carrier for granules include pulverized and screened rocks (for example, calcite, marble, pumice, sepiolite, dolomite and the like), synthetic granules of inorganic and organic powder, fine particles of organic materials (for example, sawdust, coconut shells, maize cobs, tobacco stalk and the like), and the like.

Examples of the emulsifier and/or foaming agent include nonionic and anionic emulsifiers [for example, polyoxyethylene fatty acid esters, polyoxyethylene fatty acid alcohol ethers (for example, alkylaryl polyglycol ether), alkylsulfonates, alkylsulfates, arylsulfonates and the like], albumin hydrolyzate, and the like.

Examples of the dispersant include lignin sulfite waste liquor and methylcellulose.

Fixing agents can also be used in the formulations (powders, granules, emulsions), and examples of the fixing agent include carboxymethylcellulose, natural and synthetic polymers (for example, gum arabic, polyvinyl alcohol, polyvinyl acetate, and the like) and the like.

Colorants can also be used, and examples of the colorants include inorganic pigments (for example, iron oxide, titanium oxide, Prussian Blue and the like), organic dyes such as alizarin dyes, azo dyes or metal phthalocyanine dyes, and in addition, trace elements such as the salts of iron, manganese, boron, copper, cobalt, molybdenum and zinc.

The formulations in general can contain the active ingredient in an amount ranging from 0.1 to 95% by weight, and preferably 0.5 to 90% by weight.

The compound according to the present invention can also exist as an admixture with other active compounds, for example, insecticides, poisonous baits, bactericides, miticides, nematicides, fungicides, growth regulators, herbicides and the like, in the form of their commercially useful formulation forms and in the application forms prepared from those formulations.

The content of the compound according to the present invention in a commercially useful application form can be varied within a wide range.

The concentration of the active compound according to the present invention in actual usage can be, for example, in the range of 0.0000001 to 100% by weight, and preferably 0.00001 to 1% by weight.

The compounds according to the present invention can be used through conventional methods that are appropriate for the usage form.

The active compound of the present invention have, when used against hygiene pests and pests associated with stored products, stability effective against alkali on lime materials, and also shows excellent residual effectiveness on wood and soil.

Next, the present invention is exemplified by way of the following examples, but the invention is not intended to be limited thereto.

In addition, Me stands for Methyl, Ac stands for acetyl and Ms stands for methanesulfonyl in the examples. References to room temperature means temperatures of about 18 to about 30° C.

EXAMPLE A

Synthesis of 5-[3-(3,5-dichlorophenyl)-3-(trifluoromethyl)-3,4-dihydro-2H-pyrrol-5-yl]-2-(1H-1,2,4-triazol-1-yl)benzonitrile (Compound No. 2)

Step 1. Synthesis of N-(3-bromo-4-fluorobenzyl)formamide

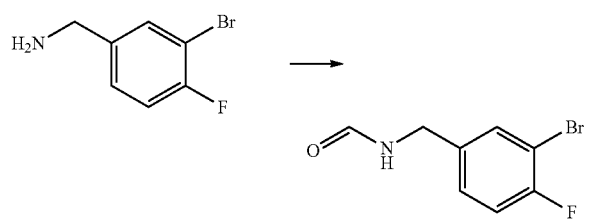

Formic acid ethyl ester (1.48 g) was added dropwise to 1-(3-bromo-4-fluorophenyl)methanamine (3.40 g) that was being stirred under ice cooling (0° C.). The reaction mixture was stirred as it was for 2 hours, then was returned to room temperature, and stirred for another 2 hours. The reaction mixture was directly subjected to purification by silica gel chromatography, to obtain N-(3-bromo-4-fluorobenzyl)formamide (2.7 g) at a yield of 69%.

1H-NMR (CDCl3) δ: 4.47 (2H, d), 7.06-7.33 (3H, m), 8.26 (1H, s)

Step 2. Synthesis of 2-(3-bromo-4-fluorophenyl)-4-(3,5-dichlorophenyl)-4-(trifluoromethyl)-3,4-dihydro-2H-pyrrole

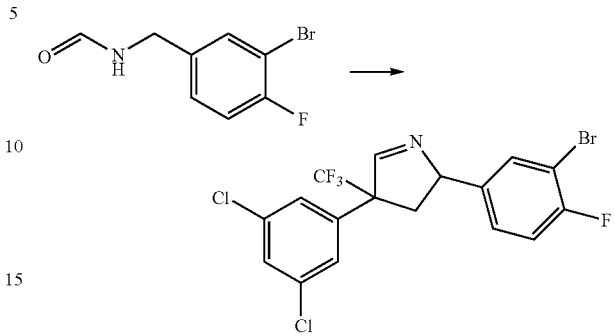

While N-(3-bromo-4-fluorobenzyl)formamide (2.70 g) and triethylamine (3.50 g) were stirred in toluene (40 ml) under ice cooling (0° C.), phosphorus oxychloride (1.90 g) was added thereto. The reaction mixture was then stirred for 3 hours at room temperature. Water (100 ml) was carefully added to the reaction mixture, and a saturated aqueous sodium hydrogen carbonate solution was added to neutralize the reaction mixture. The aqueous layer was separated and extracted with toluene (60 ml×2). The combined organic layers were washed with a saturated aqueous sodium hydrogen carbonate solution and saturated brine, subsequently dried over magnesium sulfate, and the drying agent was separated by filtration. To the filtrate, 1,3-dichloro-5-[1-(trifluoromethyl)ethenyl]benzene (2.1 g) and copper (II) oxide (0.2 g) were added. The mixture was heated to reflux for 3 days. The reaction mixture was returned to room temperature, and the filtrate was washed with a saturated aqueous solution of sodium hydrogen carbonate and saturated brine, and then dried over magnesium sulfate. After filtering the reaction mixture, the solvent was distilled off under reduced pressure, to obtain crude 2-(3-bromo-4-fluorophenyl)-4-(3,5-dichlorophenyl)-4-(trifluoromethyl)3,4-dihydro-2H-pyrrole (0.88 g).

Step 3. Synthesis of 5-(3-bromo-4-fluorophenyl)-3-(3,5-dichlorophenyl)-3-(trifluoromethyl)-3,4-dihydro-2H-pyrrole

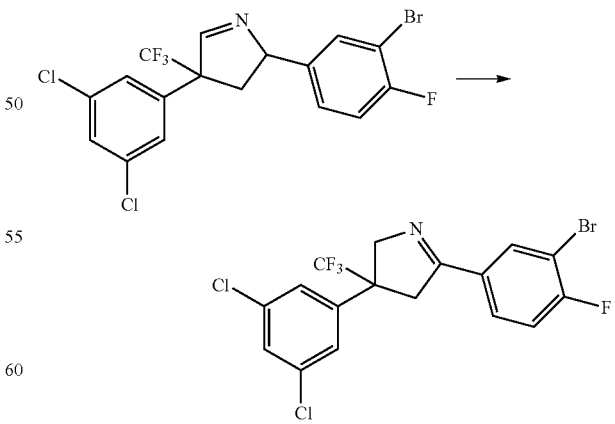

To a solution of 2-(3-bromo-4-fluorophenyl)-4-(3,5-dichlorophenyl)-4-(trifluoromethyl)-3,4-dihydro-2H-pyrrole (0.88 g) in THF (13 ml), t-BuOK (0.24 g) was added under ice cooling. The mixture was returned to room temperature and stirred for 16 hours. Water was added to the reaction mixture, and the aqueous layer was separated and extracted with ethyl acetate. The combined organic layers, were washed with saturated brine, and dried over magnesium sulfate. After filtering the reaction mixture, the solvent was distilled off under reduced pressure, and the resulting mixture was purified by silica gel chromatography, to obtain 5-(3-bromo-4-fluorophenyl)-3-(3,5-dichlorophenyl)-3-(trifluoromethyl)-3,4-dihydro-2H-pyrrole (0.88 g) at a yield of 100%.

1H-NMR (CDCl3) δ: 3.42 (2H, d), 3.75 (2H, d), 4.43 (2H, d), 4.88 (2H, d), 7.10-7.39 (3H, m), 7.86-8.08 (3H, m)

Step 4. Synthesis of 5-[3-(3,5-dichlorophenyl)-3-(trifluoromethyl)-3,4-dihydro-2H-pyrrol-5-yl]-2-fluorobenzonitrile

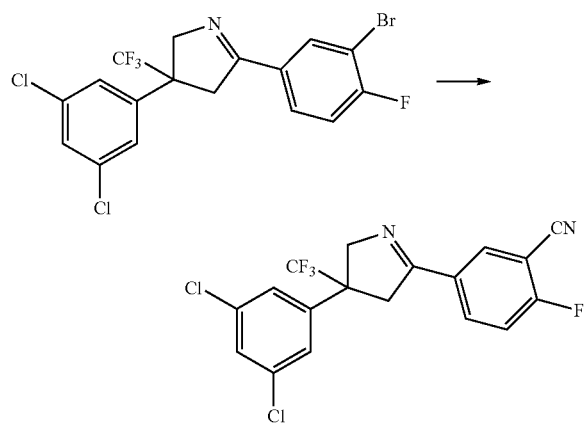

5-(3-Bromo-4-fluorophenyl)-3-(3,5-dichlorophenyl)-3-(trifluoromethyl)-3,4-dihydro-2H-pyrrole (0.88 g) was dissolved in DMF (10 ml), and the solution was deaerated and then left to stand in an argon atmosphere. To the reaction mixture, Zn(CN)2 (0.45 g) and Pd(PPh3)4 (0.67 g) were added. The mixture was stirred for 4 hours at 90° C. The reaction mixture was returned to room temperature, and then ethyl acetate was added thereto. The reaction mixture was washed with a saturated aqueous solution of sodium hydrogen carbonate, and then dried over magnesium sulfate. After filtering the reaction mixture, the solvent was distilled off under reduced pressure, and the resulting mixture was purified by silica gel chromatography, to obtain 5-[3-(3,5-dichlorophenyl)-3-(trifluoromethyl)-3,4-dihydro-2H-pyrrol-5-yl]-2-fluorobenzonitrile (0.25 g) at a yield of 32%.

1H-NMR (CDCl3) δ: 3.44 (1H, d), 3.76 (1H, d), 4.46 (1H, d), 4.91 (1H, d), 7.12-8.16 (6H, m)

Step 5. Synthesis of 5-[3-(3,5-dichlorophenyl)-3-(trifluoromethyl)-3,4-dihydro-2H-pyrrol5-yl]-2-(1H-1,2,4-triazol-1-yl)benzonitrile

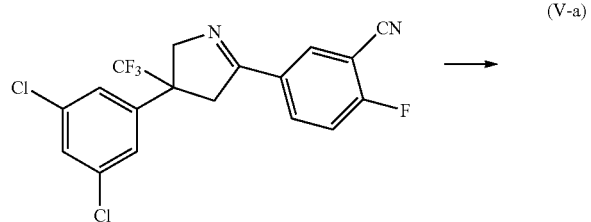

(V-a)

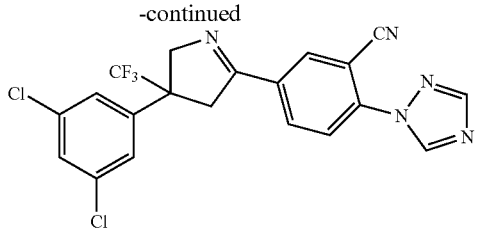

A mixed solution of 5-[3-(3,5-dichlorophenyl)-3-(trifluoromethyl)-3,4-dihydro-2H-pyrrol-5-yl]-2-fluorobenzonitirle (250 g), 1H-1,2,4-triazole (52 mg) and potassium carbonate (103 mg) in DMF (1 ml) was stirred for 3 hours at 80° C. The reaction mixture was returned to room temperature, water was added thereto, and the mixture was extracted with ethyl acetate. The organic layer was washed with saturated brine, and then dried over magnesium sulfate. After filtering the reaction mixture, the solvent was distilled off under reduced pressure, and the resulting mixture was purified by silica gel chromatography, to obtain 5-[3-(3,5-dichlorphenyl)-3-(trifluoromethyl)-3,4-dihydro-2H-pyrrol-5-yl]-2-(1H-1,2,4-triazol-1-yl)benzonitrile (130 mg) at a yield of 46%.

1H-NMR (CDCl3) δ: 3.50 (1H, d), 3.82 (1H, d), 4.5H, d), 4.96 (1H, d), 7.41 (1H, m), 7.93-8.33 (4H, m), 8.90 (1H, d)

EXAMPLE B

Synthesis of 2-(1H-1,2,4-triazol-1-yl)-5-[3-(3,4,5-trichlorophenyl)-3-(trifluoromethyl)-3,4-dihydro-2H-pyrrol-5-yl]-benzonitrile (No. 1-78)

Step 1. Synthesis of 3-bromo-4-fluoro-N-[(trimethylsilyl)methyl]benzamide

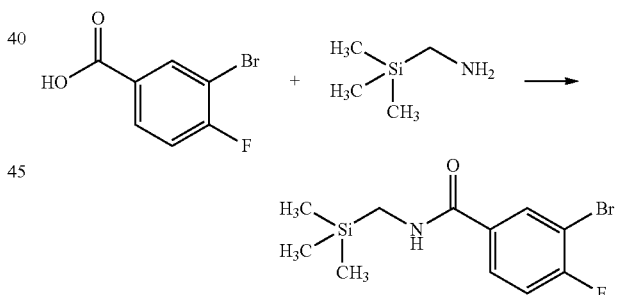

3-bromo-4-fluorobenzoic acid (5.0 g) was dissolved in ethyl acetate, and was added thionyl chloride (5.4 g) and DMF (3 drops). The mixture was heated to reflux for 2 hours and then the solvent was distilled off under reduced pressure. The residue was dissolved in THF and 1-(trimethylsilyl)methylamine (2.6 g) and triethylamine (2.9 g) were added thereto under cooling (0° C.). The reaction mixture was stirred for 3 hours at room temperature. Water was added to the reaction mixture and extracted with ethyl acetate. The organic layer was washed with a saturated aqueous sodium hydrogen carbonate solution, subsequently dried over magnesium sulfate. After filtering the reaction mixture, the solvent was distilled off under reduced pressure, and the resulting mixture was purified by silica gel chromatography, to obtain 3-bromo-4-fluoro-N-[(trimethylsilyl)methyl]benzamide (6.9 g) at a yield of 100%.

1H-NMR (CDCl3) δ: 0.11 (9H, s), 2.93 (2H, s), 5.87 (1H, s), 7.16 (1H, t), 7.66 (1H, m), 7.95 (1H, d).

Step 2. Synthesis of 3-cyano-4-fluoro-N-[(trimethylsilyl)methyl]benzamide

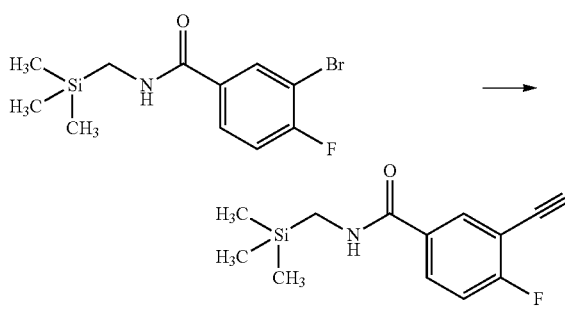

3-bromo-4-fluoro-N-[(trimethylsilyl)methyl]benzamide (5.0 g) was dissolved in DMF, and zinc cyanide (1.4 g) and tetrakis(triphenylphosphine)palladium (1.9 g) were added thereto under argon atmosphere. The reaction mixture was stirred for 4 hours at 90° C. The reaction mixture was returned to room temperature. The mixture was diluted with ethyl acetate and washed with a saturated aqueous sodium hydrogen carbonate solution, subsequently dried over magnesium sulfate. After filtering the reaction mixture, the solvent was distilled off under reduced pressure, and the resulting mixture was purified by silica gel chromatography, to obtain 3-cyano-4-fluoro-N-[trimethylsilyl)methyl]benzamide (4.0 g) at a yield of 97%.

1H-NMR (CDCl3) δ: 0.2 (9H, s), 2.97 (2H, d), 5.94 (1H, s), 7.26-7.32 (2H, m), 7.98-8.02 (2H, m).

Step 3. Synthesis of 3-cyano-4-(1H-1,2,4-triazol-1-yl)-N-[(trimethylsilyl)methyl]-benzamide

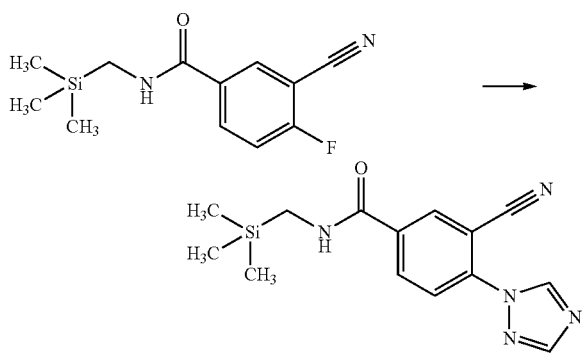

To a solution of 3-cyano-4-fluoro-N-[trimethylsilyl)methyl]benzamide 0.5 g) in DMF was added triazole (0.5 g) and potassium carbonate (1.0 g). The mixture was stirred for 3 hours at 80° C. The reaction mixture was returned to room temperature, water was added thereto, and the aqueous layer was extracted with ethyl acetate. The combined organic layers, were washed with a saturated aqueous sodium hydrogen carbonate solution, subsequently dried over magnesium sulfate. After filtering the reaction mixture, the solvent was distilled off under reduced pressure, and the resulting mixture was purified by silica gel chromatography, to obtain 3-cyano-4-(1H-1,2,4-triazol-1-yl)-N-[(trimethylsilyl)methyl]benzamide (1.1 g) at a yield of 61%.

1H-NMR (CDCl3) δ: 0.20 (9H, s), 3.01 (2H, d), 6.01 (1H, s), 7.91 (1H, d), 8.12 (1H, d), 8.21 (2H, m), 8.88 (1H, s).

Step 4. Synthesis of 3-cyano-4-(1H-1,2,4-triazol-1-yl)-N-[(trimethylsilyl)methyl]-benzene carbothioamide

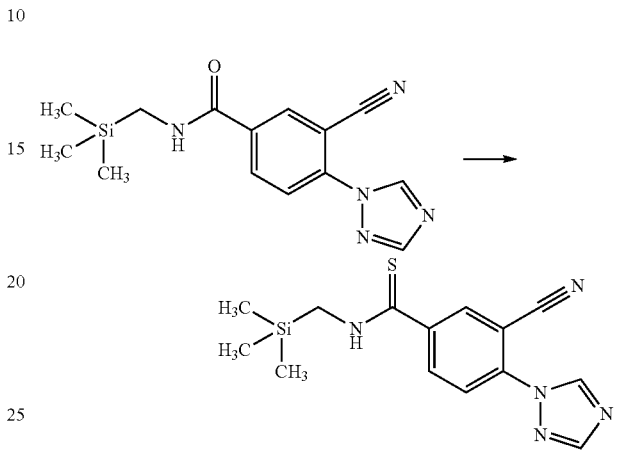

3-cyano-4-(1H-1,2,4-triazol-1-yl)-N-[(trimethylsilyl)methyl]benzamide (1.1 g) was dissolved with toluene. To the mixture was added Lawesson reagent (1.5 g) and heated to reflux for 5 hours. The reaction mixture was returned to room temperature, water was added thereto, and the aqueous layer was extracted with ethyl acetate. The combined organic layers, were washed with a saturated aqueous sodium hydrogen carbonate solution, subsequently dried over magnesium sulfate. After filtering the reaction mixture, the solvent was distilled off under reduced pressure, and the resulting mixture was purified by silica gel chromatography, to obtain 3-cyano-4-(1H-1,2,4-triazol-1-yl)-N-[(trimethylsilyl)methyl]benzenecarbothioamide (1.5 g).

1H-NMR (CDCl3) δ: 0.21 (9H, s), 3.56 (2H, d), 8.03 (5H, m).

Step 5. Synthesis of methyl 3-cyano-4-(1H-1,2,4-triazol-1-yl)-N-[(trimethylsilyl)methyl]benzenecarbimidothioate (No. 12-39)

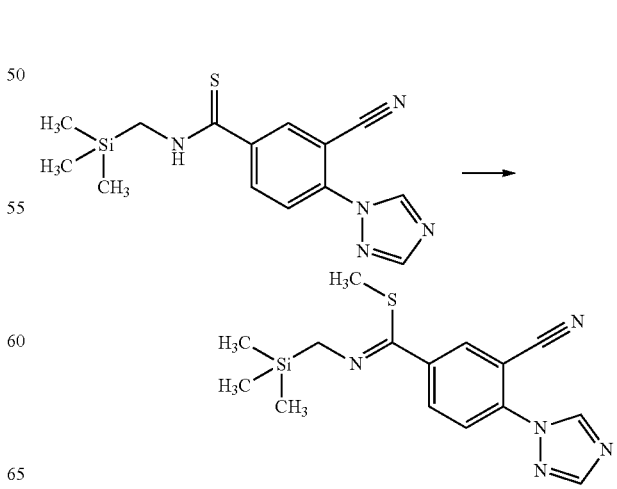

To a solution of 3-cyano-4-(1H-1,2,4-triazol-1-yl)-N-[(trimethylsilyl)methyl]benzene-carbothioamide (1.5 g) in THF was added t-BuOK (0.64 g) under cooling (0° C.). After stirring for 15 minutes, methyl iodide (0.81 g) was added dropwise to the mixture under cooling (0° C.). The reaction liquor was returned to room temperature and stirred for 2 hours. Water was added to the reaction mixture, and aqueous layer was extracted with ethyl acetate. The combined organic layer was washed with a saturated aqueous sodium hydrogen carbonate solution, subsequently dried over magnesium sulfate. After filtering the reaction mixture, the solvent was distilled off under reduced pressure, and the resulting mixture was purified by silica gel chromatography, to obtain methyl 3-cyano-4-(1H-1,2,4-triazol-1-yl)-N-[(trimethylsilyl)methyl]benzenecarbimidothioate at a yield of 64%.

1H-NMR (CDCl3) δ: 0.13 (9H, s), 2.14 (3H, s), 3.74 (2H, s), 7.81-7.87 (1H, m), 7.97-8.01 (2H, 8.08 (1H, s), 8.22 (1H, s), 8.83 (1H, s).

Step 6. Synthesis of 2-(1H-1,2,4-triazol-1-yl)-5-[3-(3,4,5-trichlorophenyl)-3-(trifluoromethyl)-3,4-dihydro-2H-pyrrol-5-yl]-benzonitrile

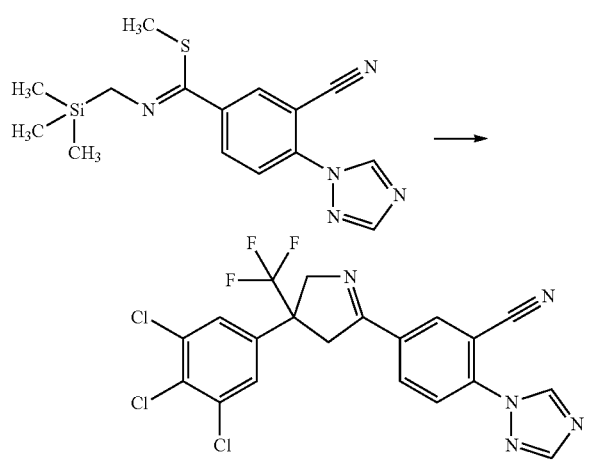

(XXXVI-a)

methyl 3-cyano-4-(1H-1,2,4-triazol-1-yl)-N-[(trimethylsilyl)methyl]benzenecarbimidothioate (0.2 g) and 1,2,3-trichloro-5-[1-(trifluoromethyl)ethenyl]benzene (0.17 g) were dissolved in THF and cooled to −5° C. to be stirring. Additionally a solution of tetrabutylammonium fluoride (0.099 mL of 1.0 M in THF) in THF was added over 10 minutes under argon atmosphere. The reaction mixture was stirred for 30 minutes at the same temperature and returned to room temperature gradually, and then stirred 4 hours. Water was added to the reaction liquor, and aqueous layer was extracted with ethyl acetate. The combined organic layers, were washed with a saturated aqueous brine, subsequently dried over magnesium sulfate. After filtering the reaction mixture, the solvent was distilled off under reduced pressure, and the resulting mixture was purified by silica gel chromatography, to obtain 2-(1H-1,2,4-triazol-1-yl)-5-[3-(3,4,5-trichlorophenyl)-3-(trifluoromethyl)-3,4-dihydro-2H-pyrrol-5-yl]benzonitrile (0.25 g) at a yield of 85%.

1H-NMR (CDCl3) δ: 3.48 (1H, d), 3.82 (1H, d), 4.50 (1H, d), 4.96 (1H, d), 7.41 (2H, s), 7.94 (1H,

EXAMPLE C

Synthesis of N-{2-bromo-4-[3-(3,5-dichlorophenyl)-3-(trifluoromethyl)-3,4-dihydro-2H-pyrrol-5-yl]benzyl}acetamide (No. 2-13)

Step 1. Synthesis of 3-bromo-4-(bromomethyl)benzoic acid

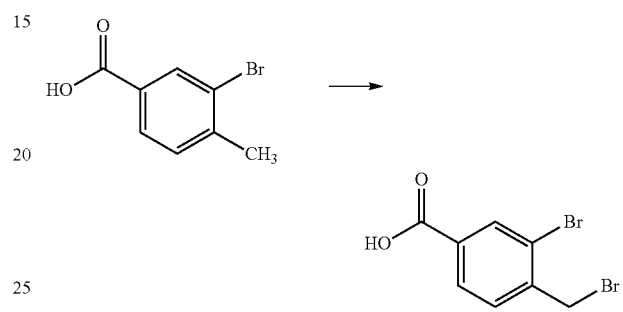

3-Bromo-4-methylbenzoic acid (10 g), N-bromosuccinimide (8.7 g) and 2,2'-azobisisobutyronitrile (0.4 g) were suspended in carbon tetrachloride (50 ml) and then heated to reflux for 2 hours. The mixture was returned to room temperature and added a 15% aqueous solution of citric acid (20 ml), and stirred for some time. Resulting crystals were filtered and washed with the 15% aqueous solution of citric acid (20 ml), and then dried, to obtain 3-bromo-4-(bromomethyl)benzoic acid (6 g).

11H-NMR (CDCl3) δ: 4.62 (2H, s), 7.57-7.58 (1H, m), 8.01-8.04 (1H, m), 8.32 (1H, d)

Step 2. Synthesis of 3-bromo-4-(bromomethyl)-N-[(trimethysilyl)methyl]benzamide

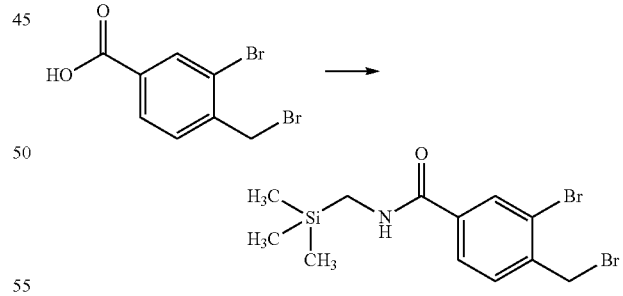

3-bromo-4-(bromomethyl)benzoic acid (5 g), 1-(trimethylsilyl)methylamine (1.76 g), N,N-dimethylaminopyridine (0.1 g) and N-(3-dimethylaminopropyl)-N'-ethylcarbodiimide hydrochloride (4.3 g) were dissolved in dichloromethane (30 ml), and stirred for 5 hours at room temperature. Water was added to the reaction mixture, and then organic layer was separated and dried over magnesium sulfate. After filtering the reaction mixture, the solvent was distilled off under reduced pressure, and the resulting mixture was purified by silica gel chromatography, to obtain 3-bromo-4-(bromomethyl)-N-[(trimethysilyl)methyl]benzamide (4 g).

1H-NMR (CDCl3) δ: 0.13 (9H, s), 2.94-2.98 (2H, m), 4.71 (2H, s), 5.99 (1H, s), 7.53-7.55 (1H, m), 7.64-7.67 (1H, m), 7.95-7.96 (1H, m)

Step 3. Synthesis of 2-bromo-4-{[(trimethysilyl)methyl]carbamoyl}benzyl acetate

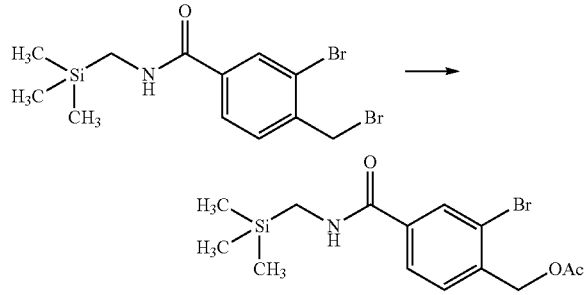

A mixed solution of sodium acetate (2.8 g), 3-bromo-4-(bromomethyl)-N-[(trimethysilyl)methyl]benzamide (6.5 g) in DMF (30 ml) was stirred for 3 hours at 70° C. The reaction liquor was returned to room temperature and diluted with t-butyl methyl ether. The mixture was washed with water and a saturated aqueous brine, subsequently dried over magnesium sulfate. After separating the drying agent by filtration, the reaction liquor was distilled off under reduced pressure, and the resulting mixture was purified by silica gel chromatography, to obtain 2-bromo-4-{[(trimethysilyl)methyl]carbamoyl}benzyl acetate (2.4 g).

1H-NMR (CDCl3) δ: 0.13 (9H, s), 2.16 (3H, s), 2.96 (2H, d), 5.21 (2H, s), 5.96 (1H, s), 7.44-7.47 (1H, m)

Step 4. Synthesis of 2-bromo-4-{[(trimethysilyl)methyl]carbamothioyl}benzyl acetate

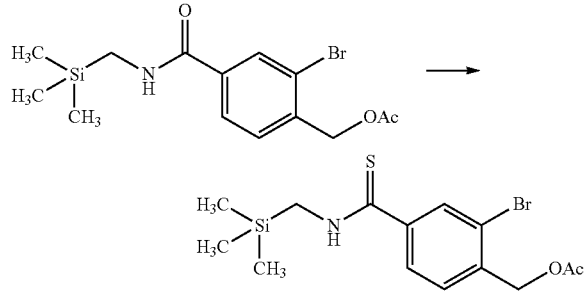

2-bromo-4-{[trimethysilyl)methyl]carbamoyl}benzyl acetate (2.4 g) and Lawesson reagent (2.7 g) were suspended with toluene. The mixture was heated to reflux for 2 hours. The reaction mixture was returned to room temperature, washed with water and a saturated aqueous brine, subsequently dried over magnesium sulfate. After filtering the reaction mixture, the solvent was distilled off under reduced pressure, and the resulting mixture was purified by silica gel chromatography, to obtain 2-bromo-4-{[(trimethysilyl)methyl]carbamothioyl}benzyl acetate (1.8 g).

1H-NMR (CDCl3) δ: 0.18 (9H, s), 2.15 (3H, s), 3.51 (2H, d), 5.18 (2H, s), 7.38-7.41 (1H, m),

Step 5. Synthesis of 2-bromo-4-[(methylsulfanyl){[(trimethysilyl)methyl]imino}methyl]benzyl acetate (No. 13-9)

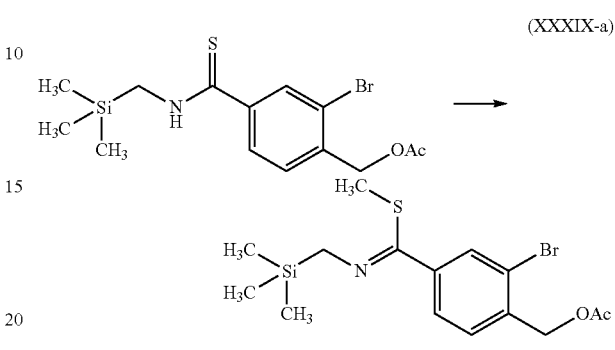

(XXXIX-a)

A mixed solution of methyl iodide (0.69 g), potassium carbonate (0.80 g) and 2-bromo-4-{[(trimethysilyl)methyl]carbamothioyl}benzyl acetate (1.8 g) in DMF (30 ml) was stirred for 2 hours at room temperature. The mixture was diluted with t-butyl methyl ether and washed with water and a saturated aqueous brine, subsequently dried over magnesium sulfate. After filtering the reaction mixture, the solvent was distilled off under reduced pressure, and the resulting mixture was purified by silica gel chromatography, to obtain 2-bromo-4-[(methylsulfanyl){[trimethysilyl)methyl]imino}methyl]benzyl acetate (0.95 g).

1H-NMR (CDCl3) δ: 0.11 (9H, s), 2.09 (3H, s), 2.14 (3H, s), 3.64 (2H, s), 5.20 (2H, s), 7.42-7.47 (2H, m), 7.71-7.74 (1H, m)

Step 6: Synthesis of 2-bromo-4-[3-(3,5-dichlorophenyl)-3-(trifluoromethyl)-3,4-dihydro-2H-pyrrol-5-yl]benzyl acetate

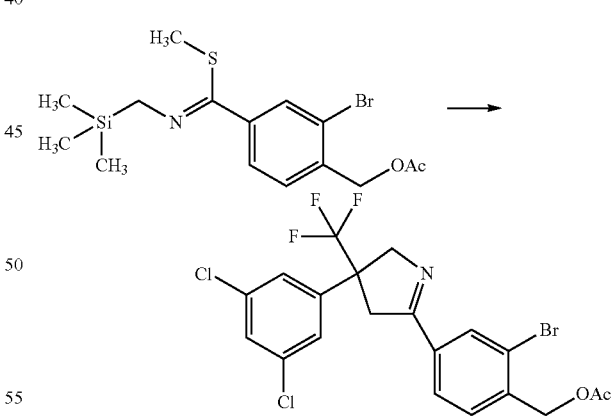

Under argon atmosphere, a mixed solution of 2-bromo-4-[(methylsulfanyl){[(trimethysilyl)methyl]imino}methyl]benzyl acetate (0.90 g) and 1,3-dichloro-5-(3,3,3-trifluoroprop-1-en-2-yl)benzene (0.56 g) in THF was cooled to −5° C. to be stirred, and a solution of tetrabutylammonium fluoride (0.56 ml, of 1.0 M in THF) was added thereto gradually. The reaction mixture was stirred for 20 hours at room temperature. The reaction mixture was diluted with t-butyl methyl ether and washed with water and a saturated aqueous brine, subsequently dried over magnesium sulfate. After filtering the reaction mixture, the solvent was distilled off under reduced pressure, and the resulting mixture was purified by silica gel chromatography, to obtain 2-bromo-4-[3-(3,5-dichlorophenyl)-3-(trifluoromethyl)-3,4-dihydro-2H-pyrrol-5-yl]benzyl acetate (1.1 g).

1H-NMR (CDCl3) δ: 2.17 (3H, s), 3.43 (1H, d), 3.73-3.79 (1H, m), 4.45 (1H, d), 4.87-4.92 (1H, m), 5.23 (2H, s), 7.25-7.28 (2H, m), 7.38-7.38 (1H, m), 7.48-7.50 (1H, m), 7.77-7.80 (1H, m), 8.07-8.08 (1H, m)

Step 7: Synthesis of {2-bromo-4-[3-(3,5-dichlorophenyl)-3-(trifluoromethyl)-3,4-dihydro-2H-pyrrol-5-yl]-phenyl}methanol

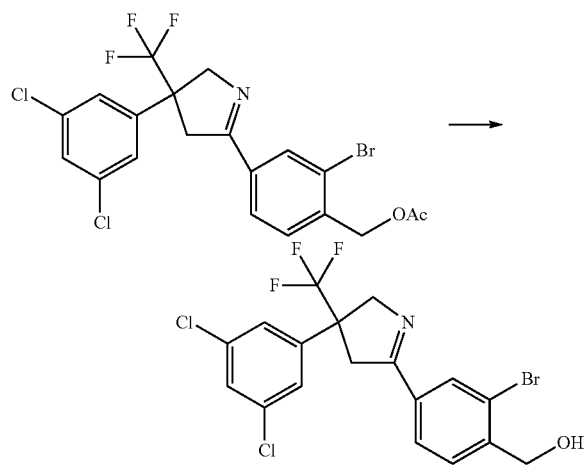

To a solution of 2-bromo-4-[3-(3,5-dichlorophenyl)-3-(trifluoromethyl)-3,4-dihydro-2H-pyrrol-5-yl]benzyl acetate (1.1 g) in methanol (20 ml) was added sodium methoxide (0.1 g), and the solution was stirred for 1 hour at room temperature. The reaction mixture was returned to room temperature and then diluted with t-butyl methyl ether, washed with water and a saturated aqueous brine and subsequently dried over magnesium sulfate. After filtering the reaction mixture, the solvent was distilled off under reduced pressure, and the resulting mixture was purified by silica gel chromatography, to obtain {2-bromo-4-[3-(3,5-dichlorophenyl)-3-(trifluoromethyl)-3,4-dihydro-2H-pyrrol-5-yl]phenyl}methanol (0.95 g).

1H-NMR (CDCl3) δ: 3.44 (1H, d), 3.74-3.80 (1H, m), 4.45 (1H, d), 4.83-4.89 (3H, m), 7.30-7.34 (3H, m), 7.59-7.61 (1H, m), 7.78-7.81 (1H, m), 8.05-8.06 (1H, m)

Step 8: Synthesis of 2-bromo-4-[3-(3,5-dichlorophenyl)-3-(trifluoromethyl)-3,4-dihydro-2H-pyrrol-5-yl]benzyl methanesulfonate

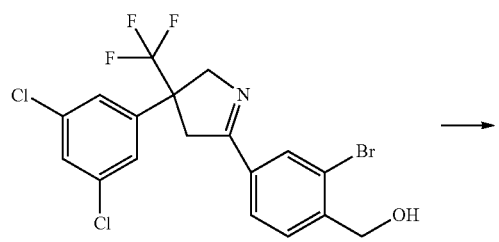

-continued

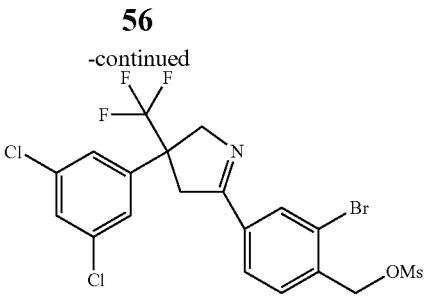

To a solution of {2-bromo-4-[3-(3,5-dichlorophenyl)-3-(trifluoromethyl)-3,4-dihydro-2H-pyrrol-5-yl]phenyl}methanol (0.95 g) and triethylamine (0.41 g) in dichloromethane was added methanesulfonyl chloride (0.35 g) gradually, and the mixture was stirred for 2 hours at room temperature. The reaction liquor was washed with water and a saturated aqueous brine, subsequently dried over magnesium sulfate. After filtering the reaction mixture, the solvent was distilled off under reduced pressure, to obtain 2-bromo-4-[3-(3,5-dichlorophenyl)-3-(trifluoromethyl)-3,4-dihydro-2H-pyrrol-5-yl]-benzyl methanesulfonate (1.0 g).

1H-NMR (CDCl3) δ: 3.07 (3H, s), 3.44 (1H, d), 3.74-3.80 (1H, m), 4.46 (1H, d), 4.88-4.94 (1H, m), 5.36 (2H, s), 7.24-7.28 (2H, m), 7.38-7.39 (1H, m), 7.58-7.60 (1H, m), 7.81-7.84 (1H, m), 8.12-8.13 (1H, m)

Step 9: Synthesis of 1-{2-bromo-4-[3-(3,5-dichlorophenyl)-3-(trifluoromethyl)-3,4-dihydro-2H-pyrrol-5-yl]phenyl}methanamine

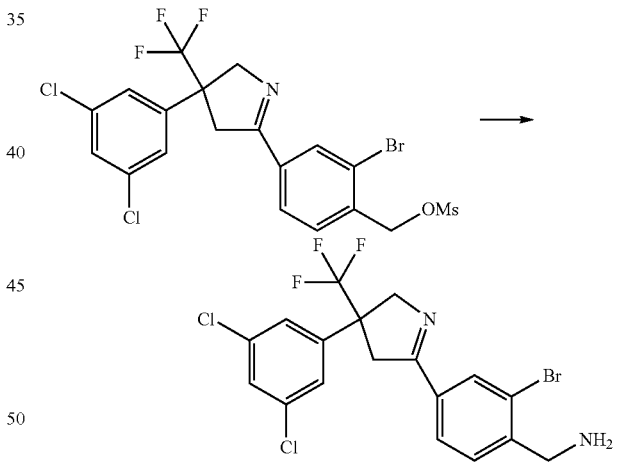

A solution of 2-bromo-4-[3-(3,5-dichlorophenyl)-3-(trifluoromethyl)-3,4-dihydro-2H-pyrrol-5-yl]benzyl methanesulfonate (1.0 g) in THF (5 ml) was added dropwise to a mixed solution of aqueous ammonia (30%, 30 ml), methanol (30 ml) and THF (30 ml), and the reaction mixture was stirred for 20 hours at room temperature. The mixture was concentrated under reduced pressure to give residual material. The residue was dissolved with t-butyl methyl ether and washed with water and a saturated aqueous brine, subsequently dried over magnesium sulfate. After separating the drying agent by filtration, the reaction liquor was distilled off under reduced pressure, to obtain 1-{2-bromo-4-[3-(3,5-dichlorophenyl)-3-(trifluoromethyl)-3,4-dihydro-2H-pyrrol-5-yl]phenyl}methanamine (0.8 g).

1H-NMR (CDCl3) δ: 3.43 (1H, d), 3.73-3.79 (1H, m), 4.43-4.48 (3H, m), 4.88 (1H, d), 7.25-7.28 (2H, m), 7.37-7.38 (1H, m), 7.59-7.62 (1H, m), 7.75-7.78 (1H, m), 8.05-8.06 (1H, m)

Step 10: Synthesis of N-{2-bromo-4-[3-(3,5-dichlorophenyl)-3-(trifluoromethyl)-3,4-dihydro-2H-pyrrol-5-yl]benzyl}acetamide

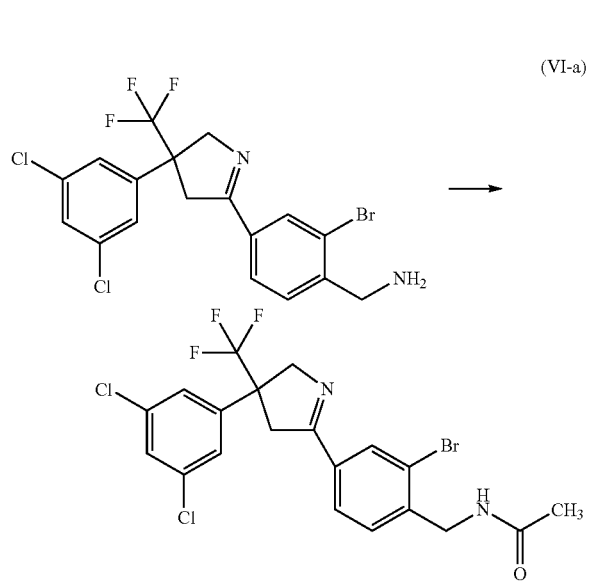

(VI-a)

To a solution of 1-(2-bromo-4-[3-(3,5-dichlorophenyl)-3-(trifluoromethyl)-3,4-dihydro-2H-pyrrol-5-yl]phenyl)methanamine (0.15 g) in THF (10 ml) was added acetic anhydride (0.04 g), and the mixture was stirred for 1 hour at room temperature. The mixture was concentrated under reduced pressure to give residual material which was purified by silica gel chromatography, to obtain N-{2-bromo-4-[3-(3,5-dichlorophenyl)-3-(trifluoromethyl)-3,4-dihydro-2H-pyrrol-5-yl]benzyl}acetamide (0.1 g).

1H-NMR (CDCl3) δ: 2.04 (3H, s), 3.41 (1H, d), 3.73-3.77 (1H, m), 4.43-4.53 (3H, m), 4.89 (1H, d), 5.98 (1H, s), 7.24-7.28 (2H, m), 7.38-7.38 (1H, m), 7.47-7.49 (1H, m), 7.71-7.78 (1H, m), 8.07-8.07 (1H, m)

EXAMPLE D

Synthesis of N-({4-[3-(3,5-dichlorophenyl)-3-(trifluoromethyl)-3,4-dihydro-2H-pyrrol-5-yl]naphthalen-1-yl}methyl)acetamide (No. 11-1)

Step 1: Synthesis of 4-(bromomethyl)naphthalen-1-carboxylic acid

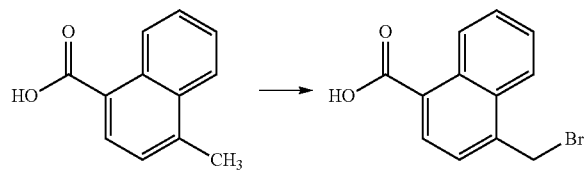

4-methylnaphthalen-1-carboxylic acid (5 g). N-bromosuccinimide (5.7 g) and 2,2'-azobisisobutyronitrile (0.2 g) were suspended in carbon tetrachloride (50 ml) and then heated to reflux for 2 hours. The mixture was returned to room temperature and added a 15% aqueous solution of citric acid (20 ml), and stirred for some time. Resulting crystals were filtered and washed with the 15% aqueous solution of citric acid (20 ml), and then dried, to obtain 4-(bromomethyl)naphthalen-1-carboxylic acid (7 g).

1H-NMR (acetone-d6) δ: 5.19 (2H, s), 7.69-7.76 (3H, m). 8.23-8.29 (2H, m), 9.04-9.06 (1H, m)

Step 2: Synthesis of 4-(bromomethyl)-N-[(trimethylsilyl)methyl]naphthalene-1-carboxamide

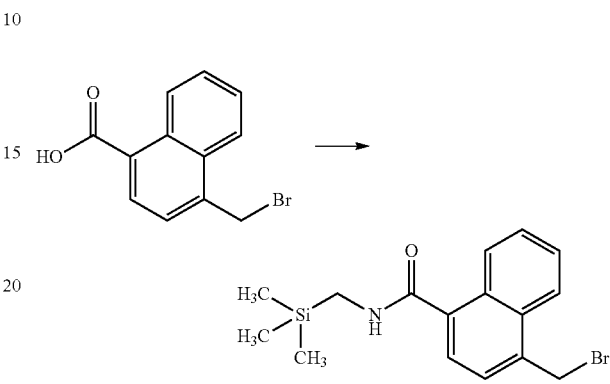

4-(bromomethyl)naphthalen-1-carboxylic acid (7 g), 1-(trimethylsilyl)methylamine (2.7 g), N,N-dimethylaminopyridine (0.1 g) and N-(3-dimethylaminopropyl)-N'-ethylcarbodiimide hydrochloride (6.6 g) were dissolved in dichloromethane (30 ml), and stirred for 5 hours at room temperature. Water was added to the reaction mixture, and then organic layers, were separated and dried over magnesium sulfate. After filtering the reaction mixture, the solvent was distilled off under reduced pressure, and the resulting mixture was purified by silica gel chromatography, to obtain 4-(bromomethyl)-N-[(trimethylsilyl)methyl]naphthalene-1-carboxamide (3 g).

1H-NMR (CDCl3) δ: 0.16 (9H, s), 3.07 (2H, d), 5.05 (2H, s), 5.80 (1H, s), 7.48-7.67 (4H, m), 8.16-8.18 (1H, m), 8.29-8.31 (1H, m)

Step 3: Synthesis of (4{[(trimethylsilyl)methyl]carbamoyl}naphthalen-1-yl)methyl acetate

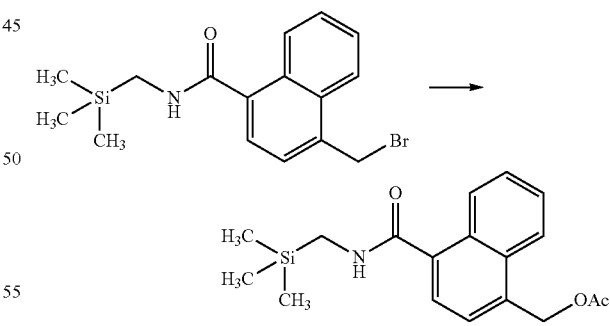

A mixed solution of sodium acetate (1.1 g), 4-(bromomethyl)-N-[(trimethylsilyl)methyl]naphthalen-1-carboxamide (2.5 g) in DMF (30 ml) was stirred for 3 hours at 70° C. The reaction mixture was returned to room temperature and diluted with t-butyl methyl ether. The mixture was washed with water and a saturated aqueous brine, subsequently dried over magnesium sulfate. After filtering the reaction mixture, the solvent was distilled off under reduced pressure, and the resulting mixture was purified by silica gel chromatography, to obtain (4{[(trimethylsilyl)methyl]carbamoyl}naphthalen-1-yl)methyl acetate (1.3 g).

1H-NMR (CDCl3) δ: 0.15 (9H, s), 2.11 (3H, s), 3.07 (2H, d), 5.57 (2H, s), 5.80 (1H, s), 7.52-7.61 (4H, m), 8.01-8.06 (1H, m), 8.29-8.33 (1H, m)

Step 4: Synthesis of (4{[(trimethylsilyl)methyl]carbamothioyl}naphthalen-1-yl)methyl acetate

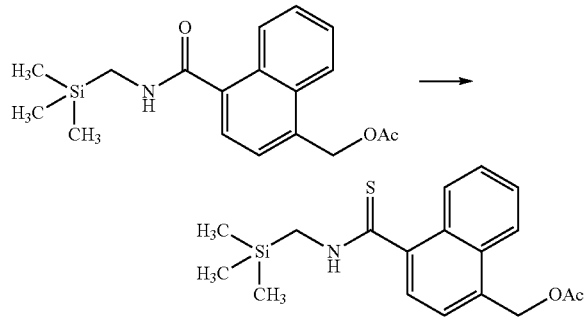

(4{[(trimethylsilyl)methyl]carbamoyl}naphthalen-1-yl)methyl acetate (2.0 g) and Lawesson reagent (2.4 g) were suspended with toluene (30 ml). The mixture was heated to reflux for 2 hours. The reaction mixture was returned to room temperature, washed with water and a saturated aqueous brine, subsequently dried over magnesium sulfate. After filtering the reaction mixture, the solvent was distilled off under reduced pressure, and the resulting mixture was purified by silica gel chromatography, to obtain (4{[(trimethylsilyl)methyl]carbamothioyl}naphthalen-1-yl)methyl acetate (1.2 g).

Step 5: Synthesis of {4-[(Z)-(methylsulfanyl){[(trimethylsilyl)methyl]imino}methyl]naphthalen-1-yl}methyl acetate (No. 15-2).

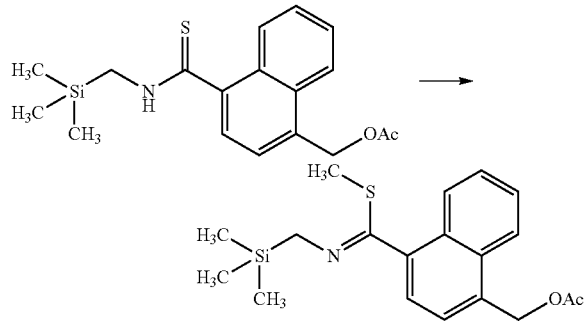

To a mixed solution of methyl iodide (0.60 g) and (4{[(trimethylsilyl)methyl]carbamothioyl}naphthalen-1-yl)methyl acetate (1.2 g) in THF (30 ml) was added potassium t-butoxide (0.45 g) gradually, and the mixture was stirred for 20 minutes at the same temperature. The mixture was diluted with t-butyl methyl ether and washed with water and a saturated aqueous brine, subsequently dried over magnesium sulfate. After filtering the reaction mixture, the solvent was distilled off under reduced pressure, to obtain {4-[(Z)-(methylsulfanyl){[(trimethylsilyl)methyl]imino}methyl]naphthalen-1-yl}methyl acetate (1.1 g).

1H-NMR (CDCl3) δ: 0.22 (9H, s), 2.14-2.15 (6H, m), 3.67 (2H, s), 5.59 (2H, s), 7.56-7.61 (4H, m), 7.82-7.83 (1H, m), 8.06-8.15 (1H, m)

Step 6: Synthesis of {4-[3-(3,4,5-trichlorophenyl)-3-(trifluoromethyl)-3,4-dihydro-2H-pyrrol-5-yl]naphthalen-1-yl}methyl acetate

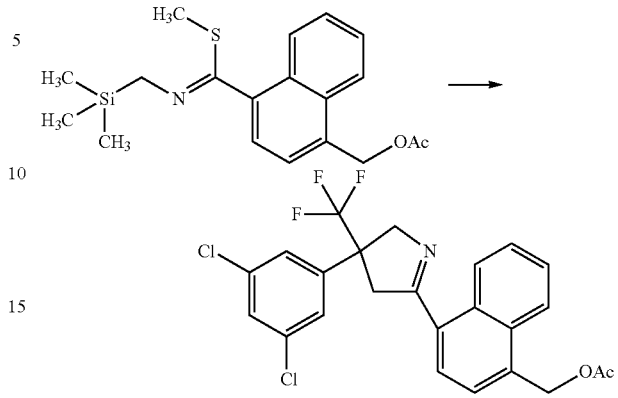

Under argon atmosphere, a mixed solution of {4-[(Z)-(methylsulfanyl){[(trimethylsilyl)methyl]imino}methyl]naphthalen-1-yl}methyl acetae (1.0 g) and 1,3-dichloro-5-(3,3,3-trifluoroprop-1-en-2-yl)benzene (0.77 g) in THF was cooled to −5° C. to be stirred, and a solution of tetrabutylammonium fluoride (0.27 mL of 1.0 M in THF) was added thereto gradually. The reaction mixture was stirred for 20 hours at room temperature. The reaction mixture was diluted with t-butyl methyl ether and washed with water and a saturated aqueous brine, subsequently dried over magnesium sulfate. After filtering the reaction mixture, the solvent was distilled off under reduced pressure, and the resulting mixture was purified by silica gel chromatography, to obtain {4-[3-(3,4,5-trichlorophenyl)-3-(trifluoromethyl)-3,4-dihydro-2H-pyrrol-5-yl]naphthalen-1-yl}methyl acetate (0.66 g).

1H-NMR (CDCl3) δ: 2.13 (3H, s), 3.63 (1H, d), 3.85-3.91 (1H, m), 4.59 (1H, d), 5.04-5.10 (1H, m), 5.60 (2H, s), 7.59-7.64 (4H, m), 8.05-8.07 (1H, m), 8.91-8.94 (1H, m)

Step 7: Synthesis of {-4-[3-(3,5-dichlorophenyl)-3-(trifluoromethyl)-3,4-dihydro-2H-pyrrol-5-yl]naphthalen-1-yl}methanol

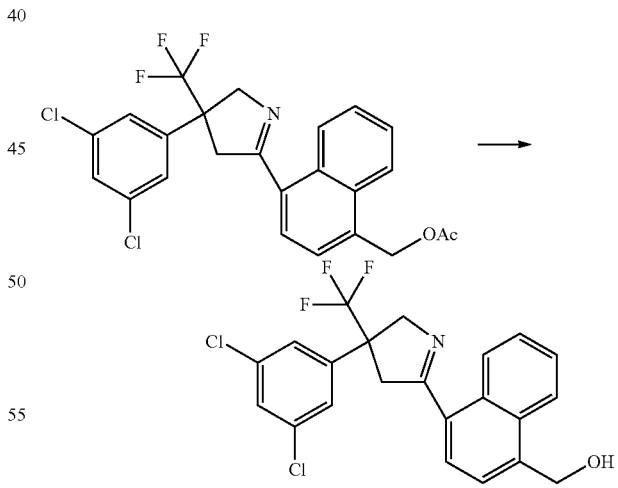

To a solution of {4-[3-(3,4,5-trichlorophenyl)-3-(trifluoromethyl)-3,4-dihydro-2H-pyrrol-5-yl]naphthalen-1-yl}methyl acetate (0.66 g) in methanol (5 ml) was added sodium methoxide (76 mg) at room temperature. The mixture was stirred for 3 hours and concentrated under reduced pressure, and then added water. The mixture was extracted with ethyl acetate, and the organic layer was dried over magnesium sulfate. After filtering the reaction mixture, the solvent was distilled off under reduced pressure, to obtain the desired compound as crude product (0.6 g).

1H-NMR (CDCl3) δ: 1.58 (1H, br s), 3.63 (1H, d), 3.89 (1H, d), 4.58 (1H, d), 5.07 (1H, d), 5.17 (2H, s), 7.4-4 (2H, s), 7.50-7.70 (4H, m). 8.06-8.09 (1H, m), 8.88-8.91 (1H, m).

Step 8: Synthesis of {4-[3-(3,5-dichlorophenyl)-3-(trifluoromethyl)-3,4-dihydro-2H-pyrrol-5-yl]naphthalen-1-yl}methyl methanesulfonate

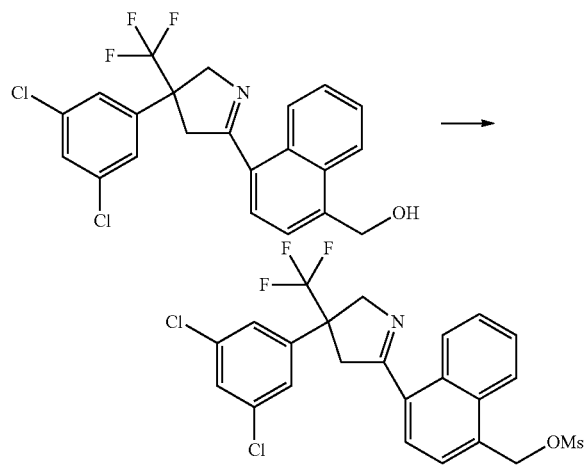

{4-[3-(3,5-dichlorophenyl)-3-(trifluoromethyl)-3,4-dihydro-2H-pyrrol-5-yl]naphthalen-1-yl}methanol (0.6 g) and triethylamine (0.35 g) were dissolved in THF (5 ml), and methanesulfonyl chloride (0.15 ml) was added gradually. The mixture was stirred for 1 hour, and then added water. The mixture was extracted with ethyl acetate, and the organic layer was dried over magnesium sulfate. After filtering the reaction mixture, the solvent was distilled off under reduced pressure, to obtain the desired compound as crude product (0.7 g).

1H-NMR (CDCl3) δ: 2.88 (3H, s), 3.64 (1H, d), 3.88 (1H, d), 4.60 (1H, d), 5.08 (1H, d), 5.74 (2H, s), 7.44 (2H, s), 7.62-7.72 (4H, m), 8.09-8.18 (1H, m), 8.86-8.93 (1H, m).

Step 9: Synthesis of 1-{4-[3-(3,5-dichlorophenyl)-3-(trifluoromethyl)-3,4-dihydro-2H-pyrrol-5-yl]naphthalen-1-yl}methanamine (No. 11-18)

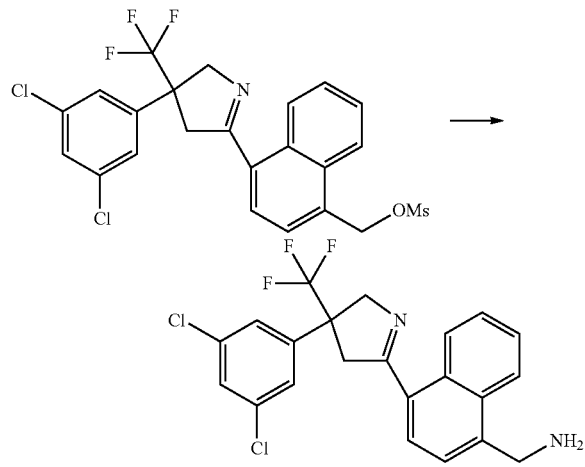

{4-[3-(3,5-dichlorophenyl)-3-(trifluoromethyl)-3,4-dihydro-2H-pyrrol-5-yl]naphthalen-1-yl}methyl methanesulfonate (0.7 g) was dissolved in a mixed solvent of THF (20 ml) and methanol (20 ml), and aqueous ammonia solution (28%, 20 ml) was added thereto. The mixture was stirred for 12 hour, and then added water. The mixture was extracted with ethyl acetate, and the organic layer was dried over magnesium sulfate. After filtering the reaction mixture, the solvent was distilled off under reduced pressure, to obtain the desired compound as crude product (0.48 g).

1H-NMR (CDCl3) δ: 1.61 (2H, s), 3.64 (1H, d), 3.90 (1H, d), 4.39 (2H, s), 4.58 (1H, d), 5.07 (H, d), 7.44 (2H, s), 7.52-7.69 (4H, m), 8.09-8.16 (1H, m). 9.00-8.94 (1H, m).

Step 10: Synthesis of N-({4-[3-(3,5-dichlorophenyl)-3-(trifluoromethyl) 3,4-dihydro-2H-pyrrol-5-yl]naphthalen-1-yl}methyl)acetamide

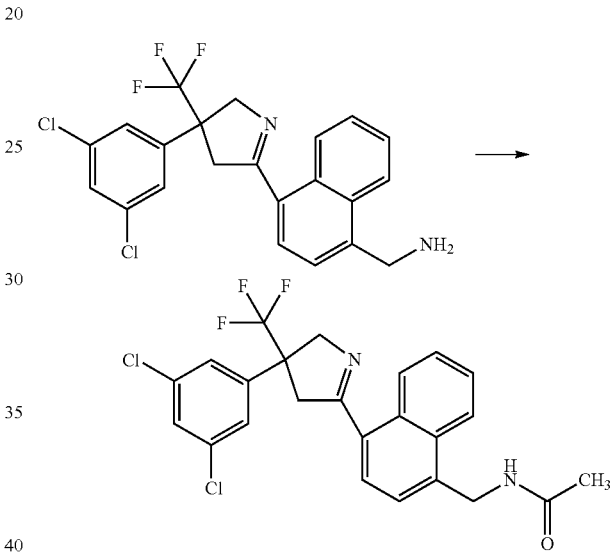

1-{4-[3-(3,5-dichlorophenyl)-3-(trifluoromethyl)-3,4-dihydro-2H-pyrrol-5-yl]naphthalen-1-yl}methanamine (0.1 g) was dissolved in THF (10 ml), and was added acetic anhydride (0.04 g) thereto. The mixture was stirred for 4 hours at room temperature. The mixture was concentrated under reduced pressure to give residual material which was purified by silica gel chromatography, to obtain the desired compound (63 mg) in a yield of 58%.

1H-NMR (CDCl3) δ: 2.04 (3H, s), 3.62 (1H, d), 3.87 (1H, d), 4.59 (1H, d), 4.93 (2H, d), 5.07 (1H, d), 5.70 (1H, br s), 7.53-7.41 (3H, m), 7.70-7.57 (3H, m), 8.15-8.01 (1H, m), 8.99-8.88 (1H, m)

The compounds of the present invention obtained according to the above synthesis examples A to D and the production methods (a) to (g) and (p) are presented in Tables 1, 2 and 11. Moreover, intermediates are presented in Tables 3 to 10 and Tables 12 to 15.

In the Tables 1 to 10 and Tables 12 to 13 and 18, A1 and A4 represent C—H.

In the tables, the abbreviations are as follows. Me: methyl, Et: ethyl, Pr: propyl, Bu: butyl, Ph: phenyl, py: pyridyl, n-Pr: normal-propyl, iso-Pr: isopropyl, tert-Bu: tertiary-butyl, cyc-Pr: cyclopropyl.

TABLE 1

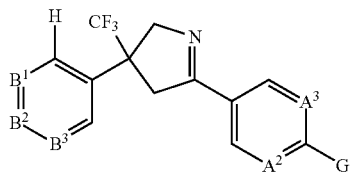

| No. | B$^1$ | B$^2$ | B$^3$ | A$^2$ | A$^3$ | G | (Z)$_k$ |
|---|---|---|---|---|---|---|---|
| 1-1 | C—Cl | C—H | C—Cl | C—H | C—H | G1 | H |
| 1-2 | C—Cl | C—H | C—Cl | C—H | C—H | G2 | H |
| 1-3 | C—Cl | C—H | C—Cl | C—H | C—H | G3 | H |
| 1-4 | C—Cl | C—H | C—Cl | C—H | C—H | G4 | H |
| 1-5 | C—Cl | C—H | C—Cl | C—H | C—H | G5 | H |
| 1-6 | C—Cl | C—H | C—Cl | C—H | C—H | G6 | H |
| 1-7 | C—Cl | C—H | C—Cl | C—H | C—H | G7 | H |
| 1-8 | C—Cl | C—H | C—Cl | C—H | C—H | G8 | H |
| 1-9 | C—Cl | C—H | C—Cl | C—H | C—H | G9 | H |
| 1-10 | C—Cl | C—H | C—Cl | C—H | C—F | G6 | H |
| 1-11 | C—Cl | C—H | C—Cl | C—H | C—F | G8 | H |
| 1-12 | C—Cl | C—H | C—Cl | C—H | C—F | G9 | H |
| 1-13 | C—Cl | C—H | C—Cl | C—H | C—Cl | G6 | H |
| 1-14 | C—Cl | C—H | C—Cl | C—H | C—Cl | G8 | H |
| 1-15 | C—Cl | C—H | C—Cl | C—H | C—Cl | G9 | H |
| 1-16 | C—Cl | C—H | C—Cl | C—H | C—Br | G1 | H |
| 1-17 | C—Cl | C—H | C—Cl | C—H | C—Br | G2 | H |
| 1-18 | C—Cl | C—H | C—Cl | C—H | C—Br | G3 | H |
| 1-19 | C—Cl | C—H | C—Cl | C—H | C—Br | G4 | H |
| 1-20 | C—Cl | C—H | C—Cl | C—H | C—Br | G5 | H |
| 1-21 | C—Cl | C—H | C—Cl | C—H | C—Br | G6 | H |
| 1-22 | C—Cl | C—H | C—Cl | C—H | C—Br | G7 | H |
| 1-23 | C—Cl | C—H | C—Cl | C—H | C—Br | G8 | H |
| 1-24 | C—Cl | C—H | C—Cl | C—H | C—Br | G9 | H |
| 1-25 | C—Cl | C—H | C—Cl | C—H | C—I | G6 | H |
| 1-26 | C—Cl | C—H | C—Cl | C—H | C—I | G8 | H |
| 1-27 | C—Cl | C—H | C—Cl | C—H | C—I | G9 | H |
| 1-28 | C—Cl | C—H | C—Cl | C—H | C—Me | G6 | H |
| 1-29 | C—Cl | C—H | C—Cl | C—H | C—Me | G8 | H |
| 1-30 | C—Cl | C—H | C—Cl | C—H | C—CF$_3$ | G6 | H |
| 1-31 | C—Cl | C—H | C—Cl | C—H | C—CF$_3$ | G8 | H |
| 1-32 | C—Cl | C—H | C—Cl | C—H | C—NO$_2$ | G6 | H |
| 1-33 | C—Cl | C—H | C—Cl | C—H | C—NO$_2$ | G8 | H |
| 1-34 | C—Cl | C—H | C—Cl | C—H | C—CN | G1 | H |
| 1-35 | C—Cl | C—H | C—Cl | C—H | C—CN | G2 | H |
| 1-36 | C—Cl | C—H | C—Cl | C—H | C—CN | G3 | H |
| 1-37 | C—Cl | C—H | C—Cl | C—H | C—CN | G4 | H |
| 1-38 | C—Cl | C—H | C—Cl | C—H | C—CN | G5 | H |
| 1-39 | C—Cl | C—H | C—Cl | C—H | C—CN | G6 | H |
| 1-40 | C—Cl | C—H | C—Cl | C—H | C—CN | G7 | H |
| 1-41 | C—Cl | C—H | C—Cl | C—H | C—CN | G8 | H |
| 1-42 | C—Cl | C—H | C—Cl | C—H | C—CN | G9 | H |
| 1-43 | C—Cl | C—H | C—Cl | C—H | C—NO$_2$ | G6 | H |
| 1-44 | C—Cl | C—H | C—Cl | C—H | C—NO$_2$ | G8 | H |
| 1-45 | C—Cl | C—H | C—Cl | C—H | C—CH$_3$ | G6 | H |
| 1-46 | C—Cl | C—H | C—Cl | C—H | C—OMe | G6 | H |
| 1-47 | C—Cl | C—H | C—Cl | C—H | C—SOMe | G6 | H |
| 1-48 | C—Cl | C—H | C—Cl | C—H | C—SO$_2$Me | G6 | H |
| 1-49 | C—Cl | C—H | C—Cl | C—H | C—SCF$_3$ | G6 | H |
| 1-50 | C—Cl | C—H | C—Cl | C—H | C—S(O)CF$_3$ | G6 | H |
| 1-51 | C—Cl | C—H | C—Cl | C—H | C—S(O)$_2$CF$_3$ | G6 | H |
| 1-52 | C—Cl | C—H | C—Cl | C—H | C—OCH$_3$ | G6 | H |
| 1-53 | C—Cl | C—H | C—Cl | C—H | C—OCF$_3$ | G6 | H |
| 1-54 | C—Cl | C—H | C—Cl | C—H | C—OH | G6 | H |
| 1-55 | C—Cl | C—H | C—Cl | C—H | C—SH | G6 | H |
| 1-56 | C—Cl | C—H | C—Cl | C—H | C—NH$_2$ | G6 | H |
| 1-57 | C—Cl | C—H | C—Cl | C—H | C—NHCOCH$_3$ | G6 | H |
| 1-58 | C—Cl | C—H | C—Cl | C—H | C—NHCO$_2$CH$_3$ | G6 | H |
| 1-59 | C—Cl | C—H | C—Cl | C—H | C—NHCO$_2$—CH$_2$CCl$_3$ | G6 | H |
| 1-60 | C—Cl | C—H | C—Cl | C—H | C—CN | G2 | 3-NO$_2$ |
| 1-61 | C—Cl | C—H | C—Cl | C—H | C—CN | G2 | 3-CN |
| 1-62 | C—Cl | C—H | C—Cl | C—H | C—CN | G6 | 3-NO$_2$ |
| 1-63 | C—Cl | C—H | C—Cl | C—H | C—CN | G6 | 3-CN |
| 1-64 | C—Cl | C—H | C—Cl | C—H | C—CN | G2 | 3-Cl |
| 1-65 | C—Cl | C—H | C—Cl | C—H | C—CN | G2 | 3-Br |
| 1-66 | C—Cl | C—H | C—Cl | C—H | C—CN | G2 | 3-CH$_3$ |
| 1-67 | C—Cl | C—H | C—Cl | C—H | C—CN | G2 | 3-CF$_3$ |
| 1-68 | C—Cl | C—H | C—H | C—H | C—CN | G6 | H |
| 1-69 | C—Cl | C—H | C—H | C—H | C—CN | G8 | H |

TABLE 1-continued

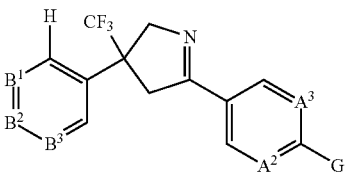

| No. | B¹ | B² | B³ | A² | A³ | G | (Z)$_k$ |
|---|---|---|---|---|---|---|---|
| 1-70 | C—CF$_3$ | C—H | C—H | C—H | C—CN | G6 | H |
| 1-71 | C—CF$_3$ | C—H | C—H | C—H | C—CN | G8 | H |
| 1-72 | C—CF$_3$ | C—H | C—CF$_3$ | C—H | C—CN | G6 | H |
| 1-73 | C—CF$_3$ | C—H | C—CF$_3$ | C—H | C—CN | G8 | H |
| 1-74 | C—NO$_2$ | C—H | C—H | C—H | C—CN | G6 | H |
| 1-75 | C—NO$_2$ | C—H | C—H | C—H | C—CN | G8 | H |
| 1-76 | C—Cl | C—Cl | C—H | C—H | C—CN | G6 | H |
| 1-77 | C—Cl | C—Cl | C—H | C—H | C—CN | G8 | H |
| 1-78 | C—Cl | C—Cl | C—Cl | C—H | C—CN | G6 | H |
| 1-79 | C—Cl | C—Cl | C—Cl | C—H | C—CN | G8 | H |
| 1-80 | C—CH$_3$ | C—H | C—H | C—H | C—CN | G6 | H |
| 1-81 | C—OCH$_3$ | C—H | C—H | C—H | C—CN | G6 | H |
| 1-82 | C—CN | C—H | C—H | C—H | C—CN | G6 | H |
| 1-83 | C—OCF$_3$ | C—H | C—H | C—H | C—CN | G6 | H |
| 1-84 | C—SCH$_3$ | C—H | C—H | C—H | C—CN | G6 | H |
| 1-85 | C—S(O)CH$_3$ | C—H | C—H | C—H | C—CN | G6 | H |
| 1-86 | C—S(O)$_2$CH$_3$ | C—H | C—H | C—H | C—CN | G6 | H |
| 1-87 | C—SCF$_3$ | C—H | C—H | C—H | C—CN | G6 | H |
| 1-88 | C—S(O)CF$_3$ | C—H | C—H | C—H | C—CN | G6 | H |
| 1-89 | C—S(O)$_2$CF$_3$ | C—H | C—H | C—H | C—CN | G6 | H |
| 1-90 | C—OH | C—H | C—H | C—H | C—CN | G6 | H |
| 1-91 | C—SH | C—H | C—H | C—H | C—CN | G6 | H |
| 1-92 | C—Cl | C—H | C—Cl | N | C—Br | G6 | H |
| 1-93 | C—Cl | C—H | C—Cl | N | C—CN | G6 | H |
| 1-94 | C—Br | C—H | C—Br | C—H | C—CN | G6 | H |
| 1-95 | C—Cl | C—H | C—CF$_3$ | C—H | C—CN | G6 | H |
| 1-96 | C—Cl | C—H | C—Cl | N | C—CN | G2 | 4-CN |
| 1-97 | C—Cl | C—H | C—Cl | N | C—CN | G2 | 4-NO2 |
| 1-98 | C—Cl | C—H | C—Cl | N | C—CN | G2 | 4-Cl |
| 1-99 | C—Cl | C—H | C—Cl | N | C—CN | G8 | 5-CH3 |
| 1-100 | C—Cl | C—H | C—Cl | N | C—CN | G9 | 5-CH3 |
| 1-101 | C—Cl | C—H | C—Cl | N | C—CN | G2 | 3-CH3, 5-NH2 |
| 1-102 | C—Cl | C—H | C—Cl | N | C—CN | G2 | 3-CH3, 5-NHCOCH3 |
| 1-103 | C—CH3 | C—NO2 | C—CH3 | C—H | C—CN | G6 | H |

TABLE 2

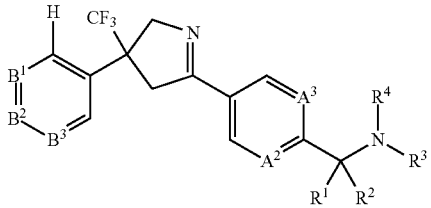

| No. | B¹ | B² | B³ | A² | A³ | R¹ | R² | R⁴ | R³ |
|---|---|---|---|---|---|---|---|---|---|
| 2-1 | C—Cl | C—H | C—Cl | C—H | C—H | H | H | MeCO | H |
| 2-2 | C—Cl | C—H | C—Cl | C—H | C—H | H | H | MeCO | MeCO |
| 2-3 | C—Cl | C—H | C—Cl | C—H | C—H | H | H | MeCO | 2-py-CO |
| 2-4 | C—Cl | C—H | C—Cl | C—H | C—H | H | H | HCO | 2-py-CH$_2$ |
| 2-5 | C—Cl | C—H | C—Cl | C—H | C—H | H | H | MeCO | 2-py-CH$_2$ |
| 2-6 | C—Cl | C—H | C—Cl | C—H | C—H | H | H | EtCO | 2-py-CH$_2$ |
| 2-7 | C—Cl | C—H | C—Cl | C—H | C—H | H | H | Me$_2$NCO | 2-py-CH$_2$ |
| 2-8 | C—Cl | C—H | C—Cl | C—H | C—H | H | H | MeSO$_2$ | 2-py-CH$_2$ |
| 2-9 | C—Cl | C—H | C—Cl | C—H | C—H | H | H | 2-py-CO | 2-py-CH$_2$ |
| 2-10 | C—Cl | C—H | C—Cl | C—H | C—H | CN | H | MeCO | H |
| 2-11 | C—Cl | C—H | C—Cl | C—H | C—H | CN | H | MeCO | 2-py-CH$_2$ |
| 2-12 | C—Cl | C—H | C—Cl | C—H | C—Br | H | H | HCO | H |
| 2-13 | C—Cl | C—H | C—Cl | C—H | C—Br | H | H | MeCO | H |
| 2-14 | C—Cl | C—H | C—Cl | C—H | C—Br | H | H | MeCO | MeCO |
| 2-15 | C—Cl | C—H | C—Cl | C—H | C—Br | H | H | MeCO | 2-py-CH$_2$ |

TABLE 2-continued

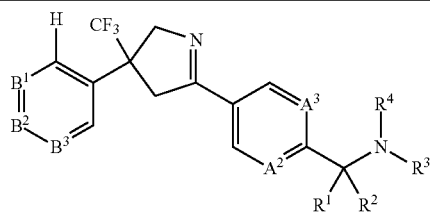

| No. | B¹ | B² | B³ | A² | A³ | R¹ | R² | R⁴ | R³ |
|---|---|---|---|---|---|---|---|---|---|
| 2-16 | C—Cl | C—H | C—Cl | C—H | C—Br | H | H | MeCO | 3-py-CH$_2$ |
| 2-17 | C—Cl | C—H | C—Cl | C—H | C—Br | H | H | MeCO | 4-py-CH$_2$ |
| 2-18 | C—Cl | C—H | C—Cl | C—H | C—Br | H | H | MeCO | Ph—CH$_2$ |
| 2-19 | C—Cl | C—H | C—Cl | C—H | C—Br | H | H | EtCO | H |
| 2-20 | C—Cl | C—H | C—Cl | C—H | C—Br | H | H | n-PrCO | H |
| 2-21 | C—Cl | C—H | C—Cl | C—H | C—Br | H | H | iso-PrCO | H |
| 2-22 | C—Cl | C—H | C—Cl | C—H | C—Br | H | H | tert-BuCO | H |
| 2-23 | C—Cl | C—H | C—Cl | C—H | C—Br | H | H | CF$_3$CO | H |
| 2-24 | C—Cl | C—H | C—Cl | C—H | C—Br | H | H | PhCO | H |
| 2-25 | C—Cl | C—H | C—Cl | C—H | C—Br | H | H | 2-py-CO | H |
| 2-26 | C—Cl | C—H | C—Cl | C—H | C—Br | H | H | 3-py-CO | H |
| 2-27 | C—Cl | C—H | C—Cl | C—H | C—Br | H | H | 4-py-CO | H |
| 2-28 | C—Cl | C—H | C—Cl | C—H | C—Br | H | H | 2-F-PhCO | H |
| 2-29 | C—Cl | C—H | C—Cl | C—H | C—Br | H | H | 3-F-PhCO | H |
| 2-30 | C—Cl | C—H | C—Cl | C—H | C—Br | H | H | 4-F-PhCO | H |
| 2-31 | C—Cl | C—H | C—Cl | C—H | C—Br | H | H | 2-Cl—PhCO | H |
| 2-32 | C—Cl | C—H | C—Cl | C—H | C—Br | H | H | 4-Cl—PhCO | H |
| 2-33 | C—Cl | C—H | C—Cl | C—H | C—Br | H | H | 3-Cl—PhCO | H |
| 2-34 | C—Cl | C—H | C—Cl | C—H | C—Br | H | H | 2-Br—PhCO | H |
| 2-35 | C—Cl | C—H | C—Cl | C—H | C—Br | H | H | 2-Me—PhCO | H |
| 2-36 | C—Cl | C—H | C—Cl | C—H | C—Br | H | H | CH$_2$=CH—CO | H |
| 2-37 | C—Cl | C—H | C—Cl | C—H | C—Br | H | H | HC≡C—CO | H |
| 2-38 | C—Cl | C—H | C—Cl | C—H | C—Br | H | H | MeSO$_2$ | H |
| 2-39 | C—Cl | C—H | C—Cl | C—H | C—Br | H | H | CF$_3$SO$_2$ | H |
| 2-40 | C—Cl | C—H | C—Cl | C—H | C—Br | H | H | MeNHCO | H |
| 2-41 | C—Cl | C—H | C—Cl | C—H | C—Br | H | H | Me$_2$NCO | H |
| 2-42 | C—Cl | C—H | C—Cl | C—H | C—Br | H | H | MeOC(=O) | H |
| 2-43 | C—Cl | C—H | C—Cl | C—H | C—Br | H | H | MeSC(=O) | H |
| 2-44 | C—Cl | C—H | C—Cl | C—H | C—Br | H | H | MeCS | H |
| 2-45 | C—Cl | C—H | C—Cl | C—H | C—Br | H | H | MeON(Me)CO | H |
| 2-46 | C—Cl | C—H | C—Cl | C—H | C—Br | H | H | MeCO | Me |
| 2-47 | C—Cl | C—H | C—Cl | C—H | C—Br | H | H | MeCO | Et |
| 2-48 | C—Cl | C—H | C—Cl | C—H | C—Br | H | H | MeCO | CH$_2$=CH— |
| 2-49 | C—Cl | C—H | C—Cl | C—H | C—Br | H | H | MeCO | HC≡C—CH$_2$— |
| 2-50 | C—Cl | C—H | C—Cl | C—H | C—Br | H | H | MeCO | PhCH$_2$ |
| 2-51 | C—Cl | C—H | C—Cl | C—H | C—Br | H | H | MeCO | CN |
| 2-52 | C—Cl | C—H | C—Cl | C—H | C—Br | H | H | MeCO | CH$_2$CF$_3$ |
| 2-53 | C—Cl | C—H | C—Cl | C—H | C—Br | H | H | MeCO | cyc-Pr |
| 2-54 | C—Cl | C—H | C—Cl | C—H | C—Br | H | H | —C(O)CH$_2$CH$_2$CH$_2$— | |
| 2-55 | C—Cl | C—H | C—Cl | C—H | C—Br | H | H | —CO—NMe—N=N— | |
| 2-56 | C—Cl | C—H | C—Cl | C—H | C—Br | H | H | —C(=N—NO$_2$)—NH—CH$_2$—CH$_2$— | |
| 2-57 | C—Cl | C—H | C—Cl | C—H | C—F | H | H | MeCO | H |
| 2-58 | C—Cl | C—H | C—Cl | C—H | C—Cl | H | H | MeCO | H |
| 2-59 | C—Cl | C—H | C—Cl | C—H | C—I | H | H | MeCO | H |
| 2-60 | C—Cl | C—H | C—Cl | C—H | C—NO$_2$ | H | H | MeCO | H |
| 2-61 | C—Cl | C—H | C—Cl | C—H | C—CN | H | H | MeCO | 2-py-CH$_2$ |
| 2-62 | C—Cl | C—H | C—Cl | C—H | C—CN | H | H | MeCO | H |
| 2-63 | C—Cl | C—H | C—Cl | C—H | C—Me | H | H | MeCO | H |
| 2-64 | C—Cl | C—H | C—Cl | C—H | C—Me | H | H | MeCO | 2-py-CH$_2$ |
| 2-65 | C—Cl | C—H | C—Cl | C—H | C—SMe | H | H | MeCO | H |
| 2-66 | C—Cl | C—H | C—Cl | C—H | C—S(O)Me | H | H | MeCO | H |
| 2-67 | C—Cl | C—H | C—Cl | C—H | C—S(O)$_2$Me | H | H | MeCO | H |
| 2-68 | C—Cl | C—H | C—Cl | C—H | C—SCF$_3$ | H | H | MeCO | H |
| 2-69 | C—Cl | C—H | C—Cl | C—H | C—S(O)CF$_3$ | H | H | MeCO | H |
| 2-70 | C—Cl | C—H | C—Cl | C—H | C—S(O)$_2$CF$_3$ | H | H | MeCO | H |
| 2-71 | C—Cl | C—H | C—Cl | C—H | C—OCH$_3$ | H | H | MeCO | H |
| 2-72 | C—Cl | C—H | C—Cl | C—H | C—OCF$_3$ | H | H | MeCO | H |
| 2-73 | C—Cl | C—H | C—Cl | C—H | C—OH | H | H | MeCO | H |
| 2-74 | C—Cl | C—H | C—Cl | C—H | C—SH | H | H | MeCO | H |
| 2-75 | C—Cl | C—H | C—Cl | C—H | C—NH$_2$ | H | H | MeCO | H |
| 2-76 | C—Cl | C—H | C—Cl | C—H | C—NHCOCH$_3$ | H | H | MeCO | H |
| 2-77 | C—Cl | C—H | C—Cl | C—H | C—NHCO$_2$CH$_3$ | H | H | MeCO | H |
| 2-78 | C—Cl | C—H | C—Cl | C—H | C—NHCO$_2$CH2CCl$_3$ | H | H | MeCO | H |
| 2-79 | C—Cl | C—H | C—Cl | C—H | C—Br | Me | H | MeCO | H |
| 2-80 | C—Cl | C—H | C—Cl | C—H | C—Br | Me | Me | MeCO | H |

TABLE 2-continued

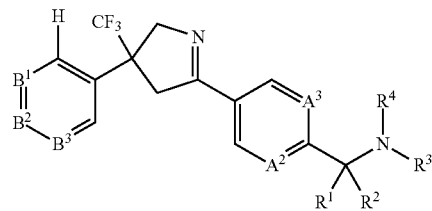

| No. | B¹ | B² | B³ | A² | A³ | R¹ | R² | R⁴ | R³ |
|---|---|---|---|---|---|---|---|---|---|
| 2-81 | C—Cl | C—H | C—Cl | C—H | C—H | cyc-Pr | H | MeCO | H |
| 2-82 | C—Cl | C—H | C—Cl | C—H | C—H | CF₃ | H | MeCO | H |
| 2-83 | C—Cl | C—H | C—Cl | C—H | C—H | CO₂Me | H | MeCO | H |
| 2-84 | C—Cl | C—H | C—Cl | C—H | C—H | CH₂=CH | H | MeCO | H |
| 2-85 | C—Cl | C—H | C—Cl | C—H | C—H | HC≡C | H | MeCO | H |
| 2-86 | C—Cl | C—H | C—Cl | C—H | C—H | —CH₂CH₂— | | MeCO | H |
| 2-87 | C—Cl | C—H | C—Cl | C—H | C—H | H | H | MeCO | H |
| 2-88 | C—Cl | C—H | C—Cl | C—H | C—H | H | H | MeCO | NH₂ |
| 2-89 | C—Cl | C—H | C—Cl | C—H | C—H | H | H | MeCO | —NHCOMe |
| 2-90 | C—Cl | C—H | C—Cl | C—H | C—Br | H | H | MeCO | —N=CMe₂ |
| 2-91 | C—Cl | C—H | C—Cl | C—H | C—H | H | H | MeCO | OH |
| 2-92 | C—Cl | C—H | C—Cl | C—H | C—H | H | H | MeCO | OMe |
| 2-93 | C—Cl | C—H | C—Cl | C—H | C—Br | H | H | MeCO | H |
| 2-94 | C—Cl | C—Cl | C—H | C—H | C—Br | H | H | MeCO | H |
| 2-95 | C—Cl | C—Cl | C—Cl | C—H | C—Br | H | H | MeCO | H |
| 2-96 | C—Cl | C—Me | C—Cl | C—H | C—Br | H | H | MeCO | H |
| 2-97 | C—F | C—F | C—F | C—H | C—Br | H | H | MeCO | H |
| 2-98 | C—Br | C—Br | C—Br | C—H | C—Br | H | H | MeCO | H |
| 2-99 | C—Cl | C—CF₃ | C—Cl | C—H | C—Br | H | H | MeCO | H |
| 2-100 | C—Cl | C—Cl | C—CF₃ | C—H | C—Br | H | H | MeCO | H |
| 2-101 | C—Cl | C—Br | C—Cl | C—H | C—Br | H | H | MeCO | H |
| 2-102 | C—Br | C—Cl | C—Br | C—H | C—Br | H | H | MeCO | H |
| 2-103 | C—Cl | C—NH₂ | C—Cl | C—H | C—Br | H | H | MeCO | H |
| 2-104 | C—Br | C—NH₂ | C—Br | C—H | C—Br | H | H | MeCO | H |
| 2-105 | C—F | C—F | C—F | C—H | C—Br | H | H | EtCO | H |
| 2-106 | C—Br | C—Br | C—Br | C—H | C—Br | H | H | EtCO | H |
| 2-107 | C—Cl | C—CF₃ | C—Cl | C—H | C—Br | H | H | EtCO | H |
| 2-108 | C—Cl | C—Cl | C—CF₃ | C—H | C—Br | H | H | EtCO | H |
| 2-109 | C—Cl | C—Br | C—Cl | C—H | C—Br | H | H | EtCO | H |
| 2-110 | C—Br | C—Cl | C—Br | C—H | C—Br | H | H | EtCO | H |
| 2-111 | C—Cl | C—NH₂ | C—Cl | C—H | C—Br | H | H | EtCO | H |
| 2-112 | C—Br | C—NH₂ | C—Br | C—H | C—Br | H | H | EtCO | H |
| 2-113 | C—F | C—H | C—H | C—H | C—Br | H | H | MeCO | H |
| 2-114 | C—Cl | C—H | C—H | C—H | C—Br | H | H | MeCO | H |
| 2-115 | C—CF₃ | C—H | C—H | C—H | C—Br | H | H | MeCO | H |
| 2-116 | C—H | C—CF₃ | C—H | C—H | C—Br | H | H | MeCO | H |
| 2-117 | C—CF₃ | C—H | C—CF₃ | C—H | C—Br | H | H | MeCO | H |
| 2-118 | C—NO₂ | C—H | C—H | C—H | C—Br | H | H | MeCO | H |
| 2-119 | C—Cl | C—H | C—Cl | N | C—H | H | H | MeCO | H |
| 2-120 | C—CH₃ | C—H | C—H | C—H | C—H | H | H | MeCO | H |
| 2-121 | C—OCH₃ | C—H | C—H | C—H | C—H | H | H | MeCO | H |
| 2-122 | C—CN | C—H | C—H | C—H | C—Br | H | H | MeCO | H |
| 2-123 | C—OCF₃ | C—H | C—H | C—H | C—H | H | H | MeCO | H |
| 2-124 | C—SCH₃ | C—H | C—H | C—H | C—H | H | H | MeCO | H |
| 2-125 | C—S(O)CH₃ | C—H | C—H | C—H | C—H | H | H | MeCO | H |
| 2-126 | C—S(O)₂CH₃ | C—H | C—H | C—H | C—H | H | H | MeCO | H |
| 2-127 | C—SCF₃ | C—H | C—H | C—H | C—H | H | H | MeCO | H |
| 2-128 | C—S(O)CF₃ | C—H | C—H | C—H | C—H | H | H | MeCO | H |
| 2-129 | C=S(O)₂CF₃ | C—H | C—H | C—H | C—H | H | H | MeCO | H |
| 2-130 | C—OH | C—H | C—H | C—H | C—H | H | H | MeCO | H |
| 2-131 | C—SH | C—H | C—H | C—H | C—H | H | H | MeCO | H |
| 2-132 | C—Cl | C—H | C—Cl | C—H | C—Br | H | H | MeCO | H |
| 2-133 | C—Cl | C—Cl | C—H | C—H | C—Br | H | H | MeCO | H |
| 2-134 | C—Cl | C—Cl | C—Cl | C—H | C—Br | H | H | MeCO | H |
| 2-135 | C—Cl | C—Me | C—Cl | C—H | C—Br | H | H | MeCO | H |
| 2-136 | C—F | C—F | C—F | C—H | C—Br | H | H | MeCO | H |
| 2-137 | C—Br | C—Br | C—Br | C—H | C—Br | H | H | MeCO | H |
| 2-138 | C—Cl | C—CF₃ | C—Cl | C—H | C—Br | H | H | MeCO | H |
| 2-139 | C—Cl | C—Cl | C—CF₃ | C—H | C—Br | H | H | MeCO | H |
| 2-140 | C—Cl | C—Br | C—Br | C—H | C—Br | H | H | MeCO | H |
| 2-141 | C—Br | C—Cl | C—Cl | C—H | C—Br | H | H | MeCO | H |
| 2-142 | C—Cl | C—NH₂ | C—NH₂ | C—H | C—Br | H | H | MeCO | H |
| 2-143 | C—Br | C—NH₂ | C—NH₂ | C—H | C—Br | H | H | MeCO | H |
| 2-144 | C—F | C—F | C—F | C—H | C—Br | H | H | EtCO | H |
| 2-145 | C—Br | C—Br | C—Br | C—H | C—Br | H | H | EtCO | H |

TABLE 2-continued

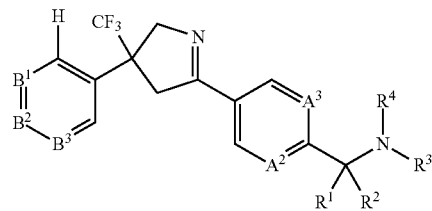

| No. | B¹ | B² | B³ | A² | A³ | R¹ | R² | R⁴ | R³ |
|---|---|---|---|---|---|---|---|---|---|
| 2-146 | C—Cl | C—CF₃ | C—Cl | C—H | C—Br | H | H | EtCO | H |
| 2-147 | C—Cl | C—Cl | C—CF₃ | C—H | C—Br | H | H | EtCO | H |
| 2-148 | C—Cl | C—Br | C—Cl | C—H | C—Br | H | H | EtCO | H |
| 2-149 | C—Br | C—Cl | C—Br | C—H | C—Br | H | H | EtCO | H |
| 2-150 | C—Cl | C—NH₂ | C—Cl | C—H | C—Br | H | H | EtCO | H |
| 2-151 | C—Br | C—NH₂ | C—Br | C—H | C—Br | H | H | EtCO | H |
| 2-152 | C—F | C—H | C—H | C—H | C—Br | H | H | MeCO | H |
| 2-153 | C—Cl | C—H | C—Cl | C—H | C—Br | H | H | cyc-PrCO | H |
| 2-154 | C—Cl | C—H | C—Cl | C—H | C—Br | H | H | CF₃CH₂CO | H |
| 2-155 | C—Cl | C—Cl | C—Cl | C—H | C—Cl | H | H | HCO | H |
| 2-156 | C—Cl | C—Cl | C—Cl | C—H | C—Cl | H | H | MeCO | H |
| 2-157 | C—Cl | C—Cl | C—Cl | C—H | C—Cl | H | H | EtCO | H |
| 2-158 | C—Cl | C—Cl | C—Cl | C—H | C—Cl | H | H | cyc-PrCO | H |
| 2-159 | C—Cl | C—Cl | C—Cl | C—H | C—Cl | H | H | CF₃CH₂CO | H |
| 2-160 | C—Cl | C—H | C—Cl | C—H | C—CF₃ | H | H | MeCO | H |
| 2-161 | C—Cl | C—Cl | C—Cl | C—H | C—CF₃ | H | H | MeCO | H |
| 2-162 | C—Cl | C—Cl | C—Cl | C—H | C—CF₃ | H | H | EtCO | H |
| 2-163 | C—Cl | C—Cl | C—Cl | C—H | C—CF₃ | H | H | c-PrCO | H |
| 2-164 | C—Cl | C—Cl | C—Cl | C—H | C—CF₃ | H | H | CF₃CH₂CO | H |
| 2-165 | C—CF₃ | C—H | C—CF₃ | C—H | C—CF₃ | H | H | MeCO | H |
| 2-166 | C—CF₃ | C—H | C—CF₃ | C—H | C—CF₃ | H | H | EtCO | H |
| 2-167 | C—CF₃ | C—H | C—CF₃ | C—H | C—CF₃ | H | H | cyc-PrCO | H |
| 2-168 | C—CF₃ | C—H | C—CF₃ | C—H | C—CF₃ | H | H | CF₃CH₂CO | H |
| 2-169 | C—Cl | C—Cl | C—Cl | C—H | C—Br | H | H | EtCO | H |
| 2-170 | C—Cl | C—Cl | C—Cl | C—H | C—Br | H | H | cyc-PrCO | H |
| 2-171 | C—Cl | C—Cl | C—Cl | C—H | C—Br | H | H | CF₃CH₂CO | H |
| 2-172 | C—Cl | C—Cl | C—CF₃ | C—H | C—Br | H | H | cyc-PrCO | H |
| 2-173 | C—Cl | C—Cl | C—CF₃ | C—H | C—Br | H | H | CF₃CH₂CO | H |
| 2-174 | C—Br | C—H | C—Br | C—H | C—Br | H | H | MeCO | H |
| 2-175 | C—Br | C—H | C—Br | C—H | C—Br | H | H | EtCO | H |
| 2-176 | C—Br | C—H | C—Br | C—H | C—Br | H | H | cyc-PrCO | H |
| 2-177 | C—Br | C—H | C—Br | C—H | C—Br | H | H | CF₃CH₂CO | H |
| 2-178 | C—CF3 | C—H | C—CF3 | C—H | C—Br | H | H | EtCO | H |
| 2-179 | C—CF3 | C—H | C—CF3 | C—H | C—Br | H | H | cyc-PrCO | H |
| 2-180 | C—CF3 | C—H | C—CF3 | C—H | C—Br | H | H | CF₃CH₂CO | H |
| 2-181 | C—Cl | C—H | C—Cl | C—H | C—CN | H | H | EtCO | H |
| 2-182 | C—Cl | C—H | C—Cl | C—H | C—CN | H | H | cyc-PrCO | H |
| 2-183 | C—Cl | C—H | C—Cl | C—H | C—CN | H | H | CF₃CH₂CO | H |
| 2-184 | C—Br | C—H | C—Br | C—H | C—CN | H | H | MeCO | H |
| 2-185 | C—Br | C—H | C—Br | C—H | C—CN | H | H | CF₃CH₂CO | H |
| 2-186 | C—CF₃ | C—H | C—CF₃ | C—H | C—CN | H | H | MeCO | H |
| 2-187 | C—CF₃ | C—H | C—CF₃ | C—H | C—CN | H | H | EtCO | H |
| 2-188 | C—CF₃ | C—H | C—CF₃ | C—H | C—CN | H | H | cyc-PrCO | H |
| 2-189 | C—CF₃ | C—H | C—CF₃ | C—H | C—CN | H | H | CF₃CH₂CO | H |
| 2-190 | C—Cl | C—Cl | C—Cl | C—H | C—CN | H | H | MeCO | H |
| 2-191 | C—Cl | C—Cl | C—Cl | C—H | C—CN | H | H | EtCO | H |
| 2-192 | C—Cl | C—Cl | C—Cl | C—H | C—CN | H | H | cyc-PrCO | H |
| 2-193 | C—Cl | C—Cl | C—Cl | C—H | C—CN | H | H | CF₃CH₂CO | H |
| 2-194 | C—Cl | C—Cl | C—Cl | C—H | C—Br | H | H | H | H |
| 2-195 | C—Cl | C—Cl | C—Cl | C—H | C—Br | H | H | EtNHCO | H |
| 2-196 | C—Cl | C—Cl | C—Cl | C—H | C—Br | H | H | n-PrNHCO | H |
| 2-197 | C—Cl | C—Cl | C—Cl | C—H | C—CF3 | H | H | tert-BuOCO | H |
| 2-198 | C—CF3 | C—Cl | C—CF3 | C—H | C—CF3 | H | H | tert-BuOCO | H |
| 2-199 | C—Cl | C—Cl | C—Cl | C—H | C—Cl | H | H | EtNHCO | H |
| 2-200 | C—CF3 | C—H | C—CF3 | C—H | C—CF3 | H | H | EtNHCO | H |
| 2-201 | C—Cl | C—Cl | C—Cl | C—H | C—CF3 | H | H | EtNHCO | H |
| 2-202 | C—Cl | C—Cl | C—Cl | C—H | C—Br | H | H | tert-BuOCO | H |
| 2-203 | C—Cl | C—Cl | C—Cl | C—H | C—Br | H | H | CF3CO | H |
| 2-204 | C—Cl | C—Cl | C—CF3 | C—H | C—CF3 | H | H | CH3CO | H |
| 2-205 | C—Cl | C—Cl | C—CF3 | C—H | C—CF3 | H | H | EtCO | H |
| 2-206 | C—Cl | C—Cl | C—CF3 | C—H | C—CF3 | H | H | CF₃CH₂CO | H |
| 2-207 | C—Cl | C—Cl | C—CF3 | C—H | C—CF3 | H | H | cyclo-PrCO | H |
| 2-208 | C—Cl | C—Cl | C—CF3 | C—H | C—CF3 | H | H | EtNHCO | H |
| 2-209 | C—Cl | C—Cl | C—Cl | C—H | C—CF3 | H | H | CH3SCH₂CO | H |
| 2-210 | C—Cl | C—H | C—Cl | C—H | C—CF₃ | H | H | EtCO | H |

TABLE 2-continued

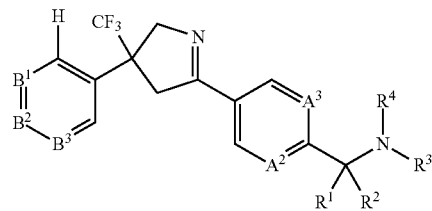

| No. | $B^1$ | $B^2$ | $B^3$ | $A^2$ | $A^3$ | $R^1$ | $R^2$ | $R^4$ | $R^3$ |
|---|---|---|---|---|---|---|---|---|---|
| 2-211 | C—Cl | C—H | C—Cl | C—H | C—CF$_3$ | H | H | CF3CH2CO | H |
| 2-212 | C—Cl | C—H | C—Cl | C—H | C—CF$_3$ | H | H | cyclo-PrCO | H |
| 2-213 | C—Cl | C—H | C—Cl | C—H | C—CF$_3$ | H | H | EtNHCO | H |
| 2-214 | C—Cl | C—H | C—Cl | C—H | C—CF$_3$ | H | H | CH3SCH2CO | H |
| 2-215 | C—Cl | C—H | C—Cl | C—H | C—CF$_3$ | H | H | CH3SOCH2CO | H |
| 2-216 | C—Cl | C—H | C—Cl | C—H | C—CF$_3$ | H | H | CH3SO2CH2CO | H |
| 2-217 | C—Cl | C—Cl | C—Cl | C—H | C—CF$_3$ | H | H | CH3SOCH2CO | H |
| 2-218 | C—Cl | C—Cl | C—Cl | C—H | C—CF$_3$ | H | H | CH3SO2CH2CO | H |
| 2-219 | C—Cl | C—Cl | C—Cl | C—H | C—Me | H | H | MeCO | H |
| 2-220 | C—Cl | C—Cl | C—Cl | C—H | C—Me | H | H | EtCO | H |
| 2-221 | C—Cl | C—Cl | C—Cl | C—H | C—Me | H | H | CF3CH2CO | H |
| 2-222 | C—Cl | C—Cl | C—Cl | C—H | C—Me | H | H | cyclo-PrCO | H |
| 2-223 | C—Cl | C—Cl | C—Cl | C—H | C—Me | H | H | EtNHCO | H |
| 2-224 | C—Cl | C—Cl | C—Cl | C—H | C—Me | H | H | CH3SCH2CO | H |
| 2-225 | C—Cl | C—Cl | C—Cl | C—H | C—Me | H | H | CH3SOCH2CO | H |
| 2-226 | C—CF3 | C—H | C—CF3 | C—H | C—Me | H | H | MeCO | H |
| 2-227 | C—CF3 | C—H | C—CF3 | C—H | C—Me | H | H | EtCO | H |
| 2-228 | C—CF3 | C—H | C—CF3 | C—H | C—Me | H | H | CF3CH2CO | H |
| 2-229 | C—CF3 | C—H | C—CF3 | C—H | C—Me | H | H | cyclo-PrCO | H |
| 2-230 | C—CF3 | C—H | C—CF3 | C—H | C—Me | H | H | EtNHCO | H |
| 2-231 | C—CF3 | C—H | C—CF3 | C—H | C—Me | H | H | CH3SCH2CO | H |
| 2-232 | C—CF3 | C—H | C—CF3 | C—H | C—Me | H | H | CH3SOCH2CO | H |
| 2-233 | C—CF3 | C—H | C—CF3 | C—H | C—Me | H | H | CH3SO2CH2CO | H |
| 2-234 | C—Cl | C—Cl | C—Cl | C—H | C—NO$_2$ | H | H | MeCO | H |
| 2-235 | C—Cl | C—Cl | C—Cl | C—H | C—NO$_2$ | H | H | EtCO | H |
| 2-236 | C—Cl | C—Cl | C—Cl | C—H | C—NO$_2$ | H | H | CF3CH2CO | H |
| 2-237 | C—Cl | C—Cl | C—Cl | C—H | C—NO$_2$ | H | H | cyclo-PrCO | H |
| 2-238 | C—Cl | C—Cl | C—Cl | C—H | C—NO$_2$ | H | H | EtNHCO | H |
| 2-239 | C—Cl | C—Cl | C—Cl | C—H | C—NO$_2$ | H | H | CH3SCH2CO | H |
| 2-240 | C—Cl | C—Cl | C—Cl | C—H | C—NO$_2$ | H | H | CH3SOCH2CO | H |
| 2-241 | C—CF3 | C—H | C—CF3 | C—H | C—NO$_2$ | H | H | MeCO | H |
| 2-242 | C—CF3 | C—H | C—CF3 | C—H | C—NO$_2$ | H | H | EtCO | H |
| 2-243 | C—CF3 | C—H | C—CF3 | C—H | C—NO$_2$ | H | H | CF3CH2CO | H |
| 2-244 | C—CF3 | C—H | C—CF3 | C—H | C—NO$_2$ | H | H | cyclo-PrCO | H |
| 2-245 | C—CF3 | C—H | C—CF3 | C—H | C—NO$_2$ | H | H | EtNHCO | H |
| 2-246 | C—CF3 | C—H | C—CF3 | C—H | C—NO$_2$ | H | H | CH3SCH2CO | H |
| 2-247 | C—CF3 | C—H | C—CF3 | C—H | C—NO$_2$ | H | H | CH3SOCH2CO | H |
| 2-248 | C—CF3 | C—H | C—CF3 | C—H | C—NO$_2$ | H | H | CH3SO2CH2CO | H |
| 2-249 | C—Cl | C—Cl | C—Cl | C—H | C—F | H | H | MeCO | H |
| 2-250 | C—Cl | C—Cl | C—Cl | C—H | C—F | H | H | EtCO | H |
| 2-251 | C—Cl | C—Cl | C—Cl | C—H | C—F | H | H | CF3CH2CO | H |
| 2-252 | C—Cl | C—Cl | C—Cl | C—H | C—F | H | H | cyclo-PrCO | H |
| 2-253 | C—Cl | C—Cl | C—Cl | C—H | C—F | H | H | EtNHCO | H |
| 2-254 | C—Cl | C—Cl | C—Cl | C—H | C—F | H | H | CH3SCH2CO | H |
| 2-255 | C—Cl | C—Cl | C—Cl | C—H | C—F | H | H | CH3SOCH2CO | H |
| 2-256 | C—CF3 | C—H | C—CF3 | C—H | C—F | H | H | MeCO | H |
| 2-257 | C—CF3 | C—H | C—CF3 | C—H | C—F | H | H | EtCO | H |
| 2-258 | C—CF3 | C—H | C—CF3 | C—H | C—F | H | H | CF3CH2CO | H |
| 2-259 | C—CF3 | C—H | C—CF3 | C—H | C—F | H | H | cyclo-PrCO | H |
| 2-260 | C—CF3 | C—H | C—CF3 | C—H | C—F | H | H | EtNHCO | H |
| 2-261 | C—CF3 | C—H | C—CF3 | C—H | C—F | H | H | CH3SCH2CO | H |
| 2-262 | C—CF3 | C—H | C—CF3 | C—H | C—F | H | H | CH3SOCH2CO | H |
| 2-263 | C—CF3 | C—H | C—CF3 | C—H | C—F | H | H | CH3SO2CH2CO | H |
| 2-264 | C—Cl | C—Cl | C—Cl | C—H | C—Cl | H | H | CH3SCH2CO | H |
| 2-265 | C—Cl | C—Cl | C—Cl | C—H | C—Cl | H | H | CH3SOCH2CO | H |
| 2-266 | C—Cl | C—Cl | C—Cl | C—H | C—Cl | H | H | CH3SO2CH2CO | H |
| 2-267 | C—CF3 | C—H | C—CF3 | C—H | C—Cl | H | H | MeCO | H |
| 2-268 | C—CF3 | C—H | C—CF3 | C—H | C—Cl | H | H | EtCO | H |
| 2-269 | C—CF3 | C—H | C—CF3 | C—H | C—Cl | H | H | CF3CH2CO | H |
| 2-270 | C—CF3 | C—H | C—CF3 | C—H | C—Cl | H | H | cyclo-PrCO | H |
| 2-271 | C—CF3 | C—H | C—CF3 | C—H | C—Cl | H | H | EtNHCO | H |
| 2-272 | C—CF3 | C—H | C—CF3 | C—H | C—Cl | H | H | CH3SCH2CO | H |
| 2-273 | C—CF3 | C—H | C—CF3 | C—H | C—Cl | H | H | CH3SOCH2CO | H |
| 2-274 | C—CF3 | C—H | C—CF3 | C—H | C—Cl | H | H | CH3SO2CH2CO | H |
| 2-275 | C—Cl | C—Cl | C—Cl | C—H | C—Br | H | H | CH3SCH2CO | H |

TABLE 2-continued

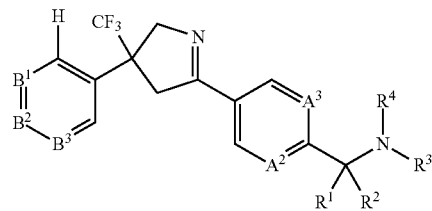

| No. | B¹ | B² | B³ | A² | A³ | R¹ | R² | R⁴ | R³ |
|---|---|---|---|---|---|---|---|---|---|
| 2-276 | C—Cl | C—Cl | C—Cl | C—H | C—Br | H | H | CH3SOCH2CO | H |
| 2-277 | C—Cl | C—Cl | C—Cl | C—H | C—Br | H | H | CH3SO2CH2CO | H |
| 2-278 | C—CF3 | C—H | C—CF3 | C—H | C—Br | H | H | CH3SCH2CO | H |
| 2-279 | C—CF3 | C—H | C—CF3 | C—H | C—Br | H | H | CH3SOCH2CO | H |
| 2-280 | C—CF3 | C—H | C—CF3 | C—H | C—Br | H | H | CH3SO2CH2CO | H |
| 2-281 | C—Cl | C—Cl | C—Cl | C—H | C—I | H | H | MeCO | H |
| 2-282 | C—Cl | C—Cl | C—Cl | C—H | C—I | H | H | EtCO | H |
| 2-283 | C—Cl | C—Cl | C—Cl | C—H | C—I | H | H | CF3CH2CO | H |
| 2-284 | C—Cl | C—Cl | C—Cl | C—H | C—I | H | H | cyclo-PrCO | H |
| 2-285 | C—Cl | C—Cl | C—Cl | C—H | C—I | H | H | EtNHCO | H |
| 2-286 | C—Cl | C—Cl | C—Cl | C—H | C—I | H | H | CH3SCH2CO | H |
| 2-287 | C—Cl | C—Cl | C—Cl | C—H | C—I | H | H | CH3SOCH2CO | H |
| 2-288 | C—CF3 | C—H | C—CF3 | C—H | C—I | H | H | MeCO | H |
| 2-289 | C—CF3 | C—H | C—CF3 | C—H | C—I | H | H | EtCO | H |
| 2-290 | C—CF3 | C—H | C—CF3 | C—H | C—I | H | H | CF3CH2CO | H |
| 2-291 | C—CF3 | C—H | C—CF3 | C—H | C—I | H | H | cyclo-PrCO | H |
| 2-292 | C—CF3 | C—H | C—CF3 | C—H | C—I | H | H | EtNHCO | H |
| 2-293 | C—CF3 | C—H | C—CF3 | C—H | C—I | H | H | CH3SCH2CO | H |
| 2-294 | C—CF3 | C—H | C—CF3 | C—H | C—I | H | H | CH3SOCH2CO | H |
| 2-295 | C—CF3 | C—H | C—CF3 | C—H | C—I | H | H | CH3SO2CH2CO | H |
| 2-296 | C—Cl | C—Cl | C—Cl | C—H | C—SMe | H | H | MeCO | H |
| 2-297 | C—Cl | C—Cl | C—Cl | C—H | C—SMe | H | H | EtCO | H |
| 2-298 | C—Cl | C—Cl | C—Cl | C—H | C—SMe | H | H | CF3CH2CO | H |
| 2-299 | C—Cl | C—Cl | C—Cl | C—H | C—SMe | H | H | cyclo-PrCO | H |
| 2-300 | C—Cl | C—Cl | C—Cl | C—H | C—SMe | H | H | EtNHCO | H |
| 2-301 | C—Cl | C—Cl | C—Cl | C—H | C—SMe | H | H | CH3SCH2CO | H |
| 2-302 | C—Cl | C—Cl | C—Cl | C—H | C—SMe | H | H | CH3SOCH2CO | H |
| 2-303 | C—CF3 | C—H | C—CF3 | C—H | C—SMe | H | H | MeCO | H |
| 2-304 | C—CF3 | C—H | C—CF3 | C—H | C—SMe | H | H | EtCO | H |
| 2-305 | C—CF3 | C—H | C—CF3 | C—H | C—SMe | H | H | CF3CH2CO | H |
| 2-306 | C—CF3 | C—H | C—CF3 | C—H | C—SMe | H | H | cyclo-PrCO | H |
| 2-307 | C—CF3 | C—H | C—CF3 | C—H | C—SMe | H | H | EtNHCO | H |
| 2-308 | C—CF3 | C—H | C—CF3 | C—H | C—SMe | H | H | CH3SCH2CO | H |
| 2-309 | C—CF3 | C—H | C—CF3 | C—H | C—SMe | H | H | CH3SOCH2CO | H |
| 2-310 | C—CF3 | C—H | C—CF3 | C—H | C—SMe | H | H | CH3SO2CH2CO | H |
| 2-311 | C—Cl | C—Cl | C—Cl | C—H | C—SCF3 | H | H | MeCO | H |
| 2-312 | C—Cl | C—Cl | C—Cl | C—H | C—SCF3 | H | H | EtCO | H |
| 2-313 | C—Cl | C—Cl | C—Cl | C—H | C—SCF3 | H | H | CF3CH2CO | H |
| 2-314 | C—Cl | C—Cl | C—Cl | C—H | C—SCF3 | H | H | cyclo-PrCO | H |
| 2-315 | C—Cl | C—Cl | C—Cl | C—H | C—SCF3 | H | H | EtNHCO | H |
| 2-316 | C—Cl | C—Cl | C—Cl | C—H | C—SCF3 | H | H | CH3SCH2CO | H |
| 2-317 | C—Cl | C—Cl | C—Cl | C—H | C—SCF3 | H | H | CH3SOCH2CO | H |
| 2-318 | C—CF3 | C—H | C—CF3 | C—H | C—SCF3 | H | H | MeCO | H |
| 2-319 | C—CF3 | C—H | C—CF3 | C—H | C—SCF3 | H | H | EtCO | H |
| 2-320 | C—CF3 | C—H | C—CF3 | C—H | C—SCF3 | H | H | CF3CH2CO | H |
| 2-321 | C—Cl | C—H | C—Cl | C—H | C—SCF3 | H | H | MeCO | H |
| 2-322 | C—Cl | C—H | C—Cl | C—H | C—SCF3 | H | H | EtCO | H |
| 2-323 | C—Cl | C—H | C—Cl | C—H | C—SCF3 | H | H | CF3CH2CO | H |
| 2-324 | C—Cl | C—H | C—Cl | C—H | C—CF3 | H | H | cyclo-PrCH2CO | H |
| 2-325 | C—Cl | C—H | C—Cl | C—H | C—CF3 | H | H | MeCOCH2CO | H |
| 2-326 | C—Cl | C—H | C—Cl | C—H | C—CF3 | H | H | cyclo-PrNHCO | H |
| 2-327 | C—Cl | C—H | C—Cl | C—H | C—CF3 | H | H | CHCCH2NHCO | H |
| 2-328 | C—Cl | C—H | C—Cl | C—H | C—CF3 | H | H | CH2=CHCH2NHCOH | |
| 2-329 | C—CF3 | C—H | C—H | C—H | C—CF3 | H | H | MeCO | H |
| 2-330 | C—CF3 | C—H | C—H | C—H | C—CF3 | H | H | EtCO | H |
| 2-331 | C—CF3 | C—H | C—H | C—H | C—CF3 | H | H | CF3CH2CO | H |
| 2-332 | C—CF3 | C—F | C—H | C—H | C—CF3 | H | H | MeCO | H |
| 2-333 | C—CF3 | C—F | C—H | C—H | C—CF3 | H | H | EtCO | H |
| 2-334 | C—CF3 | C—F | C—H | C—H | C—CF3 | H | H | cyclo-PrCO | H |
| 2-335 | C—CF3 | C—H | C—Cl | C—H | C—CF3 | H | H | MeCO | H |
| 2-336 | C—CF3 | C—H | C—Cl | C—H | C—CF3 | H | H | EtCO | H |
| 2-337 | C—CF3 | C—H | C—Cl | C—H | C—CF3 | H | H | EtNHCO | H |
| 2-338 | C—Br | C—H | C—Br | C—H | C—CF3 | H | H | MeCO | H |
| 2-339 | C—Br | C—H | C—Br | C—H | C—CF3 | H | H | EtCO | H |
| 2-340 | C—Br | C—H | C—Br | C—H | C—CF3 | H | H | cyclo-PrCH2CO | H |

TABLE 2-continued

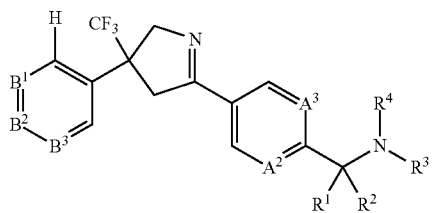

| No. | B¹ | B² | B³ | A² | A³ | R¹ | R² | R⁴ | R³ |
|---|---|---|---|---|---|---|---|---|---|
| 2-341 | C—Cl | C—CF3 | C—Cl | C—H | C—CF₃ | H | H | MeCO | H |
| 2-342 | C—Cl | C—CF3 | C—Cl | C—H | C—CF₃ | H | H | EtCO | H |
| 2-343 | C—Cl | C—CF3 | C—Cl | C—H | C—CF₃ | H | H | cyclo-PrCH2CO | H |
| 2-344 | C—Cl | C—Cl | C—H | C—H | C—CF₃ | H | H | MeCO | H |
| 2-345 | C—Cl | C—Cl | C—H | C—H | C—CF₃ | H | H | EtCO | H |
| 2-346 | C—Cl | C—Cl | C—H | C—H | C—CF₃ | H | H | cyclo-PrCO | H |
| 2-347 | C—F | C—F | C—F | C—H | C—CF₃ | H | H | MeCO | H |
| 2-348 | C—F | C—F | C—F | C—H | C—CF₃ | H | H | EtCO | H |
| 2-349 | C—F | C—F | C—F | C—H | C—CF₃ | H | H | EtNHCO | H |
| 2-350 | C—OCF3 | C—H | C—H | C—H | C—CF₃ | H | H | MeCO | H |
| 2-351 | C—OCF3 | C—H | C—H | C—H | C—CF₃ | H | H | EtCO | H |
| 2-352 | C—OCF3 | C—H | C—H | C—H | C—CF₃ | H | H | cyclo-PrCH2CO | H |
| 2-353 | C—NO2 | C—H | C—H | C—H | C—CF₃ | H | H | MeCO | H |
| 2-354 | C—NO2 | C—H | C—H | C—H | C—CF₃ | H | H | EtCO | H |
| 2-355 | C—NO2 | C—H | C—H | C—H | C—CF₃ | H | H | CF3CH2CO | H |
| 2-356 | C—Cl | C—Cl | C—Cl | C—H | C—CF₃ | Me | H | MeCO | H |
| 2-357 | C—Cl | C—Cl | C—Cl | C—H | C—CF₃ | Me | H | EtCO | H |
| 2-358 | C—Cl | C—Cl | C—Cl | C—H | C—CF₃ | Me | H | CF3CH2CO | H |
| 2-359 | C—Cl | C—Cl | C—Cl | C—H | C—CF₃ | Me | H | cyclo-PrCO | H |
| 2-360 | C—Cl | C—Cl | C—Cl | C—H | C—CF₃ | Me | H | EtNHCO | H |
| 2-361 | C—Cl | C—Cl | C—Cl | C—H | C—CF₃ | Me | H | CH3SCH2CO | H |
| 2-362 | C—Cl | C—Cl | C—Cl | C—H | C—CF₃ | Me | H | CH2SOCH2CO | H |
| 2-363 | C—Cl | C—Cl | C—Cl | C—H | C—CF₃ | Me | H | CH2SO2CH2CO | H |
| 2-364 | C—CF3 | C—H | C—CF3 | C—H | C—CF₃ | Me | H | MeCO | H |
| 2-365 | C—CF3 | C—H | C—CF3 | C—H | C—CF₃ | Me | H | EtCO | H |
| 2-366 | C—CF3 | C—H | C—CF3 | C—H | C—CF₃ | Me | H | CF3CH2CO | H |
| 2-367 | C—Cl | C—Cl | C—Cl | C—H | C—Br | Me | H | MeCO | H |
| 2-368 | C—Cl | C—Cl | C—Cl | C—H | C—Br | Me | H | EtCO | H |
| 2-369 | C—Cl | C—Cl | C—Cl | C—H | C—Br | Me | H | cyclo-PrCO | H |
| 2-370 | C—Cl | C—Cl | C—Cl | C—H | C—CF₃ | Me | Me | MeCO | H |
| 2-371 | C—Cl | C—Cl | C—Cl | C—H | C—CF₃ | Me | Me | EtCO | H |
| 2-372 | C—Cl | C—Cl | C—Cl | C—H | C—CF₃ | Me | Me | CF3CH2CO | H |
| 2-373 | C—Cl | C—Cl | C—Cl | C—H | C—CF₃ | Me | Me | cyclo-PrCO | H |
| 2-374 | C—Cl | C—Cl | C—Cl | C—H | C—CF₃ | Me | Me | EtNHCO | H |
| 2-375 | C—Cl | C—Cl | C—Cl | C—H | C—CF₃ | Me | Me | CH3SCH2CO | H |
| 2-376 | C—Cl | C—Cl | C—Cl | C—H | C—CF₃ | Me | Me | CH2SOCH2CO | H |
| 2-377 | C—Cl | C—Cl | C—Cl | C—H | C—CF₃ | Me | Me | CH3SO2CH2CO | H |
| 2-378 | C—CF3 | C—H | C—CF3 | C—H | C—CF₃ | Me | Me | MeCO | H |
| 2-379 | C—CF3 | C—H | C—CF3 | C—H | C—CF₃ | Me | Me | EtCO | H |
| 2-380 | C—CF3 | C—H | C—CF3 | C—H | C—CF₃ | Me | Me | CF3CH2CO | H |
| 2-381 | C—Cl | C—Cl | C—Cl | C—H | C—Br | Me | Me | MeCO | H |
| 2-382 | C—Cl | C—Cl | C—Cl | C—H | C—Br | Me | Me | EtCO | H |
| 2-383 | C—Cl | C—Cl | C—Cl | C—H | C—Br | Me | Me | cyclo-PrCO | H |
| 2-384 | C—Cl | C—Cl | C—Cl | C—H | C—Br | —CH2CH2— | | MeCO | H |
| 2-385 | C—Cl | C—Cl | C—Cl | C—H | C—Br | —CH2CH2— | | EtCO | H |
| 2-386 | C—Cl | C—Cl | C—Cl | C—H | C—Br | —CH2CH2— | | EtNHCO | H |
| 2-387 | C—Cl | C—Cl | C—Cl | C—H | C—Br | —CH2CH2— | | CF3CH2CO | H |
| 2-388 | C—CF3 | C—H | C—CF3 | C—H | C—Br | —CH2CH2— | | MeCO | H |
| 2-389 | C—CF3 | C—H | C—CF3 | C—H | C—Br | —CH2CH2— | | EtCO | H |
| 2-390 | C—CF3 | C—H | C—CF3 | C—H | C—Br | —CH2CH2— | | EtNHCO | H |
| 2-391 | C—CF3 | C—H | C—CF3 | C—H | C—Br | —CH2CH2— | | CF3CH2CO | H |
| 2-392 | C—CF3 | C—Cl | C—CF3 | C—H | C—CF3 | H | H | tert-BuOCO | H |

TABLE 3

| No. | B¹ | B² | B³ | R | A² | A³ | G | $(Z)_k$ |
|---|---|---|---|---|---|---|---|---|
| 3-1 | C—Cl | C—H | C—Cl | CF₃ | C—H | C—H | G1 | H |
| 3-2 | C—Cl | C—H | C—Cl | CF₃ | C—H | C—H | G2 | H |
| 3-3 | C—Cl | C—H | C—Cl | CF₃ | C—H | C—H | G3 | H |
| 3-4 | C—Cl | C—H | C—Cl | CF₃ | C—H | C—H | G4 | H |
| 3-5 | C—Cl | C—H | C—Cl | CF₃ | C—H | C—H | G5 | H |
| 3-6 | C—Cl | C—H | C—Cl | CF₃ | C—H | C—H | G6 | H |
| 3-7 | C—Cl | C—H | C—Cl | CF₃ | C—H | C—H | G7 | H |
| 3-8 | C—Cl | C—H | C—Cl | CF₃ | C—H | C—H | G8 | H |
| 3-9 | C—Cl | C—H | C—Cl | CF₃ | C—H | C—H | G9 | H |
| 3-10 | C—Cl | C—H | C—Cl | CF₃ | C—H | C—F | G6 | H |
| 3-11 | C—Cl | C—H | C—Cl | CF₃ | C—H | C—F | G8 | H |
| 3-12 | C—Cl | C—H | C—Cl | CF₃ | C—H | C—F | G9 | H |
| 3-13 | C—Cl | C—H | C—Cl | CF₃ | C—H | C—Cl | G6 | H |
| 3-14 | C—Cl | C—H | C—Cl | CF₃ | C—H | C—Cl | G8 | H |
| 3-15 | C—Cl | C—H | C—Cl | CF₃ | C—H | C—Cl | G9 | H |
| 3-16 | C—Cl | C—H | C—Cl | CF₃ | C—H | C—Br | G1 | H |
| 3-17 | C—Cl | C—H | C—Cl | CF₃ | C—H | C—Br | G2 | H |
| 3-18 | C—Cl | C—H | C—Cl | CF₃ | C—H | C—Br | G3 | H |
| 3-19 | C—Cl | C—H | C—Cl | CF₃ | C—H | C—Br | G4 | H |
| 3-20 | C—Cl | C—H | C—Cl | CF₃ | C—H | C—Br | G5 | H |
| 3-21 | C—Cl | C—H | C—Cl | CF₃ | C—H | C—Br | G6 | H |
| 3-22 | C—Cl | C—H | C—Cl | CF₃ | C—H | C—Br | G7 | H |
| 3-23 | C—Cl | C—H | C—Cl | CF₃ | C—H | C—Br | G8 | H |
| 3-24 | C—Cl | C—H | C—Cl | CF₃ | C—H | C—Br | G9 | H |
| 3-25 | C—Cl | C—H | C—Cl | CF₃ | C—H | C—I | G6 | H |
| 3-26 | C—Cl | C—H | C—Cl | CF₃ | C—H | C—I | G8 | H |
| 3-27 | C—Cl | C—H | C—Cl | CF₃ | C—H | C—I | G9 | H |
| 3-28 | C—Cl | C—H | C—Cl | CF₃ | C—H | C—Me | G6 | H |
| 3-29 | C—Cl | C—H | C—Cl | CF₃ | C—H | C—Me | G8 | H |
| 3-30 | C—Cl | C—H | C—Cl | CF₃ | C—H | C—CF₃ | G6 | H |
| 3-31 | C—Cl | C—H | C—Cl | CF₃ | C—H | C—CF₃ | G8 | H |
| 3-32 | C—Cl | C—H | C—Cl | CF₃ | C—H | C—NO₂ | G6 | H |
| 3-33 | C—Cl | C—H | C—Cl | CF₃ | C—H | C—NO₂ | G8 | H |
| 3-34 | C—Cl | C—H | C—Cl | CF₃ | C—H | C—CN | G1 | H |
| 3-35 | C—Cl | C—H | C—Cl | CF₃ | C—H | C—CN | G2 | H |
| 3-36 | C—Cl | C—H | C—Cl | CF₃ | C—H | C—CN | G3 | H |
| 3-37 | C—Cl | C—H | C—Cl | CF₃ | C—H | C—CN | G4 | H |
| 3-38 | C—Cl | C—H | C—Cl | CF₃ | C—H | C—CN | G5 | H |
| 3-39 | C—Cl | C—H | C—Cl | CF₃ | C—H | C—CN | G6 | H |
| 3-40 | C—Cl | C—H | C—Cl | CF₃ | C—H | C—CN | G7 | H |
| 3-41 | C—Cl | C—H | C—Cl | CF₃ | C—H | C—CN | G8 | H |
| 3-42 | C—Cl | C—H | C—Cl | CF₃ | C—H | C—CN | G9 | H |
| 3-43 | C—Cl | C—H | C—Cl | CF₃ | C—H | C—NO₂ | G6 | H |
| 3-44 | C—Cl | C—H | C—Cl | CF₃ | C—H | C—NO₂ | G8 | H |
| 3-45 | C—Cl | C—H | C—Cl | CF₃ | C—H | C—CH₃ | G6 | H |
| 3-46 | C—Cl | C—H | C—Cl | CF₃ | C—H | C—Sme | G6 | H |
| 3-47 | C—Cl | C—H | C—Cl | CF₃ | C—H | C—S(O)Me | G6 | H |
| 3-48 | C—Cl | C—H | C—Cl | CF₃ | C—H | C—S(O)₂Me | G6 | H |
| 3-49 | C—Cl | C—H | C—Cl | CF₃ | C—H | C—SCF₃ | G6 | H |
| 3-50 | C—Cl | C—H | C—Cl | CF₃ | C—H | C—S(O)CF₃ | G6 | H |
| 3-51 | C—Cl | C—H | C—Cl | CF₃ | C—H | C—S(O)₂CF₃ | G6 | H |
| 3-52 | C—Cl | C—H | C—Cl | CF₃ | C—H | C—OCH3 | G6 | H |
| 3-53 | C—Cl | C—H | C—Cl | CF₃ | C—H | C—OCF3 | G6 | H |
| 3-54 | C—Cl | C—H | C—Cl | CF₃ | C—H | C—OH | G6 | H |
| 3-55 | C—Cl | C—H | C—Cl | CF₃ | C—H | C—SH | G6 | H |
| 3-56 | C—Cl | C—H | C—Cl | CF₃ | C—H | C—NH₂ | G6 | H |
| 3-57 | C—Cl | C—H | C—Cl | CF₃ | C—H | C—NHCOCH₃ | G6 | H |
| 3-58 | C—Cl | C—H | C—Cl | CF₃ | C—H | C—NHCO₂CH₃ | G6 | H |
| 3-59 | C—Cl | C—H | C—Cl | CF₃ | C—H | C—NHCO₂CH₂CCl₃ | G6 | H |
| 3-60 | C—Cl | C—H | C—Cl | CF₃ | C—H | C—CN | G2 | 3-NO₂ |
| 3-61 | C—Cl | C—H | C—Cl | CF₃ | C—H | C—CN | G2 | 3-CN |
| 3-62 | C—Cl | C—H | C—Cl | CF₃ | C—H | C—CN | G6 | 3-NO₂ |
| 3-63 | C—Cl | C—H | C—Cl | CF₃ | C—H | C—CN | G6 | 3-CN |
| 3-64 | C—Cl | C—H | C—Cl | CF₃ | C—H | C—CN | G2 | 3-Cl |
| 3-65 | C—Cl | C—H | C—Cl | CF₃ | C—H | C—CN | G2 | 3-Br |
| 3-66 | C—Cl | C—H | C—Cl | CF₃ | C—H | C—CN | G2 | 3-CH₃ |
| 3-67 | C—Cl | C—H | C—Cl | CF₃ | C—H | C—CN | G2 | 3-CF₃ |
| 3-68 | C—Cl | C—H | C—H | CF₃ | C—H | C—CN | G6 | H |
| 3-69 | C—Cl | C—H | C—H | CF₃ | C—H | C—CN | G8 | H |

TABLE 3-continued

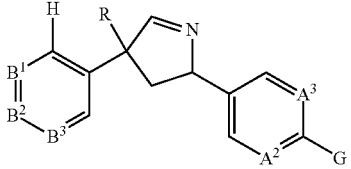

| No. | B¹ | B² | B³ | R | A² | A³ | G | (Z)$_k$ |
|---|---|---|---|---|---|---|---|---|
| 3-70 | C—CF$_3$ | C—H | C—H | CF$_3$ | C—H | C—CN | G6 | H |
| 3-71 | C—CF$_3$ | C—H | C—H | CF$_3$ | C—H | C—CN | G8 | H |
| 3-72 | C—CF$_3$ | C—H | C—CF$_3$ | CF$_3$ | C—H | C—CN | G6 | H |
| 3-73 | C—CF$_3$ | C—H | C—CF$_3$ | CF$_3$ | C—H | C—CN | G8 | H |
| 3-74 | C—NO$_2$ | C—H | C—H | CF$_3$ | C—H | C—CN | G6 | H |
| 3-75 | C—NO$_2$ | C—H | C—H | CF$_3$ | C—H | C—CN | G8 | H |
| 3-76 | C—Cl | C—Cl | C—H | CF$_3$ | C—H | C—CN | G6 | H |
| 3-77 | C—Cl | C—Cl | C—H | CF$_3$ | C—H | C—CN | G8 | H |
| 3-78 | C—Cl | C—Cl | C—Cl | CF$_3$ | C—H | C—CN | G6 | H |
| 3-79 | C—Cl | C—Cl | C—Cl | CF$_3$ | C—H | C—CN | G8 | H |
| 3-80 | C—CH$_3$ | C—H | C—H | CF$_3$ | C—H | C—CN | G6 | H |
| 3-81 | C—OCH$_3$ | C—H | C—H | CF$_3$ | C—H | C—CN | G6 | H |
| 3-82 | C—CN | C—H | C—H | CF$_3$ | C—H | C—CN | G6 | H |
| 3-83 | C—OCF$_3$ | C—H | C—H | CF$_3$ | C—H | C—CN | G6 | H |
| 3-84 | C—SCH$_3$ | C—H | C—H | CF$_3$ | C—H | C—CN | G6 | H |
| 3-85 | C—S(O)CH$_3$ | C—H | C—H | CF$_3$ | C—H | C—CN | G6 | H |
| 3-86 | C—S(O)$_2$CH$_3$ | C—H | C—H | CF$_3$ | C—H | C—CN | G6 | H |
| 3-87 | C—SCF$_3$ | C—H | C—H | CF$_3$ | C—H | C—CN | G6 | H |
| 3-88 | C—S(O)CF$_3$ | C—H | C—H | CF$_3$ | C—H | C—CN | G6 | H |
| 3-89 | C—S(O)$_2$CF$_3$ | C—H | C—H | CF$_3$ | C—H | C—CN | G6 | H |
| 3-90 | C—OH | C—H | C—H | CF$_3$ | C—H | C—CN | G6 | H |
| 3-91 | C—OH | C—H | C—H | CF$_3$ | C—H | C—CN | G6 | H |
| 3-92 | C—Cl | C—H | C—Cl | CF$_3$ | N | C—Br | G6 | H |
| 3-93 | C—Cl | C—H | C—Cl | CF$_3$ | N | C—CN | G6 | H |

TABLE 4

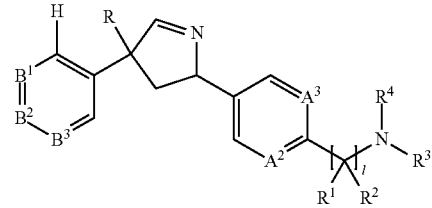

| No. | B1 | B2 | B3 | R | A2 | A3 | R1 | R2 | R4 | R3 | l |
|---|---|---|---|---|---|---|---|---|---|---|---|
| 4-1 | C—Cl | C—H | C—Cl | CF$_3$ | C—H | C—H | H | H | MeCO | H | 1 |
| 4-2 | C—Cl | C—H | C—Cl | CF$_3$ | C—H | C—H | H | H | MeCO | MeCO | 1 |
| 4-3 | C—Cl | C—H | C—Cl | CF$_3$ | C—H | C—H | H | H | MeCO | 2-py-CO | 1 |
| 4-4 | C—Cl | C—H | C—Cl | CF$_3$ | C—H | C—H | H | H | HCO | 2-py-CH$_2$ | 1 |
| 4-5 | C—Cl | C—H | C—Cl | CF$_3$ | C—H | C—H | H | H | MeCO | 2-py-CH$_2$ | 1 |
| 4-6 | C—Cl | C—H | C—Cl | CF$_3$ | C—H | C—H | H | H | EtCO | 2-py-CH$_2$ | 1 |
| 4-7 | C—Cl | C—H | C—Cl | CF$_3$ | C—H | C—H | H | H | Me$_2$NCO | 2-py-CH$_2$ | 1 |
| 4-8 | C—Cl | C—H | C—Cl | CF$_3$ | C—H | C—H | H | H | MeSO$_2$ | 2-py-CH$_2$ | 1 |
| 4-9 | C—Cl | C—H | C—Cl | CF$_3$ | C—H | C—H | H | H | 2-py-CO | 2-py-CH$_2$ | 1 |
| 4-10 | C—Cl | C—H | C—Cl | CF$_3$ | C—H | C—H | CN | H | MeCO | H | 1 |
| 4-11 | C—Cl | C—H | C—Cl | CF$_3$ | C—H | C—H | CN | H | MeCO | 2-py-CH$_2$ | 1 |
| 4-12 | C—Cl | C—H | C—Cl | CF$_3$ | C—H | C—Br | H | H | HCO | H | 1 |
| 4-13 | C—Cl | C—H | C—Cl | CF$_3$ | C—H | C—Br | H | H | MeCO | H | 1 |
| 4-14 | C—Cl | C—H | C—Cl | CF$_3$ | C—H | C—Br | H | H | MeCO | MeCO | 1 |
| 4-15 | C—Cl | C—H | C—Cl | CF$_3$ | C—H | C—Br | H | H | MeCO | 2-py-CH$_2$ | 1 |
| 4-16 | C—Cl | C—H | C—Cl | CF$_3$ | C—H | C—Br | H | H | MeCO | 3-py-CH$_2$ | 1 |
| 4-17 | C—Cl | C—H | C—Cl | CF$_3$ | C—H | C—Br | H | H | MeCO | 4-py-CH$_2$ | 1 |
| 4-18 | C—Cl | C—H | C—Cl | CF$_3$ | C—H | C—Br | H | H | MeCO | Ph—CH$_2$ | 1 |
| 4-19 | C—Cl | C—H | C—Cl | CF$_3$ | C—H | C—Br | H | H | EtCO | H | 1 |
| 4-20 | C—Cl | C—H | C—Cl | CF$_3$ | C—H | C—Br | H | H | n-PrCO | H | 1 |
| 4-21 | C—Cl | C—H | C—Cl | CF$_3$ | C—H | C—Br | H | H | iso-PrCO | H | 1 |
| 4-22 | C—Cl | C—H | C—Cl | CF$_3$ | C—H | C—Br | H | H | tert-BuCO | H | 1 |
| 4-23 | C—Cl | C—H | C—Cl | CF$_3$ | C—H | C—Br | H | H | CF3CO | H | 1 |
| 4-24 | C—Cl | C—H | C—Cl | CF$_3$ | C—H | C—Br | H | H | PhCO | H | 1 |
| 4-25 | C—Cl | C—H | C—Cl | CF$_3$ | C—H | C—Br | H | H | 2-py-CO | H | 1 |

TABLE 4-continued

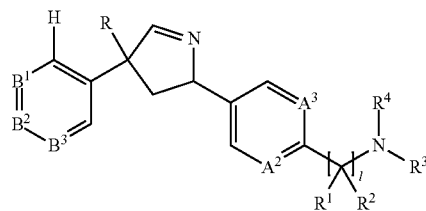

| No. | B1 | B2 | B3 | R | A2 | A3 | R1 | R2 | R4 | R3 | l |
|---|---|---|---|---|---|---|---|---|---|---|---|
| 4-26 | C—Cl | C—H | C—Cl | CF₃ | C—H | C—Br | H | H | 3-py-CO | H | 1 |
| 4-27 | C—Cl | C—H | C—Cl | CF₃ | C—H | C—Br | H | H | 4-py-CO | H | 1 |
| 4-28 | C—Cl | C—H | C—Cl | CF₃ | C—H | C—Br | H | H | 2-F—PhCO | H | 1 |
| 4-29 | C—Cl | C—H | C—Cl | CF₃ | C—H | C—Br | H | H | 3-F—PhCO | H | 1 |
| 4-30 | C—Cl | C—H | C—Cl | CF₃ | C—H | C—Br | H | H | 4-F—PhCO | H | 1 |
| 4-31 | C—Cl | C—H | C—Cl | CF₃ | C—H | C—Br | H | H | 2-Cl—PhCO | H | 1 |
| 4-32 | C—Cl | C—H | C—Cl | CF₃ | C—H | C—Br | H | H | 3-Cl—PhCO | H | 1 |
| 4-33 | C—Cl | C—H | C—Cl | CF₃ | C—H | C—Br | H | H | 4-Cl—PhCO | H | 1 |
| 4-34 | C—Cl | C—H | C—Cl | CF₃ | C—H | C—Br | H | H | 2-Br—PhCO | H | 1 |
| 4-35 | C—Cl | C—H | C—Cl | CF₃ | C—H | C—Br | H | H | 2-Me—PhCO | H | 1 |
| 4-36 | C—Cl | C—H | C—Cl | CF₃ | C—H | C—Br | H | H | CH₂=CH—CO | H | 1 |
| 4-37 | C—Cl | C—H | C—Cl | CF₃ | C—H | C—Br | H | H | HC≡C—CO | H | 1 |
| 4-38 | C—Cl | C—H | C—Cl | CF₃ | C—H | C—Br | H | H | MeSO₂ | H | 1 |
| 4-39 | C—Cl | C—H | C—Cl | CF₃ | C—H | C—Br | H | H | CF3SO₂ | H | 1 |
| 4-40 | C—Cl | C—H | C—Cl | CF₃ | C—H | C—Br | H | H | MeNHCO | H | 1 |
| 4-41 | C—Cl | C—H | C—Cl | CF₃ | C—H | C—Br | H | H | Me₂NCO | H | 1 |
| 4-42 | C—Cl | C—H | C—Cl | CF₃ | C—H | C—Br | H | H | MeOC(=O) | H | 1 |
| 4-43 | C—Cl | C—H | C—Cl | CF₃ | C—H | C—Br | H | H | MeSC(=O) | H | 1 |
| 4-44 | C—Cl | C—H | C—Cl | CF₃ | C—H | C—Br | H | H | MeCS | H | 1 |
| 4-45 | C—Cl | C—H | C—Cl | CF₃ | C—H | C—Br | H | H | MeON(Me)CO | H | 1 |
| 4-46 | C—Cl | C—H | C—Cl | CF₃ | C—H | C—Br | H | H | MeCO | Me | 1 |
| 4-47 | C—Cl | C—H | C—Cl | CF₃ | C—H | C—Br | H | H | MeCO | Et | 1 |
| 4-48 | C—Cl | C—H | C—Cl | CF₃ | C—H | C—Br | H | H | MeCO | CH₂=CH— | 1 |
| 4-49 | C—Cl | C—H | C—Cl | CF₃ | C—H | C—Br | H | H | MeCO | HC≡C—CH₂— | 1 |
| 4-50 | C—Cl | C—H | C—Cl | CF₃ | C—H | C—Br | H | H | MeCO | PhCH₂ | 1 |
| 4-51 | C—Cl | C—H | C—Cl | CF₃ | C—H | C—Br | H | H | MeCO | CN | 1 |
| 4-52 | C—Cl | C—H | C—Cl | CF₃ | C—H | C—Br | H | H | MeCO | CH₂CF3 | 1 |
| 4-53 | C—Cl | C—H | C—Cl | CF₃ | C—H | C—Br | H | H | MeCO | cyc-Pr | 1 |
| 4-54 | C—Cl | C—H | C—Cl | CF₃ | C—H | C—Br | H | H | —C(O)CH₂CH₂CH₂— | | 1 |
| 4-55 | C—Cl | C—H | C—Cl | CF₃ | C—H | C—Br | H | H | —CO—NMe—N=N— | | 1 |
| 4-56 | C—Cl | C—H | C—Cl | CF₃ | C—H | C—Br | H | H | —C(=N—NO₂)—NH—CH₂—CH₂— | | 1 |
| 4-57 | C—Cl | C—H | C—Cl | CF₃ | C—H | C—F | H | H | MeCO | H | 1 |
| 4-58 | C—Cl | C—H | C—Cl | CF₃ | C—H | C—Cl | H | H | MeCO | H | 1 |
| 4-59 | C—Cl | C—H | C—Cl | CF₃ | C—H | C—I | H | H | MeCO | H | 1 |
| 4-60 | C—Cl | C—H | C—Cl | CF₃ | C—H | C—NO2 | H | H | MeCO | H | 1 |
| 4-61 | C—Cl | C—H | C—Cl | CF₃ | C—H | C—CN | H | H | MeCO | 2-py-CH₂ | 1 |
| 4-62 | C—Cl | C—H | C—Cl | CF₃ | C—H | C—CN | H | H | MeCO | H | 1 |
| 4-63 | C—Cl | C—H | C—Cl | CF₃ | C—H | C—Me | H | H | MeCO | H | 1 |
| 4-64 | C—Cl | C—H | C—Cl | CF₃ | C—H | C—Me | H | H | MeCO | 2-py-CH2 | 1 |
| 4-65 | C—Cl | C—H | C—Cl | CF₃ | C—H | C—SMe | H | H | MeCO | H | 1 |
| 4-66 | C—Cl | C—H | C—Cl | CF₃ | C—H | C—S(O)Me | H | H | MeCO | H | 1 |
| 4-67 | C—Cl | C—H | C—Cl | CF₃ | C—H | C—S(O)₂Me | H | H | MeCO | H | 1 |
| 4-68 | C—Cl | C—H | C—Cl | CF₃ | C—H | C—SCF3 | H | H | MeCO | H | 1 |
| 4-69 | C—Cl | C—H | C—Cl | CF₃ | C—H | C—S(O)CF3 | H | H | MeCO | H | 1 |
| 4-70 | C—Cl | C—H | C—Cl | CF₃ | C—H | C—S(O)₂CF3 | H | H | MeCO | H | 1 |
| 4-71 | C—Cl | C—H | C—Cl | CF₃ | C—H | C—OCH3 | H | H | MeCO | H | 1 |
| 4-72 | C—Cl | C—H | C—Cl | CF₃ | C—H | C—OCF3 | H | H | MeCO | H | 1 |
| 4-73 | C—Cl | C—H | C—Cl | CF₃ | C—H | C—OH | H | H | MeCO | H | 1 |
| 4-74 | C—Cl | C—H | C—Cl | CF₃ | C—H | C—SH | H | H | MeCO | H | 1 |
| 4-75 | C—Cl | C—H | C—Cl | CF₃ | C—H | C—NH₂ | H | H | MeCO | H | 1 |
| 4-76 | C—Cl | C—H | C—Cl | CF₃ | C—H | C—NHCOCH3 | H | H | MeCO | H | 1 |
| 4-77 | C—Cl | C—H | C—Cl | CF₃ | C—H | C—NHCO₂CH3 | H | H | MeCO | H | 1 |
| 4-78 | C—Cl | C—H | C—Cl | CF₃ | C—H | C—NHCO₂CH₂CCl3 | H | H | MeCO | H | 1 |
| 4-79 | C—Cl | C—H | C—Cl | CF₃ | C—H | C—Br | Me | H | MeCO | H | 1 |
| 4-80 | C—Cl | C—H | C—Cl | CF₃ | C—H | C—Br | Me | Me | MeCO | H | 1 |
| 4-81 | C—Cl | C—H | C—Cl | CF₃ | C—H | C—H | cyc-Pr | H | MeCO | H | 1 |
| 4-82 | C—Cl | C—H | C—Cl | CF₃ | C—H | C—H | CF3 | H | MeCO | H | 1 |
| 4-83 | C—Cl | C—H | C—Cl | CF₃ | C—H | C—H | CO₂Me | H | MeCO | H | 1 |
| 4-84 | C—Cl | C—H | C—Cl | CF₃ | C—H | C—H | CH₂=CH | H | MeCO | H | 1 |
| 4-85 | C—Cl | C—H | C—Cl | CF₃ | C—H | C—H | HC≡C | H | MeCO | H | 1 |
| 4-86 | C—Cl | C—H | C—Cl | CF₃ | C—H | C—H | —CH₂CH₂— | | MeCO | H | 1 |
| 4-87 | C—Cl | C—H | C—Cl | CF₃ | C—H | C—H | H | H | MeCO | H | 1 |
| 4-88 | C—Cl | C—H | C—Cl | CF₃ | C—H | C—H | H | H | MeCO | NH₂ | 1 |
| 4-89 | C—Cl | C—H | C—Cl | CF₃ | C—H | C—H | H | H | MeCO | —NHCOMe | 1 |
| 4-90 | C—Cl | C—H | C—Cl | CF₃ | C—H | C—Br | H | H | MeCO | —N=CMe₂ | 1 |

TABLE 4-continued

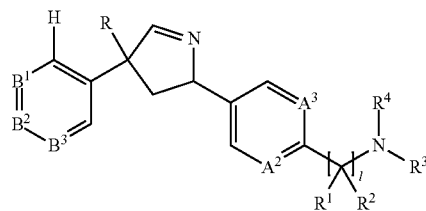

| No. | B1 | B2 | B3 | R | A2 | A3 | R1 | R2 | R4 | R3 | l |
|---|---|---|---|---|---|---|---|---|---|---|---|
| 4-91 | C—Cl | C—H | C—Cl | CF$_3$ | C—H | C—H | H | H | MeCO | OH | 1 |
| 4-92 | C—Cl | C—H | C—Cl | CF$_3$ | C—H | C—H | H | H | MeCO | OMe | 1 |
| 4-93 | C—Cl | C—H | C—Cl | CH$_3$ | C—H | C—Br | H | H | MeCO | H | 1 |
| 4-94 | C—Cl | C—Cl | C—H | CH$_3$ | C—H | C—Br | H | H | MeCO | H | 1 |
| 4-95 | C—Cl | C—Cl | C—Cl | CH$_3$ | C—H | C—Br | H | H | MeCO | H | 1 |
| 4-96 | C—Cl | C—Me | C—Cl | CH$_3$ | C—H | C—Br | H | H | MeCO | H | 1 |
| 4-97 | C—F | C—F | C—F | CH$_3$ | C—H | C—Br | H | H | MeCO | H | 1 |
| 4-98 | C—Br | C—Br | C—Br | CH$_3$ | C—H | C—Br | H | H | MeCO | H | 1 |
| 4-99 | C—Cl | C—CF3 | C—Cl | CH$_3$ | C—H | C—Br | H | H | MeCO | H | 1 |
| 4-100 | C—Cl | C—Cl | C—CF3 | CH$_3$ | C—H | C—Br | H | H | MeCO | H | 1 |
| 4-101 | C—Cl | C—Br | C—Cl | CH$_3$ | C—H | C—Br | H | H | MeCO | H | 1 |
| 4-102 | C—Br | C—Cl | C—Br | CH$_3$ | C—H | C—Br | H | H | MeCO | H | 1 |
| 4-103 | C—Cl | C—NH$_2$ | C—Cl | CH$_3$ | C—H | C—Br | H | H | MeCO | H | 1 |
| 4-104 | C—Br | C—NH$_2$ | C—Br | CH$_3$ | C—H | C—Br | H | H | MeCO | H | 1 |
| 4-105 | C—F | C—F | C—F | CH$_3$ | C—H | C—Br | H | H | EtCO | H | 1 |
| 4-106 | C—Br | C—Br | C—Br | CH$_3$ | C—H | C—Br | H | H | EtCO | H | 1 |
| 4-107 | C—Cl | C—CF | C—Cl | CH$_3$ | C—H | C—Br | H | H | EtCO | H | 1 |
| 4-108 | C—Cl | C—Cl | C—CF$_3$ | CH$_3$ | C—H | C—Br | H | H | EtCO | H | 1 |
| 4-109 | C—Cl | C—Br | C—Cl | CH$_3$ | C—H | C—Br | H | H | EtCO | H | 1 |
| 4-110 | C—Br | C—Cl | C—Br | CH$_3$ | C—H | C—Br | H | H | EtCO | H | 1 |
| 4-111 | C—Cl | C—NH$_2$ | C—Cl | CH$_3$ | C—H | C—Br | H | H | EtCO | H | 1 |
| 4-112 | C—Br | C—NH$_2$ | C—Br | CH$_3$ | C—H | C—Br | H | H | EtCO | H | 1 |
| 4-113 | C—F | C—H | C—H | CH$_3$ | C—H | C—Br | H | H | MeCO | H | 1 |
| 4-114 | C—Cl | C—H | C—H | CF$_3$ | C—H | C—Br | H | H | MeCO | H | 1 |
| 4-115 | C—CF$_3$ | C—H | C—H | CF$_3$ | C—H | C—Br | H | H | MeCO | H | 1 |
| 4-116 | C—H | C—CF$_3$ | C—H | CF$_3$ | C—H | C—Br | H | H | MeCO | H | 1 |
| 4-117 | C—CF$_3$ | C—H | C—CF3 | CF$_3$ | C—H | C—Br | H | H | MeCO | H | 1 |
| 4-118 | C—NO$_2$ | C—H | C—H | CF$_3$ | C—H | C—Br | H | H | MeCO | H | 1 |
| 4-119 | C—Cl | C—H | C—Cl | CF$_3$ | N | C—H | H | H | MeCO | H | 1 |
| 4-120 | C—CH$_3$ | C—H | C—H | CF$_3$ | C—H | C—H | H | H | MeCO | H | 1 |
| 4-121 | C—OCH$_3$ | C—H | C—H | CF$_3$ | C—H | C—H | H | H | MeCO | H | 1 |
| 4-122 | C—CN | C—H | C—H | CF$_3$ | C—H | C—Br | H | H | MeCO | H | 1 |
| 4-123 | C—OCF$_3$ | C—H | C—H | CF$_3$ | C—H | C—H | H | H | MeCO | H | 1 |
| 4-124 | C—SCH$_3$ | C—H | C—H | CF$_3$ | C—H | C—H | H | H | MeCO | H | 1 |
| 4-125 | C—S(O)CH$_3$ | C—H | C—H | CF$_3$ | C—H | C—H | H | H | MeCO | H | 1 |
| 4-126 | C—S(O)2CH$_3$ | C—H | C—H | CF$_3$ | C—H | C—H | H | H | MeCO | H | 1 |
| 4-127 | C—SCF$_3$ | C—H | C—H | CF$_3$ | C—H | C—H | H | H | MeCO | H | 1 |
| 4-128 | C—S(O)CF$_3$ | C—H | C—H | CF$_3$ | C—H | C—H | H | H | MeCO | H | 1 |
| 4-129 | C=S(O)$_2$CF$_3$ | C—H | C—H | CF$_3$ | C—H | C—H | H | H | MeCO | H | 1 |
| 4-130 | C—OH | C—H | C—H | CF$_3$ | C—H | C—H | H | H | MeCO | H | 1 |
| 4-131 | C—SH | C—H | C—H | CF$_3$ | C—H | C—H | H | H | MeCO | H | 1 |
| 4-132 | C—Cl | C—H | C—Cl | CF$_3$ | C—H | C—Br | H | H | MeCO | H | 2 |
| 4-133 | C—Cl | C—Cl | C—H | CF$_3$ | C—H | C—Br | H | H | MeCO | H | 1 |
| 4-134 | C—Cl | C—Cl | C—Cl | CF$_3$ | C—H | C—Br | H | H | MeCO | H | 1 |
| 4-135 | C—Cl | C—Me | C—Cl | CF$_3$ | C—H | C—Br | H | H | MeCO | H | 1 |
| 4-136 | C—F | C—F | C—F | CF$_3$ | C—H | C—Br | H | H | MeCO | H | 1 |
| 4-137 | C—Br | C—Br | C—Br | CF$_3$ | C—H | C—Br | H | H | MeCO | H | 1 |
| 4-138 | C—Cl | C—CF$_3$ | C—Cl | CF$_3$ | C—H | C—Br | H | H | MeCO | H | 1 |
| 4-139 | C—Cl | C—Cl | C—CF$_3$ | CF$_3$ | C—H | C—Br | H | H | MeCO | H | 1 |
| 4-140 | C—Cl | C—Br | C—Cl | CF$_3$ | C—H | C—Br | H | H | MeCO | H | 1 |
| 4-141 | C—Br | C—Cl | C—Br | CF$_3$ | C—H | C—Br | H | H | MeCO | H | 1 |
| 4-142 | C—Cl | C—NH$_2$ | C—Cl | CF$_3$ | C—H | C—Br | H | H | MeCO | H | 1 |
| 4-143 | C—Br | C—NH$_2$ | C—Br | CF$_3$ | C—H | C—Br | H | H | MeCO | H | 1 |
| 4-144 | C—F | C—F | C—F | CF$_3$ | C—H | C—Br | H | H | EtCO | H | 1 |
| 4-145 | C—Br | C—Br | C—Br | CF$_3$ | C—H | C—Br | H | H | EtCO | H | 1 |
| 4-146 | C—Cl | C—CF3 | C—Cl | CF$_3$ | C—H | C—Br | H | H | EtCO | H | 1 |
| 4-147 | C—Cl | C—Cl | C—CF$_3$ | CF$_3$ | C—H | C—Br | H | H | EtCO | H | 1 |
| 4-148 | C—Cl | C—Br | C—Cl | CF$_3$ | C—H | C—Br | H | H | EtCO | H | 1 |
| 4-149 | C—Br | C—Cl | C—Br | CF$_3$ | C—H | C—Br | H | H | EtCO | H | 1 |
| 4-150 | C—Cl | C—NH$_2$ | C—Cl | CF$_3$ | C—H | C—Br | H | H | EtCO | H | 1 |
| 4-151 | C—Br | C—NH$_2$ | C—Br | CF$_3$ | C—H | C—Br | H | H | EtCO | H | 1 |
| 4-152 | C—F | C—H | C—H | CF$_3$ | C—H | C—Br | H | H | MeCO | H | 1 |

Compounds of formula XXXIV are exemplified in the tables 5, 6, 7 and 8:

TABLE 5

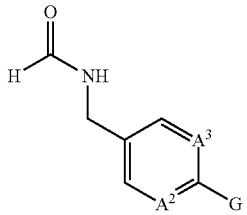

| No. | A² | A³ | G | (Z)ₖ |
|---|---|---|---|---|
| 5-1 | C—H | C—H | G1 | H |
| 5-2 | C—H | C—H | G2 | H |
| 5-3 | C—H | C—H | G3 | H |
| 5-4 | C—H | C—H | G4 | H |
| 5-5 | C—H | C—H | G5 | H |
| 5-6 | C—H | C—H | G6 | H |
| 5-7 | C—H | C—H | G7 | H |
| 5-8 | C—H | C—H | G8 | H |
| 5-9 | C—H | C—H | G9 | H |
| 5-10 | C—H | C—F | G6 | H |
| 5-11 | C—H | C—F | G8 | H |
| 5-12 | C—H | C—F | G9 | H |
| 5-13 | C—H | C—Cl | G6 | H |
| 5-14 | C—H | C—Cl | G8 | H |
| 5-15 | C—H | C—Cl | G9 | H |
| 5-16 | C—H | C—Br | G1 | H |
| 5-17 | C—H | C—Br | G2 | H |
| 5-18 | C—H | C—Br | G3 | H |
| 5-19 | C—H | C—Br | G4 | H |
| 5-20 | C—H | C—Br | G5 | H |
| 5-21 | C—H | C—Br | G6 | H |
| 5-22 | C—H | C—Br | G7 | H |
| 5-23 | C—H | C—Br | G8 | H |
| 5-24 | C—H | C—Br | G9 | H |
| 5-25 | C—H | C—I | G6 | H |
| 5-26 | C—H | C—I | G8 | H |
| 5-27 | C—H | C—I | G9 | H |
| 5-28 | C—H | C—Me | G6 | H |
| 5-29 | C—H | C—Me | G8 | H |
| 5-30 | C—H | C—CF₃ | G6 | H |
| 5-31 | C—H | C—CF₃ | G8 | H |
| 5-32 | C—H | C—SCF₃ | G6 | H |

TABLE 5-continued

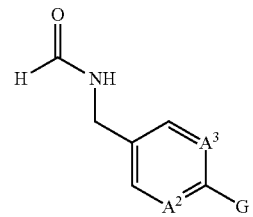

| No. | A² | A³ | G | (Z)ₖ |
|---|---|---|---|---|
| 5-33 | C—H | C—S(O)CF₃ | G6 | H |
| 5-34 | C—H | C—S(O)₂CF₃ | G6 | H |
| 5-35 | C—H | C—CN | G1 | H |
| 5-36 | C—H | C—CN | G2 | H |
| 5-37 | C—H | C—CN | G2 | 3-NO₂ |
| 5-38 | C—H | C—CN | G2 | 3-CN |
| 5-39 | C—H | C—CN | G2 | 3-Cl |
| 5-40 | C—H | C—CN | G2 | 3-Br |
| 5-41 | C—H | C—CN | G2 | 3-CH₃ |
| 5-42 | C—H | C—CN | G2 | 3-CF₃ |
| 5-43 | C—H | C—CN | G3 | H |
| 5-44 | C—H | C—CN | G4 | H |
| 5-45 | C—H | C—CN | G5 | H |
| 5-46 | C—H | C—CN | G6 | H |
| 5-47 | C—H | C—CN | G6 | 3-NO₂ |
| 5-48 | C—H | C—CN | G6 | 3-CN |
| 5-49 | C—H | C—CN | G7 | H |
| 5-50 | C—H | C—CN | G8 | H |
| 5-51 | C—H | C—CN | G9 | H |
| 5-52 | C—H | C—SMe | G6 | H |
| 5-53 | C—H | C—S(O)Me | G6 | H |
| 5-54 | C—H | C—S(O)₂Me | G6 | H |
| 5-55 | C—H | C—NH₂ | G6 | H |
| 5-56 | C—H | C—NHCO₂CH₂CCl₃ | G6 | H |
| 5-57 | C—H | C—NHCO₂CH₃ | G6 | H |
| 5-58 | C—H | C—NHCOCH₃ | G6 | H |
| 5-59 | C—H | C—NO₂ | G6 | H |
| 5-60 | C—H | C—NO₂ | G8 | H |
| 5-61 | C—H | C—OCF₃ | G6 | H |
| 5-62 | C—H | C—OH | G6 | H |
| 5-63 | C—H | C—SH | G6 | H |
| 5-64 | N | C—Br | G6 | H |
| 5-65 | N | C—CN | G6 | H |

TABLE 6

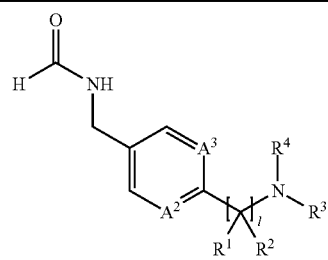

| No. | A² | A³ | R¹ | R² | R⁴ | R³ | l |
|---|---|---|---|---|---|---|---|
| 6-1 | C—H | C—H | H | H | HCO | 2-py-CH₂ | 1 |
| 6-2 | C—H | C—H | H | H | MeCO | H | 1 |
| 6-3 | C—H | C—H | H | H | MeCO | MeCO | 1 |
| 6-4 | C—H | C—H | H | H | MeCO | 2-py-CO | 1 |
| 6-5 | C—H | C—H | H | H | MeCO | 2-py-CH₂ | 1 |
| 6-6 | C—H | C—H | H | H | MeCO | NH2 | 1 |
| 6-7 | C—H | C—H | H | H | MeCO | NHCOMe | 1 |
| 6-8 | C—H | C—H | H | H | MeCO | OH | 1 |
| 6-9 | C—H | C—H | H | H | MeCO | MeO | 1 |
| 6-10 | C—H | C—H | H | H | EtCO | 2-py-CH₂ | 1 |
| 6-11 | C—H | C—H | H | H | 2-py-CO | 2-py-CH₂ | 1 |
| 6-12 | C—H | C—H | H | H | Me₂NCO | 2-py-CH₂ | 1 |

TABLE 6-continued

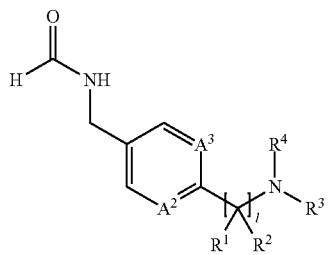

| No. | A² | A³ | R¹ | R² | R⁴ | R³ | l |
|---|---|---|---|---|---|---|---|
| 6-13 | C—H | C—H | H | H | MeSO₂ | 2-py-CH₂ | 1 |
| 6-14 | C—H | C—H | CF₃ | H | MeCO | H | 1 |
| 6-15 | C—H | C—H | CH₂CH₂ | | MeCO | H | 1 |
| 6-16 | C—H | C—H | CH₂=CH | H | MeCO | H | 1 |
| 6-17 | C—H | C—H | HC≡C | H | MeCO | H | 1 |
| 6-18 | C—H | C—H | CN | H | MeCO | H | 1 |
| 6-19 | C—H | C—H | CN | H | MeCO | 2-py-CH₂ | 1 |
| 6-20 | C—H | C—H | CO₂Me | H | MeCO | H | 1 |
| 6-21 | C—H | C—H | cyc-Pr | H | MeCO | H | 1 |
| 6-22 | C—H | C—F | H | H | MeCO | H | 1 |
| 6-23 | C—H | C—Cl | H | H | MeCO | H | 1 |
| 6-24 | C—H | C—Br | H | H | HCO | H | 1 |
| 6-25 | C—H | C—Br | H | H | MeCO | H | 1 |
| 6-26 | C—H | C—Br | H | H | MeCO | H | 2 |
| 6-27 | C—H | C—Br | H | H | MeCO | Me | 1 |
| 6-28 | C—H | C—Br | H | H | MeCO | Et | 1 |
| 6-29 | C—H | C—Br | H | H | MeCO | CH₂=CH | 1 |
| 6-30 | C—H | C—Br | H | H | MeCO | HC≡C—CH₂ | 1 |
| 6-31 | C—H | C—Br | H | H | MeCO | PhCH₂ | 1 |
| 6-32 | C—H | C—Br | H | H | MeCO | CN | 1 |
| 6-33 | C—H | C—Br | H | H | MeCO | CH₂CF₃ | 1 |
| 6-34 | C—H | C—Br | H | H | MeCO | cyc-Pr | 1 |
| 6-35 | C—H | C—Br | H | H | MeCO | 2-py-CH₂ | 1 |
| 6-36 | C—H | C—Br | H | H | MeCO | 3-py-CH₂ | 1 |
| 6-37 | C—H | C—Br | H | H | MeCO | 4-py-CH₂ | 1 |
| 6-38 | C—H | C—Br | H | H | MeCO | MeCO | 1 |
| 6-39 | C—H | C—Br | H | H | EtCO | H | 1 |
| 6-40 | C—H | C—Br | H | H | EtCO | H | 1 |
| 6-41 | C—H | C—Br | H | H | n-PrCO | H | 1 |
| 6-42 | C—H | C—Br | H | H | iso-PrCO | H | 1 |
| 6-43 | C—H | C—Br | H | H | tert-BuCO | H | 1 |
| 6-44 | C—H | C—Br | H | H | CH₂=CHCO | H | 1 |
| 6-45 | C—H | C—Br | H | H | HC≡CCO | H | 1 |
| 6-46 | C—H | C—Br | H | H | CF₃CO | H | 1 |
| 6-47 | C—H | C—Br | H | H | PhCO | H | 1 |
| 6-48 | C—H | C—Br | H | H | 2-F—PhCO | H | 1 |
| 6-49 | C—H | C—Br | H | H | 3-F—PhCO | H | 1 |
| 6-50 | C—H | C—Br | H | H | 4-F—PhCO | H | 1 |
| 6-51 | C—H | C—Br | H | H | 2-Cl—PhCO | H | 1 |
| 6-52 | C—H | C—Br | H | H | 3-Cl—PhCO | H | 1 |
| 6-53 | C—H | C—Br | H | H | 4-Cl—PhCO | H | 1 |
| 6-54 | C—H | C—Br | H | H | 2-Br—PhCO | H | 1 |
| 6-55 | C—H | C—Br | H | H | 2-Me—PhCO | H | 1 |
| 6-56 | C—H | C—Br | H | H | 2-pyridylCO | H | 1 |
| 6-57 | C—H | C—Br | H | H | 3-py-CO | H | 1 |
| 6-58 | C—H | C—Br | H | H | 4-py-CO | H | 1 |
| 6-59 | C—H | C—Br | H | H | MeSO₂ | H | 1 |
| 6-60 | C—H | C—Br | H | H | CF₃SO₂ | H | 1 |
| 6-61 | C—H | C—Br | H | H | MeHNCO | H | 1 |
| 6-62 | C—H | C—Br | H | H | Me₂NCO | H | 1 |
| 6-63 | C—H | C—Br | H | H | MeOC(=O) | H | 1 |
| 6-64 | C—H | C—Br | H | H | MeSC(=O) | H | 1 |
| 6-65 | C—H | C—Br | H | H | MeCS | H | 1 |
| 6-66 | C—H | C—Br | H | H | MeON(Me)CO | H | 1 |
| 6-67 | C—H | C—Br | H | H | —C(O)CH₂CH₂CH₂— | | 1 |
| 6-68 | C—H | C—Br | H | H | —CO—NMe—N=N— | | 1 |
| 6-69 | C—H | C—Br | H | H | —C(=N—NO₂)—NH—CH₂—CH₂— | | 1 |
| 6-70 | C—H | C—Br | H | H | MeCO | N=CMe₂ | 1 |
| 6-71 | C—H | C—Br | Me | H | MeCO | H | 1 |
| 6-72 | C—H | C—Br | Me | Me | MeCO | H | 1 |
| 6-73 | C—H | C—I | H | H | MeCO | H | 1 |
| 6-74 | C—H | C—NO₂ | H | H | MeCO | H | 1 |
| 6-75 | C—H | C—CN | H | H | MeCO | 2-py-CH₂ | 1 |
| 6-76 | C—H | C—CN | H | H | MeCO | H | 1 |
| 6-77 | C—H | C—Me | H | H | MeCO | H | 1 |

TABLE 6-continued

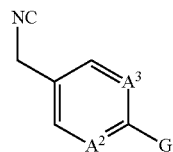

| No. | A² | A³ | R¹ | R² | R⁴ | R³ | l |
|---|---|---|---|---|---|---|---|
| 6-78 | C—H | C—Me | H | H | MeCO | 2-py-CH₂ | 1 |
| 6-79 | C—H | C—SMe | H | H | MeCO | H | 1 |
| 6-80 | C—H | C—S(O)Me | H | H | MeCO | H | 1 |
| 6-81 | C—H | C—S(O)₂Me | H | H | MeCO | H | 1 |
| 6-82 | C—H | C—CF₃S | H | H | MeCO | H | 1 |
| 6-83 | C—H | C—S(O)CF₃ | H | H | MeCO | H | 1 |
| 6-84 | C—H | C—S(O)₂CF₃ | H | H | MeCO | H | 1 |
| 6-85 | C—H | C—OCH₃ | H | H | MeCO | H | 1 |
| 6-86 | C—H | C—OCF₃ | H | H | MeCO | H | 1 |
| 6-87 | C—H | C—OH | H | H | MeCO | H | 1 |
| 6-88 | C—H | C—SH | H | H | MeCO | H | 1 |
| 6-89 | C—H | C—NH₂ | H | H | MeCO | H | 1 |
| 6-90 | C—H | C—NHCOCH₃ | H | H | MeCO | H | 1 |
| 6-91 | C—H | C—NHCO₂CH₃ | H | H | MeCO | H | 1 |
| 6-92 | C—H | C—NHCO₂CH₂CO₃ | H | H | MeCO | H | 1 |
| 6-93 | N | C—H | H | H | MeCO | H | 1 |

TABLE 7

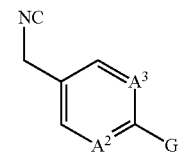

| No. | A² | A³ | G | (Z)$_k$ |
|---|---|---|---|---|
| 7-1 | C—H | C—H | G1 | H |
| 7-2 | C—H | C—H | G2 | H |
| 7-3 | C—H | C—H | G3 | H |
| 7-4 | C—H | C—H | G4 | H |
| 7-5 | C—H | C—H | G5 | H |
| 7-6 | C—H | C—H | G6 | H |
| 7-7 | C—H | C—H | G7 | H |
| 7-8 | C—H | C—H | G8 | H |
| 7-9 | C—H | C—H | G9 | H |
| 7-10 | C—H | C—F | G6 | H |
| 7-11 | C—H | C—F | G8 | H |
| 7-12 | C—H | C—F | G9 | H |
| 7-13 | C—H | C—Cl | G6 | H |
| 7-14 | C—H | C—Cl | G8 | H |
| 7-15 | C—H | C—Cl | G9 | H |
| 7-16 | C—H | C—Br | G1 | H |
| 7-17 | C—H | C—Br | G2 | H |
| 7-18 | C—H | C—Br | G3 | H |
| 7-19 | C—H | C—Br | G4 | H |
| 7-20 | C—H | C—Br | G5 | H |
| 7-21 | C—H | C—Br | G6 | H |
| 7-22 | C—H | C—Br | G7 | H |
| 7-23 | C—H | C—Br | G8 | H |
| 7-24 | C—H | C—Br | G9 | H |
| 7-25 | C—H | C—I | G6 | H |
| 7-26 | C—H | C—I | G8 | H |
| 7-27 | C—H | C—I | G9 | H |
| 7-28 | C—H | C—Me | G6 | H |
| 7-29 | C—H | C—Me | G8 | H |
| 7-30 | C—H | C—CF₃ | G6 | H |
| 7-31 | C—H | C—CF₃ | G8 | H |
| 7-32 | C—H | C—SCF₃ | G6 | H |
| 7-33 | C—H | C—S(O)CF₃ | G6 | H |
| 7-34 | C—H | C—S(O)₂CF₃ | G6 | H |
| 7-35 | C—H | C—CN | G1 | H |
| 7-36 | C—H | C—CN | G2 | H |
| 7-37 | C—H | C—CN | G2 | 3-NO₂ |
| 7-38 | C—H | C—CN | G2 | 3-CN |
| 7-39 | C—H | C—CN | G2 | 3-Cl |
| 7-40 | C—H | C—CN | G2 | 3-Br |
| 7-41 | C—H | C—CN | G2 | 3-CH₃ |
| 7-42 | C—H | C—CN | G2 | 3-CF₃ |
| 7-43 | C—H | C—CN | G3 | H |
| 7-44 | C—H | C—CN | G4 | H |
| 7-45 | C—H | C—CN | G5 | H |
| 7-46 | C—H | C—CN | G6 | H |
| 7-47 | C—H | C—CN | G6 | 3-NO₂ |
| 7-48 | C—H | C—CN | G6 | 3-CN |
| 7-49 | C—H | C—CN | G7 | H |
| 7-50 | C—H | C—CN | G8 | H |
| 7-51 | C—H | C—CN | G9 | H |
| 7-52 | C—H | C—SMe | G6 | H |
| 7-53 | C—H | C—S(O)Me | G6 | H |
| 7-54 | C—H | C—S(O)₂Me | G6 | H |
| 7-55 | C—H | C—NH₂ | G6 | H |
| 7-56 | C—H | C—NHCO₂CH₂CCl₃ | G6 | H |
| 7-57 | C—H | C—NHCO₂CH₃ | G6 | H |
| 7-58 | C—H | C—NHCOCH₃ | G6 | H |
| 7-59 | C—H | C—NO₂ | G6 | H |
| 7-60 | C—H | C—NO₂ | G8 | H |
| 7-61 | C—H | C—OCF₃ | G6 | H |
| 7-62 | C—H | C—OH | G6 | H |
| 7-63 | C—H | C—SH | G6 | H |
| 7-64 | N | C—Br | G6 | H |
| 7-65 | N | C—CN | G6 | H |

TABLE 8

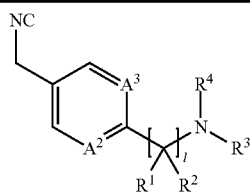

| No. | A² | A³ | R¹ | R² | R⁴ | R³ | l |
|---|---|---|---|---|---|---|---|
| 8-1 | C—H | C—H | H | H | HCO | 2-py-CH₂ | 1 |
| 8-2 | C—H | C—H | H | H | MeCO | H | 1 |
| 8-3 | C—H | C—H | H | H | MeCO | MeCO | 1 |
| 8-4 | C—H | C—H | H | H | MeCO | 2-py-CO | 1 |
| 8-5 | C—H | C—H | H | H | MeCO | 2-py-CH₂ | 1 |
| 8-6 | C—H | C—H | H | H | MeCO | NH₂ | 1 |
| 8-7 | C—H | C—H | H | H | MeCO | NHCOMe | 1 |
| 8-8 | C—H | C—H | H | H | MeCO | OH | 1 |
| 8-9 | C—H | C—H | H | H | MeCO | MeO | 1 |
| 8-10 | C—H | C—H | H | H | EtCO | 2-py-CH₂ | 1 |
| 8-11 | C—H | C—H | H | H | 2-py-CO | 2-py-CH₂ | 1 |
| 8-12 | C—H | C—H | H | H | Me₂NCO | 2-py-CH₂ | 1 |
| 8-13 | C—H | C—H | H | H | MeSO₂ | 2-py-CH₂ | 1 |
| 8-14 | C—H | C—H | CF₃ | H | MeCO | H | 1 |
| 8-15 | C—H | C—H | CH₂CH₂ | | MeCO | H | 1 |
| 8-16 | C—H | C—H | CH₂=CH | H | MeCO | H | 1 |
| 8-17 | C—H | C—H | HC≡C | H | MeCO | H | 1 |
| 8-18 | C—H | C—H | CN | H | MeCO | H | 1 |
| 8-19 | C—H | C—H | CN | H | MeCO | 2-py-CH₂ | 1 |
| 8-20 | C—H | C—H | CO₂Me | H | MeCO | H | 1 |
| 8-21 | C—H | C—H | cyc-Pr | H | MeCO | H | 1 |
| 8-22 | C—H | C—F | H | H | MeCO | H | 1 |
| 8-23 | C—H | C—Cl | H | H | MeCO | H | 1 |
| 8-24 | C—H | C—Br | H | H | HCO | H | 1 |
| 8-25 | C—H | C—Br | H | H | MeCO | H | 1 |
| 8-26 | C—H | C—Br | H | H | MeCO | H | 1 |
| 8-27 | C—H | C—Br | H | H | MeCO | Me | 1 |
| 8-28 | C—H | C—Br | H | H | MeCO | Et | 1 |
| 8-29 | C—H | C—Br | H | H | MeCO | CH₂=CH | 1 |
| 8-30 | C—H | C—Br | H | H | MeCO | HC≡C—CH₂ | 1 |
| 8-31 | C—H | C—Br | H | H | MeCO | PhCH₂ | 1 |
| 8-32 | C—H | C—Br | H | H | MeCO | CN | 1 |
| 8-33 | C—H | C—Br | H | H | MeCO | CH₂CF₃ | 1 |
| 8-34 | C—H | C—Br | H | H | MeCO | cyc-Pr | 1 |
| 8-35 | C—H | C—Br | H | H | MeCO | 2-py-CH₂ | 1 |
| 8-36 | C—H | C—Br | H | H | MeCO | 3-py-CH₂ | 1 |
| 8-37 | C—H | C—Br | H | H | MeCO | 4-py-CH₂ | 1 |
| 8-38 | C—H | C—Br | H | H | MeCO | MeCO | 1 |
| 8-39 | C—H | C—Br | H | H | EtCO | H | 1 |
| 8-40 | C—H | C—Br | H | H | EtCO | H | 1 |
| 8-41 | C—H | C—Br | H | H | n-PrCO | H | 1 |
| 8-42 | C—H | C—Br | H | H | iso-PrCO | H | 1 |
| 8-43 | C—H | C—Br | H | H | tert-BuCO | H | 1 |
| 8-44 | C—H | C—Br | H | H | CH2=CHCO | H | 1 |
| 8-45 | C—H | C—Br | H | H | HC≡CCO | H | 1 |
| 8-46 | C—H | C—Br | H | H | CF₃CO | H | 1 |
| 8-47 | C—H | C—Br | H | H | PhCO | H | 1 |
| 8-48 | C—H | C—Br | H | H | 2-F—PhCO | H | 1 |
| 8-49 | C—H | C—Br | H | H | 3-F—PhCO | H | 1 |
| 8-50 | C—H | C—Br | H | H | 4-F—PhCO | H | 1 |
| 8-51 | C—H | C—Br | H | H | 2-Cl—PhCO | H | 1 |
| 8-52 | C—H | C—Br | H | H | 3-Cl—PhCO | H | 1 |
| 8-53 | C—H | C—Br | H | H | 4-Cl—PhCO | H | 1 |
| 8-54 | C—H | C—Br | H | H | 2-Br—PhCO | H | 1 |
| 8-55 | C—H | C—Br | H | H | 2-Me—PhCO | H | 1 |
| 8-56 | C—H | C—Br | H | H | 2-pyridylCO | H | 1 |
| 8-57 | C—H | C—Br | H | H | 3-py-CO | H | 1 |
| 8-58 | C—H | C—Br | H | H | 4-py-CO | H | 1 |
| 8-59 | C—H | C—Br | H | H | MeSO₂ | H | 1 |
| 8-60 | C—H | C—Br | H | H | CF₃SO₂ | H | 1 |
| 8-61 | C—H | C—Br | H | H | MeHNCO | H | 1 |
| 8-62 | C—H | C—Br | H | H | Me₂NCO | H | 1 |
| 8-63 | C—H | C—Br | H | H | MeOC(=O) | H | 1 |
| 8-64 | C—H | C—Br | H | H | MeSC(=O) | H | 1 |
| 8-65 | C—H | C—Br | H | H | MeCS | H | 1 |
| 8-66 | C—H | C—Br | H | H | MeON(Me)CO | H | 1 |
| 8-67 | C—H | C—Br | H | H | —C(O)CH₂CH₂CH₂— | | 1 |
| 8-68 | C—H | C—Br | H | H | —CO—NMe—N=N— | | 1 |

TABLE 8-continued

| No. | A² | A³ | R¹ | R² | R⁴ | R³ | l |
|---|---|---|---|---|---|---|---|
| 8-69 | C—H | C—Br | H | H | —C(=N—NO₂)—NH—CH₂—CH₂— | | 1 |
| 8-70 | C—H | C—Br | H | H | MeCO | N=CMe₂ | 1 |
| 8-71 | C—H | C—Br | Me | H | MeCO | H | 1 |
| 8-72 | C—H | C—Br | Me | Me | MeCO | H | 1 |
| 8-73 | C—H | C—I | H | H | MeCO | H | 1 |
| 8-74 | C—H | C—NO₂ | H | H | MeCO | H | 1 |
| 8-75 | C—H | C—CN | H | H | MeCO | 2-py-CH₂ | 1 |
| 8-76 | C—H | C—CN | H | H | MeCO | H | 1 |
| 8-77 | C—H | C—Me | H | H | MeCO | H | 1 |
| 8-78 | C—H | C—Me | H | H | MeCO | 2-py-CH₂ | 1 |
| 8-79 | C—H | C—SMe | H | H | MeCO | H | 1 |
| 8-80 | C—H | C—S(O)Me | H | H | MeCO | H | 1 |
| 8-81 | C—H | C—S(O)₂Me | H | H | MeCO | H | 1 |
| 8-82 | C—H | C—CF₃S | H | H | MeCO | H | 1 |
| 8-83 | C—H | C—S(O)CF₃ | H | H | MeCO | H | 1 |
| 8-84 | C—H | C—S(O)₂CF₃ | H | H | MeCO | H | 1 |
| 8-85 | C—H | C—OCH₃ | H | H | MeCO | H | 1 |
| 8-86 | C—H | C—OCF₃ | H | H | MeCO | H | 1 |
| 8-87 | C—H | C—OH | H | H | MeCO | H | 1 |
| 8-88 | C—H | C—SH | H | H | MeCO | H | 1 |
| 8-89 | C—H | C—NH₂ | H | H | MeCO | H | 1 |
| 8-90 | C—H | C—NHCOCH₃ | H | H | MeCO | H | 1 |
| 8-91 | C—H | C—NHCO₂CH₃ | H | H | MeCO | H | 1 |
| 8-92 | C—H | C—NHCO₂CH₂CCl₃ | H | H | MeCO | H | 1 |
| 8-93 | N | C—H | H | H | MeCO | H | 1 |

Compounds of formula XXXV are exemplified in the tables 9 and 10:

TABLE 9

| No. | A² | A³ | R¹ | R² | R³ | l |
|---|---|---|---|---|---|---|
| 9-1 | C—H | C—H | H | H | H | 1 |
| 9-2 | C—H | C—H | H | H | 2-py-CH₂ | 1 |
| 9-3 | C—H | C—H | H | H | NH₂ | 1 |
| 9-4 | C—H | C—H | H | H | NHCOMe | 1 |
| 9-5 | C—H | C—H | H | H | OH | 1 |
| 9-6 | C—H | C—H | H | H | MeO | 1 |
| 9-7 | C—H | C—H | CF₃ | H | H | 1 |
| 9-8 | C—H | C—H | CH₂CH₂ | | H | 1 |
| 9-9 | C—H | C—H | CH₂=CH | H | H | 1 |
| 9-10 | C—H | C—H | HC≡C | H | H | 1 |
| 9-11 | C—H | C—H | CN | H | H | 1 |
| 9-12 | C—H | C—H | CN | H | 2-py-CH₂ | 1 |
| 9-13 | C—H | C—H | CO₂Me | H | H | 1 |
| 9-14 | C—H | C—H | cyc-Pr | H | H | 1 |
| 9-15 | C—H | C—F | H | H | H | 1 |
| 9-16 | C—H | C—Cl | H | H | H | 1 |
| 9-17 | C—H | C—Br | H | H | H | 1 |
| 9-18 | C—H | C—Br | H | H | H | 2 |
| 9-19 | C—H | C—Br | H | H | Me | 1 |
| 9-20 | C—H | C—Br | H | H | Et | 1 |
| 9-21 | C—H | C—Br | H | H | CH₂=CH | 1 |

TABLE 9-continued

| No. | A² | A³ | R¹ | R² | R³ | l |
|---|---|---|---|---|---|---|
| 9-22 | C—H | C—Br | H | H | HC≡C—CH₂ | 1 |
| 9-23 | C—H | C—Br | H | H | PhCH₂ | 1 |
| 9-24 | C—H | C—Br | H | H | CN | 1 |
| 9-25 | C—H | C—Br | H | H | CH₂CF₃ | 1 |
| 9-26 | C—H | C—Br | H | H | cyc-Pr | 1 |
| 9-27 | C—H | C—Br | H | H | 2-py-CH₂ | 1 |
| 9-28 | C—H | C—Br | H | H | 3-py-CH₂ | 1 |
| 9-29 | C—H | C—Br | H | H | 4-py-CH₂ | 1 |
| 9-30 | C—H | C—Br | H | H | MeCO | 1 |
| 9-31 | C—H | C—Br | H | H | N=CMe₂ | 1 |
| 9-32 | C—H | C—Br | Me | H | H | 1 |
| 9-33 | C—H | C—Br | Me | Me | H | 1 |
| 9-34 | C—H | C—I | H | H | H | 1 |
| 9-35 | C—H | C—NO₂ | H | H | H | 1 |
| 9-36 | C—H | C—CN | H | H | 2-py-CH₂ | 1 |
| 9-37 | C—H | C—CN | H | H | H | 1 |
| 9-38 | C—H | C—Me | H | H | H | 1 |
| 9-39 | C—H | C—Me | H | H | 2-py-CH₂ | 1 |
| 9-40 | C—H | C—SMe | H | H | H | 1 |
| 9-41 | C—H | C—S(O)Me | H | H | H | 1 |
| 9-42 | C—H | C—S(O)₂Me | H | H | H | 1 |
| 9-43 | C—H | C—SCF₃ | H | H | H | 1 |
| 9-44 | C—H | C—S(O)CF₃ | H | H | H | 1 |
| 9-45 | C—H | C—S(O)₂CF₃ | H | H | H | 1 |
| 9-46 | C—H | C—OCH₃ | H | H | H | 1 |

TABLE 9-continued

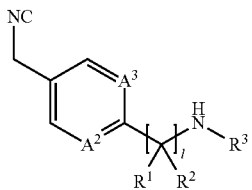

| No. | A² | A³ | R¹ | R² | R³ | l |
|---|---|---|---|---|---|---|
| 9-47 | C—H | C—OCF₃ | H | H | H | 1 |
| 9-48 | C—H | C—OH | H | H | H | 1 |
| 9-49 | C—H | C—SH | H | H | H | 1 |
| 9-50 | C—H | C—NH₂ | H | H | H | 1 |
| 9-51 | C—H | C—NHCOCH₃ | H | H | H | 1 |
| 9-52 | C—H | C—NHCO₂CH₃ | H | H | H | 1 |
| 9-53 | C—H | C—NHCO₂CH₂CCl₃ | H | H | H | 1 |
| 9-54 | N | C—H | H | H | H | 1 |

TABLE 10

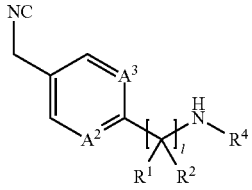

| No. | A² | A³ | R¹ | R² | R⁴ | l |
|---|---|---|---|---|---|---|
| 10-1 | C—H | C—H | H | H | HCO | 1 |
| 10-2 | C—H | C—H | H | H | MeCO | 1 |
| 10-3 | C—H | C—H | H | H | EtCO | 1 |
| 10-4 | C—H | C—H | H | H | 2-py-CO | 1 |
| 10-5 | C—H | C—H | H | H | Me₂NCO | 1 |
| 10-6 | C—H | C—H | H | H | MeSO₂ | 1 |
| 10-7 | C—H | C—H | CF₃ | H | MeCO | 1 |
| 10-8 | C—H | C—H | CH₂CH₂ | | MeCO | 1 |
| 10-9 | C—H | C—H | CH₂=CH | H | MeCO | 1 |
| 10-10 | C—H | C—H | HC≡C | H | MeCO | 1 |
| 10-11 | C—H | C—H | CN | H | MeCO | 1 |
| 10-12 | C—H | C—H | CO₂Me | H | MeCO | 1 |
| 10-13 | C—H | C—H | cyc-Pr | H | MeCO | 1 |
| 10-14 | C—H | C—F | H | H | MeCO | 1 |
| 10-15 | C—H | C—Cl | H | H | MeCO | 1 |
| 10-16 | C—H | C—Br | H | H | HCO | 1 |
| 10-17 | C—H | C—Br | H | H | MeCO | 1 |
| 10-18 | C—H | C—Br | H | H | MeCO | 2 |
| 10-19 | C—H | C—Br | H | H | EtCO | 1 |
| 10-20 | C—H | C—Br | H | H | n-PrCO | 1 |
| 10-21 | C—H | C—Br | H | H | iso-PrCO | 1 |
| 10-22 | C—H | C—Br | H | H | tert-BuCO | 1 |
| 10-23 | C—H | C—Br | H | H | CH2=CHCO | 1 |
| 10-24 | C—H | C—Br | H | H | HC≡CCO | 1 |
| 10-25 | C—H | C—Br | H | H | CF₃CO | 1 |
| 10-26 | C—H | C—Br | H | H | PhCO | 1 |
| 10-27 | C—H | C—Br | H | H | 2-F—PhCO | 1 |
| 10-28 | C—H | C—Br | H | H | 3-F—PhCO | 1 |
| 10-29 | C—H | C—Br | H | H | 4-F—PhCO | 1 |
| 10-30 | C—H | C—Br | H | H | 2-Cl—PhCO | 1 |
| 10-31 | C—H | C—Br | H | H | 3-Cl—PhCO | 1 |
| 10-32 | C—H | C—Br | H | H | 4-Cl—PhCO | 1 |
| 10-33 | C—H | C—Br | H | H | 2-Br—PhCO | 1 |
| 10-34 | C—H | C—Br | H | H | 2-Me—PhCO | 1 |
| 10-35 | C—H | C—Br | H | H | 2-py-CO | 1 |
| 10-36 | C—H | C—Br | H | H | 3-py-CO | 1 |
| 10-37 | C—H | C—Br | H | H | 4-py-CO | 1 |
| 10-38 | C—H | C—Br | H | H | MeSO₂ | 1 |
| 10-39 | C—H | C—Br | H | H | CF₃SO₂ | 1 |
| 10-40 | C—H | C—Br | H | H | MeHNCO | 1 |
| 10-41 | C—H | C—Br | H | H | Me₂NCO | 1 |
| 10-42 | C—H | C—Br | H | H | MeOC(=O) | 1 |
| 10-43 | C—H | C—Br | H | H | MeSC(=O) | 1 |

TABLE 10-continued

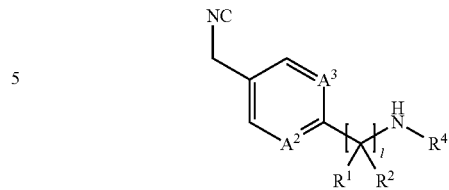

| No. | A² | A³ | R¹ | R² | R⁴ | l |
|---|---|---|---|---|---|---|
| 10-44 | C—H | C—Br | H | H | MeCS | 1 |
| 10-45 | C—H | C—Br | H | H | MeON(Me)CO | 1 |
| 10-46 | C—H | C—Br | H | H | MeCO | 1 |
| 10-47 | C—H | C—Br | Me | H | MeCO | 1 |
| 10-48 | C—H | C—Br | Me | Me | MeCO | 1 |
| 10-49 | C—H | C—I | H | H | MeCO | 1 |
| 10-50 | C—H | C—NO₂ | H | H | MeCO | 1 |
| 10-51 | C—H | C—CN | H | H | MeCO | 1 |
| 10-52 | C—H | C—CN | H | H | MeCO | 1 |
| 10-53 | C—H | C—Me | H | H | MeCO | 1 |
| 10-54 | C—H | C—Me | H | H | MeCO | 1 |
| 10-55 | C—H | C—SMe | H | H | MeCO | 1 |
| 10-56 | C—H | C—S(O)Me | H | H | MeCO | 1 |
| 10-57 | C—H | C—S(O)₂Me | H | H | MeCO | 1 |
| 10-58 | C—H | C—SCF₃ | H | H | MeCO | 1 |
| 10-59 | C—H | C—S(O)CF₃ | H | H | MeCO | 1 |
| 10-60 | C—H | C—S(O)₂CF₃ | H | H | MeCO | 1 |
| 10-61 | C—H | C—OCH₃ | H | H | MeCO | 1 |
| 10-62 | C—H | C—OCF₃ | H | H | MeCO | 1 |
| 10-63 | C—H | C—OH | H | H | MeCO | 1 |
| 10-64 | C—H | C—SH | H | H | MeCO | 1 |
| 10-65 | C—H | C—NH₂ | H | H | MeCO | 1 |
| 10-66 | C—H | C—NHCOCH₃ | H | H | MeCO | 1 |
| 10-67 | C—H | C—NHCO₂CH₃ | H | H | MeCO | 1 |
| 10-68 | C—H | C—NHCO₂CH₂CCl₃ | H | H | MeCO | 1 |
| 10-69 | N | C—H | H | H | MeCO | 1 |

TABLE 11

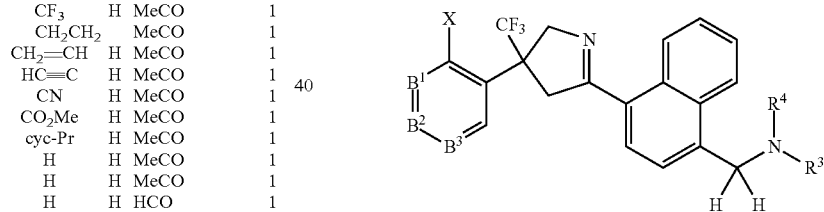

| No. | B1 | B2 | B3 | R4 | R3 |
|---|---|---|---|---|---|
| 11-1 | C—Cl | C—H | C—Cl | MeCO | H |
| 11-2 | C—Cl | C—H | C—Cl | EtCO | H |
| 11-3 | C—Cl | C—H | C—Cl | cyc-PrCO | H |
| 11-4 | C—Cl | C—H | C—Cl | CF3CH2CO | H |
| 11-5 | C—Cl | C—Cl | C—Cl | MeCO | H |
| 11-6 | C—Cl | C—Cl | C—Cl | EtCO | H |
| 11-7 | C—Cl | C—Cl | C—Cl | cyc-PrCO | H |
| 11-8 | C—Cl | C—Cl | C—Cl | CF3CH2CO | H |
| 11-9 | C—CF3 | C—H | C—CF3 | MeCO | H |
| 11-10 | C—CF3 | C—H | C—CF3 | EtCO | H |
| 11-11 | C—CF3 | C—H | C—CF3 | cyc-PrCO | H |
| 11-12 | C—CF3 | C—H | C—CF3 | CF3CH2CO | H |
| 11-13 | C—Br | C—H | C—Br | MeCO | H |
| 11-14 | C—Cl | C—Cl | C—CF3 | MeCO | H |
| 11-15 | C—Cl | C—Cl | C—CF3 | EtCO | H |
| 11-16 | C—Cl | C—Cl | C—CF3 | cyc-PrCO | H |
| 11-17 | C—Cl | C—Cl | C—CF3 | H | H |
| 11-18 | C—Cl | C—H | C—Cl | H | H |
| 11-19 | C—Cl | C—Cl | C—Cl | H | H |
| 11-20 | C—CF3 | C—H | C—CF3 | H | H |

TABLE 11-continued

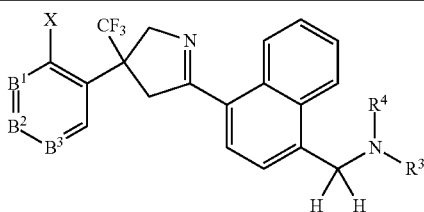

| No. | B1 | B2 | B3 | R4 | R3 |
|---|---|---|---|---|---|
| 11-21 | C—Br | C—H | C—Br | H | H |
| 11-22 | C—Cl | C—Cl | C—CF3 | H | H |

Compounds of formula (XXXIX) are exemplified in the tables 12, 13, 14, 15 and 18:

TABLE 12

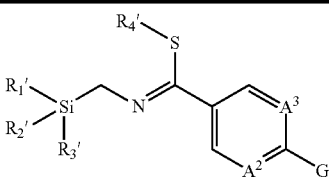

| No. | R1' | R2' | R3' | R4' | A2 | A3 | G | Z |
|---|---|---|---|---|---|---|---|---|
| 12-1 | Me | Me | Me | Me | C—H | C—H | G1 | H |
| 12-2 | Me | Me | Me | Me | C—H | C—H | G2 | H |
| 12-3 | Me | Me | Me | Me | C—H | C—H | G3 | H |
| 12-4 | Me | Me | Me | Me | C—H | C—H | G4 | H |
| 12-5 | Me | Me | Me | Me | C—H | C—H | G5 | H |
| 12-6 | Me | Me | Me | Me | C—H | C—H | G6 | H |
| 12-7 | Me | Me | Me | Me | C—H | C—H | G7 | H |
| 12-8 | Me | Me | Me | Me | C—H | C—H | G8 | H |
| 12-9 | Me | Me | Me | Me | C—H | C—H | G9 | H |
| 12-10 | Me | Me | Me | Me | C—H | C—F | G6 | H |
| 12-11 | Me | Me | Me | Me | C—H | C—F | G8 | H |
| 12-12 | Me | Me | Me | Me | C—H | C—F | G9 | H |
| 12-13 | Me | Me | Me | Me | C—H | C—Cl | G6 | H |
| 12-14 | Me | Me | Me | Me | C—H | C—Cl | G8 | H |
| 12-15 | Me | Me | Me | Me | C—H | C—Cl | G9 | H |
| 12-16 | Me | Me | Me | Me | C—H | C—Br | G1 | H |
| 12-17 | Me | Me | Me | Me | C—H | C—Br | G2 | H |
| 12-18 | Me | Me | Me | Me | C—H | C—Br | G3 | H |
| 12-19 | Me | Me | Me | Me | C—H | C—Br | G4 | H |
| 12-20 | Me | Me | Me | Me | C—H | C—Br | G5 | H |
| 12-21 | Me | Me | Me | Me | C—H | C—Br | G6 | H |
| 12-22 | Me | Me | Me | Me | C—H | C—Br | G7 | H |
| 12-23 | Me | Me | Me | Me | C—H | C—Br | G8 | H |
| 12-24 | Me | Me | Me | Me | C—H | C—Br | G9 | H |
| 12-25 | Me | Me | Me | Me | C—H | C—I | G6 | H |
| 12-26 | Me | Me | Me | Me | C—H | C—I | G8 | H |
| 12-27 | Me | Me | Me | Me | C—H | C—I | G9 | H |
| 12-28 | Me | Me | Me | Me | C—H | C—Me | G6 | H |
| 12-29 | Me | Me | Me | Me | C—H | C—Me | G8 | H |
| 12-30 | Me | Me | Me | Me | C—H | C—CF3 | G6 | H |
| 12-31 | Me | Me | Me | Me | C—H | C—CF3 | G8 | H |
| 12-32 | Me | Me | Me | Me | C—H | C—NO2 | G6 | H |
| 12-33 | Me | Me | Me | Me | C—H | C—NO2 | G8 | H |
| 12-34 | Me | Me | Me | Me | C—H | C—CN | G1 | H |
| 12-35 | Me | Me | Me | Me | C—H | C—CN | G2 | H |
| 12-36 | Me | Me | Me | Me | C—H | C—CN | G3 | H |
| 12-37 | Me | Me | Me | Me | C—H | C—CN | G4 | H |
| 12-38 | Me | Me | Me | Me | C—H | C—CN | G5 | H |
| 12-39 | Me | Me | Me | Me | C—H | C—CN | G6 | H |
| 12-40 | Me | Me | Me | Me | C—H | C—CN | G7 | H |
| 12-41 | Me | Me | Me | Me | C—H | C—CN | G8 | H |
| 12-42 | Me | Me | Me | Me | C—H | C—CN | G9 | H |
| 12-43 | Me | Me | Me | Et | C—H | C—CN | G6 | H |
| 12-44 | Me | Me | Me | PhCH2 | C—H | C—CN | G6 | H |
| 12-45 | Et | Et | Et | Me | C—H | C—CN | G6 | H |
| 12-46 | Me | Me | tert-Bu | Me | C—H | C—CN | G6 | H |

TABLE 12-continued

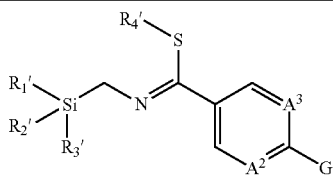

| No. | R1' | R2' | R3' | R4' | A2 | A3 | G | Z |
|---|---|---|---|---|---|---|---|---|
| 12-47 | Me | Me | Me | Et | C—H | C—Br | G6 | H |
| 12-48 | Me | Me | Me | PhCH2 | C—H | C—Br | G6 | H |
| 12-49 | Et | Et | Et | Me | C—H | C—Br | G6 | H |
| 12-50 | Me | Me | tert-Bu | Me | C—H | C—Br | G6 | H |
| 12-51 | Me | Me | Me | Et | C—H | C—H | G6 | H |
| 12-52 | Me | Me | Me | PhCH2 | C—H | C—H | G6 | H |
| 12-53 | Et | Et | Et | Me | C—H | C—H | G6 | H |
| 12-54 | Me | Me | tert-Bu | Me | C—H | C—H | G6 | H |
| 12-55 | Me | Me | Me | H | C—H | C—CN | G6 | H |
| 12-56 | Me | Me | Me | H | C—H | C—Br | G6 | H |
| 12-57 | Me | Me | Me | H | C—H | C—NO2 | G6 | H |

TABLE 13

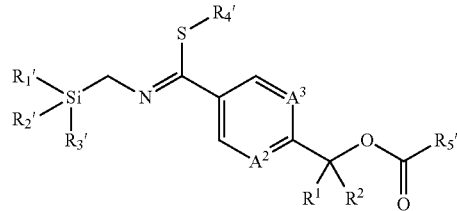

| No. | R1' | R2' | R3' | R4' | A2 | A3 | R1 | R2 | R5' |
|---|---|---|---|---|---|---|---|---|---|
| 13-1 | Me | Me | Me | Me | CH | C—H | H | H | H |
| 13-2 | Me | Me | Me | Me | CH | C—H | H | H | Me |
| 13-3 | Me | Me | Me | Me | CH | C—H | H | H | Et |
| 13-4 | Me | Me | Me | Me | CH | C—H | H | H | n-Pr |
| 13-5 | Me | Me | Me | Me | CH | C—H | H | H | i-Pr |
| 13-6 | Me | Me | Me | Me | CH | C—H | H | H | n-Bu |
| 13-7 | Me | Me | Me | Me | CH | C—H | H | H | Ph |
| 13-8 | Me | Me | Me | Me | CH | C—Br | H | H | H |
| 13-9 | Me | Me | Me | Me | CH | C—Br | H | H | Me |
| 13-10 | Me | Me | Me | Me | CH | C—Br | H | H | Et |
| 13-11 | Me | Me | Me | Me | CH | C—Br | H | H | n-Pr |
| 13-12 | Me | Me | Me | Me | CH | C—Br | H | H | i-Pr |
| 13-13 | Me | Me | Me | Me | CH | C—Br | H | H | n-Bu |
| 13-14 | Me | Me | Me | Me | CH | C—Br | H | H | Ph |
| 13-15 | Me | Me | Me | Me | CH | C—Cl | H | H | Me |
| 13-16 | Me | Me | Me | Me | CH | C—Cl | H | H | Et |
| 13-17 | Me | Me | Me | Me | CH | C—Cl | H | H | n-Pr |
| 13-18 | Me | Me | Me | Me | CH | C—Cl | H | H | i-Pr |
| 13-19 | Me | Me | Me | Me | CH | C—Cl | H | H | n-Bu |
| 13-20 | Me | Me | Me | Me | CH | C—Cl | H | H | Ph |
| 13-21 | Me | Me | Me | Me | CH | C—F | H | H | Me |
| 13-22 | Me | Me | Me | Me | CH | C—F | H | H | Et |
| 13-23 | Me | Me | Me | Me | CH | C—F | H | H | n-Pr |
| 13-24 | Me | Me | Me | Me | CH | C—F | H | H | i-Pr |
| 13-25 | Me | Me | Me | Me | CH | C—F | H | H | n-Bu |
| 13-26 | Me | Me | Me | Me | CH | C—F | H | H | Ph |
| 13-27 | Me | Me | Me | Me | CH | C—CF3 | H | H | Me |
| 13-28 | Me | Me | Me | Me | CH | C—CF3 | H | H | Et |
| 13-29 | Me | Me | Me | Me | CH | C—CF3 | H | H | n-Pr |
| 13-30 | Me | Me | Me | Me | CH | C—CF3 | H | H | i-Pr |
| 13-31 | Me | Me | Me | Me | CH | C—CF3 | H | H | n-Bu |
| 13-32 | Me | Me | Me | Me | CH | C—CF3 | H | H | Ph |
| 13-33 | Me | Me | Me | Me | CH | C—Me | H | H | Me |
| 13-34 | Me | Me | Me | Me | CH | C—Me | H | H | Et |
| 13-35 | Me | Me | Me | Me | CH | C—Me | H | H | n-Pr |
| 13-36 | Me | Me | Me | Me | CH | C—Me | H | H | i-Pr |
| 13-37 | Me | Me | Me | Me | CH | C—Me | H | H | n-Bu |
| 13-38 | Me | Me | Me | Me | CH | C—Me | H | H | Ph |
| 13-39 | Me | Me | Me | Me | CH | C—CN | H | H | Me |

TABLE 13-continued

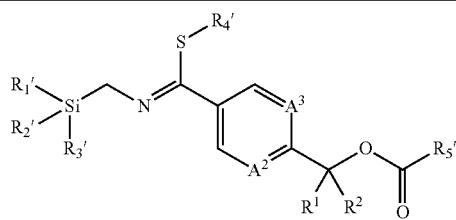

| No. | R1' | R2' | R3' | R4' | A2 | A3 | R1 | R2 | R5' |
|---|---|---|---|---|---|---|---|---|---|
| 13-40 | Me | Me | Me | Me | CH | C—CN | H | H | Et |
| 13-41 | Me | Me | Me | Me | CH | C—CN | H | H | n-Pr |
| 13-42 | Me | Me | Me | Me | CH | C—CN | H | H | i-Pr |
| 13-43 | Me | Me | Me | Me | CH | C—CN | H | H | n-Bu |
| 13-44 | Me | Me | Me | Me | CH | C—CN | H | H | Ph |
| 13-45 | Me | Me | Me | Me | CH | C—NO2 | H | H | Me |
| 13-46 | Me | Me | Me | Me | CH | C—NO2 | H | H | Et |
| 13-47 | Me | Me | Me | Me | CH | C—NO2 | H | H | n-Pr |
| 13-48 | Me | Me | Me | Me | CH | C—NO2 | H | H | i-Pr |
| 13-49 | Me | Me | Me | Me | CH | C—NO2 | H | H | n-Bu |
| 13-50 | Me | Me | Me | Me | CH | C—NO2 | H | H | Ph |
| 13-51 | Me | Me | Me | Me | CH | C—SMe | H | H | Me |
| 13-52 | Me | Me | Me | Me | CH | C—S(O)Me | H | H | Me |
| 13-53 | Me | Me | Me | Me | CH | C—S(O)2Me | H | H | Me |
| 13-54 | Me | Me | Me | Me | CH | C—SCF3 | H | H | Me |
| 13-55 | Me | Me | Me | Me | CH | C—S(O)CF3 | H | H | Me |
| 13-56 | Me | Me | Me | Me | CH | C—S(O)2CF3 | H | H | Me |
| 13-57 | Me | Me | Me | Me | CH | C—OCH3 | H | H | Me |
| 13-58 | Me | Me | Me | Me | CH | C—OCF3 | H | H | Me |
| 13-59 | Me | Me | Me | Me | CH | C—OH | H | H | Me |
| 13-60 | Me | Me | Me | Me | CH | C—SH | H | H | Me |
| 13-61 | Me | Me | Me | Me | CH | C—NH2 | H | H | Me |
| 13-62 | Me | Me | Me | Me | CH | C—NHCOCH3 | H | H | Me |
| 13-63 | Me | Me | Me | Me | CH | C—NHCO2CH3 | H | H | Me |
| 13-64 | Me | Me | Me | Me | CH | C—NHCO2CH2CCl3 | H | H | Me |
| 13-65 | Me | Me | Me | Et | CH | C—Br | H | H | Me |
| 13-66 | Me | Me | Me | PhCH2 | CH | C—Br | H | H | Me |
| 13-67 | Et | Et | Et | Me | CH | C—Br | H | H | Me |
| 13-68 | Me | Me | tert-Bu | Me | CH | C—Br | H | H | Me |
| 13-69 | Me | Me | Me | H | CH | C—H | H | H | Me |
| 13-70 | Me | Me | Me | H | CH | C—Cl | H | H | Me |
| 13-71 | Me | Me | Me | H | CH | C—Br | H | H | Me |
| 13-72 | Me | Me | Me | H | CH | C—F | H | H | Me |
| 13-73 | Me | Me | Me | H | CH | C—I | H | H | Me |
| 13-74 | Me | Me | Me | H | CH | C—Me | H | H | Me |
| 13-75 | Me | Me | Me | H | CH | C—CF3 | H | H | Me |
| 13-76 | Me | Me | Me | H | CH | C—NO2 | H | H | Me |
| 13-77 | Me | Me | Me | H | CH | C—SMe | H | H | Me |

TABLE 14

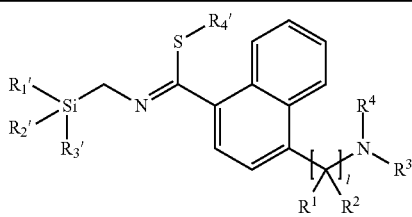

| No. | R1' | R2' | R3' | R4' | R1 | R2 | R4 | R3 | l |
|---|---|---|---|---|---|---|---|---|---|
| 14-1 | Me | Me | Me | Me | H | H | HCO | H | 1 |
| 14-2 | Me | Me | Me | Me | H | H | MeCO | H | 1 |
| 14-3 | Me | Me | Me | Me | H | H | EtCO | H | 1 |
| 14-4 | Me | Me | Me | Me | H | H | cyc-PrCO | H | 1 |
| 14-5 | Me | Me | Me | Me | H | H | CF3CH2CO | H | 1 |
| 14-6 | Me | Me | Me | Me | H | H | MeCO | 2-pyridyl-CH2 | 1 |

TABLE 14-continued

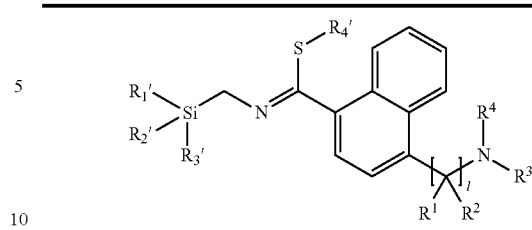

| No. | R1' | R2' | R3' | R4' | R1 | R2 | R4 | R3 | l |
|---|---|---|---|---|---|---|---|---|---|
| 14-7 | Me | Me | Me | Me | H | H | n-PrCO | H | 1 |
| 14-8 | Me | Me | Me | Me | H | H | iso-PrCO | H | 1 |
| 14-9 | Me | Me | Me | Me | H | H | tert-BuCO | H | 1 |
| 14-10 | Me | Me | Me | Me | H | H | CF3CO | H | 1 |
| 14-11 | Me | Me | Me | Me | H | H | PhCO | H | 1 |
| 14-12 | Me | Me | Me | Me | H | H | 2-pyridylCO | H | 1 |
| 14-13 | Me | Me | Me | Me | H | H | 3-pyridylCO | H | 1 |
| 14-14 | Me | Me | Me | Me | H | H | 4-pyridylCO | H | 1 |
| 14-15 | Me | Me | Me | Me | H | H | 2-F—PhCO | H | 1 |
| 14-16 | Me | Me | Me | Me | H | H | 3-F—PhCO | H | 1 |
| 14-17 | Me | Me | Me | Me | H | H | 4-F—PhCO | H | 1 |
| 14-18 | Me | Me | Me | Me | H | H | 2-Cl—PhCO | H | 1 |
| 14-19 | Me | Me | Me | Me | H | H | 3-Cl—PhCO | H | 1 |
| 14-20 | Me | Me | Me | Me | H | H | 4-Cl—PhCO | H | 1 |
| 14-21 | Me | Me | Me | Me | H | H | 2-Br—PhCO | H | 1 |
| 14-22 | Me | Me | Me | Me | H | H | 2-Me—PhCO | H | 1 |
| 14-23 | Me | Me | Me | Me | H | H | vinylCO | H | 1 |
| 14-24 | Me | Me | Me | Me | H | H | HCCCO | H | 1 |
| 14-25 | Me | Me | Me | Me | H | H | MeSO2 | H | 1 |
| 14-26 | Me | Me | Me | Me | H | H | CF3SO2 | H | 1 |
| 14-27 | Me | Me | Me | Me | H | H | MeHNCO | H | 1 |
| 14-28 | Me | Me | Me | Me | H | H | Me2NCO | H | 1 |
| 14-29 | Me | Me | Me | Me | H | H | MeOC(=O) | H | 1 |
| 14-30 | Me | Me | Me | Me | H | H | MeSC(=O) | H | 1 |
| 14-31 | Me | Me | Me | Me | H | H | MeCS | H | 1 |
| 14-32 | Me | Me | Me | Me | H | H | MeON(Me)CO | H | 1 |
| 14-33 | Me | Me | Me | Et | H | H | MeCO | H | 1 |
| 14-34 | Me | Me | Me | PhCH2 | H | H | MeCO | H | 1 |
| 14-35 | Et | Et | Et | Me | H | H | MeCO | H | 1 |
| 14-36 | Me | Me | tert-Bu | Me | H | H | MeCO | H | 1 |
| 14-37 | Me | Me | Me | H | H | H | tert-BuO(C=O) | H | 1 |

TABLE 15

| No. | R1' | R2' | R3' | R4' | R1 | R2 | R5' |
|---|---|---|---|---|---|---|---|
| 15-1 | Me | Me | Me | Me | H | H | H |
| 15-2 | Me | Me | Me | Me | H | H | Me |
| 15-3 | Me | Me | Me | Me | H | H | Et |
| 15-4 | Me | Me | Me | Me | H | H | n-Pr |
| 15-5 | Me | Me | Me | Me | H | H | i-Pr |
| 15-6 | Me | Me | Me | Me | H | H | n-Bu |
| 15-7 | Me | Me | Me | Me | H | H | Ph |
| 15-8 | Me | Me | Me | Et | H | H | Me |
| 15-9 | Me | Me | Me | PhCH2 | H | H | Me |
| 15-10 | Et | Et | Et | Me | H | H | Me |
| 15-11 | Me | Me | tert-Bu | Me | H | H | Me |
| 15-12 | Me | Me | Me | H | H | H | Me |

TABLE 16

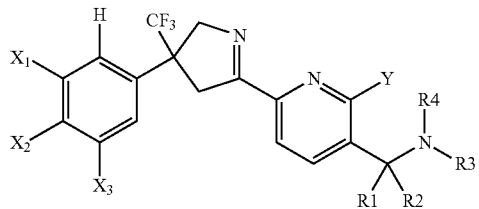

| No. | X₁ | X₂ | X₃ | Y | R¹ | R² | R⁴ | R³ |
|---|---|---|---|---|---|---|---|---|
| 16-1 | Cl | H | Cl | H | H | H | MeCO | H |
| 16-2 | Cl | H | Cl | H | H | H | MeCO | MeCO |
| 16-3 | Cl | H | Cl | H | H | H | MeCO | 2-py-CO |
| 16-4 | Cl | H | Cl | CF3 | H | H | MeCO | H |
| 16-5 | Cl | H | Cl | CF3 | H | H | EtCO | H |
| 16-6 | Cl | H | Cl | CF3 | H | H | CF3CH2CO | H |
| 16-7 | Cl | H | Cl | CF3 | H | H | cyclo-PrCO | H |
| 16-8 | Cl | H | Cl | CF3 | H | H | EtNHCO | H |
| 16-9 | Cl | H | Cl | CF3 | H | H | CH3SCH2CO | H |
| 16-10 | Cl | H | Cl | CF3 | H | H | CH3SOCH2CO | H |
| 16-11 | Cl | H | Cl | CF3 | H | H | CH3SO2CH2CO | H |
| 16-12 | Cl | Cl | Cl | CF3 | H | H | MeCO | H |
| 16-13 | Cl | Cl | Cl | CF3 | H | H | EtCO | H |
| 16-14 | Cl | Cl | Cl | CF3 | H | H | CF3CH2CO | H |
| 16-15 | Cl | Cl | Cl | CF3 | H | H | cyclo-PrCO | H |
| 16-16 | Cl | Cl | Cl | CF3 | H | H | EtNHCO | H |
| 16-17 | Cl | Cl | Cl | CF3 | H | H | CH3SCH2CO | H |
| 16-18 | Cl | Cl | Cl | CF3 | H | H | CH3SOCH2CO | H |
| 16-19 | Cl | Cl | Cl | CF3 | H | H | CH3SO2CH2CO | H |
| 16-20 | CF3 | H | CF3 | CF3 | H | H | MeCO | H |
| 16-21 | CF3 | H | CF3 | CF3 | H | H | EtCO | H |
| 16-22 | CF3 | H | CF3 | CF3 | H | H | CF3CH2CO | H |

TABLE 16-continued

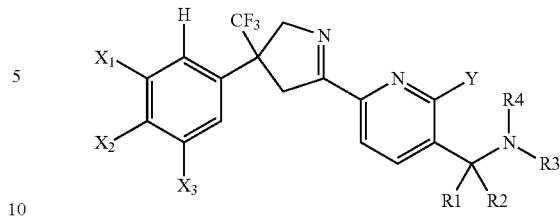

| No. | X₁ | X₂ | X₃ | Y | R¹ | R² | R⁴ | R³ |
|---|---|---|---|---|---|---|---|---|
| 16-23 | CF3 | H | CF3 | CF3 | H | H | cyclo-PrCO | H |
| 16-24 | CF3 | H | CF3 | CF3 | H | H | EtNHCO | H |
| 16-25 | CF3 | H | CF3 | CF3 | H | H | CH3SCH2CO | H |
| 16-26 | CF3 | H | CF3 | CF3 | H | H | CH3SOCH2CO | H |
| 16-27 | CF3 | H | CF3 | CF3 | H | H | CH3SO2CH2CO | H |
| 16-28 | Cl | H | Cl | CF3 | H | H | cyclo-PrCH2CO | H |
| 16-29 | Cl | H | Cl | CF3 | H | H | MeCOCH2CO | H |
| 16-30 | Cl | H | Cl | CF3 | H | H | cyclo-PrNHCO | H |
| 16-31 | Cl | H | Cl | CF3 | H | H | CHCCH2NHCO | H |
| 16-32 | Cl | H | Cl | CF3 | H | H | CH2=CHCH2NHCO | H |
| 16-33 | Cl | H | Cl | Cl | H | H | CF3CH2CO | H |
| 16-34 | Cl | H | Cl | Me | H | H | CF3CH2CO | H |
| 16-35 | Cl | H | Cl | Br | H | H | CF3CH2CO | H |
| 16-36 | Cl | H | Cl | CF3 | Me | H | cyclo-PrCO | H |
| 16-37 | Cl | H | Cl | CF3 | H | Me | EtNHCO | H |
| 16-38 | Cl | H | Cl | CF3 | Me | Me | cyclo-PrCH2CO | H |
| 16-39 | Cl | H | Cl | CF3 | Me | Me | CH2=CHCH2NHCO | H |
| 16-40 | Cl | H | Cl | CF3 | H | H | tert-BuOCO | H |
| 16-41 | Cl | Cl | Cl | CF3 | H | H | tert-BuOCO | H |
| 16-42 | CF3 | H | CF3 | CF3 | CN | H | tert-BuOCO | H |

TABLE 17

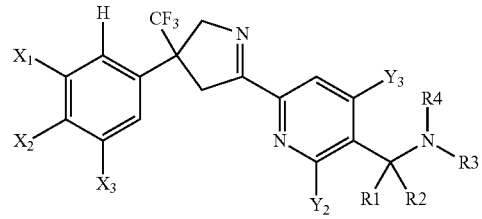

| No. | X₁ | X₂ | X₃ | Y₂ | Y₃ | R¹ | R² | R⁴ | R³ |
|---|---|---|---|---|---|---|---|---|---|
| 17-1 | Cl | H | Cl | H | H | H | H | MeCO | H |
| 17-2 | Cl | H | Cl | H | H | H | H | MeCO | MeCO |
| 17-3 | Cl | H | Cl | H | H | H | H | MeCO | 2-py-CO |
| 17-4 | Cl | H | Cl | H | CF3 | H | H | MeCO | H |
| 17-5 | Cl | H | Cl | H | CF3 | H | H | EtCO | H |
| 17-6 | Cl | H | Cl | H | CF3 | H | H | CF3CH2CO | H |
| 17-7 | Cl | H | Cl | H | CF3 | H | H | cyclo-PrCO | H |
| 17-8 | Cl | H | Cl | H | CF3 | H | H | EtNHCO | H |
| 17-9 | Cl | H | Cl | H | CF3 | H | H | CH3SCH2CO | H |
| 17-10 | Cl | H | Cl | H | CF3 | H | H | CH3SOCH2CO | H |
| 17-11 | Cl | H | Cl | H | CF3 | H | H | CH3SO2CH2CO | H |
| 17-12 | Cl | Cl | Cl | H | CF3 | H | H | MeCO | H |
| 17-13 | Cl | Cl | Cl | H | CF3 | H | H | EtCO | H |
| 17-14 | Cl | Cl | Cl | H | CF3 | H | H | CF3CH2CO | H |
| 17-15 | Cl | Cl | Cl | H | CF3 | H | H | cyclo-PrCO | H |
| 17-16 | Cl | Cl | Cl | H | CF3 | H | H | EtNHCO | H |
| 17-17 | Cl | Cl | Cl | H | CF3 | H | H | CH3SCH2CO | H |
| 17-18 | Cl | Cl | Cl | H | CF3 | H | H | CH3SOCH2CO | H |
| 17-19 | Cl | Cl | Cl | H | CF3 | H | H | CH3SO2CH2CO | H |
| 17-20 | CF3 | H | CF3 | H | CF3 | H | H | MeCO | H |
| 17-21 | CF3 | H | CF3 | H | CF3 | H | H | EtCO | H |
| 17-22 | CF3 | H | CF3 | H | CF3 | H | H | CF3CH2CO | H |
| 17-23 | CF3 | H | CF3 | H | CF3 | H | H | cyclo-PrCO | H |
| 17-24 | CF3 | H | CF3 | H | CF3 | H | H | EtNHCO | H |
| 17-25 | CF3 | H | CF3 | H | CF3 | H | H | CH3SCH2CO | H |
| 17-26 | CF3 | H | CF3 | H | CF3 | H | H | CH3SOCH2CO | H |
| 17-27 | CF3 | H | CF3 | H | CF3 | H | H | CH3SO2CH2CO | H |

TABLE 17-continued

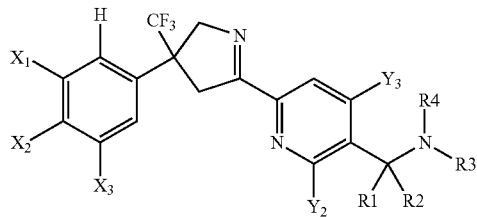

| No. | X₁ | X₂ | X₃ | Y₂ | Y₃ | R¹ | R² | R⁴ | R³ |
|---|---|---|---|---|---|---|---|---|---|
| 17-28 | Cl | H | Cl | H | CF3 | H | H | cyclo-PrCH2CO | H |
| 17-29 | Cl | H | Cl | H | CF3 | H | H | MeCOCH2CO | H |
| 17-30 | Cl | H | Cl | H | CF3 | H | H | cyclo-PrNHCO | H |
| 17-31 | Cl | H | Cl | H | CF3 | H | H | CHCCH2NHCO | H |
| 17-32 | Cl | H | Cl | H | CF3 | H | H | CH2=CHCH2NHCO | H |
| 17-33 | Cl | H | Cl | H | Cl | H | H | CF3CH2CO | H |
| 17-34 | Cl | H | Cl | H | Me | H | H | CF3CH2CO | H |
| 17-35 | Cl | H | Cl | H | Br | H | H | CF3CH2CO | H |
| 17-36 | Cl | H | Cl | H | CF3 | Me | H | cyclo-PrCO | H |
| 17-37 | Cl | H | Cl | H | CF3 | H | Me | EtNHCO | H |
| 17-38 | Cl | H | Cl | H | CF3 | Me | Me | cyclo-PrCH2CO | H |
| 17-39 | Cl | H | Cl | H | CF3 | CN | H | CH2=CHCH2NHCO | H |

TABLE 18

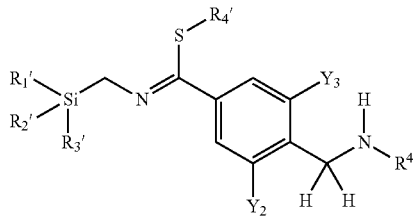

TABLE 18-continued

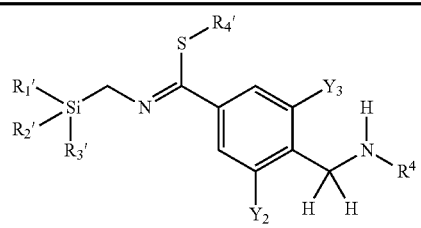

| No. | R₁' | R₂' | R₃' | R₄' | Y₂ | Y₃ | R⁴ | No. | R₁' | R₂' | R₃' | R₄' | Y₂ | Y₃ | R⁴ |
|---|---|---|---|---|---|---|---|---|---|---|---|---|---|---|---|
| 18-1 | Me | Me | Me | Me | H | H | MeCO | 18-36 | Me | Me | Me | Me | H | NO2 | tert-BuO(C=O) |
| 18-2 | Me | Me | Me | Me | H | H | EtCO | 18-37 | Me | Me | Me | Me | H | SMe | tert-BuO(C=O) |
| 18-3 | Me | Me | Me | Me | H | H | cyclo-PrCO | 18-38 | Me | Me | Me | H | H | H | MeCO |
| 18-4 | Me | Me | Me | Me | H | H | CF3CH2CO | 18-39 | Me | Me | Me | H | H | H | EtCO |
| 18-5 | Me | Me | Me | Me | H | H | EtNCO | 18-40 | Me | Me | Me | H | H | H | cyclo-PrCO |
| 18-6 | Me | Me | Me | Me | H | H | tert-BuO(C=O) | 18-41 | Me | Me | Me | H | H | H | CF3CH2CO |
| 18-7 | Me | Me | Me | Me | H | H | MeO(C=O) | 18-42 | Me | Me | Me | H | H | H | EtNCO |
| 18-8 | Me | Me | Me | Me | H | H | PhCH2OCO | 18-43 | Me | Me | Me | H | H | H | tert-BuO(C=O) |
| 18-9 | Me | Me | Me | Me | H | Br | MeCO | 18-44 | Me | Me | Me | H | H | H | MeO(C=O) |
| 18-10 | Me | Me | Me | Me | H | Br | EtCO | 18-45 | Me | Me | Me | H | H | H | PhCH2O(C=O) |
| 18-11 | Me | Me | Me | Me | H | Br | cyclo-PrCO | 18-46 | Me | Me | Me | H | H | Br | MeCO |
| 18-12 | Me | Me | Me | Me | H | Br | CF3CH2CO | 18-47 | Me | Me | Me | H | H | Br | EtCO |
| 18-13 | Me | Me | Me | Me | H | Br | EtNCO | 18-48 | Me | Me | Me | H | H | Br | cyclo-PrCO |
| 18-14 | Me | Me | Me | Me | H | Br | tert-BuO(C=O) | 18-49 | Me | Me | Me | H | H | Br | CF3CH2CO |
| 18-15 | Me | Me | Me | Me | H | Br | MeO(C=O) | 18-50 | Me | Me | Me | H | H | Br | EtNCO |
| 18-16 | Me | Me | Me | Me | H | Br | PhCH2O(C=O) | 18-51 | Me | Me | Me | H | H | Br | tert-BuO(C=O) |
| 18-17 | Me | Me | Me | Me | H | Cl | MeCO | 18-52 | Me | Me | Me | H | H | Br | MeO(C=O) |
| 18-18 | Me | Me | Me | Me | H | Cl | EtCO | 18-53 | Me | Me | Me | H | H | Br | PhCH2O(C=O) |
| 18-19 | Me | Me | Me | Me | H | Cl | cyclo-PrCO | 18-54 | Me | Me | Me | H | H | Cl | MeCO |
| 18-20 | Me | Me | Me | Me | H | Cl | CF3CH2CO | 18-55 | Me | Me | Me | H | H | Cl | EtCO |
| 18-21 | Me | Me | Me | Me | H | Cl | EtNCO | 18-56 | Me | Me | Me | H | H | Cl | cyclo-PrCO |
| 18-22 | Me | Me | Me | Me | H | Cl | tert-BuO(C=O) | 18-57 | Me | Me | Me | H | H | Cl | CF3CH2CO |
| 18-23 | Me | Me | Me | Me | H | Cl | MeO(C=O) | 18-58 | Me | Me | Me | H | H | Cl | EtNCO |
| 18-24 | Me | Me | Me | Me | H | Cl | PhCH2O(C=O) | 18-59 | Me | Me | Me | H | H | Cl | tert-BuO(C=O) |
| 18-25 | Me | Me | Me | Me | H | CF₃ | MeCO | 18-60 | Me | Me | Me | H | H | Cl | MeO(C=O) |
| 18-26 | Me | Me | Me | Me | H | CF₃ | EtCO | 18-61 | Me | Me | Me | H | H | Cl | PhCH2O(C=O) |
| 18-27 | Me | Me | Me | Me | H | CF₃ | cyclo-PrCO | 18-62 | Me | Me | Me | H | H | CF₃ | MeCO |
| 18-28 | Me | Me | Me | Me | H | CF₃ | CF3CH2CO | 18-63 | Me | Me | Me | H | H | CF₃ | EtCO |
| 18-29 | Me | Me | Me | Me | H | CF₃ | EtNCO | 18-64 | Me | Me | Me | H | H | CF₃ | cyclo-PrCO |
| 18-30 | Me | Me | Me | Me | H | CF₃ | tert-BuO(C=O) | 18-65 | Me | Me | Me | H | H | CF₃ | CF3CH2CO |
| 18-31 | Me | Me | Me | Me | H | CF₃ | MeO(C=O) | 18-66 | Me | Me | Me | H | H | CF₃ | EtNCO |
| 18-32 | Me | Me | Me | Me | H | CF₃ | PhCH2O(C=O) | 18-67 | Me | Me | Me | H | H | CF₃ | tert-BuO(C=O) |
| 18-33 | Me | Me | Me | Me | H | Me | tert-BuO(C=O) | 18-68 | Me | Me | Me | H | H | CF₃ | MeO(C=O) |
| 18-34 | Me | Me | Me | Me | H | F | tert-BuO(C=O) | 18-69 | Me | Me | Me | H | H | CF₃ | PhCH2O(C=O) |
| 18-35 | Me | Me | Me | Me | H | I | tert-BuO(C=O) | 18-70 | Me | Me | Me | H | H | Me | tert-BuO(C=O) |

TABLE 18-continued

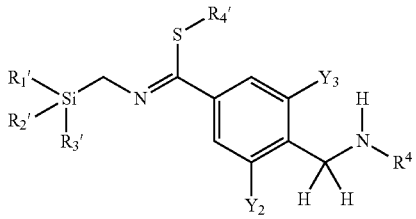

| No. | $R_1'$ | $R_2'$ | $R_3'$ | $R_4'$ | $Y_2$ | $Y_3$ | $R^4$ |
|---|---|---|---|---|---|---|---|
| 18-71 | Me | Me | Me | H | H | F | tert-BuO(C=O) |
| 18-72 | Me | Me | Me | H | H | I | tert-BuO(C=O) |

TABLE 18-continued

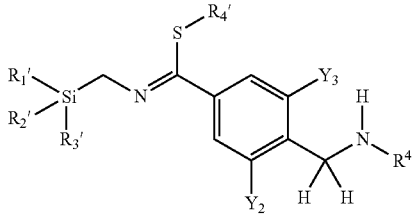

| No. | $R_1'$ | $R_2'$ | $R_3'$ | $R_4'$ | $Y_2$ | $Y_3$ | $R^4$ |
|---|---|---|---|---|---|---|---|
| 18-73 | Me | Me | Me | H | H | NO2 | tert-BuO(C=O) |
| 18-74 | Me | Me | Me | H | H | SMe | tert-BuO(C=O) |

TABLE 19

| No. | 1H-NMR |
|---|---|
| 1-21 | 1H-NMR (CDCl3) δ: 3.48 (1H, d), 3.81 (1H, d), 4.49 (1H, d), 4.94 (1H, d), 7.27 (2H, s), 7.40 (1H, t), 7.64 (1H, d), 7.94 (1H, dd), 8.16 (1H, s), 8.26 (1H, d), 8.60 (1H, s) |
| 1-35 | 1H-NMR (CDCl3) δ: 3.49 (1H, d), 3.81 (1H, dd), 4.49 (1H, d), 4.94 (1H, dd), 6.59 (1H, dd), 7.28 (2H, d), 7.40 (1H, dd0), 7.85 (1H, d), 7.95 (1H, d), 8.19 (1H, dd), 8.25 (1H, d), 8.28 (1H, d) |
| 1-36 | 1H-NMR (CDCl3) δ: 3.49 (1H, d), 3.82 (1H, dd), 4.50 (1H, d), 4.96 (1H, dd), 7.27 (2H, d), 7.31 (1H, dd), 7.40 (1H, d), 7.42 (1H, d), 7.56 (1H, d), 7.93 (1H, s), 8.23 (1H, dd), 8.30 (1H, d) |
| 1-37 | 1H-NMR (CDCl3) δ: 3.52 (1H, d), 3.84 (1H, dd), 4.52 (1H, d), 4.97 (1H, dd), 7.28 (2H, t), 7.41 (1H, dd), 7.95 (1H, d), 8.06 (1H, d), 8.28 (1H, dd), 8.37 (1H, d), 8.38 (1H, d) |
| 1-38 | 1H-NMR (CDCl3) δ: 3.50 (1H, d), 3.83 (1H, dd), 4.50 (1H, d), 4.95 (1H, dd), 7.28 (2H, d), 7.40 (1H, dd), 7.40 (2H, s), 8.24-8.23 (2H, m), 8.30 (1H, d) |
| 1-39 | 1H-NMR (CDCl3) δ: 3.50 (1H, d), 3.82 (1H, d), 4.51 (1H, d), 4.96 (1H, d), 7.27 (2H, s), 7.41 (1H, d), 7.93 (1H, d), 8.22-8.27 (2H, m), 8.32 (1H, d) |
| 1-41 | 1H-NMR (CDCl3) δ: 3.53 (1H, d), 3.85 (1H, dd), 4.53 (1H, d), 4.98 (1H, dd), 7.28 (2H, d), 7.41 (1H, dd), 8.27 (1H, d), 8.32 (1H, dd), 8.41 (1H, d), 8.82 (1H, s) |
| 1-42 | 1H-NMR (CDCl3) δ: 3.55 (1H, d), 3.86 (1H, dd), 4.53 (1H, d), 4.99 (1H, dd), 7.29 (2H, d), 7.41 (1H, dd), 8.01 (1H, d), 8.34 (1H, dd), 8.44 (1H, d), 9.36 (1H, s) |
| 1-72 | 1H-NMR (CDCl3) δ: 3.56 (1H, d), 3.95 (1H, d), 4.58 (1H, d), 5.09 (1H, d), 7.83 (2H, s), 7.93-7.98 (2H, m), 8.29 (3H, m), 8.91 (1H, d) |
| 1-74 | 1H-NMR (CDCl3) δ: 3.59 (1H, d), 3.93 (1H, d), 4.59 (1H, d), 5.06 (1H, d), 7.66 (1H, t), 7.75 (1H, d), 7.94 (1H, d), 8.22 (1H, s), 8.26-8.36 (4H, m), 8.90 (1H, s) |
| 1-78 | 1H-NMR (CDCl3) δ: 3.48 (1H, d), 3.82 (1H, d), 4.50 (1H, d), 4.96 (1H, d), 7.41 (2H, s), 7.94 (1H, d), 8.22-8.32 (3H, m), 8.90 (1H, s) |
| 1-82 | 1H-NMR (CDCl3) δ: 3.53 (1H, d), 3.88 (1H, d), 4.55 (1H, d), 5.02 (1H, d), 7.55-7.72 (4H, m), 7.94 (1H, d), 8.21-8.30 (3H, m), 8.90 (1H, s) |
| 1-83 | 1H-NMR (CDCl3) δ: 3.53 (1H, d), 3.85 (1H, d), 4.55 (1H, d), 4.99 (1H, d), 7.25-7.35 (2H, m), 7.48 (1H, t), 7.93 (1H, d), 8.22-8.29 (3H, m), 8.32 (1H, s), 8.89 (1H, s) |
| 1-94 | 1H-NMR (CDCl3) δ: 3.50 (1H, d), 3.79 (1H, d), 4.50 (1H, d), 4.96 (1H, d), 7.47 (2H, s), 7.71 (1H, s), 7.92-7.95 (1H, m), 8.21-8.34 (3H, m), 8.90 (1H, s) |
| 1-95 | 1H-NMR (CDCl3) δ: 3.51 (1H, d), 3.88 (1H, d), 4.52 (1H, d), 5.01 (1H, d), 7.65 (2H, d), 7.95 (1H, dd), 8.22-8.35 (3H, m), 8.91 (1H, s) |
| 1-96 | 1H-NMR (CDCl3) δ: 3.50 (1H, d), 3.81 (1H, dd), 4.51 (1H, d), 4.96 (1H, dd), 7.27 (2H, d), 7.41 (1H, dd), 7.92 (1H, d), 8.11 (1H, s), 8.25 (1H, dd), 8.32 (1H, d), 8.62 (1H, s) |
| 1-97 | 1H-NMR (CDCl3) δ: 3.50 (1H, d), 3.83 (1H, dd), 4.51 (1H, d), 4.97 (1H, dd), 7.27 (2H, d), 7.41 (1H, dd), 7.92 (1H, d), 8.27 (1H, dd), 8.34 (1H, d), 8.39 (1H, s), 8.88 (1H, s) |
| 1-98 | 1H-NMR (CDCl3) δ: 3.48 (1H, d), 3.81 (1H, dd), 4.49 (1H, d), 4.94 (1H, dd), 7.27 (2H, d), 7.40 (1H, dd), 7.77 (1H, d), 7.89 (1H, d), 8.19 (1H, dd), 8.26-8.25 (2H, m) |
| 1-99 | 1H-NMR (CDCl3) δ: 2.64 (3H, s), 3.56 (1H, d), 3.87 (1H, dd), 4.54 (1H, d), 4.99 (1H, d), 7.29 (2H, d), 7.41 (1H, dd), 7.68 (1H, d), 8.34 (1H, dd), 8.44 (1H, d) |
| 1-100 | 1H-NMR (CDCl3) δ: 2.72 (3H, s), 3.51 (1H, d), 3.84 (1H, dd), 4.52 (1H, d), 4.97 (1H, dd), 7.28 (2H, d), 7.41 (1H, dd), 8.22 (1H, d), 8.28 (1H, dd), 8.37 (1H, d) |
| 1-101 | 1H-NMR (CDCl3) δ: 2.27 (3H, s), 3.48 (1H, d), 3.77-3.84 (2H, m), 4.49 (1H, d), 4.94 (1H, dd), 5.72 (1H, s), 7.27 (2H, d), 7.40 (1H, dd), 7.53 (1H, d), 8.14 (1H, dd), 8.21 (1H, d) |
| 1-102 | 1H-NMR (CDCl3) δ: 2.14 (3H, s), 2.33 (3H, s), 3.49 (1H, d), 3.82 (1H, dd), 4.50 (1H, d), 4.95 (1H, dd), 6.82 (1H, s), 7.27 (2H, d), 7.40 (1H, dd), 7.52 (1H, d), 8.17 (1H, dd), 8.23 (1H, s), 8.26 (1H, d) |
| 1-103 | 1H-NMR (CDCl3) δ: 2.37 (6H, s), 3.53 (1H, d), 3.84 (1H, d), 4.54 (1H, d), 4.98 (1H, d), 7.15 (2H, s), 7.93 (1H, d), 8.22-8.36 (3H, m), 8.89 (1H, s) |
| 2-13 | 1H-NMR (CDCl3) δ: 2.04 (3H, s), 3.41 (1H, d), 3.73-3.77 (1H, m), 4.43-4.53 (3H, m), 4.89 (1H, d), 5.98 (1H, s), 7.24-7.28 (2H, m), 7.38-7.38 (1H, m), 7.47-7.49 (1H, m), 7.71-7.78 (1H, m), 8.07-8.07 (1H, m) |
| 2-19 | 1H-NMR (CDCl3) δ: 1.18 (3H, t), 2.27 (2H, q), 3.41 (1H, d), 3.72-3.78 (1H, m), 4.43-4.54 (3H, m), 4.87-4.90 (1H, m), 5.93 (1H, s), 7.26-7.28 (2H, m), 7.38-7.38 (1H, m), 7.47-7.49 (1H, m), 7.71-7.74 (1H, m), 8.07-8.08 (1H, m) |
| 2-117 | 1H-NMR (CDCl3) δ: 2.04 (3H, s), 3.47 (1H, d), 3.87 (1H, d), 4.50-4.54 (3H, m), 5.01 (1H, d), 5.96 (1H, s), 7.50 (1H, d), 7.76 (1H, dd), 7.81 (2H, s), 7.91 (1H, s), 8.09 (1H, d) |

TABLE 19-continued

| No. | 1H-NMR |
|---|---|
| 2-153 | 1H-NMR (CDCl3) δ: 0.75-0.79 (2H, m), 0.99-1.01 (2H, m), 1.36-1.44 (1H, m), 2.04 (3H, s), 3.41 (1H, d), 3.72-3.78 (1H, m), 4.44 (1H, d), 4.56 (2H, d), 4.88 (1H, d), 6.16-6.19 (1H, m), 7.26-7.26 (2H, m), 7.38-7.38 (1H, m), 7.47-7.49 (1H, m), 7.71-7.74 (1H, m), 8.07-8.07 (1H, m) |
| 2-154 | 1H-NMR (CDCl3) δ: 3.12 (2H, q), 3,42 (1H, d), 3.75 (1H, d), 4.44 (1H, d), 4.60 (2H, d), 4.89 (1H, d), 6.22-6.25 (1H, m), 7.24-7.27 (2H, m), 7.38-7.39 (1H, m), 7.45-7.48 (1H, m), 7.73-7.75 (1H, m), 8.09 (1H, d) |
| 2-156 | 1H-NMR (CDCl3) δ: 2.04 (3H, s), 3.40 (1H, d), 3.72-3.78 (1H, m), 4.42 (1H, d), 4.55 (2H, d), 4.86-4.89 (1H, m), 6.01-6.04 (1H, m), 7.39 (2H, s), 7.48 (1H, d), 7.66-7.69 (1H, m), 7.88 (1H, d) |
| 2-157 | 1H-NMR (CDCl3) δ: 2.26 (2H, q), 3.40 (1H, d), 3.73-3.76 (1H, m), 4.43 (1H, d), 4.56 (2H, d), 4.88 (1H, d), 5.89-5.93 (1H, m), 7.39 (2H, s), 7.49 (1H), 7.66-7.69 (1H, m), 7.89 (1H, d) |
| 2-158 | 1H-NMR (CDCl3) δ: 0.75-0.79 (2H, m), 0.99-1.01 (2H, m), 1.38-1.41 (1H, m), 3.40 (1H, d), 3.72-3.78 (1H, m), 4.43 (1H, d), 4.58 (2H, d), 4.85-4.91 (1H, m), 6.13-6.16 (1H, m), 7.39 (2H, s), 7.47-7.49 (1H, m), 7.66-7.69 (1H, m), 7.88-7.89 (1H, m) |
| 2-161 | 1H-NMR (CDCl3) δ: 2.04 (3H, s), 3.44 (1H, d), 3.79 (1H, d), 4.44 (1H, d), 4.64 (2H, d), 4.88-4.91 (1H, m), 6.03-6.05 (1H, m), 7.41 (2H, s), 7.65-7.68 (1H, m), 7.94-7.97 (1H, m), 8.12-8.15 (1H, m) |
| 2-162 | 1H-NMR (CDCl3) δ: 1.18 (3H, t), 2.27 (2H, q), 3.45 (1H, d), 3.77-3.82 (1H, m), 4.45 (1H, d), 4.66 (2H, d), 4.87-4.93 (1H, m), 5.99-6.01 (1H, m), 7.42 (2H, s), 7.66-7.69 (1H, m), 7.95-7.98 (1H, m), 8.13-8.16 (1H, m) |
| 2-163 | 1H-NMR (CDCl3) δ: 0.74-0.81 (2H, m), 0.98-1.05 (2H, m), 1.36-1.44 (1H, m), 3.44 (1H, d), 3.76-3.82 (1H, m), 4.45 (1H, d), 4.67 (2H, d), 4.87-4.93 (1H, m), 6.16-6.18 (1H, m), 7.41 (2H, s), 7.65-7.69 (1H, m), 7.94-7.97 (1H, m), 8.14-8.14 (1H, m) |
| 2-164 | 1H-NMR (CDCl3) δ: 3.11-3.15 (2H, m), 3.45 (1H, d), 3.77-3.82 (1H, m), 4.45 (1H, d), 4.70 (2H, dz), 4.88-4.94 (1H, m), 6.23-6.26 (1H, m), 7.40 (2H, s), 7.64-7.66 (1H, m), 7.96-7.99 (1H, m), 8.17 (1H, s) |
| 2-165 | 1H-NMR (CDCl3) δ: 2.04 (3H, s), 3.52 (1H, d), 3.88-3.94 (1H, m), 4.53 (1H, d), 4.65 (2H, d), 5.00-5.06 (1H, m), 6.05-6.07 (1H, m), 7.68 (1H, d), 7.83 (2H, s), 7.92 (1H, s), 7.99 (1H, d), 8.16 (1H, s). |
| 2-166 | 1H-NMR (CDCl3) δ: 1.18 (3H, t), 2.27 (2H, q), 3.52 (1H, d), 3.88-3.94 (1H, m), 4.53 (1H, d), 4.66 (2H, d), 5.00-5.06 (1H, m), 5.98 (1H, t), 7.68 (1H, d), 7.83 (2H, s), 7.92 (1H, s), 7.97-8.00 (1H, m), 8.16 (1H, d) |
| 2-167 | 1H-NMR (CDCl3) δ: 0.76-0.80 (2H, m), 0.96-1.07 (2H, m), 1.39-1.41 (1H, m), 3.50-3.53 (1H, m), 3.88-3.94 (1H, m), 4.52 (1H, d), 4.68 (2H, d), 5.00-5.06 (1H, m), 6.13-6.15 (1H, m), 7.68 (1H, d), 7.83 (2H, s), 7.92 (1H, s), 7.97-8.00 (1H, m), 8.16 (1H, s) |
| 2-168 | 1H-NMR (CDCl3) δ: 3.12-3.15 (2H, m), 3.53 (1H, d), 3.89-3.95 (1H, m), 4.53 (1H, d), 4.69 (2H, d), 5.03 (1H, d), 6.54 (1H, s), 7.64 (1H, d), 7.83 (2H, s), 7.92 (1H, s), 7.99 (1H, d), 8.17 (1H, s) |
| 2-170 | 1H-NMR (CDCL3) δ: 1.09-0.77 (4H, m), 1.40 (1H, m), 3.40 (1H, d), 3.75 (1H, d), 4.40 (1H, d), 4.56 (2H, d), 4.88 (1H, d), 6.17 (1H, s), 7.37 (2H, d), 7.48 (1H, d), 7.72 (1H, d), 8.06 (1H, s) |
| 2-134 | 1H-NMR (CDCl3) δ: 2.07 (3H, s), 3.40 (1H, d), 3.75 (1H, d), 4.43 (1H, d), 4.55 (2H, d), 4.88 (1H, d), 5.97 (1H, s), 7.40 (2H, s), 7.49 (1H, d), 7,73 (1H, dd), 8.07 (1H, d) |
| 2-139 | 1H-NMR (CDCl3) δ: 2.05 (3H, s), 3.41 (1H, d), 3.80 (1H, d), 4.45 (1H, d), 4.54 (2H, dz), 4.93 (1H, d), 5.96 (1H, s), 7.49 (1H, d), 7.59 (1H, s), 7.68 (1H, s), 7.74 (1H, dd), 8.07 (1H, d) |
| 2-172 | 1H-NMR (CDCl3) δ: 0.74-1.08 (7H, m), 1.39-1.42 (1H, m), 3.44 (1H, d), 3.80 (1H, d), 4.45 (1H, d), 4.57 (2H, d), 4.93 (1H, d), 6.21 (1H, s), 7.49 (1H, m), 7.59 (1H, s), 7.70-7.77 (2H, m), 8.06 (1H, d) |
| 2-159 | 1H-NMR (CDCl3) δ: 3.14-3.20 (2H, m), 3.42 (1H, d), 3.77 (1H, d), 4.44 (1H, d), 4.60 (2H, d), 4.89 (1H, dd), 6.35-6.39 (1H, m), 7.39 (2H, s), 7.46 (1H, d), 7.67-7.70 (1H, m), 7.89 (1H, s) |
| 2-160 | 1H-NMR (CDCl3) δ: 2.04 (3H, s), 3.46 (1H, d), 3.79 (1H, dd), 4.45 (1H, d), 4.64 (3H, d), 4.91 (1H, dd), 6.02-6.04 (1H, m), 7.27 (2H, s), 7.38-7.39 (1H, m), 7.67 (1H, d), 7.96 (1H, d), 8.14 (1H, s) |
| 2-171 | 1H-NMR (CDCl3) δ: 3.10-3.14 (2H, m), 3.40 (1H, d), 3.75 (1H, dd), 4.42-4.45 (1H, m), 4.59 (2H, d), 4.88 (1H, dd), 6.29-6.30 (1H, m), 7.39-7.48 (3H, m), 7.72-7.75 (1H, m), 8.08-8.09 (1H, m) |
| 2-173 | 1H-NMR (CDCL3) δ: 3.14 (2H, q), 3.43 (1H, d), 3.80 (1H, d), 4.45 (1H, d), 4.58 (2H, d), 4.93 (1H, d), 6.43 (1H, s), 7.45 (1H, d), 7.59 (1H, s), 7.84-7.68 (2H, m), 8.06 (1H, s) |
| 2-174 | 1H-NMR (CDCl3) δ: 2.04 (3H, s), 3.40 (1H, d), 3.74 (1H, d), 4.43 (1H, d), 4.54 (2H, d), 4.88 (1H, d), 5.97 (1H, s), 7.46-7.48 (3H, m), 7.68-7.75 (2H, m), 8.07 (1H, d) |
| 2-176 | 1H-NMR (CDCl3) δ: 0.74-1.08 (4H, m), 1.32-1.44 (1H, m), 3.41 (1H, d), 3.74 (1H, d), 4.42 (1H, d), 4.57 (2H, d), 4.88 (1H, d), 6.19 (1H, d), 7.45-7.48 (3H, m), 7.70-7.75 (2H, m), 8.07 (1H, d) |
| 2-177 | 1H-NMR (CDCL3) δ: 3.12 (2H, q), 3.41 (1H, d), 3.75 (1H, d), 4.43 (1H, d), 4.60 (2H, d), 4.89 (1H, d), 6.25 (1H, s), 7.45 (3H, m), 7.76-7.68 (2H, m), 8.09 (1H, s) |
| 2-179 | 1H-NMR (CDCl3) δ: 0.76-0.79 (2H, m), 0.99-1.02 (2H, m), 1.35-1.44 (1H, m), 3.47 (1H, d), 3.88 (1H, d), 4.50-4.56 (3H, m), 5.01 (1H, d), 6.13 (1H, s), 7.50 (1H, d), 7.74-7.81 (3H, m), 7.91 (1H, s), 8.09 (1H, d) |
| 2-194 | 1H-NMR (CDCl3) δ: 3.40-3.43 (1H, m), 3.76 (1H, dd), 3.97 (2H, s), 4.43 (1H, d), 4.88 (1H, d), 7.40 (2H, s), 7.50 (1H, d,), 7.76-7.78 (1H, m), 8.04-8.05 (1H, m). |
| 2-195 | 1H-NMR (CDCl3) δ: 1.14 (3H, t), 3.20-3.25 (2H, m), 3.37-3.42 (1H, m), 3.72-3.77 (1H, m), 4.25-4.26 (1H, m), 4.43-4.46 (4H, m), 4.78-4.90 (2H, m), 7.39 (2H, s), 7.52 (1H, d), 7.71-7.74 (1H, m), 8.05-8.06 (1H, m) |
| 2-196 | 1H-NMR (CDCl3) δ: 0.91 (3H, t), 1.48-1.55 (2H, m), 3.12-3.16 (2H, m), 3.39 (1H, d), 3.74 (1H, dd), 4.36-4.46 (3H, m), 4.84-4.88 (2H, m), 7.39 (2H, s), 7.52 (1H, d), 7.71-7.73 (1H, m), 8.05-8.05 (1H, m) |
| 2-197 | 1H-NMR (CDCl3) δ: 1,46 (9H, s), 3.44 (1H, d), 3.79 (1H, d), 4.44-4.53 (3H, m), 4.90-4.95 (2H, m), 7.41 (2H, s), 7.68 (1H, d), 7.97-8.00 (1H, m), 8.13 (1H, s) |
| 2-199 | 1H-NMR (CDCl3) δ: 1.13 (3H, t), 3.19-3.24 (2H, m), 3.40 (1H, d), 3.75 (1H, dd), 4.37-4.48 (4H, m), 4.84-4.89 (2H, m), 7.39 (2H, s), 7.51 (1H, d), 7.67 (1H, dd), 7.86 (1H, d) |
| 2-200 | 1H-NMR (CDCl3) δ: 1.09-1.15 (3H, m), 3.16-3.25 (2H, m), 3.50 (1H, d), 3.90 (1H, d), 4.48-4.62 (4H, m), 5.00-5,02 (2H, m), 7.72 (1H, d), 7.83 (2H, s), 7.93-7.96 (2H, m), 8.13 (1H, s) |

TABLE 19-continued

| No. | 1H-NMR |
|---|---|
| 2-201 | 1H-NMR (CDCl3) δ: 1.13 (3H, t), 3.19-3.24 (2H, m), 3.43 (1H, d), 3.78 (1H, dd), 4.43-4.45 (2H, m), 4.60 (2H, d), 4.84-4.90 (2H, m), 7.40 (2H, s), 7.73 (1H, d), 7.95 (1H, d), 8.12 (1H, s) |
| 2-202 | 1H-NMR (CDCl3) δ: 1.45 (9H, s), 3.40 (1H, d), 3.76 (1H, d), 4.41-4.44 (3H, m), 4.88 (1H, d), 5.07-5.10 (1H, m), 7.42-7.45 (3H, m), 7.73-7.76 (1H, m), 8.05-8.05 (1H, m) |
| 2-203 | 1H-NMR (CDCl3) δ: 3.41 (1H, d), 3.75 (1H, dd), 4.44 (1H, d), 4.65 (2H, d), 4.88 (1H, d), 6.92-6.95 (1H, m), 7.41-7.45 (3H, m), 7.74-7.77 (1H, m), 8.10-8.10 (1H, m) |
| 2-204 | 1H-NMR (CDCl3) δ: 2.04 (3H, s), 3.47 (1H, d), 3.84 (1H, dd), 4.47 (1H, d), 4.66 (2H, d), 4.95 (1H, dd), 6.08-6.10 (1H, m), 7.61-7.70 (3H, m), 7.97 (1H, d), 8.15 (1H, s) |
| 2-205 | 1H-NMR (CDCl3) δ: 1.14-1.19 (3H, m), 2.23-2.31 (2H, m), 3.47 (1H, d), 3.84 (1H, dd), 4.47, (1H, d) 4.65 (2H, d), 4.95 (1H, dd), 6.04 (1H, m), 7.61-7.70 (3H, m), 7.95-7.98 (1H, m), 8.15 (1H, s) |
| 2-206 | 1H-NMR (CDCl3) δ: 3.08-3.19 (2H, m), 3.46 (1H, d), 3.85 (1H, dd), 4.48 (1H, d), 4.71 (2H, d), 4.93-4.99 (1H, m), 6.20-6.23 (1H, m), 7.60-7.69 (3H, m), 7.97-8.00 (1H, m), 8.18 (1H, s) |
| 2-207 | 1H-NMR (CDCl3) δ: 0.76-0.80 (2H, m), 0.99-1.02 (2H, m), 1.38-1.41 (1H, m), 3.46 (1H, d), 3.84 (1H, d), 4.47 (1H, d), 4.67 (2H, d), 4.95 (1H, dd), 6.13-6.15 (1H, m), 7.63-7.67 (3H, m), 7.97 (1H, d), 8.15 (1H, s) |
| 2-208 | 1H-NMR (CDCl3) δ: 1.08 (3H, t), 3.13-3.16 (2H, m), 3.44 (1H, d), 3.82 (1H, dd), 4.44-4.52 (3H, m), 4.90-4.97 (2H, m), 5.35-5.37 (1H, m), 7.60-7.70 (3H, m), 7.92 (1H, d), 8.07-8.07 (1H, m) |
| 2-209 | 1H-NMR (CDCl3) δ: 2.11 (3H, s), 3.23-3.27 (3H, m), 3.48 (1H, d), 3.82 (1H, dd), 4.47 (1H, d), 4.71 (2H, d), 4.92 (1H, d), 7.43 (2H, s), 7.66 (1H, d), 7.97 (1H, d), 8.15 (1H, s) |
| 2-210 | 1H-NMR (CDCl3) δ: 1.17 (3H, t), 2.26 (2H, q), 3.45 (1H, d), 3.79 (1H, dd), 4.45 (1H, d), 4.66 (2H, d), 4.91 (1H, dd), 5.90-5.92 (1H, m), 7.27 (2H, s), 7.38-7.39 (1H, m), 7.67 (1H, d), 7.96 (1H, d), 8.14 (1H, s) |
| 2-211 | 1H-NMR (CDCl3) δ: 3.11-3.21 (2H, m), 3.48 (1H, d), 3.81 (1H, dd), 4.47 (1H, d), 4.69 (2H, d), 4.92 (1H, dd), 6.39-6.41 (1H, m), 7.27 (2H, s), 7.38-7.39 (1H, m), 7.62 (1H, d), 7.97 (1H, d), 8.15 (1H, s) |
| 2-212 | 1H-NMR (CDCl3) δ: 0.75-0.79 (2H, m), 0.98-1.07 (2H, m), 1.35-1.44 (1H, m), 3.45 (1H, d), 3.79 (1H, dd), 4.46 (1H, d), 4.67 (2H, d), 4.91 (1H, dd), 6.13-6.16 (1H, m), 7.29 (2H, s), 7.38-7.39 (1H, m), 7.67 (1H, d), 7.96 (1H, d), 8.14 (1H, s) |
| 2-213 | 1H-NMR (CDCl3) δ: 1.11 (3H, t), 3.18-3.23 (2H, m), 3.44 (1H, d), 3.78 (1H, dd), 4.43-4.57 (4H, m), 4.86-5.00 (2H, m), 7.27 (2H, s), 7.38-7.39 (1H, m), 7.71 (1H, d), 7.94 (1H, d), 8.11 (1H, s) |
| 2-214 | 1H-NMR (CDCl3) δ: 2.09 (3H, s), 3.23-3.26 (3H, m), 3.47 (1H, d), 3.80 (1H, dd), 4.47 (1H, d), 4.71 (2H, d), 4.92 (1H, dd), 7.27 (2H, s), 7.38-7.39 (1H, m), 7.66 (1H, d), 7.98 (1H, d), 8.16 (1H, s) |
| 2-392 | 1H-NMR (CDCl3) δ: 1.46 (9H, s), 3.51 (1H, d), 3.90-3.93 (1H, m), 4.49-4.55 (3H, m), 5.00-5.05 (2H, m), 7.69 (1H, d), 7.82 (2H, s), 7.92 (1H, s), 8.01 (1H, d), 8.15 (1H, s) |
| 11-5 | 1H-NMR (CDCl3) δ: 2.04 (3H, s), 3.62 (1H, d), 3.87 (1H, d), 4.59 (1H, d), 4.93 (2H, d), 5.07 (1H, d), 5.70 (1H, br s), 7.53-7.41 (3H, m), 7.70-7.57 (3H, m), 8.15-8.01 (1H, m), 8.99-8.88 (1H, m). |
| 11-6 | 1H-NMR (CDCl3) δ: 1.18 (3H, t), 2.25 (2H, q), 3.62 (1H, d), 3.87 (1H, d), 4.58 (1H, d), 4.92 (2H, d), 5.06 (1H, d), 5.76 (1H, br s), 7.40-7.51 (3H, m), 7.55-7.69 (3H, m), 8.01-8.13 (1H, m), 8.96-8.86 (1H, m). |
| 11-7 | 1H-NMR (CDCl3) δ: 0.82-0.70 (2H, m), 0.99-1.10 (2H, m), 1.30-1.41 (1H, m), 3.62 (1H, d), 3.87 (1H, d), 4,58 (1H, d), 4.94 (2H, d), 5.06 (1H, d), 5.95 (1H, brs), 7.66-7.41 (6H, m), 8.12-8.02 (1H, m), 8.98-8.90 (1H, m). |
| 11-8 | 1H-NMR (CDCl3) δ: 3.11 (2H, q), 3.62 (1H, d), 3.87 (1H, d), 4.58 (1H, d), 4.89-5.14 (3H, m), 6.02 (1H, br s), 7.40-7.52 (3H, m), 7.56-7.69 (3H, m), 8.07-7.92 (1H, m), 8.99-8.87 (1H, m). |
| 12-39 | 1H-NMR (CDCl3) δ: 0.13 (9H, s), 2.14 (3H, s), 3.74 (2H, s), 7.81-7.87 (1H, m), 7.97-8.01 (2H, m), 8.08 (1H, s), 8.22 (1H, s), 8.83 (1H, s) |
| 12-55 | 1H-NMR (CDCl3) δ: 0.21 (9H, s), 3.56 (2H, s), 7.63 (1H, brs), 7.84 (1H, d), 8.06 (1H, dd), 8.14 (1H, d), 8.21 (1H, s), 8.85 (1H, s) |
| 13-9 | 1H-NMR (CDCl3) δ: 0.11 (9H, s), 2.09 (3H, s), 2.14 (3H, s), 3.64 (2H, s), 5.20 (2H, s), 7.42-7.47 (2H, m), 7.71-7.74 (1H, m) |
| 13-15 | 1H-NMR (CDCl3) δ: 0.11 (9H, s), 2.10 (3H, s), 2.14 (3H, s), 3.64 (2H, s), 5.22 (2H, s), 7.41-7.45 (2H, m), 7.53-7.56 (1H, m) |
| 13-27 | 1H-NMR (CDCl3) δ: 0.12 (9H, s), 2.09 (3H, s), 2.15 (3H, s), 3.68 (2H, s), 5.32 (2H, s), 7.57-7.60 (1H, m), 7.72-7.75 (1H, m), 7.84-7.87 (1H, m) |
| 13-70 | 1H-NMR (CDCl3) δ: 0.13 (9H, s), 2.16 (3H, s), 2.94-2.96 (3H, m), 5.24 (2H, s), 5.91-5.94 (1H, m), 7.46-7.76 (4H, m) |
| 13-71 | 1H-NMR (CDCl3) δ: 0.18 (9H, s), 2.15 (3H, s), 3.51 (2H, d), 5.18 (2H, s), 7.40 (1H, d), 7.58-7.60 (2H, m), 7.90 (1H, d) |
| 13-75 | 1H-NMR (CDCl3) δ: 0.19 (9H, s), 2.14 (3H, s), 3.53-3.55 (2H, m), 5.30 (2H, s), 7.56-7.59 (2H, m), 7.83 (1H, d, J = 8.1 Hz), 7.99 (1H, s) |
| 15-2 | 1H-NMR (CDCl3) δ: 0.22 (9H, s), 2.14-2.15 (6H, m), 3.67 (2H, s), 5.59 (2H, s), 7.56-7.61 (4H, m), 7.82-7.83 (1H, m), 8.06-8.15 (1H, m) |
| 18-14 | 1H-NMR (CDCl3) δ: 0.12 (9H, s), 1.45 (9H, s), 2.09 (3H, s), 3.17-3.20 (2H, m), 4.38-4.40 (2H, m), 5.03-5.06 (1H, m), 7.39-7.46 (2H, m), 7.69 (1H, d) |
| 18-30 | 1H-NMR (CDCl3) δ: 0.12 (9H, s), 1.46 (9H, s), 2.08 (3H, s), 3.21 (1H, s), 3.67 (1H, s), 4.51-4.54 (2H, m), 4.94-5.00 (1H, m), 7,60-7.70 (2H, m), 7.79 (1H, s) |
| 18-51 | 1H-NMR (CDCl3) δ: 0.18 (9H, s), 1.45 (9H, s), 3.51 (2H, d), 4.36 (2H, d), 5.06-5.10 (1H, m), 7.36-7.39 (1H, m), 7.53-7.56 (2H, m), 7.90 (1H, d) |
| 18-67 | 1H-NMR (CDCl3) δ: 0.17 (9H, s), 1.44 (9H, s), 3.52 (2H, d), 4.41 (2H, d), 5.15-5.16 (1H, m), 7.45 (1H, dz), 7.70-7.72 (1H, m), 7.94 (1H, s), 8.14-8.17 (1H, m) |

BIOLOGICAL EXAMPLES

Unless nomentioned otherwise, the test solutions were prepared as follows:
Containing as solvent: Dimethylformamide, 3 parts by weight; and as emulsifier: Polyoxyethylene alkyl phenyl ether, 1 part by weight
To prepare the test solution, 1 part by weight of an active compound is mixed with the above-mentioned amount of solvent containing the above-mentioned amount of emulsifier, and the mixture is diluted with water to the desired concentration.

BIOLOGICAL TEST EXAMPLE 1

Test Against Tobacco Cutworm (*Spodoptera litura*) Larvae

The leaves of sweet potato were immersed in the test solution at the appropriate concentration, and the leaves were dried in air. The leaves were then placed in a petri dish having a diameter of 9 cm, and ten third-instar larvae of tobacco cutworm were released therein. The petri dish was placed in a temperature chamber at 25° C. After 2 days and 4 days sweet potato leaves were additionally added. After 7 days, the number of dead larvae was counted, to calculate the insecticidal activity. An insecticidal activity of 100% means that all larvae were killed, whereas an insecticidal activity of 0% means that no larva was killed. In the current test, the results of two petri dishes for each partition were averaged.

In the Biological Test Example 1, the compounds Nos. 1-21, 1-39, 1-72, 1-78, 1-94, 1-95, 2-13, 2-19, 2-153, 2-154, 2-156, 2-157, 2-158, 2-159, 2-160, 2-161, 2-162, 2-163, 2-164, 2-165, 2-166, 2-167, 2-168, 2-170, 2-171, 2-172, 2-173, 2-179, 2-180, 2-195, 2-205, 2-209, 2-211, 2-212, 11-5, 11-6, 11-7, 11-8, showed an insecticidal insecticidal activity of 100% at an active compound concentration of 100 ppm.

The compounds Nos. 1-35, 1-37, 1-36, 1-41, 1-42, 1-96, 1-97, 1-98, 1-99, 2-117, 2-134, 2-139, 2-147, 2-174, 2-176, 2-177, 2-194, 2-196, 2-197, 2-199, 2-200, 2-201, 2-202, 2-203, 2-204, 2-206, 2-207, 2-208, 2-210, 2-211, 2-212, 2-213, 2-214, 2-392, showed an insecticidal activity of $\geq 80\%$ at an active compound concentration of 100 ppm.

BIOLOGICAL TEST EXAMPLE 2

Test Against Two-Spotted Spider Mite (*Tetranvchus urticae*)

50 to 100 adult two-spotted spider mites were inoculated onto the leaves of kidney beans at the two-true leaf stage, which plant had been cultivated in a pot having a diameter of 6 cm. After one day, test solution at the appropriate concentration was sprayed thereon in a sufficient amount using a spray gun. After the spraying, the plant pot was placed inside a greenhouse, and after 7 days, the acaricidal activity was calculated. An acaricidal activity of 100% means that all mites were killed, whereas an acaricidal activity of 0% means that no mite was killed.

Compounds Nos. 1-21, 1-72, 1-78, 1-94, 1-95, 2-154, 2-156, 2-157, 2-158, 11-5, 11-6, 11-7, 11-8, 2-159, 2-160, 2-161, 2-162, 2-163, 2-164, 2-165, 2-166, 2-167, 2-168, 2-170, 2-171, 2-172, 2-173, 2-179, 2-180, 2-195, 2-205, 2-209, 2-211, 2-212 showed an acaricidal activity of 100% at an active compound concentration of 100 ppm. The compound No. 1-39 showed an acaricidal activity rate of 98% at a concentration of 100 ppm.

BIOLOGICAL TEST EXAMPLE 3

Test Against Cucurbit Leaf Beetle (*Aulacophora femoralis*)

Cucumber leaves were immersed in the test solution at the appropriate concentration, and the leaves were dried in air. The leaves were then placed in a plastic cup containing aseptically sterilized black soil, and five second-instar larvae of cucurbit leaf beetle were released therein. After 7 days, the number of dead larvae was counted, and thus the insecticidal activity was calculated. An insecticidal activity of 100% means that all beetles were killed, whereas an insecticidal activity of 0% means that no beetle was killed.

Compounds Nos. 1-21, 1-39, 1-72, 1-78, 1-94, 1-95, 2-19, 2-153, 2-154, 2-156, 2-157, 2-158, 11-5, 11-6, 11-7, 11-8, 2-159, 2-160, 2-161, 2-162, 2-163, 2-164, 2-165, 2-166, 2-167, 2-168, 2-170, 2-171, 2-172, 2-173, 2-179, 2-180, 2-195, 2-205, 2-209, 2-211, 2-212 showed an insecticidal activity of 100% at an active compound concentration of 100 ppm.

BIOLOGICAL TEST EXAMPLE 4

Test Against a Strain of Green Peach Aphid (*Mvzus persicas*) which is Resistant to Organic Phosphorus and Carbamate Agents About 30 to 50 of the resistant green peach aphids were inoculated per seedling, onto the leaves of egg plant at the two-true leaf stage, which plant had been cultivated in a pot having a diameter of 6 cm. One day after the inoculation, the test solution at the appropriate concentration was sprayed thereon in a sufficient amount using a spray gun. After the spraying, the plant pot was placed in a greenhouse at 28° C., and after 7 days, the insecticidal activity was calculated. An insecticidal activity of 100% means that all aphids were killed, whereas an insecticidal activity of 096 means that no aphid was killed. The test was repeated two times.

Compounds Nos. 1-21, 1-72, 1-78, 1-94, 1-95, 2-156, 2-157, 2-158, 11-5, 11-6, 11-7, 11-8, 2-159, 2-160, 2-161, 2-162, 2-163, 2-164, 2-165, 2-166, 2-167, 2-168, 2-170, 2-171, 2-172, 2-173, 2-179, 2-180, 2-195, 2-205, 2-209, 2-211, 2-212 showed an insecticidal activity of 100% at an active compound concentration of 500 ppm, and the compound no. 1-39 showed control effects of an insecticidal activity of 98% at a concentration of 500 ppm.

Compounds Nos. 1-39, 1-42, 1-72, 1-78, 1-94, 1-95, 2-71, 2-134, 2-139, 2-157, 2-158, 2-159, 2-160, 2-161, 2-162, 2-163, 2-164, 2-165, 2-166, 2-167, 2-168, 2-172, 2-176, 2-174, 2-179, 2-197, 2-199, 2-201, 2-202, 2-173, 2-147, 2-209, 2-210, 2-211, 2-212, 2-214, 2-392, 11-5, 11-6, 11-7 and 11-8 showed an insecticidal activity of $\geq 80\%$ at an active compound concentration of 100 ppm.

BIOLOGICAL TEST EXAMPLE 5

Test Against Cat Fleas (*Ctenocephalides fells*)

Solvent: Dimethylsulfoxide
In order to make a suitable test solution, 10 mg of an active compound is dissolved in 0.5 ml of the above-mentioned solvent, and the mixture is diluted with the blood of a domestic animal to a predetermined concentration.

About 10 to 15 adult cat fleas are provided in a container exclusive for fleas. An exclusive container containing the test solution is covered with Parafilm, reversed upside down, and then mounted on top of the flea container, so that the cat fleas can suck the blood in the container. The test solution is maintained at 37° C., and the flea container is maintained at room temperature. After 2 days the mortality rate of the cat fleas is measured. 100% means that all of the cat fleas have been killed, while 0% means that all are alive.

Compounds Nos. 1-21 showed a mortality rate of at least 90% at an active compound concentration of 100 ppm, and the compounds of Compound No. 1-39 showed a mortality rate of 100% at 100 ppm.

Additionally, compounds Nos 1-35, 1-72, 1-78, 1-94, 1-95, 1-100, 2-13, 2-19, 2-117, 2-134, 2-139, 2-147, 2-153, 2-154, 2-156, 2-157, 2-158, 2-159, 2-160, 2-161, 2-162, 2-163, 2-164, 2-165, 2-166, 2-167, 2-168, 2-170, 2-171, 2-172, 2-173, 2-174, 2-176, 2-177, 2-179, 2-180, 2-194, 2-195, 2-196, 2-197, 2-199, 2-200, 2-201, 2-202, 2-203, 2-205, 2-209, 2-211, 2-212, 11-5, 11-6, 11-7, 11-8, 15-2 showed an mortality rate of ≧80% at an active compound concentration of 100 ppm.

BIOLOGICAL TEST EXAMPLE 6

Test Against Cattle Tick (*Boophilus microplus*)

Solvent: Dimethylsulfoxide

In order to make a suitable test solution, 10 mg of an active compound is dissolved in 0.5 ml of the above mentioned solvent, and the mixture is diluted with water to a predetermined concentration.

The test solution is injected into the abdomens of five fully-fed female adult cattle ticks. The cattle ticks are transferred to a replica plate, and are bred in a breeding vessel for a certain time period. Egg deposition of fertile eggs is monitored.

After 7 days the mortality rate of the cattle ticks is measured. 100% means that all eggs are infertile; and 0% means that all eggs are fertile.

Compounds Nos. 1-21 and 1-39 showed an mortality rate of 100% at an active compound concentration of 20 μg/animal.

Additionally, compounds Nos. 1-35, 1-72, 1-78, 1-94, 1-95, 1-99, 1-100, 2-13, 2-19, 2-117, 2-134, 2-139, 2-147, 2-153, 2-154.2-156, 2-157, 2-158, 2-159, 2-160, 2-161, 2-162, 2-163, 2-164, 2-165, 2-166, 2-167, 2-168, 2-170, 2-171, 2-172, 2-173, 2-174, 2-176, 2-177, 2-179, 2-180, 2-194, 2-195, 2-196, 2-197, 2-199, 2-200, 2-201, 2-202, 2-203, 2-205, 2-209, 2-211, 2-212, 2-392, 11-5, 1-6, 11-7, 11-8, 15-2 showed mortality rate of ≧80% at an active compound concentration of 20 μg/animal.

BIOLOGICAL TEST EXAMPLE 7

Test Against Sheep Blowfly (*Lucillia cuprina*)

Solvent: Dimethylsulfoxide

In order to make a suitable test solution, 10 mg of an active compound is dissolved in 0.5 ml of the solvent, and the mixture is diluted with water to a predetermined concentration.

Minced horse meat having a size of 1 square centimeter, and 0.5 ml of the test solution are placed in a test tube, and about 20 to 30 adult sheep blowflies are introduced therein.

After 2 days the mortality rate of the sheep blowflies is measured. 100% means that all of the sheep blowflies have been killed, and 0% means that all are alive.

Compounds Nos. 1-21 and 1-39 showed a mortality rate of 100% at an active compound concentration of 100 ppm.

Additionally, compounds Nos. 1-35, 1-72, 1-78, 1-94, 1-95, 1-99, 1-100, 2-1, 2-19, 2-117, 2-134, 2-139, 2-147, 2-153, 2-154, 2-156, 2-157, 2-158, 2-159, 2-160, 2-161, 2-162, 2-163, 2-164, 2-165, 2-166, 2-167, 2-168, 2-170, 2-171, 2-172, 2-173, 2-174, 2-176, 2-177, 2-179, 2-180, 2-194, 2-195, 2-196, 2-197, 2-199, 2-200, 2-201, 2-202, 2-203, 2-205, 2-209, 2-211, 2-212, 2-392, 11-5, 11-6, 11-7, 11-8, 15-2 showed a mortality rate of ≧80% at an active compound concentration of 100 ppm.

BIOLOGICAL TEST EXAMPLE 8

Test Against Housefly (*Musca domestica*)

Solvent: Dimethylsulfoxide

In order to make a suitable test solution, 10 mg of an active compound is dissolved in 0.5 ml of the solvent, and the mixture is diluted with water to a predetermined concentration.

In a preliminary stage of the test, a piece of sponge having a certain size is soaked with a mixture of sugar and the test solution is placed in a test container. Ten adult houseflies are introduced to the container, and the container is covered with a perforated lid.

After 2 days, the mortality rate of the houseflies is measured. At that time, 100% means that all of the houseflies have been killed, and 0% means that all are alive.

Compounds Nos. 1-21 and 1-39 showed a mortality rate of 100% at active compound concentration of 100 ppm.

Additionally, compounds Nos. 1-35, 1-72, 1-78, 1-94, 1-95, 2-13, 2-19, 2-117, 2-134, 2-139, 2-147, 2-153, 2-154, 2-156, 2-157, 2-158, 2-159, 2-160, 2-161, 2-162, 2-163.2-164, 2-165, 2-166, 2-167, 2-168, 2-170, 2-171, 2-172, 2-173, 2-174, 2-176, 2-177, 2-179, 2-180, 2-194, 2-195, 2-196, 2-199, 2-200, 2-201, 2-203, 2-205, 2-209, 2-211, 2-212, 11-5, 11-6, 11-7, 11-8 and 15-2 showed a mortality rate of ≧80% at an active compound concentration of 100 ppm.

BIOLOGICAL TEST EXAMPLE 9

*Amblyomma hebraeum*—Test

Solvent: Dimethylsulfoxide

To produce a suitable preparation of active compound. 1 part by weight of active compound is mixed with the stated amount of solvent, and the concentrate is diluted with containing solvent to the desired concentration.

Nymphs of the tick *Amblyomma hebraeum* are placed in perforated plastic beakers and immersed in aqueous compound solution for one minute. Ticks are transferred to a filter paper in a Petri dish and incubated in a climate chamber for 42 days.

After 2 days mortality in % is determined. 100% means that all the ticks have been killed; 0% means that none of the ticks have been killed.

In this test compounds Nos. 1-39, 1-78, 1-95, 1-94, 2-134, 2-139, 2-147, 2-156, 2-157, 2-158, 2-162, 2-163, 2-164, 2-170, 2-173, 2-177, 11-5, 11-6, 11-7, 15-2, showed an activity of ≧80% at an application rate of 100 ppm.

BIOLOGICAL TEST EXAMPLE 10

*Boophilus microplus*

Solvent: Dimethylsulfoxid

To produce a suitable preparation of active compound, 10 mg of active compound are dissolved in 0.5 ml solvent, and the concentrate is diluted with water to the desired concentration.

Eight to ten adult engorged female *Boophilus microplus* ticks are placed in perforated plastic beakers and immersed in aqueous compound solution for one minute. Ticks are transferred to a filter paper in a plastic tray. Egg deposition of fertile eggs is monitored after.

After 7 days mortality in % is determined. 100% means that all the ticks have been killed; 0% means that none of the ticks have been killed.

The following compounds showed an activity of ≧80% at application rate of 100 ppm:

1-39, 1-72, 1-78, 1-94, 1-95, 2-13, 2-19, 2-117, 2-134, 2-139, 2-147, 2-153, 2-154, 2-156, 2-157, 2-158, 2-159, 2-160, 2-161, 2-162, 2-163, 2-164, 2-165, 2-166, 2-167, 2-168, 2-170, 2-171, 2-172, 2-173, 2-174, 2-176, 2-177, 2-179, 2-180, 2-195, 2-197, 2-199, 2-201, 2-202, 2-203, 2-204, 2-205, 2-206, 2-208, 2-209, 2-211, 2-212, 11-5, 11-6, 11-7, 11-8, 15-2.

FORMULATION EXAMPLES

Formulation Example 1

Granules

To a mixture of 10 parts of Compound No. 1-39, 30 parts of bentonite (montmorillonite), 58 parts of talc and 2 parts of lignin sulfonate, 25 parts of water is added. The mixture is thoroughly kneaded. The product is fabricated into particles of 10 to 40 mesh by extruding through an extruder type granulating machine, and dried at 40 to 50° C. to obtain a granular preparation.

Formulation Example 2

Granules 95 parts of clay mineral particles having a particle size distribution in the range of 0.2 to 2 mm is introduced into a rotary mixer, and while rotating, 5 parts of Compound No. 1-39 is sprayed together with a liquid diluent to uniformly wet the particles. Then, the particles are dried at 40 to 50° C. to obtain a granular preparation.

Formulation Example 3

Emulsion 30 parts of Compound No. 1-19, 55 parts of xylene. 8 parts of polyoxyethylene alkyl phenyl ether and 7 parts of calcium alkylbenzenesulfonate are mixed and stirred to obtain an emulsion preparation.

Formulation Example 4

Wettable Powder 15 parts of Compound No. 1-39, 80 parts of a mixture of white carbon (finely powdered amorphous hydrous silicon oxide) and clay powder (1:5). 2 parts of sodium alkylbenzenesulfonate and 3 parts of sodium alkylnaphthalenesulfonate-formalin condensate are pulverized and mixed to obtain a wettable powder preparation.

Formulation Example 5

Wettable Granules 20 parts of Compound No. 1-39, 30 parts of sodium lign-insulfonate, 15 parts of bentonite and 35 parts of calcined diatomaceous earth powder are sufficiently mixed, and water is added thereto. The mixture is extruded through a screen of 0.3 mm and dried to obtain a wettable granule preparation.

The novel arylpyrroline derivatives of the present invention have an excellent insecticidal action and can be used as an insecticide as demonstrate though the Examples.

The invention claimed is:

1. An arylpyrroline compound of formula (I)

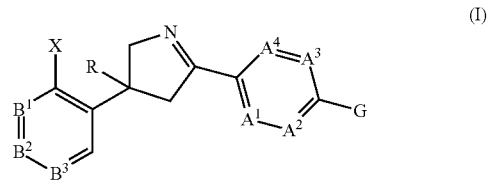

wherein

G represents an optionally substituted saturated or unsaturated 5- or 6-membered heterocyclic group, or represents a chemical-group of the following formula:

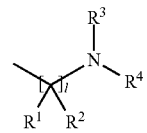

wherein $R^1$ and $R^2$ each independently represent hydrogen; optionally substituted alkyl, cycloalkyl, haloalkyl, cyclohaloalkyl, alkenyl, alkynyl, haloalkenyl, haloalkynyl; cyano; optionally substituted alkoxycarbony, or alkoxythiocarbonyl; or $R^1$ and $R^2$ together with the carbon atom to which they are attached form a 3 to 6-membered carbocyclic ring;

$R^3$ represents hydrogen; amino; hydroxyl; optionally substituted alkoxy, alkylcarbonylamino, alkylimino, alkyl, cycloalkyl, haloalkyl; cyano; optionally substituted alkenyl, alkynyl, alkylcarbonyl, or is selected from the following groups $CH_2$—$R^5$, $C(=O)R^5$, $C(=S)R^5$;

$R^4$ is selected from the group consisting of hydrogen; cyano; carbonyl; thiocarbonyl; optionally substituted alkylcarbonyl, alkylthiocarbonyl, haloalkylcarbonyl, haloalkylthiocarbonyl, alkylaminocarbonyl, alkylaminothiocarbonyl, dialkylaminocarbonyl, dialkylaminothiocarbonyl, alkoxyaminocarbonyl, alkoxyaminothiocarbonyl, alkoxycarbonyl, alkoxythiocarbonyl, thioalkoxycarbonyl, thioalkoxythiocarbonyl, alkylsulfonyl, haloalkylsulfonyl, or a chemical group selected among cycloalkylcarbonyl, alkenylcarbonyl, alkynylcarbonyl, cycloalkylalkylcarbonyl, alkylsulfenylarkylcarbonyl, alkylsulfinylarkylcarbonyl, alkylsulfonylalkylcarbonyl, alkylcarbonylalkylcarbonyl, cyclalkylaminocrbonyl, alkenylaminocarbonyl, and alkynylaminocarbonyl or is selected from the groups $C(=O)R^5$ and $C(=S)R^5$;

or $R^3$ and $R^4$ together with the nitrogen atom to which they are bound, form a 3- to 6-membered heterocyclic ring which may be substituted with a substituent X, or may be substituted with a keto, thioketo or nitroimino group;

$R^5$ represents optionally substituted phenyl, or an optionally substituted heterocyclic ring;

R represents optionally substituted alkyl, or haloalkyl;

$A^1$, $A^2$, $A^3$ and $A^4$ each independently represents a group C—Y; or nitrogen, under the proviso that only 2 of the chemical groups $A^1$, $A^2$, $A^3$ and $A^4$ may stand for nitrogen at the same time or if $A^1$ and $A^2$ both represent C—Y, then both Y, together with the carbon atoms to which they are attached to, may form a 5- or 6-membered aromatic ring;

$B^1$, $B^2$ and $B^3$ each independently represent C—X or nitrogen; under the proviso that only two of the chemical groups $B^1$, $B^2$, and $B^3$ may stand for nitrogen at the same time;

X each independently represents hydrogen, halogen, optionally substituted haloalkyl; nitro; optionally substituted alkyl, alkoxyl; cyano, optionally substituted haloalkoxyl, alkylsulfenyl, alkylsulfinyl, alkylsulfonyl, haloalkylsulfenyl, haloalkylsulfinyl, haloalkylsulfonyl; hydroxyl, thiol, amino, optionally substituted acylamino, alkoxycarbonylamino, haloalkoxycarbonylamino, alkoxyimino, haloalkoxyimino, alkylsulfonylamino; or sulfur pentafluoride;

Y each independently represents hydrogen; halogen; optionally substituted haloalkyl; nitro; optionally substituted alkyl, cycloalkyl, cyclohaloalkyl, alkoxyl; cyano, optionally substituted haloalkoxyl, alkylsulfenyl, alkylsulfinyl, alkylsulfonyl, haloalkylsulfenyl, haloalkylsulfinyl, haloalkylsulfonyl, alkylsulfonyloxy, haloalkylsulfonyloxy, alkylaminosulfonyl, haloalkylaminosulfonyl, dialkylaminosulfonyl, di(haloalkyl) aminosulfonyl; hydroxyl; thiol; amino; optionally substituted alkylamino, dialkylamino, acylamino, alkoxycarbonylamino, haloalkoxycarbonylamino, alkylsulfonylamino, haloalkylsulfonylamino, trialkylsilyl, alkoxyimino, haloalkoxyimino, alkoxyiminoalkyl, haloalkoxy-iminoalkyl, alkylsulfinylimino, alkylsulfinyliminoalkyl, alkylsulfinyliminoalkylcarbonyl, alkylsulfoxyimino, alkylsulfoxyiminoalkyl, alkoxycarbonyl, alkylcarbonyl, aminocarbonyl, alkylaminocarbonyl, aminothiocarbonyl, alkylaminothiocarbonyl, dialkylaminocarbonyl, or dialkylaminothiocarbonyl; and l stands for 1, 2 or 3.

2. A compound according to claim 1, wherein

G is selected from the group consisting of optionally substituted 5-membered heterocyclic groups G1 to G9:

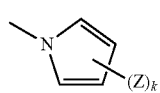
G1

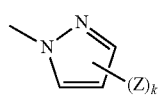
G2

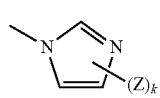
G3

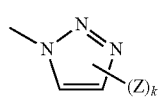
G4

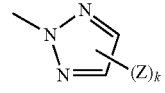
G5

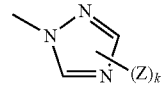
G6

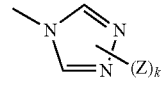
G7

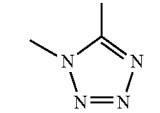
G8

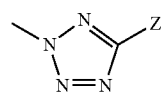
G9 or represents a chemical group of the following formula:

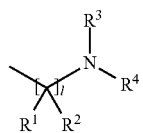

wherein $R^1$ and $R^2$ each independently represent hydrogen; optionally substituted $C_{1-12}$ alkyl, $C_{3-8}$ cycloalkyl, $C_{1-12}$ haloalkyl, $C_{3-8}$cyclohaloalkyl, $C_{2-12}$ alkenyl, $C_{2-12}$ alkynyl, $C_{2-12}$ haloalkenyl, $C_{2-12}$ haloalkynyl; cyano; optionally substituted $C_{1-12}$ alkoxy-carbonyl, $C_{1-12}$ alkoxythiocarbonyl, or $R^1$ and $R^2$ together with the carbon atom to which they are attached may form a 3 to 6-membered carbocyclic ring;

$R^3$ represents hydrogen; amino; hydroxyl; optionally substituted $C_{1-12}$ alkoxy, $C_{1-12}$ alkyl-carbonylamino, $C_{1-12}$ alkylimino, $C_{1-12}$ alkyl, $C_{3-8}$cycloalkyl, $C_{1-12}$ haloalkyl, cyano, $C_{2-12}$ alkenyl, $C_{2-12}$ alkynyl, $C_{1-12}$ alkyl-carbonyl; or is selected from the following groups $CH_2$—$R^5$, $C(=O)R^5$, $C(=S)R^5$;

$R^4$ a chemical group selected among represents hydrogen; cyano; carbonyl; thiocarbonyl; optionally substituted $C_{1-12}$ alkyl-carbonyl, $C_{1-12}$ alkyl-thiocarbonyl, $C_{1-12}$ haloalkyl-carbonyl, $C_{1-12}$ haloalkyl-thiocarbonyl, $C_{1-12}$ alkylamino-carbonyl, $C_{1-12}$ alkylamino-thiocarbonyl, $C_{2-24}$ (total carbon number) dialkylamino-carbonyl, $C_{2-24}$ (total carbon number) dialkylamino-thiocarbonyl, $C_{1-12}$ alkoxyamino-carbonyl, $C_{1-12}$ alkoxyamino-thiocarbonyl, $C_{1-12}$ alkoxy-carbonyl, $C_{1-12}$ alkoxy-thiocarbonyl, $C_{1-12}$ thioalkoxy-carbonyl, $C_{1-12}$ thioalkoxy-thiocarbonyl, $C_{1-12}$ alkylsulfonyl, $C_{1-12}$ haloalkylsulfonyl, or a chemical group selected among $C_{4-13}$ cycloalkylcarbonyl, $C_{3-13}$ alkenylcarbonyl, $C_{3-13}$ alkynylcarbonyl, $C_{5-25}$ cycloalkylalkylcarbonyl, $C_{3-25}$ alkylsulfenylarkylcarbonyl, $C_{3-25}$ alkylsulfinylarkylcarbonyl, $C_{3-25}$ alkylsulfonylalkylcarbonyl, $C_{4-26}$ alkylcarbonylalkylcarbonyl, $C_{4-13}$ cyclalkylaminocrbonyl, $C_{3-13}$ alkenylaminocarbonyl, $C_{3-13}$ alkynylaminocarbonyl, or is selected from the groups $C(=O)R^5$ and $C(=S)R^5$;

or $R^3$ and $R^4$ together with the nitrogen atom to which they are bound, form a 3- to 6-membered heterocyclic ring which may be substituted with a substituent X, or may be substituted with a keto, thioketo or nitroimino group;

$R^5$ represents optionally substituted phenyl, or an optionally substituted saturated or unsaturated heterocyclic ring;

Z each independently represents halogen, optionally substituted $C_{1-12}$ haloalkyl; nitro; optionally substituted $C_{1-12}$ alkoxyl; cyano; optionally substituted $C_{1-12}$ haloalkoxyl, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl; hydroxyl or thiol;

k represents 0, 1, 2, 3 or 4;

R represents optionally substituted $C_{1-12}$ alkyl, or $C_{1-12}$ haloalkyl;

$A^1$, $A^2$, $A^3$ and $A^4$ each independently represents a group C—Y; or nitrogen, under the proviso that only 2 of the chemical groups $A^1$, $A^2$, $A^3$ and $A^4$ may stand for nitrogen at the same time; or if A1 and A2 both represent C—Y, then both Y, together with the carbon atoms to which they are attached to, may form a 5- or 6-membered aromatic ring;

$B^1$, $B^2$ and $B^3$ each independently represents a group C—X; or nitrogen under the proviso that only 2 of the chemical groups $B^1$, $B^2$, and $B^3$ may stand for nitrogen at the same time;

X each independently represents hydrogen; halogen; optionally substituted $C_{1-12}$ haloalkyl; nitro; optionally substituted $C_{1-12}$ alkyl, $C_{1-12}$ alkoxyl, cyano, optionally substituted $C_{1-12}$ haloalkoxyl, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl; hydroxyl, thiol; amino; optionally substituted $C_{1-12}$ acylamino, $C_{1-12}$ alkoxy-carbonylamino, $C_{1-12}$ haloalkoycarbonylamino, $C_{1-12}$ alkoxy-imino, $C_{1-12}$ haloalkoxyimino, $C_{1-12}$ alkylsulfonylamino; or sulfur pentafluoride;

Y each independently represents hydrogen; halogen; optionally substituted $C_{1-12}$ haloalkyl; nitro; optionally substituted $C_{1-12}$ alkyl, $C_{3-8}$ cycloalkyl, $C_{3-8}$cyclohaloalkyl, $C_{1-12}$ alkoxyl; cyano, optionally substituted $C_{1-12}$ haloalkoxyl, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylsulfonyloxy, $C_{1-12}$ haloalkylsulfonyloxy, $C_{1-12}$ alkylaminosulfonyl, $C_{1-12}$ haloalkylaminosulfonyl, $C_{2-24}$ (total carbon number) dialkylaminosulfonyl, $C_{2-24}$ (total carbon number)di(haloalkyl)aminosulfonyl; hydroxyl; thiol; amino; optionally substituted $C_{1-12}$ alkylamino, $C_{2-24}$ (total carbon number)dialkylamino, $C_{1-12}$ acylamino, $C_{1-12}$ alkoxycarbonylamino, $C_{1-12}$ haloalkoxycarbonylamino, $C_{1-12}$ alkylsulfonylamino, $C_{1-12}$ haloalkylsulfonylamino, $C_{1-12}$ trialkylsilyl, $C_{1-12}$ alkoxyimino, $C_{1-12}$ haloalkoxyimino, $C_{1-12}$ alkoxyiminoalkyl, $C_{1-12}$ haloalkoxy-iminoalkyl, $C_{1-12}$ alkylsulfinylimino, $C_{1-12}$ alkylsulfinyliminoalkyl, $C_{1-12}$ alkylsulfinylimino-$C_{1-12}$ alkylcarbonyl, $C_{1-12}$ alkylsulfoxyimino, $C_{1-12}$ alkylsulfoxyimino-$C_{1-12}$ alkyl, $C_{1-12}$ alkoxycarbonyl, $C_{1-12}$ alkylcarbonyl, aminocarbonyl, $C_{1-12}$ alkylaminocarbonyl, aminothiocarbonyl, $C_{1-12}$ alkylaminothiocarbonyl, $C_{2-12}$ (total carbon number)dialkylaminocarbonyl, or $C_{2-12}$ (total carbon number)dialkylaminothiocarbonyl; and l stands for 1, 2 or 3.

3. A composition, comprising at least one compound according to claim 1 for controlling animal pests.

4. A method for controlling animal pests, comprising applying a compound according to claim 1 to an animal pest and/or a habitat thereof.

5. A composition for controlling arthropods comprising at least one compound of claim 1.

6. Seed of a conventional or transgenic plant treated with at least one compound of claim 1.

7. A compound of formula (II) useful for the preparation of a compound according to claim 1

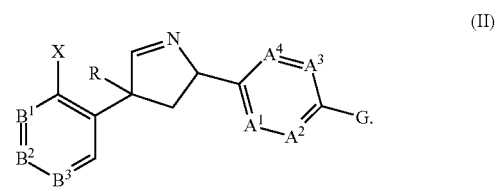

(II)

8. A method for the preparation of a compound according to claim 1, comprising reacting a compound (XII)

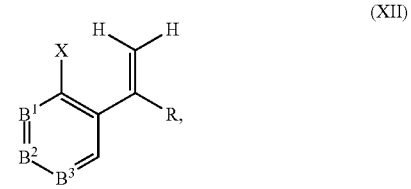

(XII)

with a compound (XXXIX)

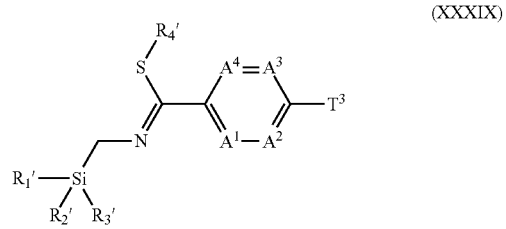

(XXXIX)

wherein $T^3$ stands for F, Cl, Br, I, the chemical group G, or for one of the following chemical groups

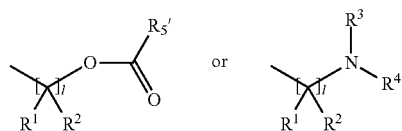

wherein $R_1'$, $R_2'$ and $R_3'$ each independently represents optionally substituted $C_{1-6}$ alkyl or phenyl; and $R_4'$ represents hydrogen, or is selected among optionally substituted $C_{1-6}$alkyl, $C_{2-6}$alkenyl, $C_{2-6}$alkynyl; optionally substituted benzyl, and $R_5'$ represents hydrogen, optionally substituted $C_{1-6}$alkyl or optionally substituted phenyl wherein R4' does not stand for H, in the presence of fluorine reagent.

9. A method for the preparation of a compound according to claim 1, comprising reacting a compound (XII)

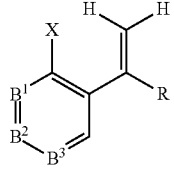
(XII)

with a compound (XXXIX)

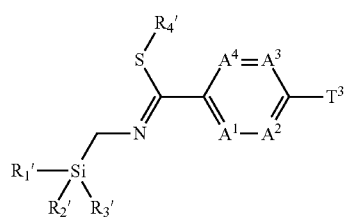
(XXXIX)

wherein $T^3$ stands for F, Cl, Br, I, the chemical group G, or for one of the following chemical groups

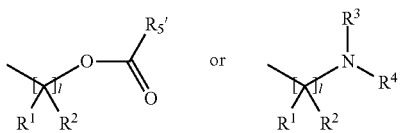

wherein $R_1'$, $R_2'$ and $R_3'$ each independently represents optionally substituted $C_{1-6}$alkyl or phenyl; and $R_4'$ represents hydrogen, or is selected among optionally substituted $C_{1-6}$alkyl, $C_{2-6}$alkenyl, $C_{2-6}$alkynyl; optionally substituted benzyl, and $R_5'$ represents hydrogen, optionally substituted $C_{1-6}$alkyl or optionally substituted phenyl wherein R4' stands for H, in a one pot reaction by firstly adding an alkyl halide and secondly adding a fluorine reagent.

10. A method for the preparation of a compound according to claim 1, comprising reacting a compound (XII)

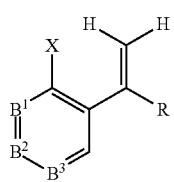
(XII)

with (i) a compound (XXXIV)

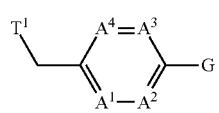
(XXXIV)

wherein $T^1$ stand for —N—CH=O or —N—C; or (ii) a compound (XXXV)

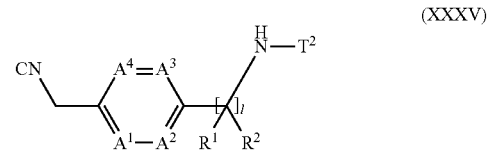
(XXXV)

wherein $T^2$ stands for $R^3$ or $R^4$
yielding a compound of formula (II)

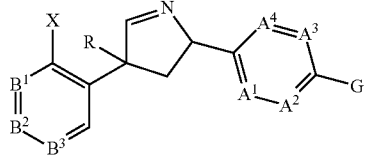
(II)

and further reacting the compound of formula (II) in the presence of an alkali metal base.

11. A compound according to claim 1, wherein the compound is

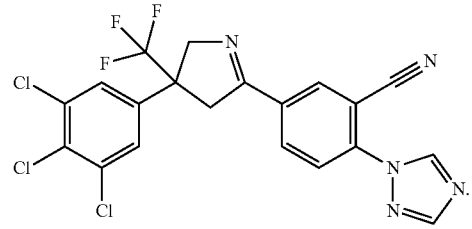

12. A compound according to claim 1, wherein
   G represents an optionally substituted saturated or unsaturated 5- or 6-membered heterocyclic group.
13. A compound according to claim 2, wherein
   G is G1 to G9.
14. A method for controlling animal pests according to claim 4, wherein
   G represents an optionally substituted saturated or unsaturated 5- or 6-membered heterocyclic group.
15. A compound according to claim 7, wherein
   G represents an optionally substituted saturated or unsaturated 5- or 6-membered heterocyclic group.
16. A method for controlling animal pests, comprising applying a compound according to claim 1 to an animal pest and/or habitation thereof, wherein the compound is

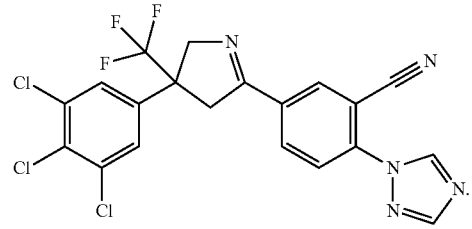

17. A method for controlling animal pests, comprising applying a compound according to claim 1 to an animal pest and/or habitation thereof, wherein G is selected from the group consisting of optionally substituted 5-membered heterocyclic groups G1 to G9:

 G1

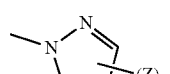 G2

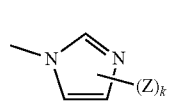 G3

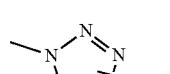 G4

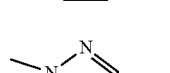 G5

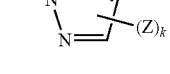 G6

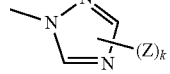 G7

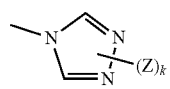 G8

 G9

-continued

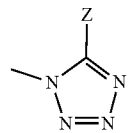 G8

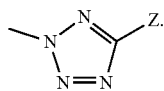 G9

18. A compound according to claim 1, wherein

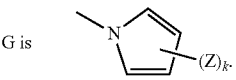 G1

G is

19. A compound according to claim 1, wherein

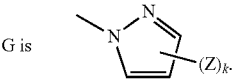 G2

G is

20. A compound according to claim 1, wherein

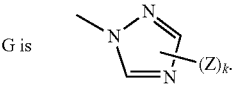 G6

G is

* * * * *